US011591300B2

(12) United States Patent
Blumberg et al.

(10) Patent No.: US 11,591,300 B2
(45) Date of Patent: Feb. 28, 2023

(54) OXAZOLE CONTAINING COMPOUNDS AS ACTIVATORS OF IDO1 AND AHR

(71) Applicants: Shankar S. Iyer, Medford, MA (US); Amadeu Llebaria, Barcelona (ES); The Brigham and Women's Hospital, Inc., Boston, MA (US)

(72) Inventors: Richard S. Blumberg, Weston, MA (US); Shankar S. Iyer, Medford, MA (US); Amit Ghandi, Billerica, MA (US); Amadeu Llebaria, Barcelona (ES)

(73) Assignee: The Brigham and Women's Hospital, Inc., Boston, MA (US)

(*) Notice: Subject to any disclaimer, the term of this patent is extended or adjusted under 35 U.S.C. 154(b) by 84 days.

(21) Appl. No.: 16/955,417

(22) PCT Filed: Dec. 21, 2018

(86) PCT No.: PCT/US2018/067189
§ 371 (c)(1),
(2) Date: Jun. 18, 2020

(87) PCT Pub. No.: WO2019/126697
PCT Pub. Date: Jun. 27, 2019

(65) Prior Publication Data

US 2021/0009535 A1 Jan. 14, 2021

Related U.S. Application Data

(60) Provisional application No. 62/608,784, filed on Dec. 21, 2017.

(51) Int. Cl.

| | |
|---|---|
| ***C07D 263/32*** | (2006.01) |
| ***C07D 263/48*** | (2006.01) |
| ***C07D 277/46*** | (2006.01) |
| ***C07D 417/04*** | (2006.01) |

(52) U.S. Cl.
CPC ......... *C07D 263/32* (2013.01); *C07D 263/48* (2013.01); *C07D 277/46* (2013.01); *C07D 417/04* (2013.01)

(58) Field of Classification Search
CPC ........................... C07D 263/32; C07D 277/46
See application file for complete search history.

(56) References Cited

U.S. PATENT DOCUMENTS

| | | | |
|---|---|---|---|
| 2013/0281525 A1 | 10/2013 | Sherr et al. | |
| 2015/0182592 A1 | 7/2015 | Salford et al. | |

FOREIGN PATENT DOCUMENTS

| | | |
|---|---|---|
| WO | 2008150899 A1 | 12/2008 |

OTHER PUBLICATIONS

Shibazaki et al., "Suppression by p38 MAP kinase inhibitors (pyridinyl imidazole compounds) of Ah receptor target gene activiation by 2,3,7,8-tetrachlorodibenzo-p-dioxin and the possible mechanism", Journal of Biol. Chem., 279, 3869-3876, (2004).

Yang et al., "Acetylsalicylic acid enhances the anti-inflammatory effect of fluoxetine through inhibition of NF-kB, p38-MAPK and ERK1/2 activation in lipopolysaccharide-induced BV-2 microglia cells", Neuroscience, 275, 296-304, (2014).

*Primary Examiner* — Kamal A Saeed
(74) *Attorney, Agent, or Firm* — Nixon Peabody LLP; David S. Resnick; Ravinderjit S. Braich

(57) ABSTRACT

Provided herein are methods and compositions related to a method of stimulating the immune system in a subject in need thereof by administering an agent that increases the level or activity of indoleamine 2,3-dioxygenase (IDO1) and/or aryl hydrocarbon receptor (Ahr).

16 Claims, 46 Drawing Sheets

Specification includes a Sequence Listing.

TMC
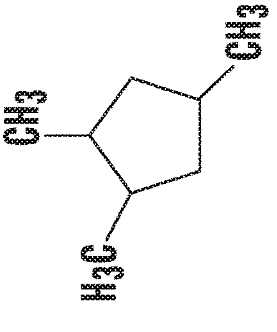
1-MP
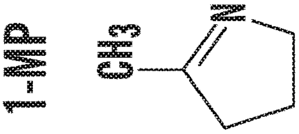
Oxazolone
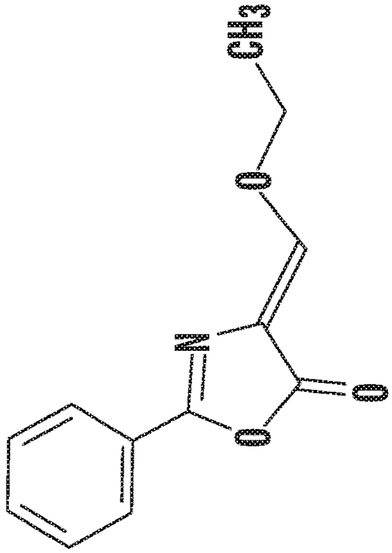
TMO
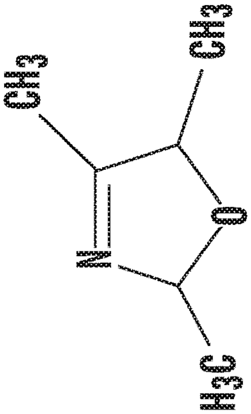
Vinclozolin
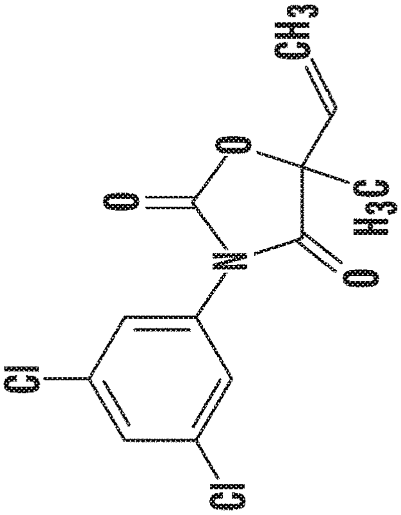
*FIG. 1A*

Anti-DNA Gyrase

Yes

Frag-oztz

Frag-tzoz

No

Frag-tz

Frag-oz

Table 1: Summary of CD1d-restricted responses and aryl hydrocarbon receptor (AhR) activation in MODE-K cells for experimentally tested naturally occurring metabolites

| Compound | Molecular Weight (D | CAS | Human Metabolomics Database | % of CD1d-restricted response (relativ | AhR Activatio | Source (Human Metabolomics Database) |
|---|---|---|---|---|---|---|
| 2,4,5-Trimethyl-2,5-dihydro-1,3-oxazole | 113.16 | 22694-96-9 | HMDB31199 | 45.6 +/- 4.9 | YES | boiled beef, roasted peanuts, flavor enhancer in fish products |
| 2,4,5-Trimethyloxazole | 111.14 | 20662-84-4 | HMDB40148 | 56.7 +/- 3.2 | YES | heated beef, cocoa, cooked pork, french fries, autolyzed yeast, cooked egg, fried chicken |
| 2,4-Dimethyloxazole | 97.11 | 7208-05-1 | HMDB40518 | 68.2 +/- 1.2 | YES | cooked beef, fried bacon, fried chicken, roasted peanuts |
| 4,5-dimethyloxazole | 97.11 | 20662-83-3 | HMDB32970 | 66.8 +/- 1.7 | YES | arabica coffee aroma |
| 5-ethyl-4-methyloxazole | 111.14 | 29584-92-7 | HMDB37863 | 91.2 +/- 2.5 | NO | arabica coffee aroma, yeast extract aromas |
| 2-ethyl-4,5-dimethyloxazole | 125.17 | 53833-30-0 | HMDB37865 | 89.4 +/- 3.2 | NO | french fries, arabica coffee |

*FIG. 13*

IDO1 mediated conversion of Tryptophan to kynurenine precursors

L-Tryptophan

N'-Formylkynurenine

L-Kynurenine

Trimethyl cyclopentane (TMC)

2,4,5,-trimethyl-2,5-dihydro-1,3-oxazole (TMO)

Oxazolone

Frag-oz

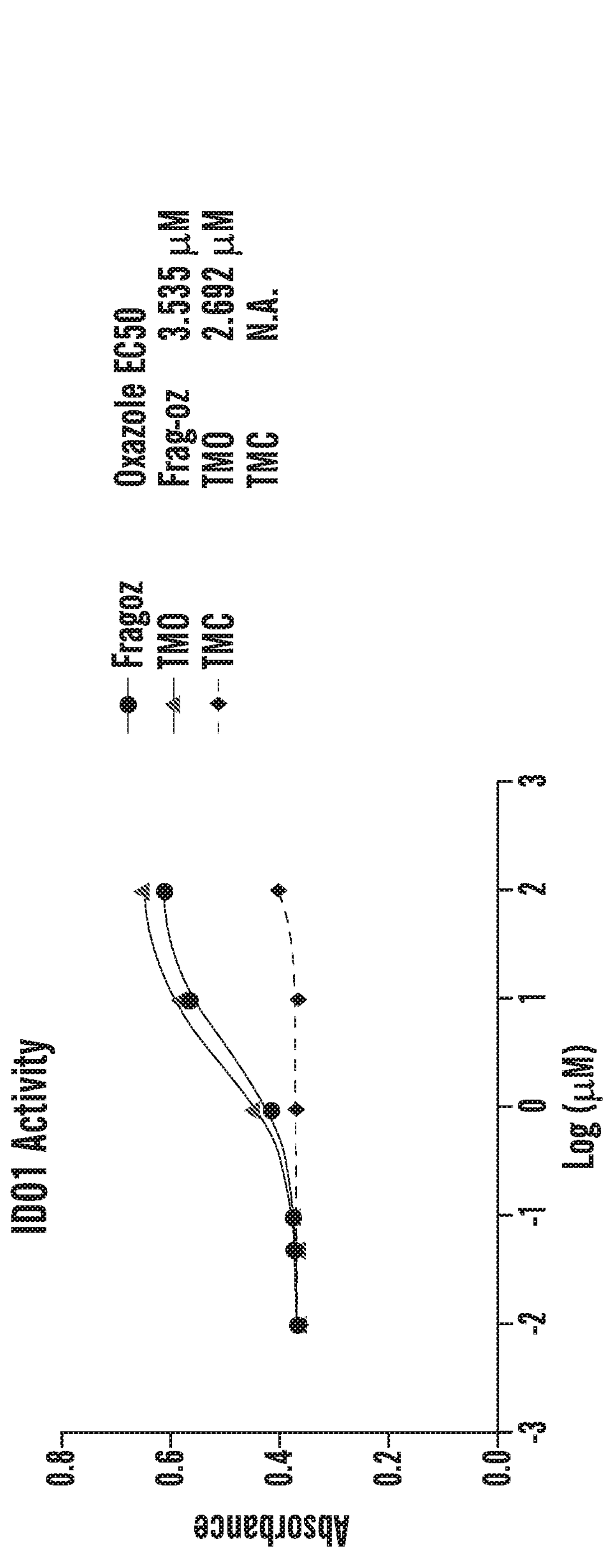
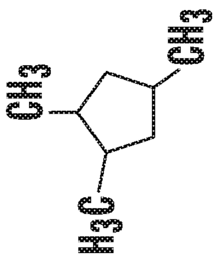
Trimethyl
cyclopentane
(TMC)
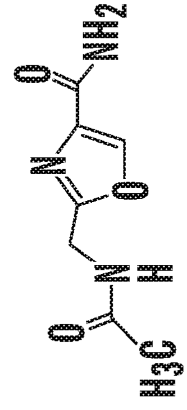
Frag-oz
*Microbial*
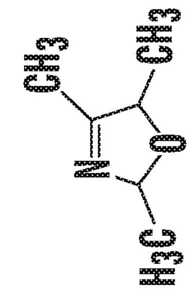
2,4,5,-trimethyl-2,5-dihydro-
1,3-oxazole (TMO)
*Dietary*
*FIG. 19*

4 Synthetic Compounds
1.
5(4H)-Oxazolone, 4-methyl-
EC50: 2.766 μM
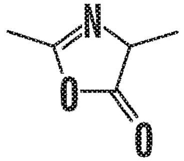
$C_5H_7NO_2$
2.
4(5H)-Oxazolone
EC50: 2.134 μM
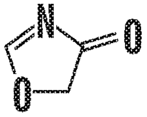
$C_3H_3NO_2$
3.
5(4H)-Oxazolone, 2-(2-furanyl)-
EC50: No Enhancer
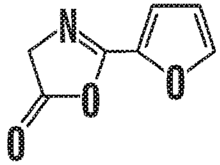
$C_7H_5NO_3$
4.
5(4H)-Oxazolone, 2-phenyl-
No Enhancer
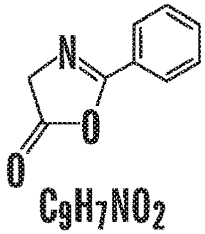
$C_9H_7NO_2$
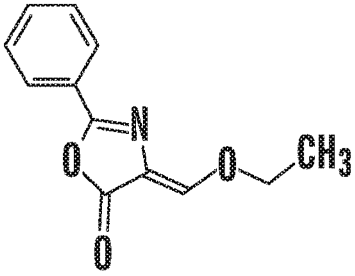
5. Oxazolone
4 Dietary Compounds
6.
2,4,5,-trimethyl-2,5-dihydro-1,3-oxazole (TMO)
EC50: 2.692 μM
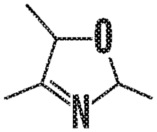
7.
2,4-dimethyloxazole
EC50: 13.16 μM
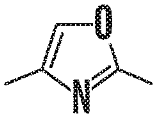
8.
Ethyl-4-methyloxazole-5-carboxylate
No Enhancer
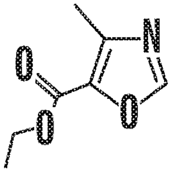
9.
2,4,5,-trimethyloxazole
EC50: 4.517 μM
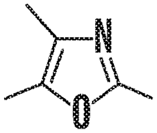
*FIG. 20*

Bacterial Compounds
10 McbB17
No Enhancer
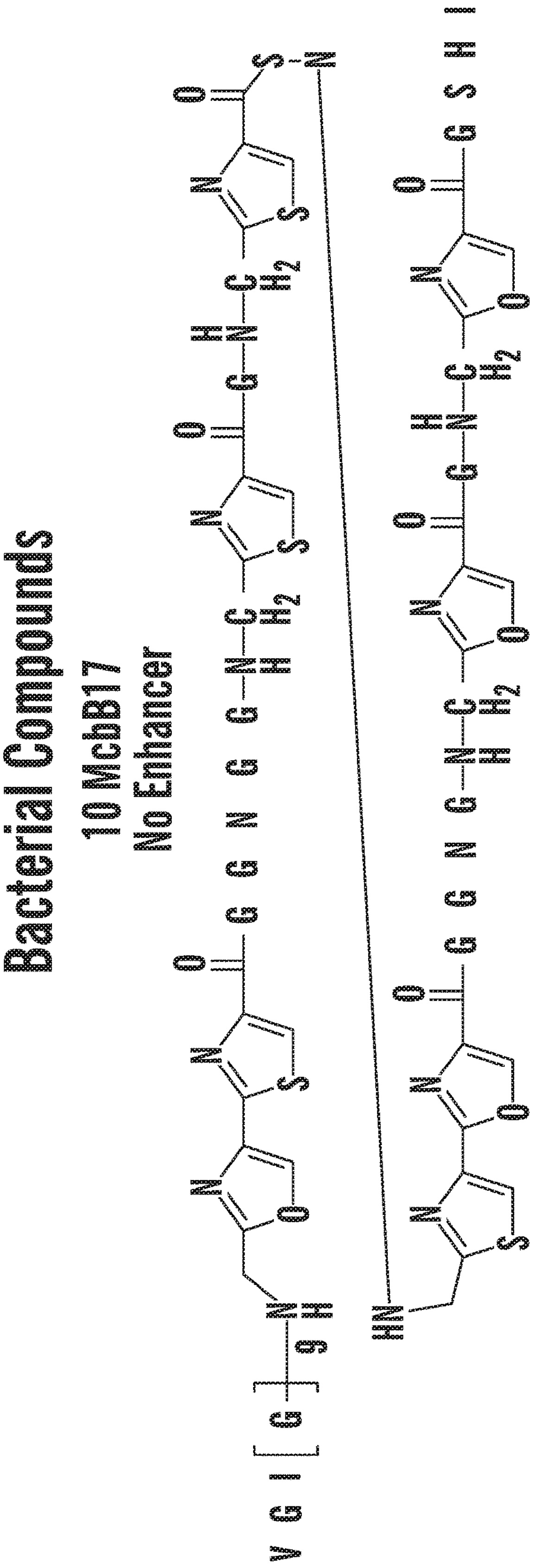
11 McB/SHI
No Enhancer
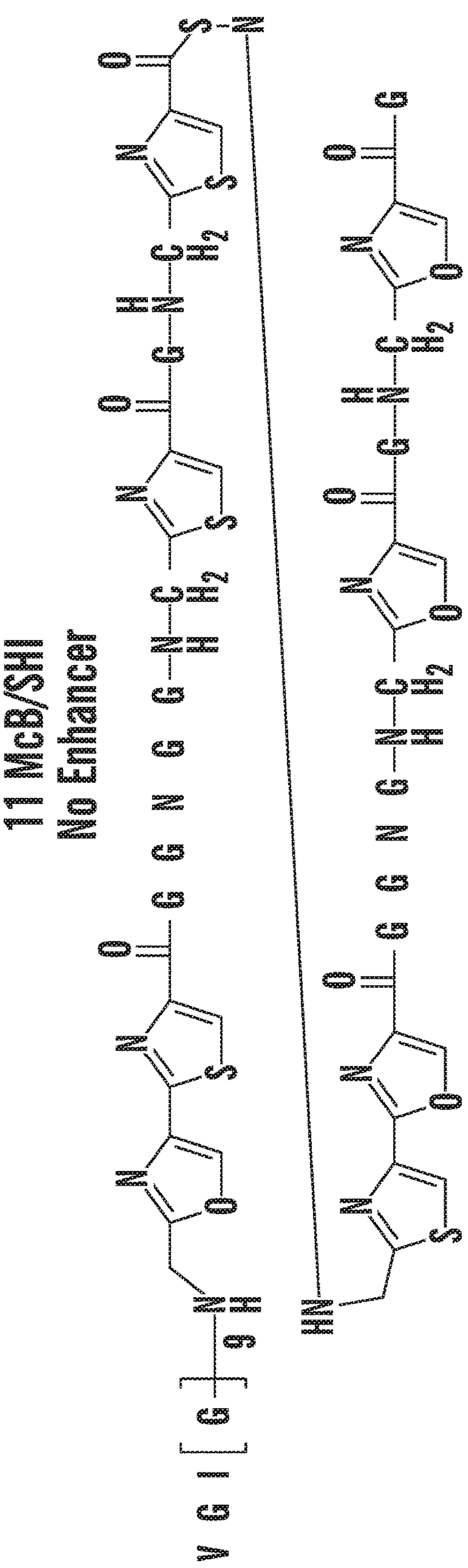
FIG. 21

12 McBΔHI
No Enhancer

13 Frag-C-term
No Enhancer

14 Frag-Hept1
No Enhancer
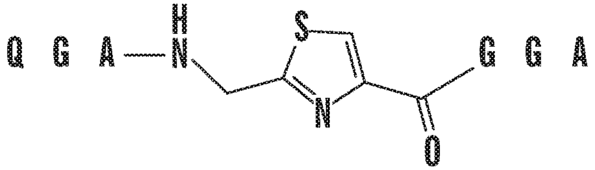
15 Frag-QN
No Enhancer
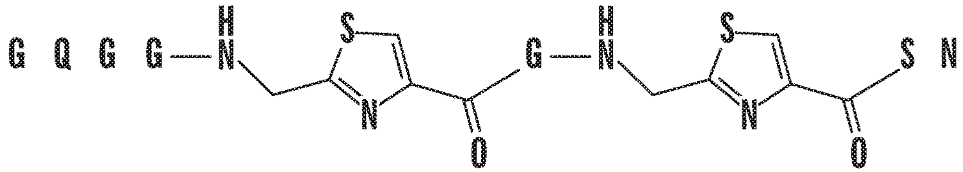
*FIG. 21 (cont.)*

16 Frag-EN
No Enhancer
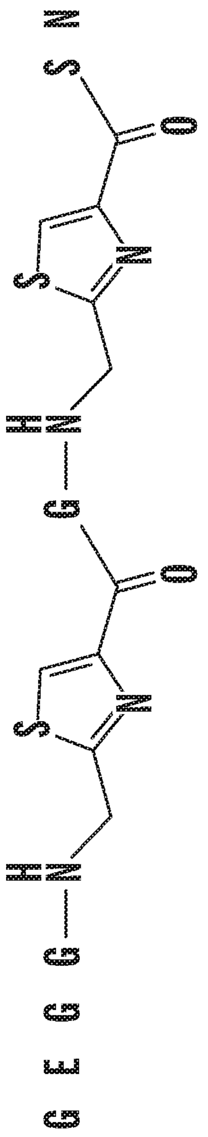
17 Frag-QD
No Enhancer
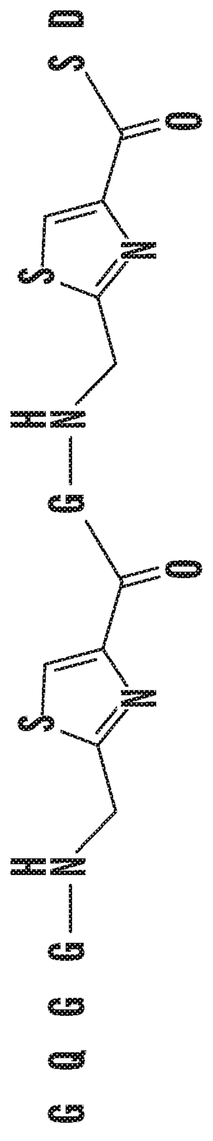
*FIG. 21 (cont.)*

18 Frag-ED
No Enhancer
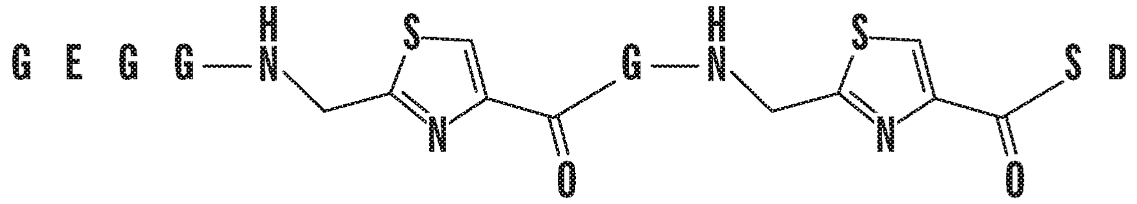
19 Frag-oztz
EC50: 4.027μM
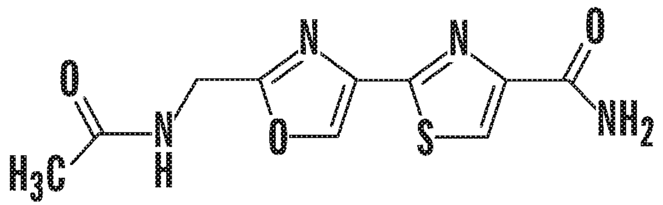
FIG. 21 (cont.)

20 Frag-tzoz
EC50: 5.507 μM
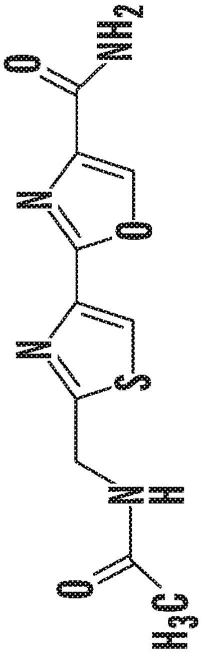
21 Frag-tz
EC50: 4.33 μM
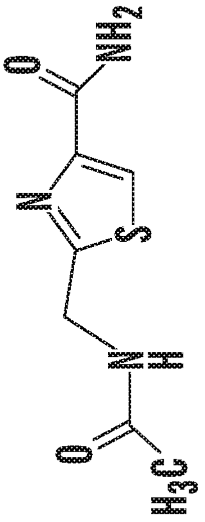
*FIG. 21 (cont.)*

22 Frag-oz
EC50: 3.535μM

| | Compound Name | CAS# | EC50 (μM) |
|---|---|---|---|
| 1 | 5(4H)-Oxazolone, 2,4-dimethyl- | CAS-69773-71-3 | 2.766 |
| 2 | 4(5H)-Oxazolone | CAS-6542-34-3 | 2.134 |
| 5 | 4-Ethoxymethylene-2-phenyl-2-oxazolin-5-one (oxazolone) | 15646-46-5 | |
| 6 | 2,4,5-Trimethyl-2,5-dihydro-1,3-oxazole | 22694-96-8 | 2.692 |
| 7 | 2,4-Dimethyloxazole | 7208-05-1 ( | 13.16 |
| 8 | Ethyl 4-methyloxazole-5-carboxylate | 84027-96-3 | 4.02 |
| 9 | 2,4,5-Trimethyloxazole | 20662-84-4 | 4.517 |
| 19 | frag-oztz | | 4.027 |
| 20 | frag-tzoz | | 5.507 |
| 21 | frag-tz | | 4.33 |
| 22 | frag-oz | | 3.535 |

OXAZOLE CONTAINING COMPOUNDS AS ACTIVATORS OF IDO1 AND AHR

CROSS-REFERENCE TO RELATED APPLICATIONS

This application is a 35 U.S.C. § 371 National Phase Entry Application of International Application No. PCT/US2018/067189 filed Dec. 21, 2018, which designates the U.S. and claims benefit under 35 U.S.C. § 119(e) of U.S. Provisional Application No. 62/608,784 filed Dec. 21, 2017 the contents of which are incorporated herein by reference in their entireties.

GOVERNMENT SUPPORT

This invention was made with government support under Contract Nos. DK044319, DK053056, DK051362, DK088199, 5P01AI073748 awarded by the National Institute of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Oct. 28, 2022, is named "043214-091250USPX_SL_ST25.txt" and is 92,490 bytes in size.

TECHNICAL FIELD

The technology described herein relates to methods of stimulating the immune system and uses thereof.

BACKGROUND

Indoleamine 2,3,dioxygenase 1 (IDO1), is a cell marker highly expressed in the colon of patients suffering from inflammatory bowel disease (IBD) as well as in many animal models of colitis. In the hematopoietic system, elevated IDO1 expression and subsequent aryl hydrocarbon receptor (AhR) activation have been associated with immune tolerance implicating this pathway in maintaining intestinal homeostasis. Furthermore, an increase in IDO1 expression has been associated with improved survival for certain cancers. Thus, there is a need for agents that target IDO1 and AhR to modulate immune responses in patients affected by cancer, immunosuppressive disorders, autoimmune disease, infection, or to prevent infection following surgical procedures.

SUMMARY

Provided herein is a method of stimulating an immune response in a subject. In part, the methods provided herein are based on the discovery that activators of indoleamine 2,3,dioxygenase 1 (IDO1) and aryl hydrocarbon receptor (AhR) promote inflammation by reducing the secretion of anti-inflammatory cytokines (e.g. IL-10) and increasing the activity of immune cells (e.g. natural killer T-cells).

In one aspect, provided herein is a method of stimulating the immune system in a subject in need thereof, the method comprising: administering an agent that increases the level or activity of indoleamine 2,3-dioxygenase (IDO1) to the subject.

In another aspect, provided herein is a method of vaccinating a subject, the method comprising administering the agent provided herein to the subject.

In another aspect, provided herein is a method of stimulating the immune system in a subject in need thereof, the method comprising: administering an agent that increases the level or activity of aryl hydrocarbon receptor (Ahr) to the subject.

In one embodiment of any of the aspects, the agent is selected from the group consisting of: a small molecule, an antibody, a peptide, a genome editing system, a vector, a miRNA, and a siRNA.

In another embodiment of any of the aspects, the agent is an activator of IDO1.

In another embodiment of any of the aspects, the agent is an agonist of AhR.

In another embodiment of any of the aspects, the agent is the compound of Formula (I), Formula (II), Formula (III), Formula (IV) or any derivative thereof.

In another embodiment of any of the aspects, the agent is formulated in a pharmaceutical composition.

In another embodiment of any of the aspects, the subject has or is diagnosed as having cancer, an immune deficiency, an autoimmune disease, an infection, or has had surgery.

In another embodiment of any of the aspects, the cancer is selected from the group consisting of: gastrointestinal cancer, prostate cancer, ovarian cancer, breast cancer, head and neck cancer, lung cancer, non-small cell lung cancer, cancer of the nervous system, kidney cancer, retinal cancer, melanoma skin cancer, stomach cancer, liver cancer, pancreatic cancer, genital-urinary cancer, prostate cancer, colorectal cancer, and bladder cancer.

In another embodiment of any of the aspects, the agent is formulated with at least one pharmaceutically acceptable carrier and an adjuvant.

In another aspect, provided herein is a method of vaccinating a subject, the method comprising administering the agent provided herein to the subject.

In one embodiment of any of the aspects, the subject is a mammal.

In another embodiment of any of the aspects, the subject is a human.

In another embodiment of any of the aspects, the method further comprises administering at least one immunotherapeutic agent or cell.

In another embodiment of any of the aspects, the immunotherapeutic agent is a chemotherapeutic agent.

In another embodiment of any of the aspects, the chemotherapeutic agent is selected from the group consisting of: alemtuzumab, atezolizumab, ipilimumab, nivolumab, ofatumumab, pembrolizumab, rituximab, and durvalumab.

In another embodiment of any of the aspects, the chemotherapeutic cell is a genetically engineered T cell, a dendritic cell, or a natural killer cell.

In another embodiment of any of the aspects, the genetically engineered T cell is a chimeric antigen receptor (CAR) T cell.

In another aspect, provided herein is an assay for identifying an agent that modulates the immune response of a biological sample, the assay comprising: a. contacting the biological sample with an agent; and b. detecting the level or activity of IDO1 wherein detecting a change in IDO1 levels or activity after contacting step (a) identifies the agent as one that can modulate the immune response.

In one embodiment of any of the aspects, the biological sample is a tissue, blood sample, tumor, or plurality of cells.

In another embodiment of any of the aspects, the assay further comprises detecting the level of aryl hydrocarbon receptor (Ahr); N'-formyl-kynurenine; L-kynurenine; kynurenic acid; xanthurenic acid; cluster of differentiation 1d (CD1d); interleukin (IL)-10; IL-13, interferon-γ (IFN-γ); microsomal triglyceride transfer protein (Mttp); and/or cytochrome P450 family 1, member A1 (Cyp1a1).

In another embodiment of any of the aspects, the assay further comprises detecting the activity or induction of Cyp1a1.

In another embodiment of any of the aspects, the assay further comprises detecting the level or activity of IDO1 from a biological sample that is not contacted with the agent as an appropriate control.

BRIEF DESCRIPTION OF THE DRAWINGS

FIGS. 1A-1H demonstrates the minimal oxazole structure modulates expression of specific gene targets and attenuates CD1d restricted in intestinal epithelial cells leading to colonic inflammation. FIG. 1A shows a panel of oxazole containing and control heterocylic natural compounds. FIG. 1B shows relative transcript abundance of Mttp and Cyp1a1 in MODE-K cells normalized to β-actin. FIG. 1C shows interleukin 10 production in MODE-K cells conditioned with the indicated compounds, loaded with α-Galactosyl Ceramide (α-GC) followed by 24.7 iNKT hybridoma co-culture. FIG. 1D-E shows representative traces and quantification of surface CD1d loaded with α-GC in MODE-K cells conditioned with indicated compounds. FIG. 1F shows weight change after intra-rectal administration of 1% TMO or EtOH (50% v/v) vehicle in wildtype (WT) or CD1d-deficient (KO) animals (n=10-12). *p<0.05 (Mann-Whitney U-test) FIG. 1G shows quantitative scoring for colitis after intra-rectal administration of 1% TMO or EtOH (50% v/v) vehicle in wildtype (WT) or CD1d-deficient (KO) animals. FIG. 1H shows quantification (ELISA) of Interleukin 13 and IFN-γ production from colon explants 2 days after intra-rectal administration of 1% TMO, TMC or EtOH (50% v/v) vehicle (n=3). ** p<0.01 (Student's t-test). *p<0.05 p<0.01' *p<0.001 (Student's t-test).

FIG. 2A-B shows interleukin 10 response in MODE-K cells pre-conditioned with vehicle (DMSO) or indicated compounds. FIG. 2A shows lysates from bacterial transformants (empty/pUC19, B17) were grown in Luria Broth or M63 supplement. FIG. 2B shows purified MccB17 (B17) microcin and/or B17 microcin proteolytic digest (subtilisin, trypsin), and subsequently loaded with α-GC followed by 24.7 iNKT hybridoma co-culture. FIG. 2C shows relative transcript abundance of target genes in MODE-K cells to β-actin in MODE-K pre-conditioned as in FIG. 2B. FIG. 2D shows the panel of synthetic analogs of B17 microcin proteolysis products with indicated anti-microbial activity. FIG. 2E shows the interleukin 10 response in MODE-K cells pre-conditioned with vehicle, oxazolone, or synthetic MccB17 microcin analogs, and subsequently loaded with α-GC followed by 24.7 iNKT hybridoma co-culture. FIG. 2F shows relative transcript abundance of target genes in MODE-K cells to β-actin in MODE-K pre-conditioned as in FIG. 2E. *p<0.05; p<0.01; *p<0.001 (Student's t-test).

FIG. 3A shows quantitative scoring for colitis after intra-rectal administration of 1% TMO or EtOH (50% v/v) vehicle in wildtype (WT) or CD1d-deficient (KO) littermates (n=8). FIG. 3B shows quantification of interleukin 13 and IFN-γ production from colon explants 2 days after intra-rectal administration of 1% TMO or EtOH (50% v/v) vehicle (n=6). FIG. 3C shows weight change after intra-rectal administration of 1% Frag-oz or EtOH (50% v/v) vehicle in Germ Free, SPF or animals conventionalized prior to birth with SPF microbiota (n=10). p<0.01; *p<0.001 (Mann-Whitney U-test). FIG. 3D shows quantification of Mttp and FIG. 3E shows Cyp1a1 transcripts (normalized to β-actin) from mucosal scraping 2 days after intra-rectal administration of 1% Frag-oz, or EtOH (50% v/v) vehicle (n=4). p<0.01; *p<0.001 (Student's t-test) FIG. 3F shows quantitative scoring for colitis after intra-rectal administration of 1% TMO or EtOH (50% v/v) vehicle in germ free, SPF or animals conventionalized prior to birth with SPF microbiota (n=8). **p<0.01; p<0.001 (Student's t-test).

FIG. 4A shows Aryl Hydrocarbon Receptor promoter-reporter activity after MODE-K cells conditioned with indicated compounds. MODE-K cells transfected with scrambled (solid fill) or siRNA targeted against AhR (clear fill), conditioned with indicated compounds and then loaded with α-GC followed by 24.7 iNKT hybridoma co-culture. FIG. 4B shows Interleukin 10 production. FIG. 4C shows quantification of surface CD1d loaded with α-GC. FIG. 4D shows quantification of Interleukin 10 from colon explants 3 days after intra-rectal administration of 1% oxazolone or 1% Frag-oz EtOH (50% v/v) vehicle in WT or animals with AhR-deficiency in epithelial compartment (AhrΔIEC). (n=4). FIG. 4E, G shoes weight change after intra-rectal administration of 1% oxazolone or EtOH (50% v/v) vehicle (FIG. 4E) or 1% Frag-oz or EtOH (50% v/v) vehicle (FIG. 4G) in WT or animals with AhR-deficiency in epithelial compartment (AhrΔIEC). * p<0.001 (Mann-Whitney U-test) FIG. 4F, H shows quantitative scoring for colitis after intra-rectal administration of oxazolone (FIG. 4F) or frag-oz (FIG. 4**H) in EtOH (50% v/v) in WT or animals with AhR-deficiency in epithelial compartment (AhrΔIEC). *p<0.05;  p<0.01; *p<0.001 (Student's t-test).

FIG. 5A shows recombinant IDO1 was incubated with L-tryptophan in the presence of oxazole (oxazolone, TMO, Frag-oz), control (TMC) compounds or vehicle and formyl-kyneurenine production measured via a calorimetric assay. FIG. 5B shows MODE-K cells cultured with tryptophan deficient media or media supplemented with exogenous L-tryptophan and CD1d-restricted Interleukin 10 responses measured in MODE-K cells pre-conditioned with vehicle or indicated compounds. FIG. 5C shows CD1d-restricted Interleukin 10 responses in MODE-K cells pre-conditioned with the indicated compounds and supplemented with L-tryptophan, kynurenic acid, or xanthurenic acid. FIG. 5D shows CD1d-restricted Interleukin 10 responses in MODE-K cells pre-conditioned with vehicle or oxazolone in tryptophan deficient media with supplementation with L-tryptophan, DL-methyl tryptophan, kyneurenine, kyneurenic acid, or xanthurenic acid and then loaded with α-GC followed by 24.7 iNKT hybridoma co-culture. FIG. 5E shows CD1d-restricted Interleukin 10 production by MODE-K cells transfected with scrambled (solid fill) or siRNA targeted against AhR (clear fill) in tryptophan deficient media. CD1d-restricted Interleukin 10 responses were measured following pre-conditioning with vehicle, TMC, oxazolone, TMO or frag-oz with or without supplementation of L-tryptophan or kyneurenic acid. ***p<0.001 (Student's t-test).

FIG. 7A shows relative transcript abundance in MODE-K cells conditioned with the indicated compounds, normalized to β-actin. p<0.01 (Student's t test). FIG. 7B-C shows CD1d-restricted Interleukin 10 production in the absence of exogenous lipid supplementation in MODE-K cells conditioned with the indicated compounds followed by co-culture with (FIG. 7B) invariant NKT (24.8) or (FIG. 7C) non-invariant NKT (14S.6) hybridomas. *p<0.001 (Student's t test). FIG. 7D shows interferon γ production in bone marrow derived dendritic cells conditioned with the indicated compounds followed by loading with a-galactosyl ceramide and co-cultured with 24.7 iNKT hybridoma.

FIG. 9D shows quantitative colitis scoring was assessed on colons harvested 3 days after intra-rectal challenge. ***p<0.001 (Student's t-test).

FIG. 10A shows Cyp1a1 transcripts. FIG. 10B shows IDO1 transcripts. FIG. 10C shows Mttp transcripts. ***p<0.001 (Student's t-test).

FIG. 12A shows a schematic outline for synthesis of MccB17 derived product Frag-oz. FIG. 12B shows a schematic outline for synthesis of MccB17 derived product Frag-tz.

FIG. 13 shows a table summarizing the CD1d-restricted responses and aryl hydrocarbon receptor activation in MODE-K cells for experimentally tested metabolites.

FIG. 14A shows IDO1 mediated conversion of tryptophan to kynurenine precursors. FIG. 14B shows oxazoles enhance production of AhR agonists in IDO1-dependent manner in intestinal epithelial cells.

FIG. 19 shows dietary and microbial oxazole enhance IDO1 activity.

FIG. 20 shows results from the screening assay featuring synthetic and dietary compounds.

DETAILED DESCRIPTION

Figure 1B:
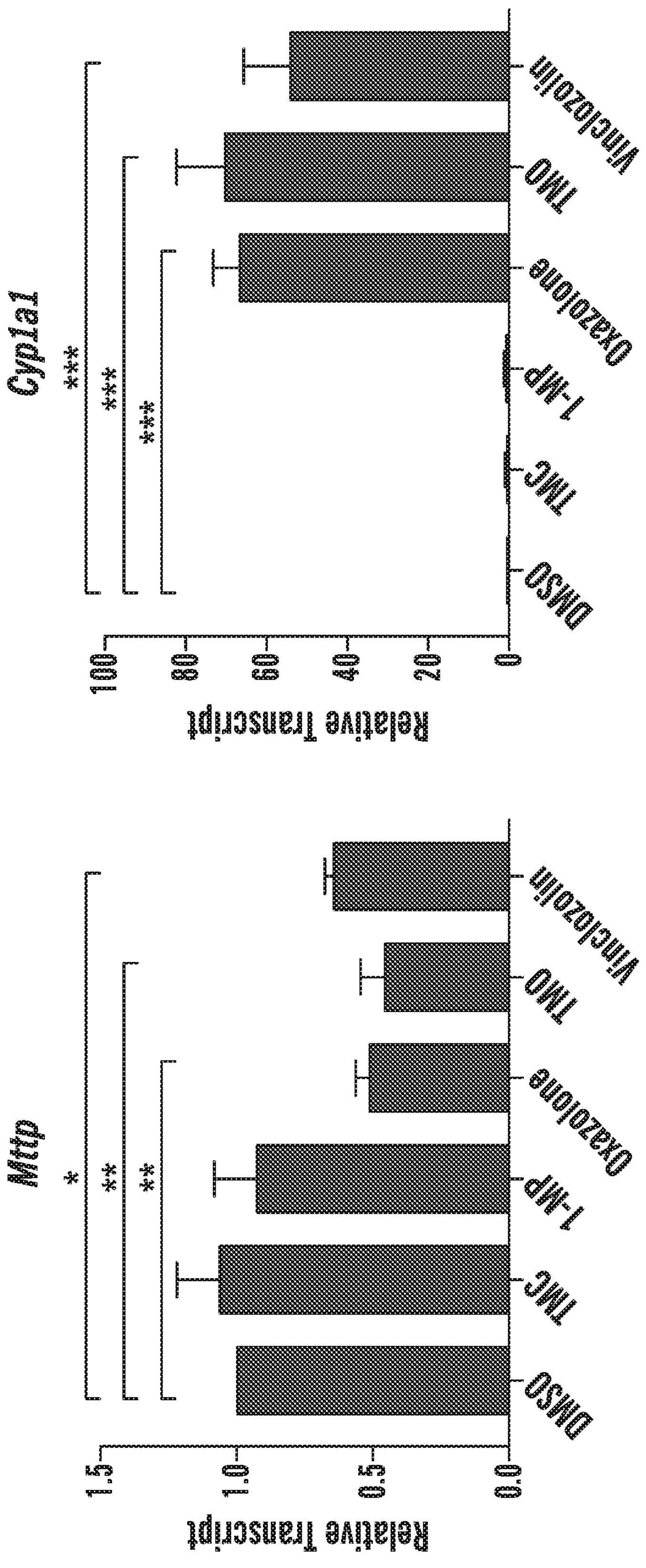

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

In one aspect, provided herein is method of stimulating the immune system in a subject in need thereof, the method comprising: administering an agent that increases the level or activity of indoleamine 2,3-dioxygenase (IDO1) to the subject.

In another aspect, provided herein is method of stimulating the immune system in a subject in need thereof, the method comprising: administering an agent that increases the level or activity of aryl hydrocarbon receptor (Ahr) to the subject.

In one embodiment of any of the aspects, the agent is an activator of IDO1. In another embodiment of any of the aspects, the agent is an agonist of Ahr.

As used herein, the term "indoleamine 2,3-dioxygenase" or "IDO1," refers to an enzyme that is expressed in epithelial cells, cancer cells, immune cells, and T cells, among others. Specifically, IDO1 is a major component in maintaining the homeostasis of the immune system and contributes to tumor-induced tolerance. IDO has been identified as a major immune regulatory molecule, which is part of several negative feedback mechanisms by which immune responses are kept under control. In this manner, IDO1 also exerts critical immunosuppressive function in cancer and stimulating effects in the gastrointestinal tract. IDO1 can refer to human IDO1, including naturally occurring variants, molecules, purified, or genetically engineered IDO1, and alleles thereof. IDO1 refers to the mammalian IDO1 of, e.g., mouse, rat, rabbit, dog, cat, cow, horse, pig, and the like. IDO is present in humans in five forms: IDO, IDOA, IDOB, IDOC and IDOLIKE (also known in the literature as IDO2). IDO is a 403 amino acid residue long polypeptide as disclosed in SEQ ID NO:1, and is the preferred IDO in the present text.

As used herein, the terms "IDO1 activity" or "activity of IDO1" refers to the cellular functions of the IDO1, for example, the metabolism and degradation of tryptophan. Some of the biological effects of IDO are mediated through local depletion of tryptophan, whereas others are mediated via immunomodulatory tryptophan metabolites.

As used herein, the term "aryl hydrocarbon receptor" or "AhR' refers to a receptor transcription factor that regulates gene expression in a variety of cell types and mediates a broad spectrum of physiological processes upon binding to its ligand. The AhR is a ligand-activated transcription factor which, after binding a ligand, translocates into the cell nucleus, where it forms a dimer with another transcription factor, namely the aryl hydrocarbon receptor nuclear translocator (ARNT), binds to regulatory gene sequences and induces the transcription of various genes, e.g. CYP1A1. AhR has a central role in the detoxification of exogenous contaminants.

As used herein, the terms "AhR activity" or "activity of AhR" refers to the cellular functions of the AhR (e.g. inflammation). For example, responses mediated by AhR include expression of P450 family genes (e.g. CYPA1), cell proliferation or differentiation, apoptosis, immune suppression and activation, vitamin A depletion, inhibition of adipose differentiation, waste syndrome, vascular development and remodeling, tumorigenicity or anti-tumorigenicity, and estrogenicity or anti-estrogenicity (Schmidt & Bradfield, 1996; Alexander et al., 1998; Whitlock, 1999; Poellinger, 2000; Elizondo et al. 2000; Safe, 2001; Vorderstrasse et al., 2001; Nilsson & Hakansson, 2002; Safe & Wormke, 2003; Walisser et al., 2004; Puga et al., 2005).

In another embodiment of any of the aspects, the agent is selected from the group consisting of: a small molecule, an antibody, a peptide, a genome editing system, a vector, a miRNA, and a siRNA.

The term "agent" as used herein means any compound or substance such as, but not limited to, a small molecule, nucleic acid, polypeptide, peptide, drug, ion, etc. An "agent" can be any chemical, entity or moiety, including without limitation, synthetic and naturally-occurring proteinaceous and non-proteinaceous entities. In some embodiments of any of the aspects, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

The agent can be a molecule from one or more chemical classes, e.g., organic molecules, which may include organometallic molecules, inorganic molecules, genetic sequences, etc. Agents may also be fusion proteins from one or more proteins, chimeric proteins (for example domain switching or homologous recombination of functionally significant regions of related or different molecules), synthetic proteins or other protein variations including substitutions, deletions, insertion and other variants.

In various embodiments, the agent is a small molecule that preferentially binds to IDO1 or AhR and/or increases activity of IDO1 or AhR. As used herein, the term "small molecule" refers to a chemical agent which can include, but is not limited to, a metabolite, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. In some embodiments of any of the aspects, the agent or compound provided herein has a molecular weight of 220 Da or less.

The term “derivative” as used herein means any chemical, conservative substitution, or structural modification of an agent. The derivative can improve characteristics of the agent or small molecule such as pharmacodynamics, pharmacokinetics, absorption, distribution, delivery, targeting to a specific receptor, or efficacy. For example, for a small molecule, the derivative can consist essentially of at least one chemical modification to about ten modifications. The derivative can also be the corresponding salt of the agent (e.g. sodium propionate as a derivative of propionate). The derivative can be the pro-drug of the small molecule as described herein.

In some embodiments of the various aspects disclosed herein, the agent is a 1,3-oxazole substituted with at least two substituents, provided that the substituted 1,3-oxazole has a molecular weight of 500 Da or less. Without limitations, said at least two substituents can be selected independently from the group consisting of C1-C6alkyl, —(CH2)nC(O)R51, —(CH2)nNHC(O)—R51, —(CH2)nC(O)N(R51)2, C2-C6 alkenyl, C2-C6alkynyl, N(R7)2, —(CH2)nC(O)OR51, halogen, CF3, SR51, OR51, aryl, heteroaryl, cyclyl or heterocyclyl, each of which can be optionally substituted; where R51 is H, C1-C6alkyl, heterocyclyl, heteroaryl, aryl, cyclyl, C2-C6alkenyl, or C2-C6alkynyl, each of which can be optionally substituted; and n is 0, 1, 2, 3, 4, 5 or 6.

Said at least two substituents on the 1,3-oxazole can be same or different. Further, the said at least two substituents can be located at any position of the 1,3-oxazole. For example, the 1,3-oxazole can comprise one substituent at the 2-position, i.e., the 1,3-oxazole is substituted at the 2-position. The 1,3-oxazole can comprise one substituent at the 4-position, i.e., the 1,3-oxazole is substituted at the 4-position. The 1,3-oxazole can comprise one substituent at the 5-position, i.e., the 1,3-oxazole is substituted at the 5-position. The 1,3-oxazole can comprise one substituent at the 2-position and one substituent at the 4-position, i.e., the 1,3-oxazole is substituted at the 2- and 4-positions. The 1,3-oxazole can comprise one substituent at the 2-position and one substituent at the 5-position, i.e., the 1,3-oxazole is substituted at the 2- and 5-positions. The 1,3-oxazole can comprise one substituent at the 4-position and one substituent at the 5-position, i.e., the 1,3-oxazole is substituted at the 4- and 5-positions.

In some embodiments of the various aspects disclosed herein, the 1,3-oxazole substituted with at least two substituents is 2,5-dihydro-1,3-oxazole substituted with at least two substituents.

In some embodiments, the 1,3-oxazole substituted with at least two substituents has a molecular weight of 450 Da or less, 400 Da or less, 350 Da or less, 300 Da or less, 250 Da or less, or 220 Da or less.

In some embodiments of the various aspects disclosed herein, the agent is a 1,3-thiazole substituted with at least two substituents, provided that the substituted 1,3-thiazole has a molecular weight of 500 Da or less. Without limitations, said at least two substituents can be selected independently from the group consisting of C1-C6alkyl, —(CH2)nC(O)R51, —(CH2)nNHC(O)—R51, —(CH2)nC(O)N(R51)2, C2-C6 alkenyl, C2-C6alkynyl, N(R7)2, —(CH2)nC(O)OR51, halogen, CF3, SR51, OR51, aryl, heteroaryl, cyclyl or heterocyclyl, each of which can be optionally substituted; where R51 is H, C1-C6alkyl, heterocyclyl, heteroaryl, aryl, cyclyl, C2-C6alkenyl, or C2-C6alkynyl, each of which can be optionally substituted; and n is 0, 1, 2, 3, 4, 5 or 6.

Said at least two substituents on the 1,3-thiazole can be same or different. Further, the said at least two substituents can be located at any position of the 1,3-thiazole. For example, the 1,3-thiazole can comprise one substituent at the 2-position, i.e., the 1,3-thiazole is substituted at the 2-position. The 1,3-thiazole can comprise one substituent at the 4-position, i.e., the 1,3-thiazole is substituted at the 4-position. The 1,3-thiazole can comprise one substituent at the 5-position, i.e., the 1,3-thiazole is substituted at the 5-position. The 1,3-thiazole can comprise one substituent at the 2-position and one substituent at the 4-position, i.e., the 1,3-thiazole is substituted at the 2- and 4-positions. The 1,3-thiazole can comprise one substituent at the 2-position and one substituent at the 5-position, i.e., the 1,3-thiazole is substituted at the 2- and 5-positions. The 1,3-thiazole can comprise one substituent at the 4-position and one substituent at the 5-position, i.e., the 1,3-thiazole is substituted at the 4- and 5-positions.

In some embodiments of the various aspects disclosed herein, the 1,3-thiazole substituted with at least two substituents is 2,5-dihydro-1,3-thiazole substituted with at least two substituents.

In some embodiments, the 1,3-thiazole substituted with at least two substituents has a molecular weight of 450 Da or less, 400 Da or less, 350 Da or less, 300 Da or less, 250 Da or less, or 220 Da or less.

In some embodiments of the various aspects disclosed herein, the agent is an oxazolone, which can be optionally substituted with one, two or three independently selected substituents, provided that the optionally substituted oxazolone has a molecular weight of 500 Da or less. Without limitations the optional substituents can be selected independently from the group consisting of C1-C6alkyl, —(CH2)nC(O)R51, —(CH2)nNHC(O)—R51, —(CH2)nC(O)N(R51)2, C2-C6 alkenyl, C2-C6alkynyl, N(R7)2, —(CH2)nC(O)OR51, halogen, CF3, SR51, OR51, aryl, heteroaryl, cyclyl or heterocyclyl, each of which can be optionally substituted; where R51 is H, C1-C6alkyl, heterocyclyl, heteroaryl, aryl, cyclyl, C2-C6alkenyl, or C2-C6alkynyl, each of which can be optionally substituted; and n is 0, 1, 2, 3, 4, 5 or 6.

In some embodiments, the optionally substituted oxazolone has a molecular weight of 450 Da or less, 400 Da or less, 350 Da or less, 300 Da or less, 250 Da or less, or 220 Da or less.

In some embodiments, the optionally substituted oxazolone is optionally substituted 5(4H)-oxazolone or optionally substituted 4(5H)-oxazolone.

In some embodiments of any of the aspects, the agent is the compound of Formula (I).

The compound of Formula (I) is:

FORMULA (I)

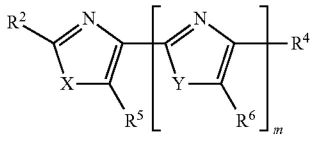

wherein:

m is 0, 1 or 2;

X and Y are independently O or S;

$R^2$, $R^4$, $R^5$ and $R^6$ are independently H, $C_1$-$C_6$alkyl, —$(CH_2)_n$C(O)$R^7$, —$(CH_2)_n$NHC(O)—$R^7$, —$(CH_2)_n$C(O)N$(R^7)_2$, $C_2$-$C_6$ alkenyl, $C_2$-$C_6$alkynyl, N$(R^7)_2$, —$(CH_2)_n$C(O)O$R^7$, halogen, $CF_3$, S$R^7$, O$R^7$, aryl, heteroaryl, cyclyl or heterocyclyl, each of which can be optionally substituted;

$R^7$ is H, $C_1$-$C_6$alkyl, heterocyclyl, heteroaryl, aryl, cyclyl, $C_2$-$C_6$alkenyl, or $C_2$-$C_6$alkynyl, each of which can be optionally substituted; and n is 0, 1, 2, 3, 4, 5 or 6, or a pharmaceutically acceptable salt thereof.

In some compounds of Formula (I), m is 0 or 1. For example, in some compounds m is 0. In some other compounds m is 1.

In some embodiments, X and Y are the same. For example, X and Y are O or S. In some other embodiments, X and Y are different. For example, X is O and Y is S, or X is S and Y is O.

In some compounds of Formula (I), $R^2$ can be H, $C_1$-$C_6$ alkyl, —$(CH_2)_n$C(O)$R^7$, or —$(CH_2)_n$NHC(O)—$R^7$. For example, $R^2$ can be methyl, ethyl, propyl, isopropyl, butyl, pentyl, hexyl, —$(CH_2)_n$C(O)$R^7$, or —$(CH_2)_n$NHC(O)—$R^7$, where n is 0 or 1, and $R^7$ $C_1$-$C_6$alkyl. In some preferred embodiments, $R^2$ is methyl or —$CH_2$NHC(O)$R^7$, where $R^7$ is methyl, ethyl or propyl. Preferably, $R^7$ is methyl.

In some embodiments, $R^4$ can be —$(CH_2)_n$C(O)$R^7$, or —$(CH_2)_n$NHC(O)—$R^7$, where n is 0 or 1; and $R^7$ is methyl, ethyl, propyl, isopropyl, butyl, pentyl, or hexyl. In some preferred embodiments, $R^4$ is methyl or —C(O)$NH_2$.

In some compounds of Formula (I), $R^5$ can be H, $C_1$-$C_6$alkyl, or —$(CH_2)_n$C(O)—O$R^7$, where n is 0 or 1, and $R^7$ is $C_1$-$C_6$alkyl. For example, $R^5$ can be H, methyl, ethyl, propyl, isopropyl, butyl, pentyl, hexyl, or —C(O)O$R^7$, where $R^5$ is methyl, ethyl, propyl, isopropyl, butyl, pentyl, or hexyl. In some embodiments, $R^5$ is H, methyl or —C(O)O$CH_2CH_3$. Preferably, $R^5$ is H or methyl. More preferably, $R^5$ is H.

In some embodiments, $R^6$ is H or $C_1$-$C_6$alkyl. For example, $R^6$ is H, methyl, ethyl, propyl, isopropyl, butyl, pentyl, or hexyl. Preferably, $R^6$ is H, methyl, or ethyl, and more preferably, $R^6$ is H.

In some embodiments, the compound of Formula (I) is selected from the group consisting of: (i) 2,4-dimethyloxazole having the structure:

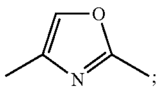;

(ii) ethyl-4-methyloxazole-5-carboxylate having the structure:

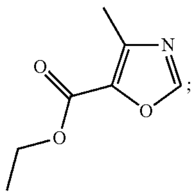;

(iii) 2,4,5-trimethyloxazole having the structure:

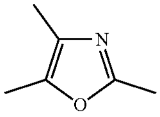;

(iv) Frag-oztz having the structure:

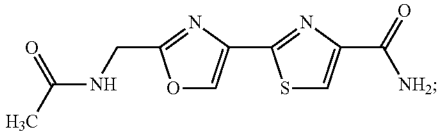 [SMILES: CC(=O)NCc1nc(-c2nc(C(N)=O)cs2)co1]

(v) Frag-tzoz having the structure:

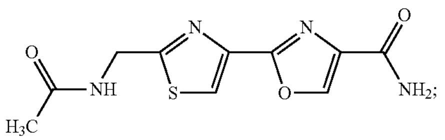

(vi) Frag-tz having the structure:

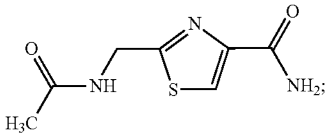

and (vii) Frag-oz having the structure:

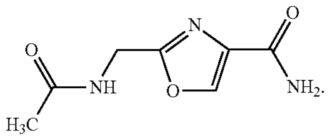

In some embodiments, the compound of Formula (I) is not ethyl-4-methyloxazole-5-carboxylate having the structure:

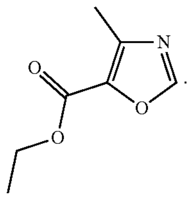

In some embodiments of an of the aspects the ent is the compound of Formula (II):

FORMULJA (II)

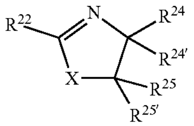

wherein:

X is O or S;

$R^2$ is H, $C_1$-$C_6$ alkyl, —$(CH_2)_n$C(O)$R^{26}$, —$(CH_2)_n$NHC(O)—$R^6$, —$(CH_2)_n$C(O)N$(R^6)_2$, $C_2$-$C_6$ alkenyl, $C_2$-$C_6$alkynyl, N$(R^{26})_2$, —$(CH_2)_n$C(O)O$R^{26}$, halogen, $CF_3$, S$R^{26}$, O$R^{26}$, aryl, heteroaryl, cyclyl or heterocyclyl, each of which can be optionally substituted;

$R^{24}$ is H, $C_1$-$C_6$ alkyl, —$(CH_2)_n$C(O)$R^{26}$, —$(CH_2)_n$NHC(O)—$R^{26}$, —$(CH_2)_n$C(O)N$(R^{26})_2$, $C_2$-$C_6$ alkenyl, $C_2$-$C_6$alkynyl, N$(R^2)_2$, —$(CH_2)_n$C(O)O$R^{26}$, halogen, $CF_3$, S$R^{26}$, O$R^{26}$, aryl, heteroaryl, cyclyl or heterocyclyl, each of which can be optionally substituted;

$R^{24'}$ is H, or $R^{24}$ and $R^{24'}$ together form ═O or ═S;

$R^{25}$ is H, $C_1$-$C_6$ alkyl, —$(CH_2)_n$C(O)$R^{26}$, —$(CH_2)_n$NHC(O)—$R^{26}$, —$(CH_2)_n$C(O)N(Re)$_2$, $C_2$-$C_6$ alkenyl, $C_2$-$C_6$alkynyl, N$(R^{26})_2$, —$(CH_2)_n$C(O)O$R^{26}$, halogen, $CF_3$, S$R^{26}$, O$R^{26}$, aryl, heteroaryl, cyclyl or heterocyclyl, each of which can be optionally substituted;

$R^{25'}$ is H, or $R^{25}$ and $R^{25'}$ together form ═O or ═S;

$R^{26}$ is H, $C_1$-$C_6$ alkyl, heterocyclyl, heteroaryl, aryl, cyclyl, $C_2$-$C_6$ alkenyl, or $C_2$-$C_6$alkynyl, each of which can be optionally substituted; and n is 0, 1, 2, 3, 4, 5 or 6, or a pharmaceutically acceptable salt thereof.

In some compounds of Formula (II), X is O.

In some compounds of Formula (II), $R^{22}$ is H or $C_1$-$C_6$alkyl. For example, $R^{22}$ is H, methyl, ethyl, propyl, isopropyl, butyl, pentyl, or hexyl. In some preferred embodiments, $R^{22}$ is H or methyl.

In some compounds of Formula (II), $R^{24}$ and $R^{24'}$ together form ═O. In some other compounds of Formula (II), $R^{24'}$ is H and $R^{24}$ is H or $C_1$-$C_6$alkyl.

In some compounds of Formula (II), $R^{25}$ and $R^{25'}$ together form ═O. In some other compounds of Formula (II), $R^{25'}$ is H and $R^{25}$ is H or $C_1$-$C_6$alkyl.

Exemplary compounds of Formula (II) include, but are not limited to 4-methyl-5(4H)-oxazolone having the structure:

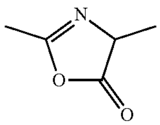, and

4(5H)-oxazolone having the structure:

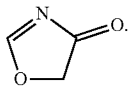

In some embodiments of any of the aspects, the agent is the compound of Formula (III):

FORMULA (III)

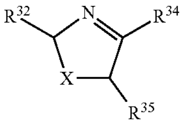

wherein:

X is O or S;

$R^{32}$, $R^{34}$, and $R^{35}$ are independently H, $C_1$-$C_6$ alkyl, —$(CH_2)_n$C(O)R, —$(CH_2)_n$NHC(O)—$R^3$, —$(CH_2)_n$C(O)N$(R^3)_2$, $C_2$-$C_6$ alkenyl, $C_2$-$C_6$alkynyl, N$(R^3)_2$, —$(CH_2)_n$C(O)O$R^3$, halogen, $CF_3$, S$R^3$, O$R^3$, aryl, heteroaryl, cyclyl or heterocyclyl, each of which can be optionally substituted;

$R^{36}$ is H, $C_1$-$C_6$ alkyl, heterocyclyl, heteroaryl, aryl, cyclyl, $C_2$-$C_6$ alkenyl, or $C_2$-$C_6$alkynyl, each of which can be optionally substituted; and n is 0, 1, 2, 3, 4, 5 or 6, or a pharmaceutically acceptable salt thereof.

In some compounds of Formula (III), $R^{32}$ can be H, $C_1$-$C_6$ alkyl, —$(CH_2)_n$C(O)$R^{36}$, or —$(CH_2)_n$NHC(O)—$R^{36}$. For example, $R^{32}$ can be methyl, ethyl, propyl, isopropyl, butyl, pentyl, hexyl, —$(CH_2)_n$C(O)$R^{36}$, or —$(CH_2)_n$NHC(O)—$R^{36}$, where n is 0 or 1, and $R^{36}$ $C_1$-$C_6$alkyl. In some preferred embodiments, $R^{32}$ is methyl.

In some compounds of Formula (III), $R^{34}$ can be H, $C_1$-$C_6$ alkyl, —$(CH_2)_n$C(O)$R^{36}$, or —$(CH_2)_n$NHC(O)—$R^{36}$. For example, $R^{34}$ can be methyl, ethyl, propyl, isopropyl, butyl, pentyl, hexyl, —$(CH_2)_n$C(O)$R^{36}$, or —$(CH_2)_n$NHC(O)—$R^{36}$, where n is 0 or 1, and $R^{36}$ $C_1$-$C_6$alkyl. In some preferred embodiments, $R^3$ is methyl.

In some compounds of Formula (III), $R^{35}$ can be H, $C_1$-$C_6$ alkyl, —$(CH_2)_n$C(O)$R^{36}$, or —$(CH_2)_n$NHC(O)—$R^{36}$. For example, $R^3$ can be methyl, ethyl, propyl, isopropyl, butyl, pentyl, hexyl, —$(CH_2)_n$C(O)$R^{36}$, or —$(CH_2)_n$NHC(O)—$R^{36}$, where n is 0 or 1, and $R^{36}$ $C_1$-$C_6$alkyl. In some preferred embodiments, $R^{35}$ is methyl.

Exemplary compounds of Formula (III) include, but are limited to, 2,4,5-trimethyl-2,5-dihydro-1,3-oxazole (TMO) having the structure:

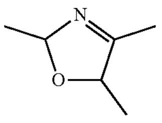.

In some embodiments, the compound of Formula (III) is not 2-(2-furanyl)-5(4H)-oxazolone having the structure:

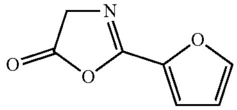, or 2-phenyl-5(4H)-oxazolone having the structure:

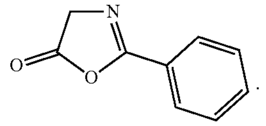 [SMILES: O=C1CN=C(c2ccccc2)O1]

In some embodiments of any of the aspects, the agent is the compound of Formula (IV):

FORMULA (III)

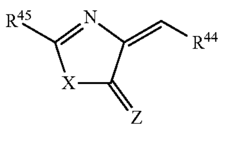

wherein:

X is O or S;

Z is O or S;

$R^{42}$ is H, aryl, heteroaryl, cyclyl, heterocyclyl, $C_1$-$C_6$ alkyl, $-(CH_2)_nC(O)R^4$, $-(CH_2)_nNHC(O)-R^{45}$, $-(CH_2)_nC(O)N(R^{45})_2$, $C_2$-$C_6$ alkenyl, $C_2$-$C_6$alkynyl, $N(R^{45})_2$, $-(CH_2)_nC(O)OR^{45}$, halogen, $CF_3$, $SR^{45}$, or $OR^{45}$, each of which can be optionally substituted;

$R^{44}$ is H, $C_1$-$C_6$ alkyl, $-(CH_2)_nC(O)R^{45}$, $-(CH_2)_nNHC(O)-R^{45}$, $-(CH_2)_nC(O)N(R^{45})_2$, $C_2$-$C_6$ alkenyl, $C_2$-$C_6$alkynyl, $N(R^{45})_2$, $-(CH_2)_nC(O)OR^{45}$, halogen, $CF_3$, $SR^{45}$, or $OR^{45}$, each of which can be optionally substituted;

$R^{45}$ is H, $C_1$-$C_6$ alkyl, heterocyclyl, heteroaryl, aryl, cyclyl, $C_2$-$C_6$ alkenyl, or $C_2$-$C_6$alkynyl, each of which can be optionally substituted; and n is 0, 1, 2, 3, 4, 5 or 6, or a pharmaceutically acceptable salt thereof.

In some compounds of Formula (IV) X and Z are the same. For example, X and Z are O. In some other compounds of Formula (IV), X and Z are different. For example, X is O and Z is S, or X is S and Z is O.

In some compounds of Formula (IV), $R^{42}$ is an optionally substituted aryl. In some embodiments, $R^{42}$ is an optionally substituted phenyl. In some preferred embodiments, $R^{42}$ is a unsubstituted phenyl In some compounds of Formula (IV), $R^{44}$ is $OR^{45}$. In some preferred embodiments, $R^{44}$ is $OR^{45}$ and $R^{45}$ is $C_1$-$C_6$alkyl. For example, $R^{45}$ is methyl, ethyl, propyl, isopropyl, butyl, pentyl or hexyl. In some preferred embodiments, $R^{45}$ is ethyl.

Exemplary compounds of Formula (IV) include, but are not limited to, 4-ethoxymethylene-2-phenyl-2-oxazolin-5-one (oxazolone) having the structure:

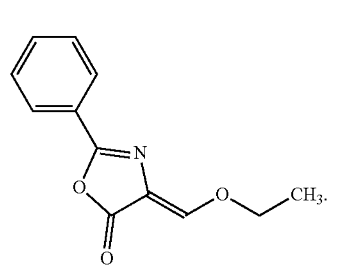 [SMILES: CCO/C=C1\N=C(c2ccccc2)OC1=O]

In some embodiments, the compound of Formula (I), (II), (III) or (IV) has a molecular weight of 500 Da or less. For example, the compound has a molecular weight of 450 Da or less, 400 Da or less, 350 Da or less, 300 Da or less, 250 Da or less. In some embodiments, the compound of Formula (I), (II), (III) or (IV) has a molecular weight of 220 Da or less.

The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $-CH_2O-$ is equivalent to $-OCH_2-$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons) An alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, $-CH_2CH_2CH_2CH_2-$. Typically, an alkyl (or alkylene) group will have from 1 to 24 carbon atoms, with those groups having 10 or fewer carbon atoms being preferred in the present invention. An alkylene is au uncyclized chain. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. A heteroalkyl is an uncyclized chain. The heteroatom(s) O, N, P, S, B, As, and Si may be placed at any interior position of the heteroalkyl group or at the position at which the alkyl group is attached to the remainder of the molecule Examples include, but are not limited to $-CH_2-CH_2-O-CH_3$, $-CH-CH_2-NH-CH_3$, $-CH_2-CH_2-N(CH_3)-CH_3$, $-CH-S-CH_2-CH_3$, $-CH_2-CH_2$, $-S(O)-CH_3$, $-CH_2-CH_2-S(O)_2-CH_3$, $-CH{=}CH-O-CH_3$, $-Si(CH_3)_3$, $-CH_2-CH{=}N-OCH_3$, $-CH{=}CH-N(CH_3)-CH_3$, $-O-CH_3$, $-O-CH_2-CH_3$, and $-CN$. Up to two or three heteroatoms may be consecutive, such as, for example, $-CH_2-NH-OCH_3$ and $-CH_2-O-Si(CH_3)_3$.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkylenoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. A heteroalkylene is an uncyclized chain. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl." by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. A cycloalkyl or heteroalkyl is not aromatic Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydopyridyl), 1-piperidyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O— bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substitutents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings Substituents for individual rings within spirocyclic rings are the substituents for the same ring when not part of spirocyclic rings (e.g. substitutents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spircyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

Each of the above terms (e.g., "alkyl," "heteroalkyl." "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR'. =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —$NO_2$, —NR'SO$_2$R", —NR'C=(O)R", —NR'C(O)—OR", —NR'OR", in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2$OCH, and the like).

Similar to the substituents described for the alkyl radical, substituents for the aryl and heteroaryl groups are varied and are selected from, for example: —OR', —NR'R", —SR', -halogen, —SiR'R"R', —OC(O)R', —C(O)R', —$CO_2$R', —CONR'R", —OC(O)NR'R", —NR"C(O)R', —NR'—C(O)NR"R'", —NR"C(O)R', —NR—C(NR'R'")=NR"", —NR—C(NR"R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, —NR'SO$_2$R", —NR'C=(O)R", —NR'C(O)—OR", —NR'OR", in a number ranging from zero to the total number of open valences on the aromatic ring system: and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings) When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R', R', R", and R" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted an, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)NH, —$NHSO_2H$, —NHC═(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, halogen, —CF, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC(O)$NH_2$, —$NHSO_2H$, —NHC═(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, and unsubstituted heteroaryl.

In some embodiments, each substituted group described in the compounds herein is substituted with at least one substituent group More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_8$alkylene, each substituted or unsubstituted heteroalkyene is a substituted or unsubstituted 2 to 8 membered heteroalkylene, each substituted or unsubstituted cycloalkylene is a substituted or unsubstituted $C_3$-$C_7$cycloalkylene, and/or each substituted or unsubstituted heterocycloalkylene is a substituted or unsubstituted 3 to 7 membered heterocycloalkylene.

Certain compounds of the present invention possess asymmetric carbon atoms (optical or chiral centers) or double bonds; the enantiomers, racemates, diasteromers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

The term "silyl ether" as used herein, refers to a chemical compound containing a silicon atom covalently bonded to an alkoxy group generally having the structure $R^wR^xR^ySi—O—R^z$, wherein $R^w$, $R^x$, $R^y$, and $R^z$ are independently alkyl or aryl groups.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*. 1977, 66, 1-19) Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention Illustrative examples of salts include mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. The term salt also refers to formation of a salt between two compounds.

Certain compounds of the present invention possess asymmetric carbon atoms (optical or chiral centers) or double bonds: the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure: i.e., the R and S configurations for each asymmetric center Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

In various embodiments of any of the aspects, the agent is an antibody or antigen-binding fragment thereof, or an antibody reagent that is specific for IDO1 or AhR or a regulator of IDO1 or AhR. As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and Fab fragments, $F(ab')_2$, Fd fragments, Fv fragments, scFv, CDRs, and domain antibody (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include midibodies, nanobodies, humanized antibodies, chimeric antibodies, and the like.

In one embodiment of any of the aspects, the agent is a humanized, monoclonal antibody or antigen-binding fragment thereof, or an antibody reagent. As used herein, "humanized" refers to antibodies from non-human species (e.g., mouse, rat, sheep, etc.) whose protein sequence has been modified such that it increases the similarities to antibody variants produce naturally in humans. In one embodiment of any of the aspects, the humanized antibody is a humanized monoclonal antibody. In one embodiment of any of the aspects, the humanized antibody is a humanized polyclonal antibody. In one embodiment of any of the aspects, the humanized antibody is for therapeutic use.

In one embodiment of any of the aspects, the anti-IDO1 or AhR antibody is any known anti-IDO1 or AhR antibodies in the art, or any anti-IDO1 or AhR antibodies that are yet to be discovered. Exemplary anti-IDO1 or AhR antibodies known in the art include, but are not limited to, anti-IDO1 or AhR antibodies sold by hermo Fisher Scientific (Waltham, Mass.). In one embodiment of any of the aspects, the anti-IDO1 or AhR antibody is a humanized anti-IDO or AhR antibody derived from any known, or yet to be discovered, non-human anti-IDO1 or AhR antibody.

In one embodiment of any of the aspects, the antibody or antibody reagent binds to an amino acid sequence that corresponds to the amino acid sequence encoding IDO1 or AhR.

In another embodiment of any of the aspects, the anti-IDO1 or AhR antibody or antibody reagent binds to an amino acid sequence that comprises the sequence of SEQ ID NO: 1 or SEQ ID NO: 2; or binds to an amino acid sequence that comprises a sequence with at least 80%, at least 85%, at least 90%, at least 95%, at least 96%, at least 97%, at least 98%, at least 99% or greater sequence identity to the sequence of SEQ ID NO: 1 or SEQ ID NO: 2. In one embodiment of any of the aspects, the anti-IDO1 or AhR antibody or antibody reagent binds to an amino acid sequence that comprises the entire sequence of SEQ ID NO: 1 or SEQ ID NO: 2 In another embodiment, of any of the aspects, the antibody or antibody reagent binds to an amino acid sequence that comprises a fragment of the sequence of SEQ ID NO: 1 or SEQ ID NO: 2, wherein the fragment is sufficient to bind its target, e.g., IDO1 or AhR or a metabolite that is a ligand for IDO1 or AhR, and result in the activation of IDO or AhR level and/or activity. The antibody can directly or indirectly affect IDO1 or AhR levels, e.g. by binding to a transcriptional repressor protein of IDO1 or AhR gene expression thereby increasing gene expression of IDO1 or AhR.

In one embodiment of any of the aspects, the agent that increases IDO1 or AhR is an antisense oligonucleotide. As used herein, an "antisense oligonucleotide" refers to a synthesized nucleic acid sequence that is complementary to a DNA or mRNA sequence, such as that of a microRNA. Antisense oligonucleotides are typically designed to block expression of a DNA or RNA target by binding to the target and halting expression at the level of transcription, translation, or splicing. Antisense oligonucleotides as described herein are complementary nucleic acid sequences designed to hybridize under cellular conditions to a gene. Thus, oligonucleotides are chosen that are sufficiently complementary to the target, i.e., that hybridize sufficiently well and with sufficient specificity in the context of the cellular environment, to give the desired effect. For example, an antisense oligonucleotide that activates or increases levels of IDO1 or AhR directly or indirectly may comprise at least 5, at least 10, at least 15, at least 20, at least 25, at least 30, or more bases complementary to a portion of the coding sequence of the human IDO1 or AhR gene (e.g., SEQ ID NO: 3 and SEQ ID NO: 4), respectively. Furthermore, the antisense oligonucleotide can target transcription factors that regulate the expression of IDO1 or AhR or any other transcription factors known in the art.

In one embodiment of any of the aspects, IDO1 or AhR is increased in the cell's genome using any genome editing system including, but not limited to, zinc finger nucleases, TALENS, meganucleases, and CRISPR/Cas systems. In one embodiment of any of the aspects, the genomic editing system used to incorporate the nucleic acid encoding one or more guide RNAs into the cell's genome is not a CRISPR/Cas system; this can prevent undesirable cell death in cells that retain a small amount of Cas enzyme/protein. It is also contemplated herein that either the Cas enzyme or the sgRNAs are each expressed under the control of a different inducible promoter, thereby allowing temporal expression of each to prevent such interference. The gene editing system can directly or indirectly modulate levels of IDO1 or AhR expression, e.g. by inhibiting transcriptional repressors of IDO1 or AhR that results in an increase in IDO or AhR transcription.

When a nucleic acid encoding one or more sgRNAs and a nucleic acid encoding an RNA-guided endonuclease each need to be administered in vivo, the use of an adenovirus associated vector (AAV) is specifically contemplated. Other vectors for simultaneously delivering nucleic acids to both components of the genome editing/fragmentation system (e.g., sgRNAs, RNA-guided endonuclease) include lentiviral vectors, such as Epstein Barr, Human immunodeficiency virus (HIV), and hepatitis B virus (HBV). Each of the components of the RNA-guided genome editing system (e.g., sgRNA and endonuclease) can be delivered in a separate vector as known in the art or as described herein.

In one embodiment of any of the aspects, the agent activates or increases IDO1 or AhR activity by RNA insertion or increasing RNA transcripts. Activators of the expression of a given gene can be an activating nucleic acid or transcription factor for IDO1 or AhR. In some embodiments, of any of the aspects, the inhibitory nucleic acid is an inhibitory RNA (iRNA). The RNAi can be single stranded or double stranded. The RNAi can directly or indirectly modulate IDO or AhR expression, e.g. inhibiting transcriptional repressors of IDO1 or AhR and thereby increasing IDO1 or AhR.

The iRNA can be siRNA, shRNA, endogenous microRNA (miRNA), or artificial miRNA. In one embodiment of any of the aspects, an iRNA as described herein affects inhibition of the expression and/or activity of a target, e.g. a transcriptional repressor of IDO1 or AhR. In some embodiments of any of the aspects, the agent is siRNA that inhibits transcriptional repressors of IDO1 or AhR. In some embodiments of any of the aspects, the agent is shRNA that inhibits a transcriptional repressor of IDO1 or AhR, thereby increasing IDO1 or AhR expression.

One skilled in the art would be able to design siRNA, shRNA, or miRNA to target IDO1 or AhR directly or indirectly by inhibiting a transcriptional repressor of IDO1 or AhR, e.g., using publically available design tools, siRNA, shRNA, or miRNA is commonly made using companies such as Dharmacon (Layfayette, Colo.) or Sigma Aldrich (St. Louis, Mo.).

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions.

The RNA of an iRNA can be chemically modified to enhance stability or other beneficial characteristics. The nucleic acids as described herein may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference.

In one embodiment of any of the aspects, the agent is miRNA that activates or increases IDO1 or AhR activity. MicroRNAs are small non-coding RNAs with an average length of 22 nucleotides. These molecules act by binding to complementary sequences within mRNA molecules, usually in the 3' untranslated (3'UTR) region, thereby promoting target mRNA degradation or inhibited mRNA translation. The interaction between microRNA and mRNAs is mediated by what is known as the "seed sequence", a 6-8-nucleotide region of the microRNA that directs sequence-specific binding to the mRNA through imperfect Watson-Crick base pairing. More than 900 microRNAs are known to be expressed in mammals. Many of these can be grouped into families on the basis of their seed sequence, thereby identifying a "cluster" of similar microRNAs. A miRNA can be expressed in a cell, e.g., as naked DNA. A miRNA can be encoded by a nucleic acid that is expressed in the cell, e.g., as naked DNA or can be encoded by a nucleic acid that is contained within a vector. The miRNA can directly or indirectly modulate IDO1 or AhR expression. For example, the miRNA can inhibit transcriptional repressors of IDO1 or AhR.

The agent may be contained in and thus further include a vector. Many such vectors useful for transferring exogenous genes into target mammalian cells are available. The vectors may be episomal, e.g. plasmids, virus-derived vectors such cytomegalovirus, adenovirus, etc., or may be integrated into the target cell genome, through homologous recombination or random integration, e.g. retrovirus-derived vectors such as MMLV, HIV-1, ALV, etc. In some embodiments, combinations of retroviruses and an appropriate packaging cell line may also find use, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "expression vector" refers to a vector that directs expression of an RNA or polypeptide (e.g., IDO1 or AhR or a modulator of IDO or AhR) from nucleic acid sequences contained therein linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

Integrating vectors have their delivered RNA/DNA permanently incorporated into the host cell chromosomes. Non-integrating vectors remain episomal which means the nucleic acid contained therein is never integrated into the host cell chromosomes. Examples of integrating vectors include retroviral vectors, lentiviral vectors, hybrid adenoviral vectors, and herpes simplex viral vector.

One example of a non-integrative vector is a non-integrative viral vector. Non-integrative viral vectors eliminate the risks posed by integrative retroviruses, as they do not incorporate their genome into the host DNA. One example is the Epstein Barr oriP/Nuclear Antigen-1 ("EBNA1") vector, which is capable of limited self-replication and known to function in mammalian cells. As containing two elements from Epstein-Barr virus, oriP and EBNA1, binding of the EBNA1 protein to the virus replicon region oriP maintains a relatively long-term episomal presence of plasmids in mammalian cells. This particular feature of the oriP/EBNA1 vector makes it ideal for generation of integration-free host cells. Another non-integrative viral vector is adenoviral vector and the adeno-associated viral (AAV) vector.

Another non-integrative viral vector is RNA Sendai viral vector, which can produce protein without entering the nucleus of an infected cell. The F-deficient Sendai virus vector remains in the cytoplasm of infected cells for a few passages, but is diluted out quickly and completely lost after several passages (e.g., 10 passages).

Another example of a non-integrative vector is a minicircle vector. Minicircle vectors are circularized vectors in which the plasmid backbone has been released leaving only the eukaryotic promoter and cDNA(s) that are to be expressed.

As used herein, the term "viral vector" refers to a nucleic acid vector construct that includes at least one element of viral origin and has the capacity to be packaged into a viral vector particle. The viral vector can contain a nucleic acid encoding a polypeptide as described herein in place of non-essential viral genes. The vector and/or particle may be utilized for the purpose of transferring nucleic acids into cells either in vitro or in vivo. Numerous forms of viral vectors are known in the art.

In the various embodiments of any of the aspects, it is contemplated that variants (naturally occurring or otherwise), alleles, homologs, conservatively modified variants, and/or conservative substitution variants of any of the particular polypeptides described are encompassed. As to amino acid sequences (e.g. SEQ ID NO:1 and SEQ ID NO: 2), one of ordinary skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. ligand-mediated receptor activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments of any of the aspects, a "peptide" or "polypeptide" as described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to an assay known in the art or described below herein. A functional fragment can comprise conservative substitutions of the sequences disclosed herein.

In some embodiments of any of the aspects, a polypeptide as described herein can be a variant of a polypeptide or molecule as described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity of the non-variant polypeptide. A wide variety of PCR-based site-specific mutagenesis approaches are known in the art and can be applied by the ordinarily skilled artisan.

A variant amino acid or DNA sequence can be at least 80%, at least 90%, at least 91%, at least 92%, at least 93%, at least 94%, at least 95%, at least 96%, at least 97%, at least 98%, at least 99%, identical to a native or reference sequence (e.g. SEQ ID NO: 1 or SEQ ID NO: 2). The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of a polypeptide also can be substituted, generally with serine, to improve the oxidative stability of the molecule and prevent aberrant crosslinking. Conversely, cysteine bond(s) can be added to a polypeptide to improve its stability or facilitate oligomerization.

For administering to a subject, the agents and compounds of Formula (I)-(IV) can be formulated in pharmaceutical compositions. A "pharmaceutical composition" refers to a chemical or biological composition suitable for administration to a mammalian subject. Such compositions may be specifically formulated for administration via one or more of a number of routes, including but not limited to, oral, parenteral, intravenous, intraarterial, subcutaneous, intranasal, sublingual, intraspinal, intracerebroventricular, and the like.

An agent or pharmaceutical composition described herein is considered effective for increasing the levels or activity of IDO1 or AhR if, for example, upon administration, it increases the presence, amount, activity and/or level of IDO1 or AhR in a cell.

An agent can increase or activate e.g., the transcription, or the translation of IDO1 or AhR in the cell. An agent can increase the activity or alter the activity (e.g., such that the activity increases, is enhanced or occurs properly (e.g., as compared to wild-type IDO1 or AhR activity), or occurs at an increased rate) of IDO1 or AhR in the cell (e.g., IDO1 or AhR's expression).

The terms "decrease", "reduced", "reduction", or "inhibit" are all used herein to mean a decrease or lessening of a property, level, or other parameter by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased," "increase," "increases," or "enhance" or "activate" are all used herein to generally mean an increase of a property, level, or other parameter by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level. For example, increasing activity can refer to activating IDO1 or aryl hydrocarbon receptor or increasing levels of IDO1 or AhR directly or indirectly.

As used herein, a "reference level" refers to a normal, otherwise unaffected cell population or tissue (e.g., a biological sample obtained from a healthy subject, or a biological sample obtained from the subject at a prior time point, e.g., a biological sample obtained from a patient prior to being diagnosed with a disease, or a biological sample that has not been contacted with an agent or composition disclosed herein).

In one embodiment of any of the aspects, activating IDO1 or AhR is increasing IDO1 or AhR activity. The IDO1 activity can be any currently known, or yet to be discovered activity of function of the IDO1 or the AhR gene or gene product. For example, increased metabolites of tryptophan by IECs. In one embodiment of any of the aspects, the activity of IDO1 or AhR is increased by at least 5%, 10%, 15%, 20%, 25%, 30%, 35%, 40%, 45%, 50%, 55%, 60%, 65%, 70%, 75%, 80%, 85%, 90%, 95%, 99%, or more as compared to an appropriate control.

As used herein, an "appropriate control" refers to an untreated, otherwise identical cell or population (e.g., a biological sample that was not contacted by an agent or composition described herein, or not contacted in the same manner, e.g., for a different duration, as compared to a non-control cell). As used herein, an appropriate control would be the level of IDO1 or AhR activity in an otherwise identical sample that is not contacted by an agent or composition described herein, or is the level of IDO1 or AhR activity in a subject prior to administration of an agent or composition. Further, an appropriate control can be the level of IDO1 or AhR activity in a healthy subject, e.g., an individual that does not have a disease. One skilled in the art can determine the activity of IDO1 or AhR using functional readouts of IDO1 or AhR's activity, for example, by measuring/assessing the secretion of IL-10, IL-13, IFN-γ, gene products, or metabolites of tryptophan.

In another embodiment, of any of the aspects, activating IDO1 or AhR is increasing IDO1 or AhR levels in the cell, e.g., gene expression levels or gene product levels. In one embodiment of any of the aspects, IDO or AhR levels are increased by at least 5%, 10%, 15%, 20%, 25%, 30%, 35%, 40%, 45%, 50%, 55%, 60%, 65%, 70%, 75%, 80%, 85%, 90%, 95%, 99%, or more as compared to an appropriate control.

As used herein, an appropriate control would be the level of IDO1 or AhR in an otherwise identical sample that is not contacted by an agent or composition described herein, or is the level of IDO1 or AhR in a subject prior to administration of an agent or composition. Further, an appropriate control can be the level of IDO1 or AhR in a healthy subject, e.g., an individual that does not have a disease. One skilled in the art can determine the activity of IDO1 or AhR using functional readouts of their activity, for example, by measuring/assessing the activation and secretion of IL-10 or metabolites of tryptophan. One skilled in the art can assess/measure the protein and mRNA levels of IDO1 or AhR and downstream targets or secretions from the cells of interest, e.g., using western blotting or PCR-based assays, respectively.

The phrase "therapeutically-effective amount" as used herein means that amount of a compound, material, or composition comprising a compound described herein which is effective for producing some desired therapeutic effect in at least a sub-population of cells in a subject at a reasonable benefit/risk ratio applicable to any medical treatment. Thus, "therapeutically effective amount" means that amount which, when administered to a subject for treating a disease, is sufficient to affect such treatment for the disease.

Determination of an effective amount is well within the capability of those skilled in the art. Generally, the actual effective amount can vary with the specific compound, the use or application technique, the desired effect, the duration of the effect and side effects, the subject's history, age, condition, sex, as well as the severity and type of the medical condition in the subject, and administration of other pharmaceutically active agents. Accordingly, an effective dose of compound described herein is an amount sufficient to produce at least some desired therapeutic effect in a subject.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of use or administration utilized.

The effective dose can be estimated initially from cell culture assays. A dose can be formulated in animal models to achieve a circulating plasma concentration range that includes the ICs (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay. The effective plasma concentration for a compound as disclosed herein can be about 0.01 μM to about 10 μM, about 0.2 μM to about 5 μM, or about 0.8 to about 3 μM in a subject, such as a rat, dog, or human.

Generally, the compositions are administered so that a compound of the disclosure herein is used or given at a dose from 1 μg/kg to 1000 mg/kg; 1 μg/kg to 500 mg/kg; 1 μg/kg to 150 mg/kg, 1 μg/kg to 100 mg/kg, 1 μg/kg to 50 mg/kg, 1 μg/kg to 20 mg/kg, 1 μg/kg to 10 mg/kg, 1 μg/kg to mg/kg, 100 μg/kg to 100 mg/kg, 100 μg/kg to 50 mg/kg, 100 μg/kg to 20 mg/kg, 100 μg/kg to 10 mg/kg, 100 μg/kg to mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. Further contemplated is a dose (either as a bolus or continuous infusion) of about 0.1 mg/kg to about 10 mg/kg, about 0.3 mg/kg to about 5 mg/kg, or 0.5 mg/kg to about 3 mg/kg. It is to be further understood that the ranges intermediate to those given above are also within the scope of this disclosure, for example, in the range 1 mg/kg to 10 mg/kg, for example use or dose ranges such as 2 mg/kg to 8 mg/kg, 3 mg/kg to 7 mg/kg, 4 mg/kg to 6 mg/kg, and the like.

The compounds described herein can be administered at once, or can be divided into a number of smaller doses to be administered at intervals of time. It is understood that the precise dosage and duration of treatment will be a function of the location of where the composition is parenterally administered, the carrier and other variables that can be determined empirically using known testing protocols or by extrapolation from in vivo or in vitro test data. It is to be noted that concentrations and dosage values can also vary with the age of the individual treated. It is to be further understood that for any particular subject, specific dosage regimens can need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The compound can be administered as a single bolus or multiple boluses, as a continuous infusion, or a combination thereof. For example, the compound can be administered as a single bolus initially, and then administered as a continuous infusion following the bolus. The rate of the infusion can be any rate sufficient to maintain effective concentration, for example, to maintain effective plasma concentration. Some contemplated infusion rates include from 1 μg/kg/min to 100 mg/kg/min, or from 1 μg/kg/hr to 1000 mg/kg/hr. Rates of infusion can include 0.2 to 1.5 mg/kg/min, or more specifically 0.25 to 1 mg/kg/min, or even more specifically 0.25 to 0.5 mg/kg/min. It will be appreciated that the rate of infusion can be determined based upon the dose necessary to maintain effective plasma concentration and the rate of elimination of the compound, such that the compound is administered via infusion at a rate sufficient to safely maintain a sufficient effective plasma concentration of compound in the bloodstream.

The terms "co-administration" or the like, as used herein, are meant to encompass administration of the selected therapeutic agents to a single patient and are intended to include treatment regimens in which the agents are administered by the same or different route of administration or at the same or different time.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably.

In some embodiments, the pharmaceutical composition is a liquid dosage form or solid dosage form. Liquid dosage forms for oral administration include, but are not limited to, pharmaceutically acceptable emulsions, microemulsions, solutions, suspensions, syrups and elixirs. In addition to the compound of any of Formula (I)-(IV), the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the compound of any of Formula (I)-(IV) are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcelhdose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quatemary ammonium compounds, g) wetting agents such as, for example, cetyl alcohol and glycerol monosteamte, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols, and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polethylene glycols, and the like.

The agents or compounds of any of Formula (I)-(IV) provided herein can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms, the compound of any of Formula (I)-(IV) can be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

In some embodiments, the carrier or excipient is an enteric coating or enteric-coated drug delivery device. As used herein, the terms "enteric coating" or "enteric-coated drug delivery device" refers to any drug delivery method that can be administered orally but is not degraded or activated until the device enters the intestines. Such methods can utilize a coating or encapsulation that is degraded using e.g., pH dependent means, permitting protection of the delivery device and the agent to be administered or transplanted throughout the gastrointestinal tract until the device reaches the alkaline pH of the intestines (e.g. cecum or colon).

Pharmaceutical compositions include formulations suitable for oral administration may be provided as discrete units, such as tablets, capsules, cachets, syrups, elixirs, prepared food items, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

Accordingly, formulations suitable for rectal administration include gels, creams, lotions, aqueous or oily suspensions, dispersible powders or granules, emulsions, dissolvable solid materials, douches, and the like can be used. The formulations are preferably provided as unit-dose suppositories comprising the active ingredient in one or more solid carriers forming the suppository base, for example, cocoa butter. Suitable carriers for such formulations include petroleum jelly, lanolin, polyethyleneglycols, alcohols, and combinations thereof. Alternatively, colonic washes with the rapid recolonization deployment agent of the present disclosure can be formulated for colonic or rectal administration.

The terms "administered" and "subjected" are used interchangeably in the context of treatment of a disease or disorder.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are orally administered. Without limitations, oral administration can be in the form of solutions, suspensions, tablets, pills, capsules, sustained-release formulations, oral rinses, powders and the like.

The dosage of the agent as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further agents, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

In one embodiment of any of the aspects, the agent or compositions described herein are used as a monotherapy. In one embodiment of any of the aspects, the agents described herein can be used in combination with other known agents and therapies for a disease. Administered "in combination," as used herein, means that two (or more) different treatments are delivered to the subject during the course of the subject's affliction with the disorder, e.g., the two or more treatments are delivered after the subject has been diagnosed with the disorder (a disease) and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The agents described herein and the at least one additional therapy can be administered simultaneously, in the same or in separate compositions, or sequentially. For sequential administration, the agent described herein can be administered first, and the additional agent can be administered second, or the order of administration can be reversed. The agent and/or other therapeutic agents, procedures or modalities can be administered during periods of active disorder, or during a period of remission or less active disease. The agent can be administered before another treatment, concurrently with the treatment, post-treatment, or during remission of the disorder.

When administered in combination, the agent or composition and the additional agent (e.g., second or third agent), or all, can be administered in an amount or dose that is higher, lower or the same as the amount or dosage of each agent used individually, e.g., as a monotherapy. In certain embodiments, the administered amount or dosage of the agent, the additional agent (e.g., second or third agent), or all, is lower (e.g., at least 20%, at least 30%, at least 40%, or at least 50%) than the amount or dosage of each agent used individually. In other embodiments, the amount or dosage of agent, the additional agent (e.g., second or third agent), or all, that results in a desired effect (e.g., treatment of a disease) is lower (e.g., at least 20%, at least 30%, at least 40%, or at least 50% lower) than the amount or dosage of each agent individually required to achieve the same therapeutic effect.

In one embodiment of any of the aspects, the methods provided herein further comprises administering at least one immunotherapeutic agent or cell.

In another embodiment of any of the aspects, the immunotherapeutic agent is a chemotherapeutic agent.

As used herein, an "immunotherapeutic agent" is an agent that is known to stimulate the immune system or recruit immune cells to a target tissue in a subject. Immunotherapeutic agents include, but are not limited to, 3622W94, 4B5, ANA Ab, anti-FLK-2, anti-VEGF, ATRAGEN, AVASTIN (bevacizumab; Genentech), BABS, BEC2, BEXXAR (tositumomab; GlaxoSmithKline), C225, CAMPATH (alemtuzumab; Genzyme Corp.), CEACIDE, CMA 676, EMD-72000, ERBITUX (cetuximab; ImClone Systems, Inc.), Gliomab-H, GNI-250, HERCEPTIN (trastuzumab; Genentech), IDEC-Y2B8, ImmuRAIT-CEA, ior c5, ior egf.r3, ior t6, LDP-03, LymphoCide, MDX-11, MDX-22, MDX-210, MDX-220, MDX-260, MDX-447, MELIMMUNE-1, MELIMMUNE-2, Monopharm-C, NovoMAb-G2, Oncolym, OV103, Ovarex, Panorex, Pretarget, Quadramet, Ributaxin, RITUXAN (rituximab; Genentech), SMART 1D10 Ab, SMART ABL 364 Ab, SMART M195, TNT, and ZENAPAX (daclizumab; Roche).

Anti-cancer therapies for use with the compositions and methods described herein include cancer medicaments, radiation, and surgical procedures. As used herein, a "chemotherapeutic agent" refers to an agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

Non-limiting examples of chemotherapeutic agents include methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, famesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Ince/X-710, VX-853, ZD0101, ISI641, ODN 698, TA 2516/Marmistat, BB2516/Marmistat, CDP 845, D2163, PD183805, DX8951f, Lemonal DP 2202, FK 317, picibanil/OK-432, AD 32/Valrubicin, Metastron/strontium derivative, Temodal/ITemozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT(Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate.

In another embodiment of any of the aspects, the chemotherapeutic agent is selected from the group consisting of: alemtuzumab, atezolizumab, ipilimumab, nivolumab, ofatumumab, pembrolizumab, rituximab, and durvalumab.

In another embodiment of any of the aspects, the chemotherapeutic cell is a genetically engineered T cell, a dendritic cell, or a natural killer cell. In another embodiment of any of the aspects, the genetically engineered T cell is a chimeric antigen receptor (CAR) T cell.

Chemotherapeutic cell and cell vaccine therapies are known in the art (See for example U.S. Pat. Nos. 6,207,147B1, 5,484,596A, and US20080206286A1).

As used herein, the terms "treat," "treatment," "treating," or "amelioration" refer to therapeutic treatments, wherein the object is to reverse, alleviate, ameliorate, inhibit, slow down or stop the progression or severity of a condition associated with disease, e.g. ulcerative colitis. The term "treating" includes reducing or alleviating at least one adverse effect or symptom of disease, for example, diarrhea, bleeding, loss of appetite, discomfort, or vomiting. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein "preventing" or "prevention" refers to any methodology where the disease state does not occur due to the actions of the methodology (such as, for example, administration of an agent as described herein). In one aspect, it is understood that prevention can also mean that the disease is not established to the extent that occurs in untreated controls. Accordingly, prevention of a disease encompasses a reduction in the likelihood that a subject can develop the disease, relative to an untreated subject (e.g. a subject who is not treated with the methods or compositions described herein).

The term "subject" includes human and other mammalian subjects that receive therapeutic treatment. Accordingly, the term "subject" refers to any living organism which can be administered compound and/or pharmaceutical compositions of the present invention. The term includes, but is not limited to, humans, non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult and newborn subjects, whether male or female, are intended to be covered. The term "subject" is also intended to include living organisms susceptible to conditions or disease states as generally disclosed, but not limited to, throughout this specification. Examples of subjects include humans, dogs, cats, cows, goats, and mice. The term subject is further intended to include transgenic species. The term "subject" and "individual" are used interchangeably herein, and refer to an animal, for example a human or non-human mammals/animals, to whom treatment, including prophylactic treatment, with the compounds and compositions according to the present invention, is provided. The term "non-human animals" and "non-human mammals" are used interchangeably herein and include all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

Preferably, the subject is a mammal. The mammal can be a human, non-human primate, mouse, rat, dog, cat, horse, or cow, but is not limited to these examples. Mammals other than humans can be advantageously used as subjects that represent animal models of a disease. A subject can be male or female.

In one embodiment of any of the aspects, the subject has been previously diagnosed with having a disease. In another embodiment of any of the aspects, the subject is diagnosed with a disease prior to the administering of the agent. In another embodiment of any of the aspects, the subject is a mammal. In another embodiment of any of the aspects, the subject is a human.

A subject can be one who has been previously diagnosed with or identified as suffering from or having a disease or disorder in need of treatment (e.g., cancer) or one or more complications related to such a disease or disorder, and optionally, have already undergone treatment for the disease or disorder or the one or more complications related to the disease or disorder. Alternatively, a subject can also be one who has not been previously diagnosed as having such disease or disorder or related complications. For example, a subject can be one who exhibits one or more risk factors for the disease or disorder or one or more complications related to the disease or disorder or a subject who does not exhibit risk factors.

In one aspect of any embodiment, described herein is a method for treating or preventing a disease by stimulating the immune system, the method comprises administering to a subject an agent that increases the level or activity of IDO1 or AhR in the subject.

As used herein, the term "stimulating the immune system," "inflammation" or "inflamed" refers to activation or recruitment of the immune system or immune cells (e.g. T cells, B cells, macrophages, or natural killer cells). A tissue that has inflammation can become reddened, white, swollen, hot, painful, exhibit a loss of function, or have a film or mucus. Methods of identifying inflammation are well known in the art. Inflammation typically occurs following injury or infection by a microorganism.

In one aspect, provided here is a method of vaccinating a subject, the method comprises administering the agent described herein to the subject.

In one embodiment of any of the aspects, the administering of the agents or compounds as provided herein increases inflammation. In another embodiment of any of the aspects, the subject has or is diagnosed as having cancer, an immune deficiency, an autoimmune disease, an infection, or has had surgery.

"Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Hemopoietic cancers, such as leukemia, are able to outcompete the normal hemopoietic compartments in a subject, thereby leading to hemopoietic failure (in the form of anemia, thrombocytopenia and neutropenia) ultimately causing death.

A metastasis is a region of cancer cells, distinct from the primary tumor location, resulting from the dissemination of cancer cells from the primary tumor to other parts of the body. At the time of diagnosis of the primary tumor mass, the subject may be monitored for the presence of metastases. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Cancers include, but are not limited to, basal cell carcinoma, biliary tract cancer; bladder cancer; bone cancer; brain and central nervous system (CNS) cancer; breast cancer; cervical cancer; choriocarcinoma; colon and rectum cancer; connective tissue cancer; cancer of the digestive system; endometrial cancer; esophageal cancer; eye cancer; cancer of the head and neck; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; sarcoma; skin cancer; stomach cancer; testicular cancer; thyroid cancer; uterine cancer; cancer of the urinary system, as well as other carcinomas, adenocarcinomas, and sarcomas.

In another embodiment of any of the aspects, the cancer is selected from the group consisting of: gastrointestinal cancer, prostate cancer, ovarian cancer, breast cancer, head and neck cancer, lung cancer, non-small cell lung cancer, cancer of the nervous system, kidney cancer, retinal cancer, melanoma skin cancer, stomach cancer, liver cancer, pancreatic cancer, genital-urinary cancer, prostate cancer, colorectal cancer, and bladder cancer.

In another embodiment of any of the aspects, the infection as provided herein is due to a microorganism. In another embodiment of any of the aspects, the microorganism is a bacterium, virus, fungus, parasite, yeast, prion, or any other microorganism known in the art. As used herein, "microbe" or "microorganism" refers to an organism which is microscopic. A microbe can be a single-celled organism. In some embodiments of any of the aspects, a microbe can be a bacterium. As used herein, the term "pathogen" refers to an organism or molecule that causes a disease or disorder in a subject. For example, pathogens include but are not limited to viruses, fungi, bacteria, parasites and other infectious organisms, or molecules therefrom, as well as taxonomically related macroscopic organisms within the categories algae, fungi, yeast and protozoa or the like.

In another embodiment of any of the aspects, the bacterium is a *Clostridium, Staphalococcus, Streptococcus. Escherichia* (e.g. *E. coli*). *Mycobacterium, Pseudomonas, Burkholderiz, Trichomonas, Campylobacter, Shingella, Salmonella, Citrobacter*, or any other bacteria known in the art. In another embodiment of any of the aspects, the virus is influenza virus, coronavirus, retrovirus, or any other virus known in the art.

In one aspect, provided herein is an assay for identifying an agent that modulates the immune response of a biological sample, the assay comprising: (a) contacting the biological sample with an agent; and (b) detecting the level or activity of IDO1 wherein detecting a change in IDO1 levels after contacting step (a) identifies the agent as one that can modulate the immune response.

In one embodiment of any of the aspects, the biological sample is a tissue, blood sample, tumor, or plurality of cells.

In another embodiment of any of the aspects, comprising detecting the level or activity of aryl hydrocarbon receptor (Ahr); N'-formyl-kynurenine; L-kynurenine; kynurenic acid; xanthurenic acid; cluster of differentiation 1d (CD1d); interleukin (IL)-10; IL-13, interferon-γ (IFN-γ); microsomal triglyceride transfer protein (Mttp); and/or cytochrome P450 family 1, member A1 (Cyp1a1). Methods of detecting the levels or activity of these proteins and metabolites are known in the art.

In another embodiment of any of the aspects, the assay further comprises detecting the activity or induction of Cyp1a1.

In another embodiment of any of the aspects, the assay further comprises detecting the level or activity of IDO1 from a biological sample that is not contacted with the agent as an appropriate control.

In another embodiment of any of the aspects, the detecting is accomplished by RT-PCR, flow cytometry, immunohistochemistry, Western Blot, enzyme-linked immunosorbent assay (ELISA), mass spectrometry, calorimetric assay, or microscopy. These methods are well known in the art.

For the assay, cells can be optionally allowed to grow for a period time before contacting with the agent. In some embodiments, a practitioner can obtain cells (e.g. intestinal epithelial cells or cancer cells) that are already plated in the appropriate vessel and allowed to grow for a period of time. In other embodiments, the practitioner plates the cell in the appropriate vessel and allow the cells to grow for a period time, e.g., at least one day, at least two days, at least three days, at least four days, at least five days, at least six days, at least seven days or more before contacting with the test compound.

After the agent or test compound has been in contact with the cell or population of cells (e.g. intestinal epithelial cells or cancer cells) for a sufficient period of time, amount of reporter (e.g., expression or activity) is measured and compared to a control or reference. For example, contact time can be from seconds to days or weeks. The practitioner can optimize the contact time for obtaining an optimal signal-to-noise ratio, time constraints, amount of test compound to be tested, number of cells, test volume, availability of reagents for the assay, and the like.

As used herein, the term "test compound" refers to compounds, agents as described herein, and/or pharmaceutical compositions that are to be screened for their ability to stimulate and/or increase and/or promote IDO1 or AhR activity or expansion of intestinal epithelial cell or cancer cell populations. The test compounds can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; an extract made from biological materials such as bacteria, plants, fungi, or animal cells; animal tissues; naturally occurring or synthetic compositions; and any combinations thereof. In some embodiments of any of the aspects, the agent or test compound is a small molecule. In some embodiments of any of the aspects, the agent or test compound is the compound of any one of Formula (I), (II), (III), or (IV) as provided herein.

The number of possible test compounds runs into millions. Methods for developing small molecule, polymeric and genome based libraries are described, for example, in Ding, et al. J Am. Chem. Soc. 124: 1594-1596 (2002) and Lynn, et al., J. Am. Chem. Soc. 123: 8155-8156 (2001). Commercially available compound libraries can be obtained from, e.g., ArQule, Pharmacopia, Graffinity, Panvera, Vitas-M Lab, Biomol International and Oxford. These libraries can be screened using the screening devices and methods described herein. Chemical compound libraries such as those from NIH Roadmap, Molecular Libraries Screening Centers Network (MLSCN) can also be used. A comprehensive list of compound libraries can be found at www.broad.harvard.edu/chembio/platform/screening/compound_libraries/index.htm. A chemical library or compound library is a collection of stored chemicals usually used ultimately in high-throughput screening or industrial manufacture, e chemical library can consist in simple terms of a series of stored chemicals. Each chemical has associated information stored in some kind of database with information such as the chemical structure, purity, quantity, and physiochemical characteristics of the compound.

Depending upon the particular embodiment being practiced, the test compounds can be provided free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds can be screened individually, or in groups. Group screening is particularly useful where hit rates for effective test compounds are expected to be low such that one would not expect more than one positive result for a given group.

The test compound can be tested at any desired concentration. For example, the test compound can be tested at a final concentration of from 0.01 nanomolar to about 10 millimolar. Further, the test can be tested at 2 or more (e.g., 2, 3, 4, 5, 6, 7, 8, 9, 10 or more) different concentrations. This can be helpful if the test compound is active only in a range of concentration. When the test compound is tested at 2 or more different concentrations, the concentration difference can range from 10-10,000 fold (e.g., 10-5000 fold, 10-1000 fold, 10-500 fold, or 10-250 fold).

In some embodiments of any of the aspects, the agent or test compound is assayed more than once and selected if it reproducibly modulates IDO1 or AhR expression or activity.

In some embodiments of any of the aspects, the assay further comprises the step of determining of the compound has scored on any other screens. This can be accomplished by looking at the various chemical databases that describe activity of compounds in various assays. This can help in identifying compounds that are unique to the present assay.

In some embodiments of any of the aspects, the selected test compound exhibits dose-dependent modulation of IDO1 or AhR expression or activity. In some embodiments of any of the aspects, selected test compound exhibits maximal modulation of IDO1 or AhR expression or activity in the assay. This can be helpful because some highly potent modulators (based on EC50) can yield only weak maximal activation, whereas other less potent modulators (based on EC50) can produce significantly greater activation, even at doses below their EC50.

The assay can be performed any suitable container or apparatus available to one of skill in the art for cell culturing. For example, the assay can be performed in 24-, 96-, or 384-well plates. In one embodiment of any of the aspects, the assay is performed in a 384-well plate.

Cells for the aspects disclosed herein can be obtained from any source available to one of skill in the art. Additionally, cells can be of any origin. Accordingly, in some embodiments, the cell is from a mammalian source. In some embodiments, of any of the aspects, the cells are cancer cells, or intestinal epithelial cells.

In some embodiments of any of the aspects, the cell is from a subject, e.g., a patient. In some embodiments of any of the aspects, the cell is from the blood, tumor, skin, esophagus, small intestine, large intestine, or colon of the subject. In some embodiments of any of the aspects, the subject, is a patient in need of treatment for a disease.

Some Selected Definitions

Unless defined otherwise, all technical and scientific terms used herein have the same meaning as those commonly understood to one of ordinary skill in the art to which this invention pertains. Although any known methods, devices, and materials can be used in the practice or testing of the invention, the methods, devices, and materials in this regard are provided herein.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects provided herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as provided herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages can mean 1%.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type provided herein and/or which will become apparent to those persons skilled in the art upon reading this disclosure and so forth.

Although methods and materials similar or equivalent to those provided herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The present invention is further illustrated by the following Examples, which in no way should be construed as further limiting.

Some embodiments of the various aspects described herein can be described as in the following numbered paragraphs:

1. A method of stimulating the immune system in a subject in need thereof, the method comprising: administering an agent that increases the level or activity of indoleamine 2,3-dioxygenase (IDO1) to the subject.
2. The method of paragraph 1, wherein the agent is an activator of IDO1.
3. The method of paragraph 1, wherein the agent is selected from the group consisting of: a small molecule, an antibody, a peptide, a genome editing system, a vector, a miRNA, and a siRNA.
4. The method of paragraph 1, wherein the agent is the compound of Formula (I):

FORMULA (I)

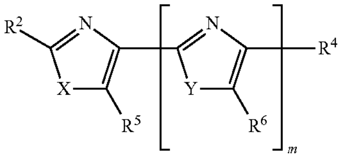

wherein:

m is 0, 1 or 2;

X and Y are independently O or S;

$R^2$, $R^4$, $R^5$ and $R^6$ are independently H, $C_1$-$C_6$alkyl, $-(CH_2)_nC(O)R^7$, $-(CH_2)_nNHC(O)-R^7$, $-(CH_2)_nC(O)N(R^7)_2$, $C_2$-$C_6$ alkenyl, $C_2$-$C_6$alkynyl, $N(R^7)_2$, $-(CH_2)_nC(O)OR^7$, halogen, $CF_3$, $SR^7$, $OR^7$, aryl, heteroaryl, cyclyl or heterocyclyl, each of which can be optionally substituted;

$R^7$ is H, $C_1$-$C_6$alkyl, heterocyclyl, heteroaryl, aryl, cyclyl, $C_2$-$C_6$alkenyl, or $C_2$-$C_6$alkynyl, each of which can be optionally substituted; and n is 0, 1, 2, 3, 4, 5 or 6, or a pharmaceutically acceptable salt thereof.

5. The method of paragraph 4, wherein the compound is selected from the group consisting of: (i) 2,4-dimethyloxazole having the structure:

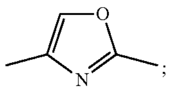

;

(ii) ethyl-4-methyloxazole-5-carboxylate having the structure:

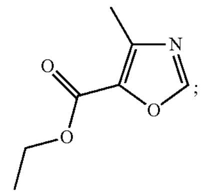

(iii) 2,4,5-trimethyloxazole having the structure:

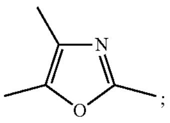

(iv) Frag-oztz having the structure:

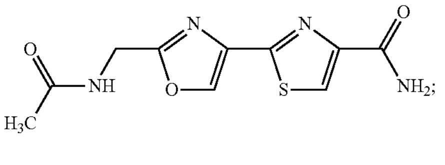 [SMILES: CC(=O)NCc1nc(-c2nc(C(N)=O)cs2)co1]

(v) Frag-tzoz having the structure:

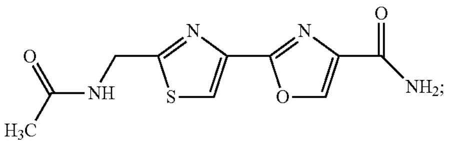

(vi) Frag-tz having the structure:

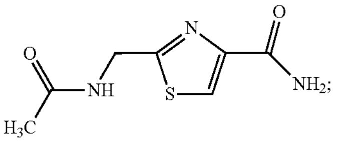

and (vii) Frag-oz having the structure:

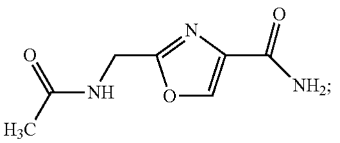

6. The method of paragraph 1, wherein the agent is the compound of Formula (II):

FORMULA (II)

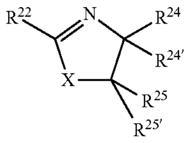

wherein:

X is O or S;

$R^{22}$ is H, $C_1$-$C_6$ alkyl, —$(CH_2)_n C(O)R^{26}$, —$(CH_2)_n$NHC(O)—$R^6$, —$(CH_2)_n C(O)N(R^6)_2$, $C_2$-$C_6$ alkenyl, $C_2$-$C_6$alkynyl, $N(R^2)_2$, —$(CH_2)_n C(O)OR^{26}$, halogen, $CF_3$, $SR^{26}$, $OR^{26}$, aryl, heteroaryl, cyclyl or heterocyclyl, each of which can be optionally substituted;

$R^{24}$ is H, $C_1$-$C_6$ alkyl, —$(CH_2)_n C(O)R^{26}$, —$(CH_2)_n$NHC(O)—$R^2$, —$(CH_2)_n C(O)N(Re)_2$, $C_2$-$C_6$ alkenyl, $C_2$-$C_6$alkynyl, $N(R^2)_2$, —$(CH_2)_n C(O)OR^{26}$, halogen, $CF_3$, $SR^{26}$, $OR^{26}$, aryl, heteroaryl, cyclyl or heterocyclyl, each of which can be optionally substituted;

$R^{24'}$ is H, or $R^{24}$ and $R^{24'}$ together form ═O or ═S;

$R^{25}$ is H, $C_1$-$C_6$ alkyl, —$(CH_2)_n C(O)R^{26}$, —$(CH_2)_n$NHC(O)—$R^{26}$, —$(CH_2)_n C(O)N(R^{26})_2$, $C_2$-$C_6$ alkenyl, $C_2$-$C_6$alkynyl, $N(R^{26})_2$, —$(CH_2)_n C(O)OR^{26}$, halogen, $CF_3$, $SR^{26}$, $OR^{26}$, aryl, heteroaryl, cyclyl or heterocyclyl, each of which can be optionally substituted;

$R^{25'}$ is H, or $R^2$ and $R^{2'}$ together form ═O or ═S;

$R^{26}$ is H, $C_1$-$C_6$ alkyl, heterocyclyl, heteroaryl, aryl, cyclyl, $C_2$-$C_6$ alkenyl, or $C_2$-$C_6$alkynyl, each of which can be optionally substituted; and n is 0, 1, 2, 3, 4, 5 or 6, or a pharmaceutically acceptable salt thereof.

7. The method of paragraph 6, wherein the compound is 4-methyl-5(4H)-oxazolone having the structure:

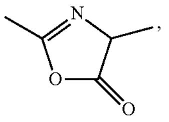

or 4(5H)-oxazolone having the structure:

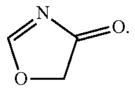

8. The method of paragraph 1, wherein the agent is the compound of Formula (III):

FORMULA (III)

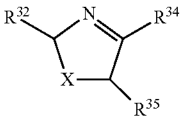

wherein:

X is O or S;

$R^{32}$, $R^{34}$, and $R^{35}$ are independently H, $C_1$-$C_6$ alkyl, —$(CH_2)_n C(O)R^6$, —$(CH_2)_n$NHC(O)—$R^6$, —$(CH_2)_n C(O)N(R^3)_2$, $C_2$-$C_6$ alkenyl, $C_2$-$C_6$alkynyl, $N(R^3)_2$, —$(CH_2)_n C(O)OR^3$, halogen, $CF_3$, $SR^3$, $OR^3$, aryl, heteroaryl, cyclyl or heterocyclyl, each of which can be optionally substituted;

$R^3$ is H, $C_1$-$C_6$ alkyl, heterocyclyl, heteroaryl, aryl, cyclyl, $C_2$-$C_6$ alkenyl, or $C_2$-$C_6$alkynyl, each of which can be optionally substituted; and n is 0, 1, 2, 3, 4, 5 or 6, or a pharmaceutically acceptable salt thereof.

9. The method of paragraph 8, wherein the compound is 2,4,5-trimethyl-2,5-dihydro-1,3-oxazole (TMO) having the structure:

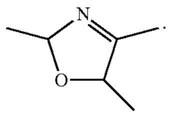

10. The method of paragraph 1, wherein the agent is the compound of Formula (IV):

FORMULA (III)

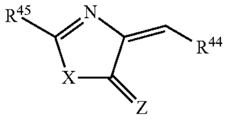

wherein:

X is O or S;

Z is O or S;

$R^{42}$ is H, aryl, heteroaryl, cyclyl, heterocyclyl, $C_1$-$C_6$ alkyl, —$(CH_2)_n C(O)R^{45}$, —$(CH_2)_n NHC(O)$—$R^{45}$, —$(CH_2)_n C(O)N(R^{45})_2$, $C_2$-$C_6$ alkenyl, $C_2$-$C_6$alkynyl, $N(R^{45})_2$, —$(CH_2)_n C(O)OR^{45}$, halogen, $CF_3$, $SR^{45}$, or $OR^{45}$, each of which can be optionally substituted;

$R^{44}$ is H, $C_1$-$C_6$ alkyl, —$(CH_2)_n C(O)R^{45}$, —$(CH_2)_n NHC(O)$—$R^{45}$, —$(CH_2)_n C(O)N(R^{45})_2$, $C_2$-$C_6$ alkenyl, $C_2$-$C_6$alkynyl, $N(R^{45})_2$, —$(CH_2)_n C(O)OR^{45}$, halogen, $CF_3$, $SR^{45}$, or $OR^{45}$, each of which can be optionally substituted;

$R^{45}$ is H, $C_1$-$C_6$ alkyl, heterocyclyl, heteroaryl, aryl, cyclyl, $C_2$-$C_6$ alkenyl, or $C_2$-$C_6$alkynyl, each of which can be optionally substituted; and n is 0, 1, 2, 3, 4, 5 or 6, or a pharmaceutically acceptable salt thereof.

11. The method of paragraph 10, wherein the compound is 4-ethoxymethylene-2-phenyl-2-oxazolin-5-one (oxazolone) having the structure:

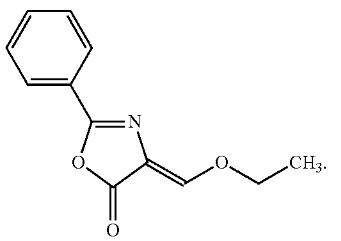 [SMILES: CCO/C=C1\N=C(c2ccccc2)OC1=O]

12. The method of any one of paragraphs 4-11, wherein the compound has a molecular weight of 220 Da or less.

13. The method of any one of paragraphs 1-12, wherein the agent is formulated in a pharmaceutical composition.

14. The method of paragraph 1, wherein the subject has or is diagnosed as having cancer, an immune deficiency, an autoimmune disease, an infection, or has had surgery.

15. The method of paragraph 14, wherein the cancer is selected from the group consisting of: gastrointestinal cancer, prostate cancer, ovarian cancer, breast cancer, head and neck cancer, lung cancer, non-small cell lung cancer, cancer of the nervous system, kidney cancer, retinal cancer, melanoma skin cancer, stomach cancer, liver cancer, pancreatic cancer, genital-urinary cancer, prostate cancer, colorectal cancer, and bladder cancer.

16. The method of paragraph 1, wherein the agent is formulated with at least one pharmaceutically acceptable carrier and an adjuvant.

17. A method of vaccinating a subject, the method comprising administering the agent of any one of paragraphs 1-16 to the subject.

18. The method of paragraph 17, wherein the subject is a mammal.

19. The method of paragraph 18, wherein the subject is a human.

20. The method of any one of paragraphs 1-19, further comprising administering at least one immunotherapeutic agent or cell.

21. The method of paragraph 20, wherein the immunotherapeutic agent is a chemotherapeutic agent.

22. The method of paragraph 21, wherein the chemotherapeutic agent is selected from the group consisting of: alemtuzumab, atezolizumab, ipilimumab, nivolumab, ofatumumab, pembrolizumab, rituximab, and durvalumab.

23. The method of paragraph 20, wherein the chemotherapeutic cell is a genetically engineered T cell, a dendritic cell, or a natural killer cell.

24. The method of paragraph 23, wherein the genetically engineered T cell is a chimeric antigen receptor (CAR) T cell.

25. A method of stimulating the immune system in a subject in need thereof, the method comprising: administering an agent that increases the level or activity of aryl hydrocarbon receptor (Ahr) to the subject.

26. The method of paragraph 25, wherein the agent is an agonist of Ahr.

27. The method of paragraph 25, wherein the agent is selected from the group consisting of: a small molecule, an antibody, a peptide, a genome editing system, a vector, a miRNA, and a siRNA.

28. The method of paragraph 25, wherein the agent is the compound of Formula (I), Formula (II), Formula (III), Formula (IV) or any derivative thereof.

29. The method of any one of paragraphs 25-28, wherein the agent is formulated in a pharmaceutical composition.

30. The method of paragraph 25, wherein the subject has or is diagnosed as having cancer, an immune deficiency, an autoimmune disease, an infection, or has had surgery.

31. The method of paragraph 30, wherein the cancer is selected from the group consisting of: gastrointestinal cancer, prostate cancer, ovarian cancer, breast cancer, head and neck cancer, lung cancer, non-small cell lung cancer, cancer of the nervous system, kidney cancer, retinal cancer, melanoma skin cancer, stomach cancer, liver cancer, pancreatic cancer, genital-urinary cancer, prostate cancer, colorectal cancer, and bladder cancer.

32. The method of paragraph 25, wherein the agent is formulated with at least one pharmaceutically acceptable carrier and an adjuvant.

33. A method of vaccinating a subject, the method comprising administering the agent of any one of paragraphs 25-29 to the subject.

34. The method of paragraph 33, wherein the subject is a mammal.

35. The method of paragraph 34, wherein the subject is a human.

36. The method of any one of paragraphs 25-35, further comprising administering at least one immunotherapeutic agent or cell.

37. The method of paragraph 36, wherein the immunotherapeutic agent is a chemotherapeutic agent.

38. The method of paragraph 37, wherein the chemotherapeutic agent is selected from the group consisting of: alemtuzumab, atezolizumab, ipilimumab, nivolumab, ofatumumab, pembrolizumab, rituximab, and durvalumab.

39. The method of paragraph 36, wherein the chemotherapeutic cell is a genetically engineered T cell, a dendritic cell, or a natural killer cell.

40. The method of paragraph 39, wherein the genetically engineered T cell is a chimeric antigen receptor (CAR) T cell.

41. An assay for identifying an agent that modulates the immune response of a biological sample, the assay comprising:

a. contacting the biological sample with an agent; and b. detecting the level or activity of IDO1 wherein detecting a change in IDO1 levels or activity after contacting step (a) identifies the agent as one that can modulate the immune response.

42. The assay of paragraph 41, wherein the biological sample is a tissue, blood sample, tumor, or plurality of cells.

43. The assay of paragraph 41, further comprising detecting the level of aryl hydrocarbon receptor (Ahr); N'-formyl-kynurenine; L-kynurenine; kynurenic acid; xanthurenic acid; cluster of differentiation 1d (CD1d); interleukin (IL)-10; IL-13, interferon-γ (IFN-γ); microsomal triglyceride transfer protein (Mttp); and/or cytochrome P450 family 1, member A1 (Cyp1a1).

44. The assay of paragraph 41, further comprising detecting the activity or induction of Cyp1a1.

45. The assay of paragraph 41, further comprising detecting the level or activity of IDO from a biological sample that is not contacted with the agent as an appropriate control.

EXAMPLES

Example 1: Dietary and Microbial Oxazoles Induce Intestinal Inflammation by Modulating Epithelial Derived Aryl Hydrocarbon Receptor Responses Summary Genome-wide association studies have identified numerous risk loci associated with the development of inflammatory bowel disease (IBD). Yet epidemiological studies have emphasized that disease pathogenesis likely requires host interactions with environmental elements whose source, structure and mechanism of action have yet to be precisely defined. Here a class of environmental triggers of inflammation in the gastrointestinal tract, derived from dietary, microbial and industrial sources that are characterized by the presence of a 5-membered oxazole ring, an abundant structural feature within the class of hetero-polycyclic aromatics are identified. The activity of minimal oxazole structures were evaluated, originating from these sources including a class of bacterial derived peptides, termed thiazole/oxazole modified microcins (TOMMs), and found that the colitogenic potential of these compounds depends on cell intrinsic intestinal epithelial cell (IEC) responses that modulate natural killer T cell dependent inflammation in a CD1d dependent manner. Furthermore, CD1d-restricted production of interleukin 10 by the IEC is limited by the activity of the aryl hydrocarbon receptor (AhR) pathway in response to oxazole induction of tryptophan metabolites such that genetic elimination of AhR in the intestinal epithelium abrogates oxazole-induced inflammation. This study identifies oxazoles as a new class of environmental and microbial triggers of CD1d-dependent intestinal responses associated with inflammation that occurs through the AhR pathway in the intestinal epithelium.

Introduction

Inflammatory bowel disease (IBD) is a complex disorder that evolves from the interactions between poorly understood environmental factors and a host's genetic framework that together define susceptibility to and severity of disease. Pathology is influenced by specific host elements that include the autochthonous commensal microbiota, which is acquired at birth, the intestinal epithelial cell barrier and subjacent immune cells within the intestinal mucosa (Kaser et al. 2010). One of the great challenges of understanding IBD pathogenesis stems from efforts to elucidate the molecular details surrounding the environmental basis for these disorders (Kaplan and Ng 2017). This is increasingly important as epidemiologic studies have revealed a rapid global expansion of these diseases that includes geographic regions, which have heretofore been unaffected (Molodecky and Kaplan 2010).

A potential opportunity to investigate this question has emerged from recent studies on the role of CD1d and natural killer T cells (NKT) in mucosal biology. CD1d is a non-polymorphic, major histocompatibility complex (MHC) class I-related molecule in non-covalent association with β2-microglobulin that presents cell associated and microbial lipid antigens to NKT cells (Barral and Brenner 2007). In the intestines, CD1d is expressed by parenchymal cells, such as the intestinal epithelial cell (IEC), and hematopoietic cells such as professional antigen presenting cells (APC) residing in the lamina propria (Brigl and Brenner 2004, RossJohn et al. 2012, Van de waal et al 2003, Colgan et al. 1999, Dougan et al. 2007). CD1d-bearing IEC and APC present endogenous (self) or exogenous lipid antigens to NKT cells expressing an invariant T cell receptor (TCR) a chain (iNKT cells) or a semi-diverse (d) set of TCR-α chains (dNKT), which are present in human and mouse intestines (Brennan et al. 2013).

Both types of NKT cells have been implicated in the pathogenesis of IBD through studies of human tissues and an experimental mouse model of IBD involving the chemical induction of colitis using a classic chemical hapten, oxazolone (Wirtz et al. 2007). Boirevant and colleagues first demonstrated that administration of oxazolone directly to the colon in ethanol of SJLJJ mice, or in later studies indirectly after skin painting and sensitization suggesting a model of haptenization, resulted in a severe acute, superficial inflammation due to the production of interleukin (IL)-4 and IL-13 that was counter-balanced by tumor growth factor-α which delimited the inflammation to the distal colon (Boirevant et al. 1998). This restriction to type 2 cytokines was eventually recognized to be genetically based as similar studies in C57B/6 mice revealed inflammation in association with oxazolone that was due to type 1 cytokines (namely interferon-y) derived from hematopoietic cells (Olszak et al. 2014, Iijima et al. 2004). In later groundbreaking studies by Heller and colleagues, it was recognized that oxazolone-induced colitis was dependent upon CD1d and iNKT cells as an inflammatory response to oxazolone was abrogated by the deletion of Cd1d or Jα18, encoding the invariant TCR-α chain (Heller et al. 2002). Moreover, the pro-inflammatory effects of CD1d-iNKT cell interactions in response to oxazolone were primarily derived from the activity of professional APC in the lamina propria using bone marrow chimeras (Olszak et al. 2014). In contrast, CD1d-expressing IECs were shown to secrete anti-inflammatory IL-10 in response to iNKT cells in a CD1d-dependent manner, which serves to restrain oxazolone-induced inflammation derived from the hematopoeitic system (Colgan et al. 1999, Olzsak et al. 2014). As such, when CD1d-restricted pathways in the IEC are specifically eliminated by conditional genetic deletion of Cd1d, microsomal triglyceride transfer protein (Mttp), an endoplasmic reticulum resident protein which serves to regulate CD1d lipidation and its ability to function, or I110, oxazolone-induced colitis is unrestrained and severe (Dougan et al. 2005, 2007, Sagiv et al. 2007, Olszak et al. 2014). Human studies have further identified a potential role for dNKT cells in IBD by showing elevated IL-13 production by lamina propria mononuclear cells in response to sulfatide, a CD1d-restricted self antigen which can activate iNKT and dNKT cells (Fuss et al. 2004, Fuss et al. 2014). Further, T cell receptor (TCR) transgenic mice expressing a non-invariant CD1d-restricted TCR develop colitis (Wang et al. 2017). Moreover, some studies have shown that T cells expressing V□24, the TCRAV chain expressed by iNKT cells, are increased in the intestinal mucosa and blood of patients with IBD; although others have reported the opposite observations suggesting a decrease of TCRAV bearing cells or their receptor upon activation (Fuss et al. 2004, Grose et al. 2007, van der Vliet et al. 2001). These studies together suggest that NKT cells may play a role in the pathogenesis of IBD.

Importantly, these host inflammatory responses to oxazolone occur even in animals raised under germ free (GF) conditions, indicating that NKT cell mediated response to self (rather than microbial) lipid antigens presented by CD1d on professional and/or non-professional antigen presenting cells (APC) is sufficient for pathogenesis (Olszak et al. 2012). Instead, commensal bacteria themselves can modulate the magnitude of NKT cell responses either by directly altering the CD1d-restricted lipid antigen reservoir (An et al. 2014, Wieland Brown et al. 2013) or indirectly by regulating the quantity of iNKT cells in the colon (Olszak et al. 2012). In the latter case, the absence of appropriate microbial signals in early life leads to elevated levels of iNKT cells in the colon that in later life makes the host susceptible to the colitogenic effects of oxazolone (Olszak et al. 2012). Conversely, CD1d itself plays a critical role in regulating the composition and extent of colonization by both commensal and pathogenic microbial species through disruption of the anti-microbial activity of Paneth cells (Nieuwenhuis et al. 2005, Nieuwenhuis et al. 2009, Farin et al. 2014).

The similarities between these biological observations in mouse models and current hypotheses for IBD pathogenesis wherein environmental triggers activate inflammation in a susceptible host lead us to hypothesize that oxazolone may be an example of a much larger collection of environmental chemical moieties capable of triggering CD1d-restricted iNKT cell responses. Evidence for the existence of oxazolone-related chemicals in the environment and microbiota capable of inducing intestinal inflammation were investigated. In so doing, environmental mimetics of oxazolone that are derived from dietary, industrial or microbial sources have been identified which are characterized by the presence of a 5-membered oxazole ring and capable of driving CD d-dependent inflammation through activation of the aryl hydrocarbon receptor pathway within IECs of the colon. As efforts to define and evaluate natural and synthetic chemicals involved in homeostasis or disease have generally been elusive, these results have broad implications for understanding the environmental basis of mucosal diseases such as IBD.

Results

Defining a Structural Moiety that Modulates Epithelial Derived CD1d Dependent Inflammatory Responses.

4-ethoxymethylene-2-phenyl-2-oxazol-5-one, (referred to as oxazolone, FIG. 1A) has been widely utilized in models of contact hypersensitivity and when applied to the mucosa has been proposed to cause colitis through its properties as a hapten (Gorbachev and Fairchild 2001). However to date there is limited evidence for hapten-specific antibody production or responses following topical oxazolone sensitization or hapten modified autologous proteins or luminal antigens identified at mucosal sites (Singleton et al. 2016, Yanaba et al. 2008, Wirtz et al. 2007). Interestingly, upon analysis of previously published microarray studies derived from epithelial enriched colon fractions following intrarectal oxazolone challenge (Olszak et al. 2014), it was observed decreased transcripts for microsomal triglyceride transfer protein (Mttp, MTP) and increased transcripts for elements associated with aryl hydrocarbon receptor (AhR) signaling, including P450 enzymes (cyp1a1) and indoleamine 2,3-dioxygenase (Ido1). It was then determined whether oxazolone could affect the expression of these transcripts in the intestinal epithelium in a cell intrinsic manner by directly stimulating an immortalized intestinal epithelial cell line (IEC) derived from mouse small intestine, MODE-K, with oxazolone. It was observed that down-regulation of Mttp and induction of metabolic genes cyp1a1 and Ido1 (FIG. 1B, FIG. 7A-D).

Figure 1D:
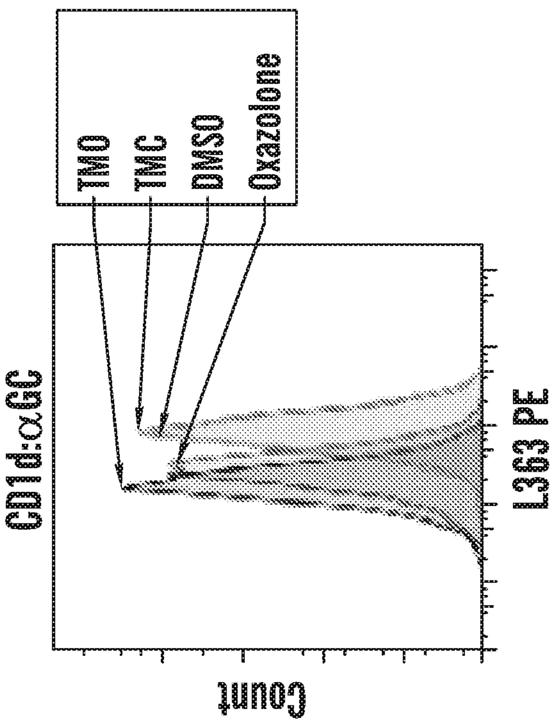
Figure 1C:
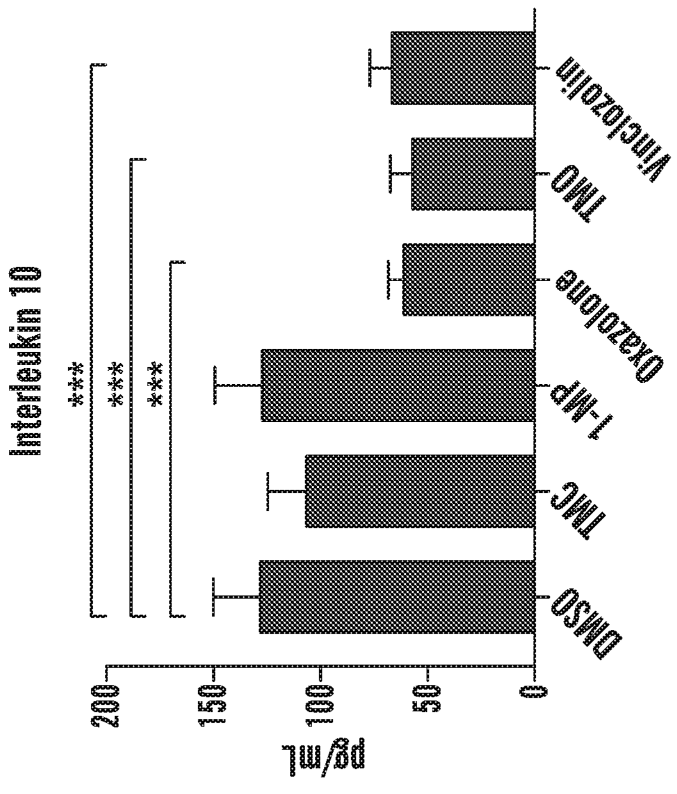
Figure 8A:
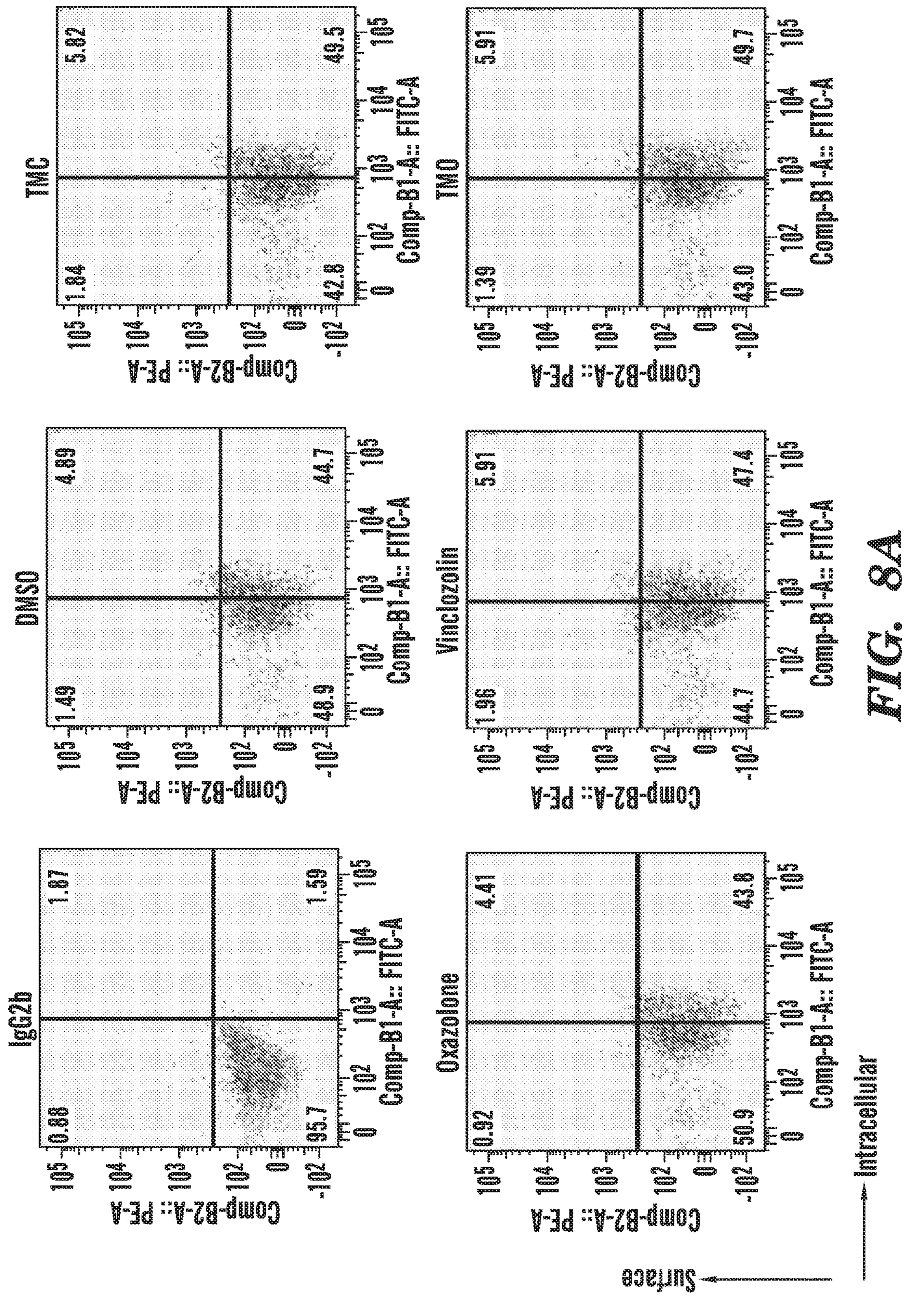
FIG. 8A-B shows a minimal oxazole structure does not alter CD1d protein expression or cellular distribution. Quantification of surface and intra-cellular CD1d protein expression in MODE-K cells conditioned with the indicated compounds for 48 hr, as measured by FIG. 8A shows flow cytometry and, FIG. 8B shows relative proportions of intracellular and cell surface CD1d expression.
Figure 8B:
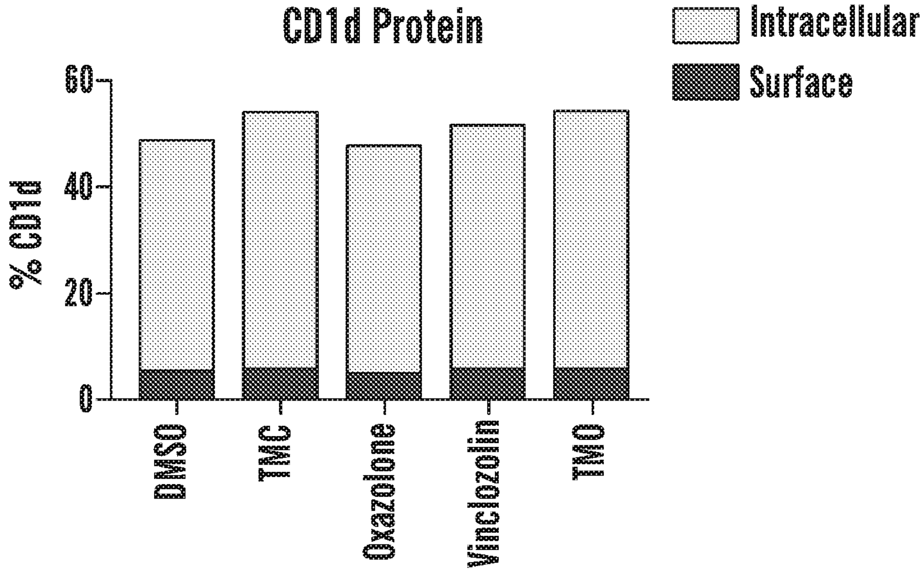

MTP is a critical regulator of mucosal homeostasis that promotes epithelial barrier activity by controlling CD1d-restricted IL-10 production by epithelial cells (Colgan et al. 1999, Olszak et al. 2014). Thus IEC specific deletion of Mttp results in decreased CD1d-stimulated IL-10 production by the IEC leading to the exaggerated inflammatory activity of hematopoietic cells in response to oxazolone challenge resulting in increased colitis (Olszak et al. 2014). It was therefore modeled interactions between NKT cells and IECs using MODE-K cells and CD1d-restricted T cell hybridomas in a previously described CD1d-dependent co-culture system (van de Wal et al. 2003). These studies have shown that loading of CD1d with alpha-galactosyl ceramide (α-GC), a cognate lipid antigen, in this co-culture system, leads to MTP-dependent, CD1d-restricted IL-10 production that is primarily derived from the IEC (Brozovic et al. 2004, Colgan et al. 1999, Olzsak et al. 2014). Here, it was found that MODE-K cells pre-conditioned with oxazolone exhibited attenuated IL-10 production in response to α-GC when placed in co-culture with an iNKT cell hybridoma (24.7), which specifically reacts to α-GC presented on CD1d (FIG. 1C). Interestingly, epithelial derived IL-10 was also suppressed when IECs pre-conditioned with oxazolone were co-cultured with an autoreactive iNKT cell hybridoma (24.8) or an autoreactive non-invariant dNKT cell hybridoma (14S.6) in the absence of exogenously administered α-GC (FIG. 8A-B). These effects were specific to the IEC as co-culture of bone marrow-derived dendritic cells with the 24.7iNKT cell hybridoma and α-GC did not lead to the production of IL-10 (data not shown) but rather to IFN-γ which was not affected by oxazolone or any of the oxazolone-related compounds described below (FIG. 9A-D).

Figure 1E:
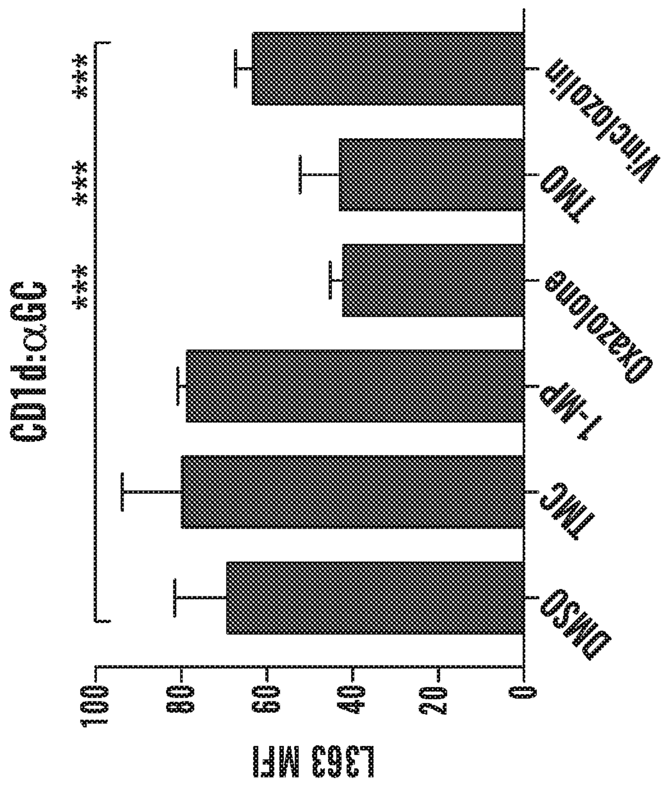

In light of the decreased MTP expression observed in oxazolone treated IECs (FIG. 1B) and given that MTP loss alters the ability of CD1d to acquire exogenous antigens, such as α-GC, and CD1d elicited IL-10 responses by epithelial cells (Dougan et al. 2005, Dougan et al. 2007, Zeissig et al 2017, Sagiv et al. 2007, Brozovic et al. 2004, Olszak et al. 2014), it was investigated whether CD1d expression and lipid loading on oxazolone conditioned IECs. IECs stimulated with oxazolone did not display altered CD1d protein expression or distribution between intracellular and cell surface pools (FIG. 8A-B), but instead exhibited decreased loading of α-GC on CD1d at the cell surface based upon staining with the CD1d-α-GC complex specific monoclonal antibody (L363) which revealed decreased mean fluorescence intensity on IECs exposed to oxazolone (FIG. 1D, 1E). These results were consistent with the decreased CD1d-restricted IL-10 protein production it was observed in MODE-K:iNKT cell co-cultures (FIG. 1C, FIG. 8A-B), and suggest that oxazolone induced alterations in MTP expression were associated with decreased CD1d function affecting IL-10 production in response to iNKT cells, supporting previous observations of MTP activity (Dougan et al. 2005, Dougan et al. 2007).

Oxazolone is administered in experimental models of colitis and contact sensitivity but is also widely used in industry and pharmaceuticals as a pharmacophore for the generation of synthetic compounds suggesting it may act as a potential environmental trigger of inflammation in sensitive hosts (Turchi 2008). A library of structural mimetics of oxazolone and test whether these molecules behaved in a similar manner. A two part in silico screen was performed against three chemical databases of naturally occurring compounds (Human Metabolome Database, Super Natural II database, Dictionary of Natural Products) (Banerjee et al. 2015, Wishart et al. 2007) thereby limiting the search to compounds within a defined human envirome. Natural compounds were queried in the standard SMILES format and Tanimoto similarities between oxazolone and test compounds were computed with the ChemMine Similarity Workbench, which calculated maximum common substructure (MCS) similarities with the Tanimoto coefficient. Further, Euclidean distance scores were calculated using a non-continuous atom matching structural similarity function (NAMS) (Cao et al. 2008, Teixeira et al. 2013). An initial screen identified 33 compounds with MCS>0.5 and Euclidean distance scores cutoff of 0.9.

Oxazolone consists of four major functional moieties: a 5-membered oxazole ring, a 2' phenylgroup, a 4' ethoxymethylene substituent, and the 5'-carbonyl lactone. The computational screen revealed the oxazole ring to be a distinctive and shared chemical sub-structure between the 33 compounds identified, all of which derived from dietary, microbial and/or industrial sources, a second screen using the same parameters was employed but instead substituting a minimal oxazole ring as the template structure. The analysis led to the identification of 63 naturally occurring oxazole-containing (OxC) compounds (including the 33 described above), 6 of which were commercially available in purified form. Of particular interest, it was discovered that many of these compounds derived from three major sources: diet, microbes, and agriculture. Therefore, it was investigated whether oxazolone is a molecular prototype for a broader class of environmental stimuli that feature an oxazole sub-structure capable of modulating epithelial CD1d-restricted responses in a cell intrinsic manner.

To test this, a systematic in vitro system was devised to assess transcriptional and CD1d-restricted responses in IECs in response to stimulation with dietary OxC structures, including 2,4,5-trimethyl-2,5-dihydro-1,3-oxazole (referred to as TMO, FIG. 1A) found in coffee, peanuts, meats and utilized as a food additive, which lacks the 2-phenyl ring, 5-ketone, and 4-ethoxymethylene present in oxazolone (Vitzthum et al. 1975, Stoffesima et al. 1968, Lee et al. 1981, Chang et al. 1968, Ho and Hartman 1968). Like oxazolone, TMO suppressed Mttp and induced cyp1a1 and Ido1 transcripts in IECs (FIG. 1B, FIG. 7A-D). In contrast two structurally related non-OxC heterocyclic aromatic compounds 1,2,4-trimethyl cyclopentane (MCS=0.5, referred to as TMC) and 2-methyl-1-pyrroline (MCS=0.83, referred to as 1-MP), that substitute carbons at the 1'-oxygen and/or 3'-nitrogen, did not elicit any transcriptional changes in the target genes assessed (FIG. 1B). Moreover, IECs conditioned with oxazolone or TMO but not TMC or 1-MP limited CD1d-restricted IL-10 production in co-cultures with an iNKT hybridoma (24.7) and the ability of CD1d to be lipidated with exogenously administered α-GC as revealed by decreased cell surface staining with the L363 monoclonal antibody (FIG. 1C-E). Overall, 5 of 7 tested naturally occurring dietary OxC as well as vinclozolin (FIG. 1A), an OxC fungicide used in agriculture, phenocopied the transcriptional and CD1d-restricted epithelial responses observed after oxazolone stimulation (FIG. 13).

A Minimal Oxazole Structure Induces Colonic Inflammation in a CD1d Dependent Manner.

Figure 1F:
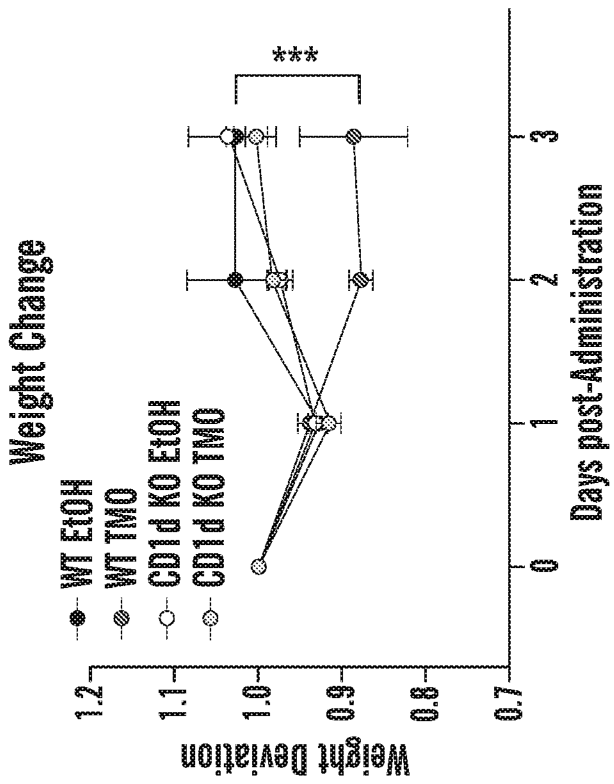
Figure 1G:
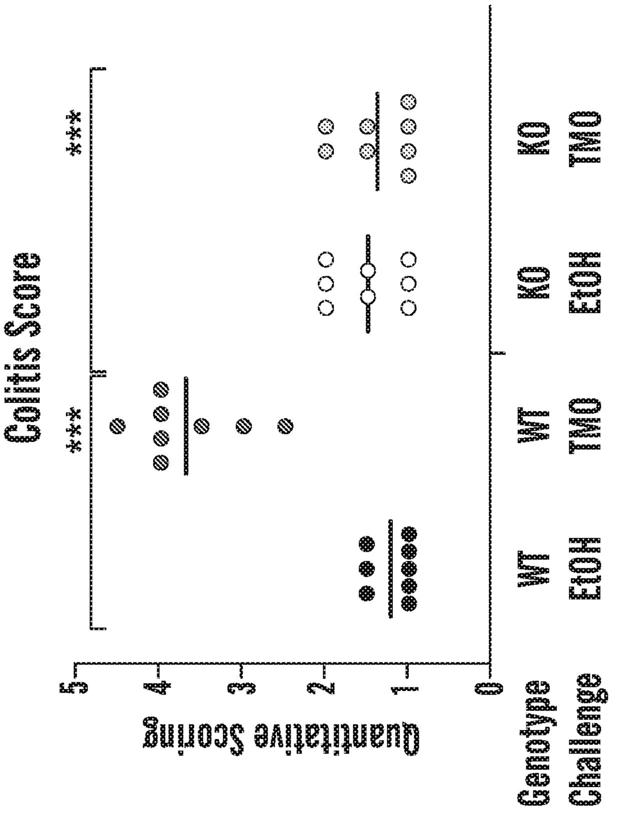
Figure 1H:
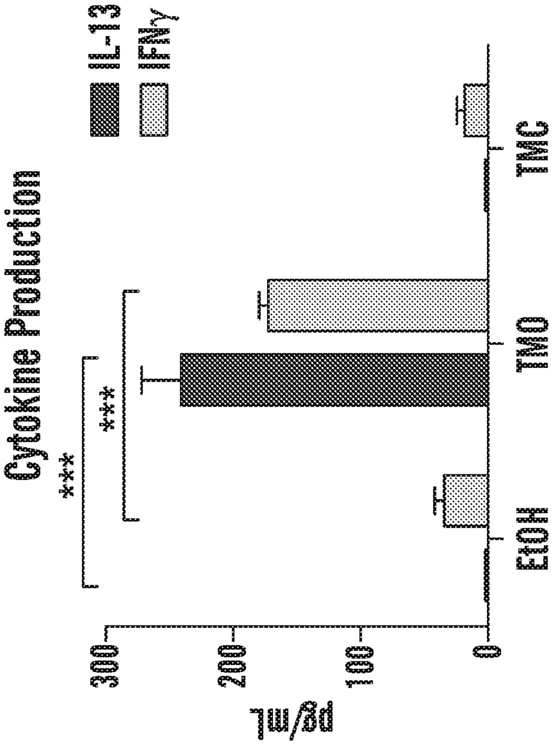
Figure 9B:
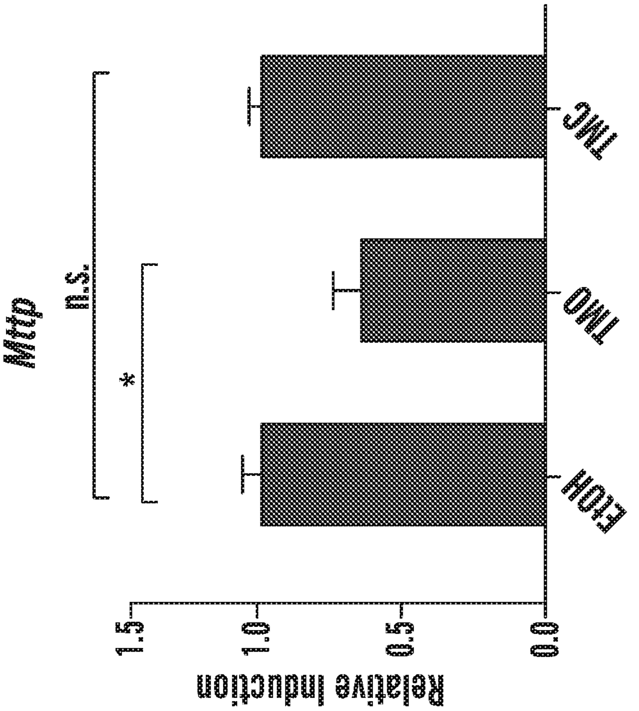
FIG. 9A-D shows intestinal inflammation and pathology to oxazole containing compounds does not require apriori host sensitization. Animals were sensitized by topical application of the indicated compounds followed by intra-rectal administration of 1% TMO, 1% oxazolone, or EtOH (50% v/v) vehicle in wildtype C57Bl/6 animals.
Figure 9A:
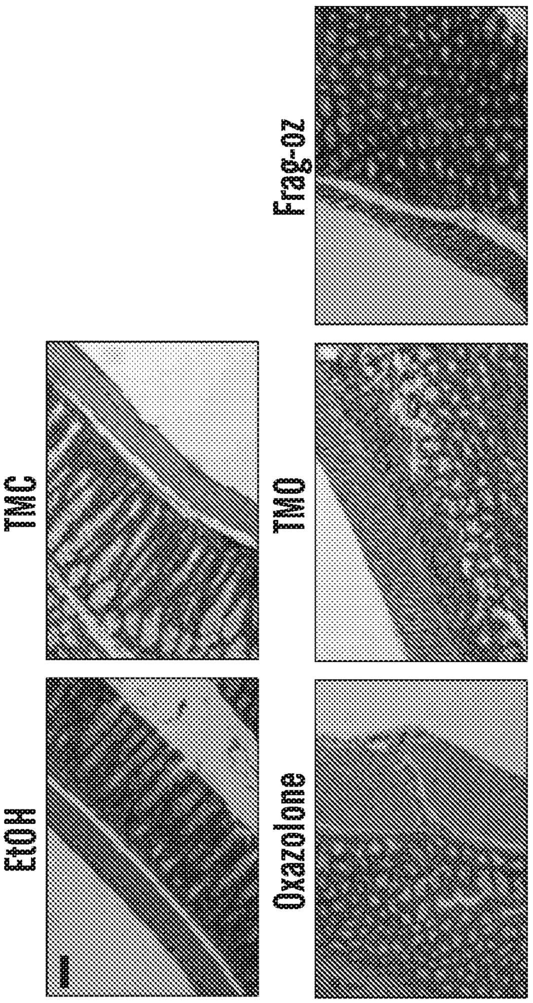
Figure 9D:
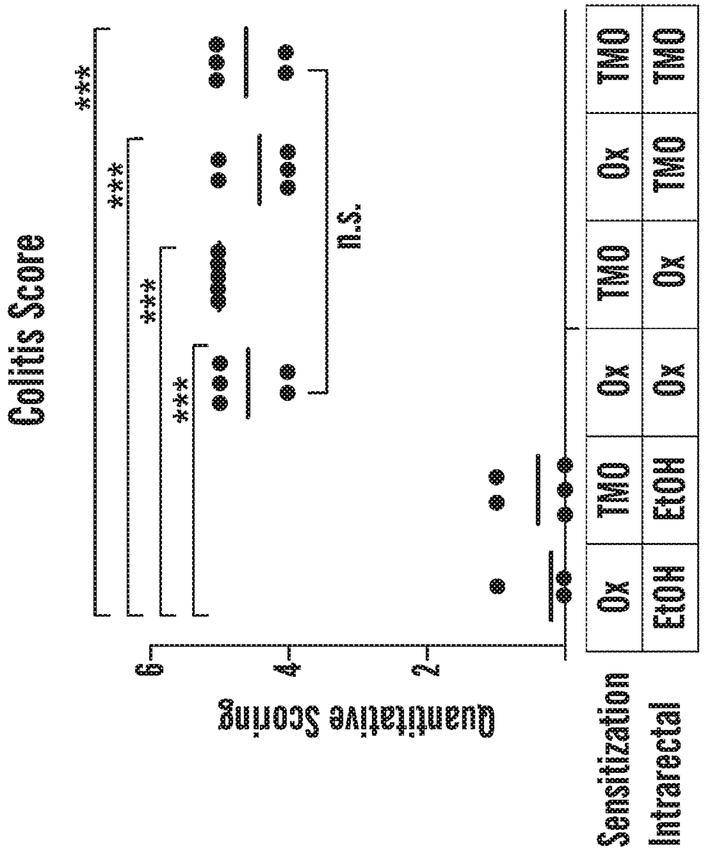
Figure 9C:
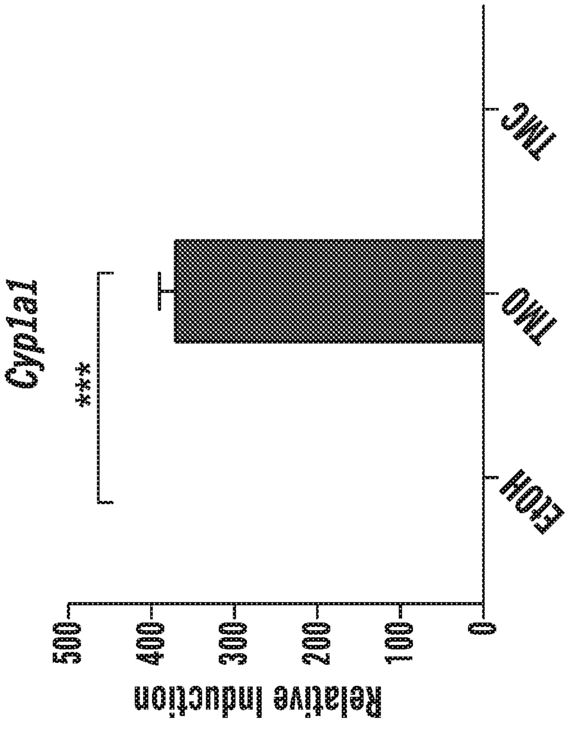
Figure 12A:
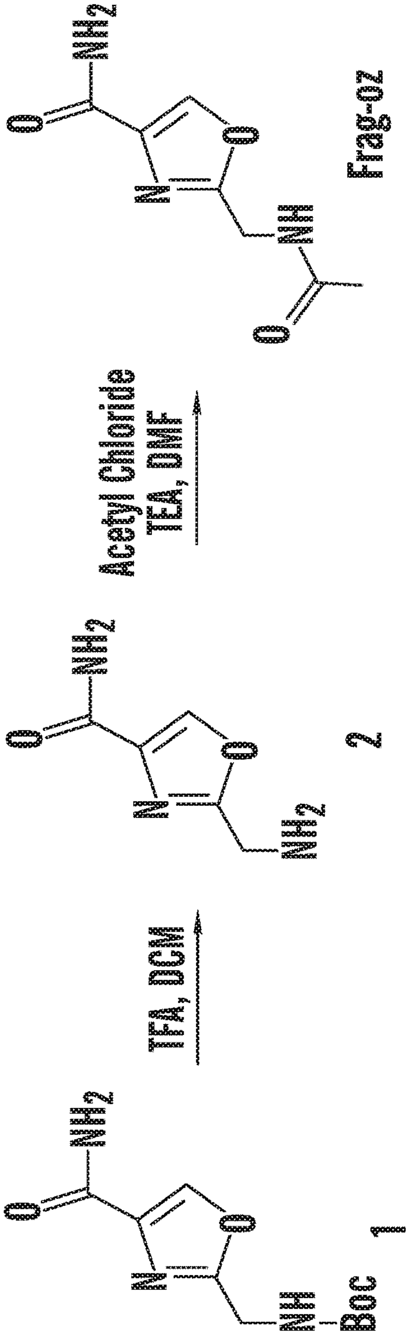
FIG. 12A-B shows synthesis of Frag-oz and Frag-tz.
Figure 12B:
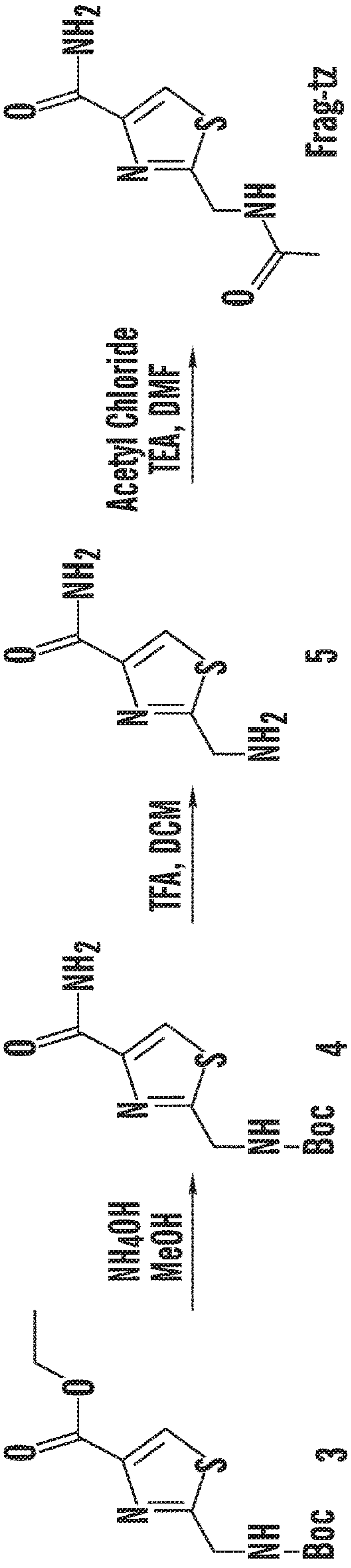

It was tested whether a dietary sourced minimal oxazole structure was sufficient to induce intestinal inflammation in vivo. Indeed, intra-rectal administration of TMO was observed to lead to increased weight loss, colon shortening, and histological pathology characterized by superficial inflammation of the gut wall, neutrophil accumulation and ulceration of the epithelial layer of the colon that was similar to the inflammation associated with oxazolone (FIG. 1F-G, FIG. 9A) (Heller et al. 2002). The immune response to TMO but not 1,2,4-trimethylcyclopentane (TMC) or vehicle was characterized by production of Th2 and Th1 cytokines including IL-13 and IFN-γ from colon explants consistent with the genetic background of the hosts, C57Bl/6 (FIG. 1H) (Iijima et al. 2004). Importantly, intestinal inflammation after TMO challenge was dependent on the presence of iNKT cells, as CD1d-deficient animals displayed no evidence of clinical symptoms or pathology (FIG. 1F-G) as previously shown for oxazolone (Boirevant et al. 1998, Heller et al. 2002). In addition, the host in vivo IEC responses to TMO but not TMC or vehicle recapitulated the transcriptional changes observed in microarray and in vitro analyses including downregulation of Mttp and induction of cyp1a1 (FIG. 12A-B). Importantly, these studies were performed by direct administration of TMO to the colonic epithelium by rectal challenge without preceding skin sensitization further suggesting that the OxC-induced effects observed were direct and did not require prior immune activation as would be expected from a hapten-induced model. To confirm this, the ability of oxazolone skin pre-sensitization to affect the responses to rectal challenge with TMO and vice-versa (FIG. 9D). These studies showed that pre-sensitization with oxazolone or TMO did not affect rectal responses to TMO or oxazolone, respectively; providing further evidence that oxazolone or TMO were having direct effects on the colonic mucosa.

A Microbial Derived Oxazole Structure Modulates Epithelial Responses and Leads to Intestinal Inflammation.

Figure 2A:
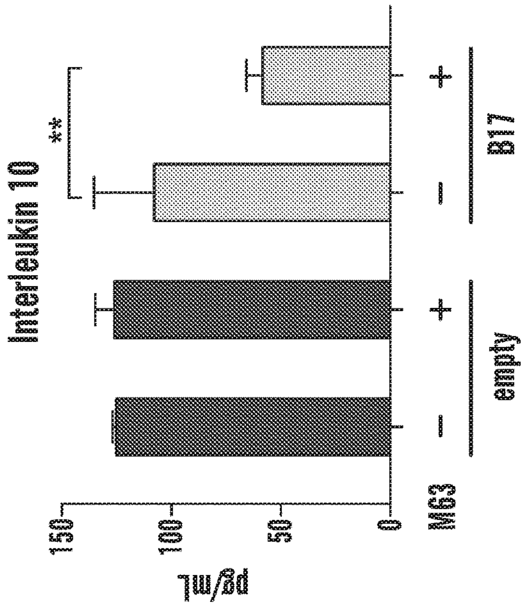
FIG. 2A-F demonstrates that microbial derived oxazoles modulate CD1d restricted responses and regulate transcriptional targets in epithelial cells.
Figure 2B:
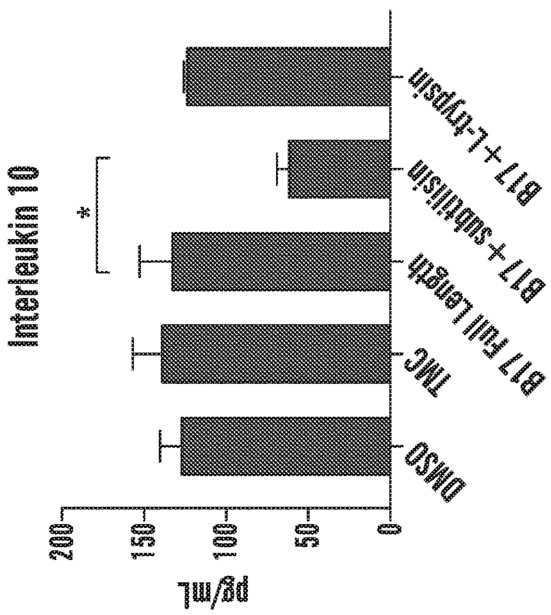
Figure 2C:
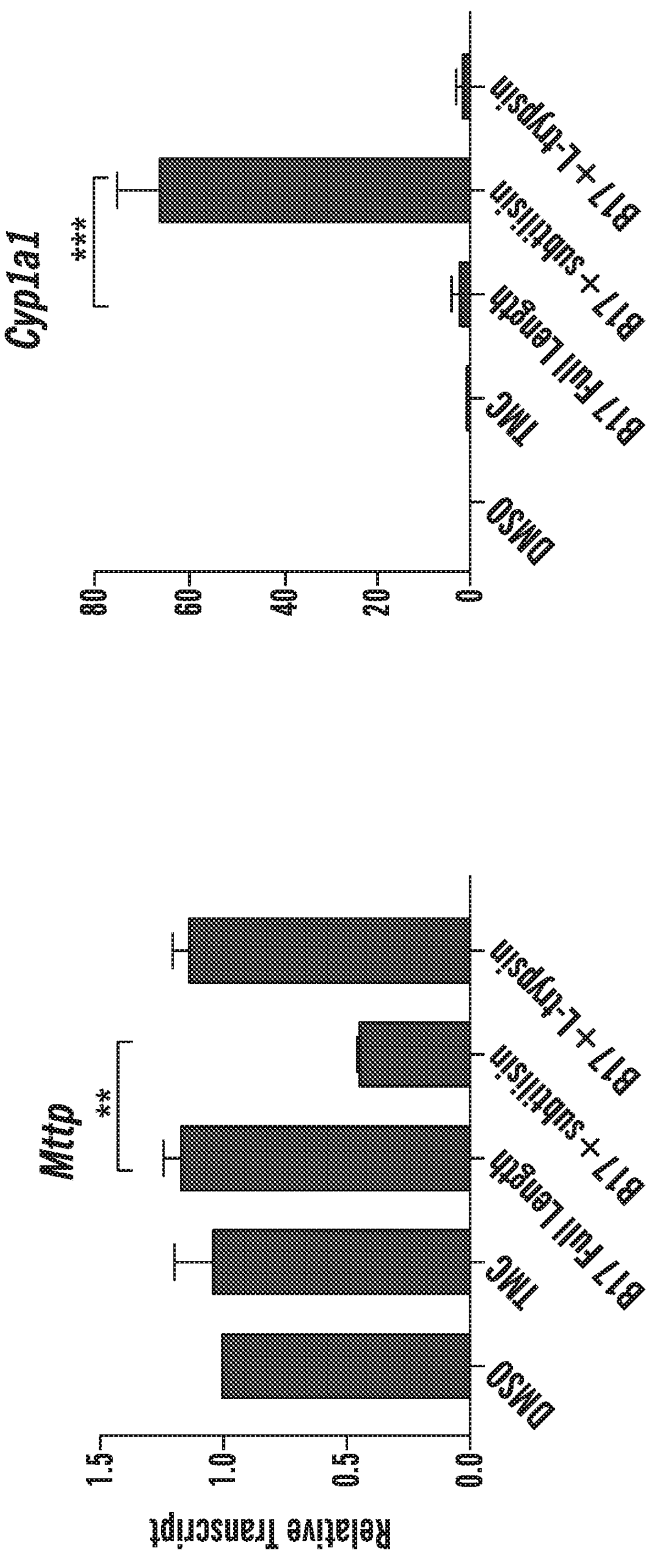

The in silico analysis also identified a class of bacterial derived toxins featuring oxazole moieties with a high degree of similarity to a minimal oxazole template. These are termed thiazole/oxazole modified microcins (TOMMs), a family of anti-microbial peptides featuring the presence of thiazol(in)e and oxazol(in)e heterocycles derived from cysteine, serine, and threonine residues on a ribosomally produced precursor peptide that confer a range of anti-microbial activities including DNA gyrase inhibitors, translation inhibitors and hemolytic toxins (Melby et al. 2011, Collin et al. 2013, Vizan et al. 1991, Lee et al. 2008, Sassone-Corsi et al. 2016). Though chemically and functionally diverse, as a rule TOMM biosynthetic gene clusters encode a leader peptide, enzymatic machinery including a cyclodehydratase and cyclodehydrogenase, that mediate post-translational installation of oxazole/thiazole moieties required for biological activity, and in some cases an immunity gene that protects the host strain from the anti-microbial activities of the TOMM itself (Melby et al. 2011). Importantly, many TOMM biosynthetic gene clusters (BGC) have been described in a variety of human commensal communities as a means of providing host strains with ecological fitness advantages (Donia et al. 2014, Lee et al. 2008, Sassone-Corsi et al. 2016). Within the commensal populations, these BGC encoded small molecule bacterial signaling factors collectively have an enormous potential to mediate microbe-microbe interactions (Donia et al. 2014, Wyatt et al. 2010, Nougayrede et al. 2006, Mazmanian et al. 2005, 2008, An et al. 2014, Wieland-Brown et al. 2013, Yoshimoto et al. 2013). Therefore, it was contemplated that that microcins also regulated microbe-host interactions. It was then determined whether oxazole containing microcin products modulated epithelial derived CD1d immune responses in the host as did other OxC compounds. To address this question, Microcin B17 (MccB17, MCS=0.75) was the focus, originally isolated from strains of *Escherichia coli* (*E. coli*) from the intestinal tract of newborns whose expression is linked to a plasmid (pMccB17) that carries a 7 gene mcb operon, encoding the MccB17 toxin that acts as a DNA gyrase inhibitor (Yorgey et al. 1994, Li et al. 1996). The mcb operon was previously cloned into a pUC19 vector (Collin et al. 2013) and transformed into a competent *E. coli* BSL1 human commensal strain (MG1655). MccB17 production is induced by growing bacteria in nutrient rich M63 media (Collin et al. 2013). Bacteria transformed with mcb or empty plasmid was grown in Luria Broth or M63 supplemented media and bacterial lysates incubated with IECs after which CD1d-restricted responses were measured upon co-culture with an iNKT cell hybridoma. It was observed that lysates from bacterial isolates transformed with mcb and grown under MccB17 permissive conditions, but not non-transformed bacteria, attenuated CD1d-restricted IL-10 production in MODE-K:iNKT cell co-cultures, whereas lysates isolated from bacteria grown under non-permissive conditions or transformed with empty plasmid had no effect (FIG. 2A). To further examine whether suppression of CD1d-restricted responses was due to a MccB17 product, full length mature MccB17 was purified by High Performance Liquid Chromatography (HPLC) and examined in the aforementioned IEC:iNKT co-culture assay. Surprisingly, purified MccB17 exerted no effects on CD1d dependent IL-10 production (FIG. 2B). However, although the full length MccB17 microcin consists of a 3093 Da peptide, several smaller heterocyclic mcb derived heterocyclic species have been identified by MALDI-ToF mass spectrometry analysis which may or may not retain DNA gyrase inhibitory activity suggesting that the immunomodulatory effects of the MccB17 positive lysate might be a result of proteolytic and/or degradative products rather than the mature full length MccB17 itself (Collin et al. 2013, Sinha Roy et al. 1998). B17 microcin is sensitive to cleavage by subtilisin but not trypsin (Asensio and Perez-Diaz 1976). Therefore, digested purified full length B17 with each protease were completed and CD1d-restricted IL-10 responses were measured in the IEC:iNKT cell co-culture assay to these proteolytic products (FIG. 2B). In this case, cleavage products from subtilisin but not trypsin were able to attenuate IL-10 production in IEC:iNKT co-cultures with α-GC. Similarly, decreased Mttp was observed and induction of Cyp1a1 transcripts in MODE-K cells incubated with MccB17 subtilisin proteolytic products but not full length B17 or MccB17 digested with trypsin (FIG. 2C).

Figure 2E:
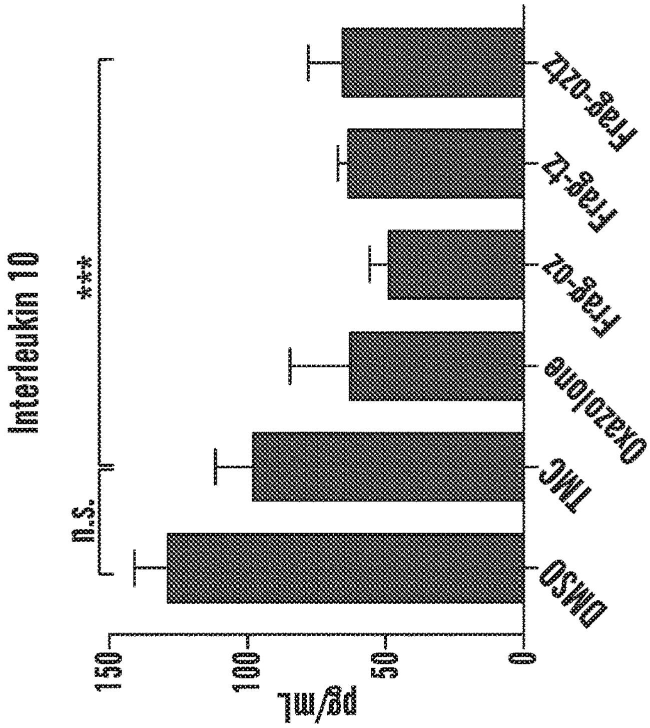
Figure 2D:
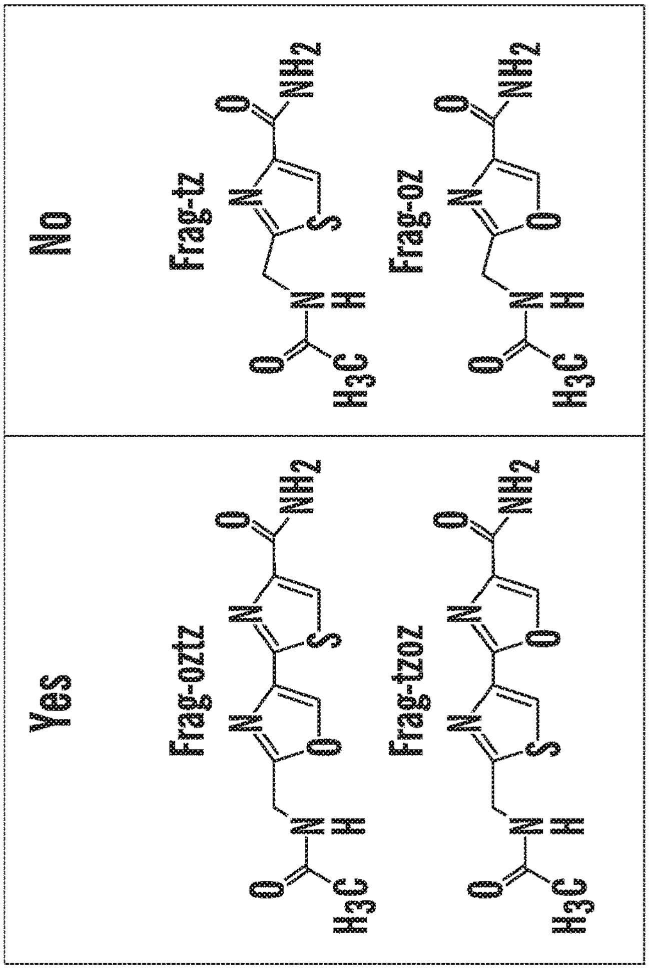
Figure 2F:
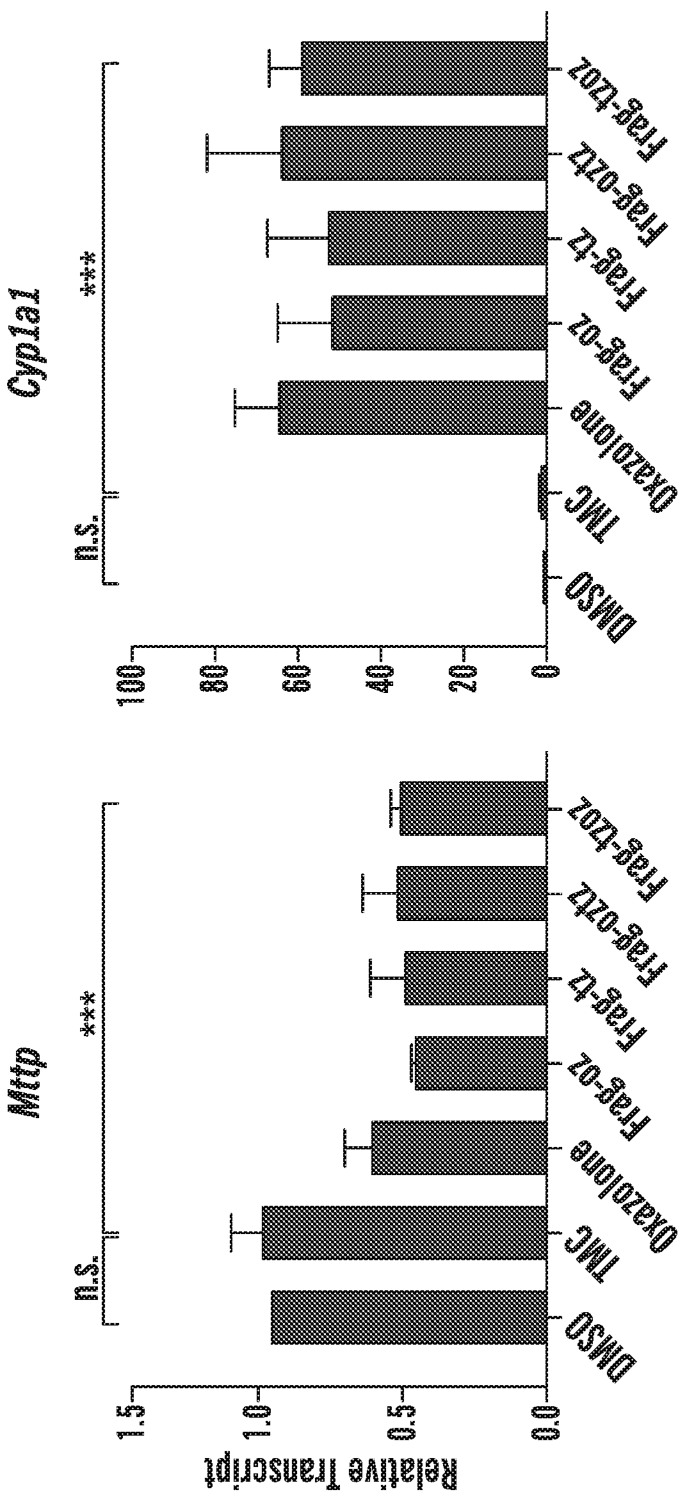

Taken together, these results suggested that the ability of MccB17 derived toxins to affect epithelial transcriptional and CD1d-restricted responses is limited by the size of the product. To clarify this size restriction, a library of 8 synthetic MccB17 derived products were screened with molecular weights ranging from 183.17-857.82 Da that are analogous to naturally produced MccB17 fragments and whose anti-DNA gyrase activity has been previously described (FIG. 2D) (Collin et al. 2013). Consistent with the hypothesis, four fragments, containing permutations of 1 or 2 oxazole/thiazole moieties, with MW<270 Da were able to modulate CD1d dependent IL-10 production and regulate Mttp and Cyp1a1 whereas synthetic products >500 Da were not (FIG. 2E-F and data not shown). Importantly, synthetic analogs capable of exerting immunomodulatory effects were within the relative size range of both oxazolone (217.22 Da) and 2,4,5-trimethyl-2,5,-dihydro-1,3-oxazole (113.16 Da) but surprisingly even synthetic products that did not confer anti-DNA gyrase activity were able to generate epithelial responses (FIG. 2D-F). Furthermore, both oxazole and thiazole containing compounds generated similar effects consistent with their shared physico-chemical properties (FIG. 2D-F).

A Synthetic B17 Microcin Derivative Induces Colonic Inflammation in a CD1d-Dependent Manner Independent of Anti-Microbial Activity.

Figure 3B:
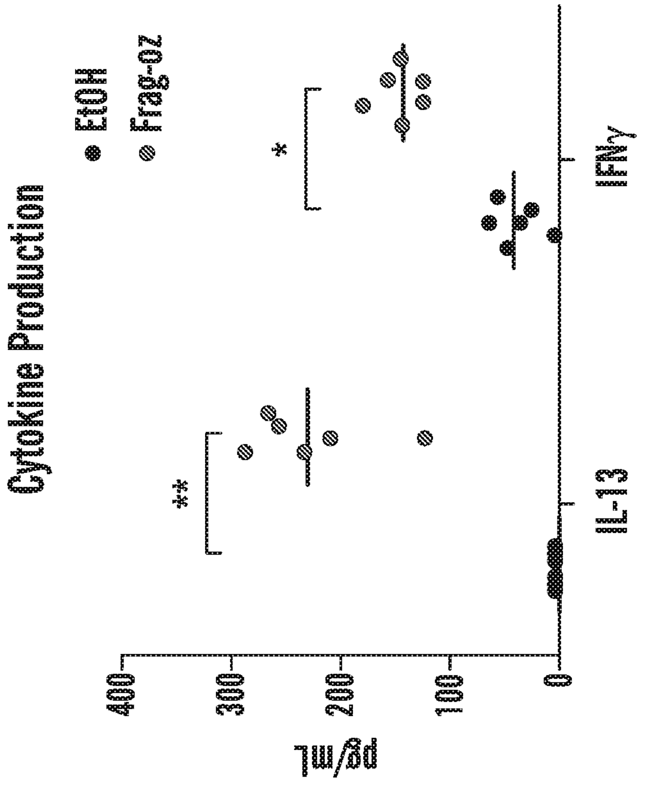
FIG. 3A-F demonstrates that NKT cells are required for colonic inflammation induced by Frag-oz.
Figure 3A:
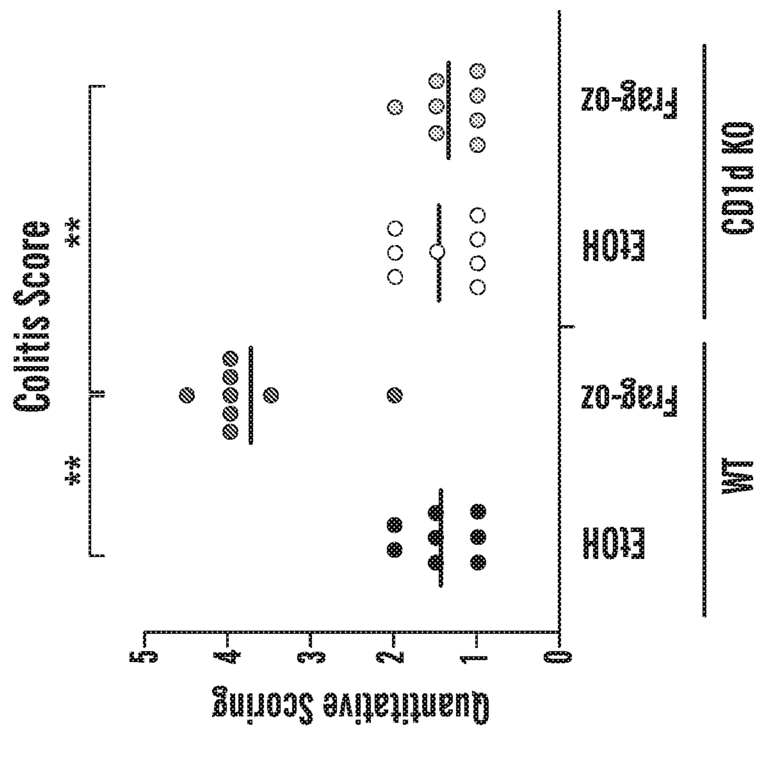
Figure 3C:
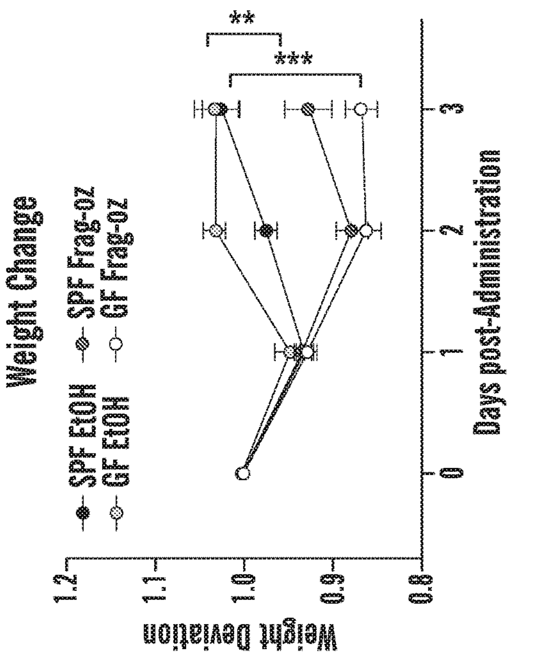
Figure 3D:
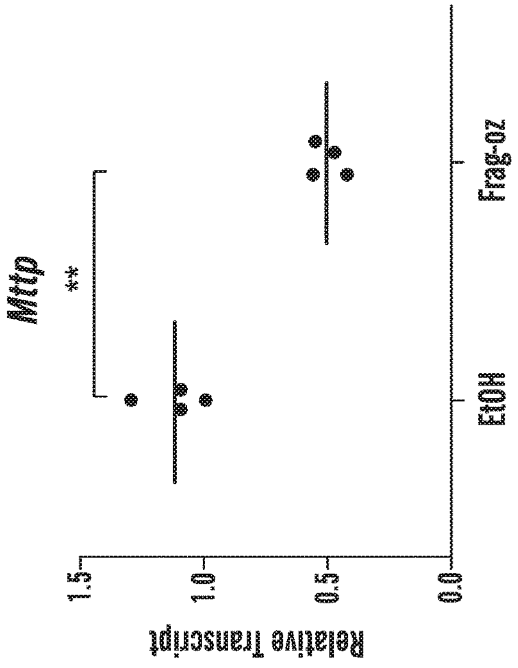
Figure 3F:
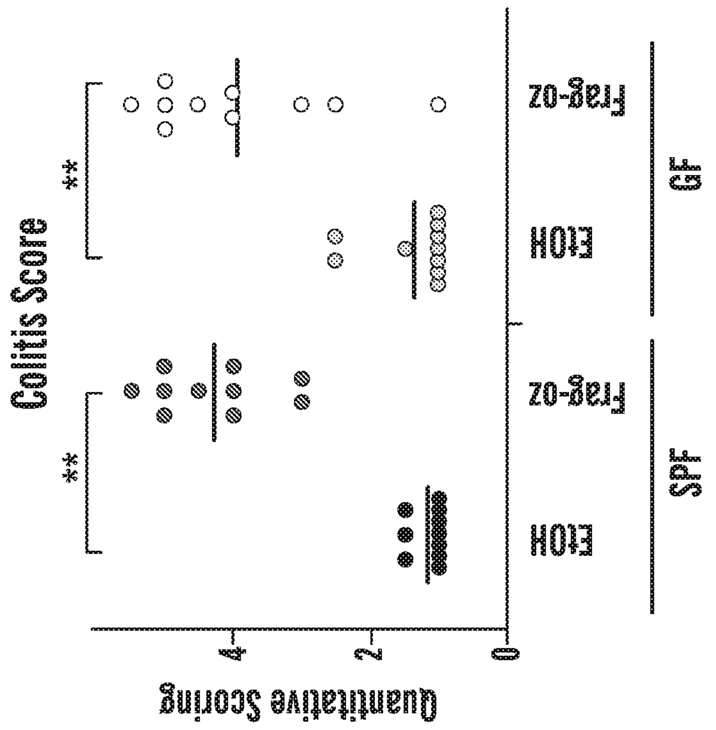
Figure 3E:
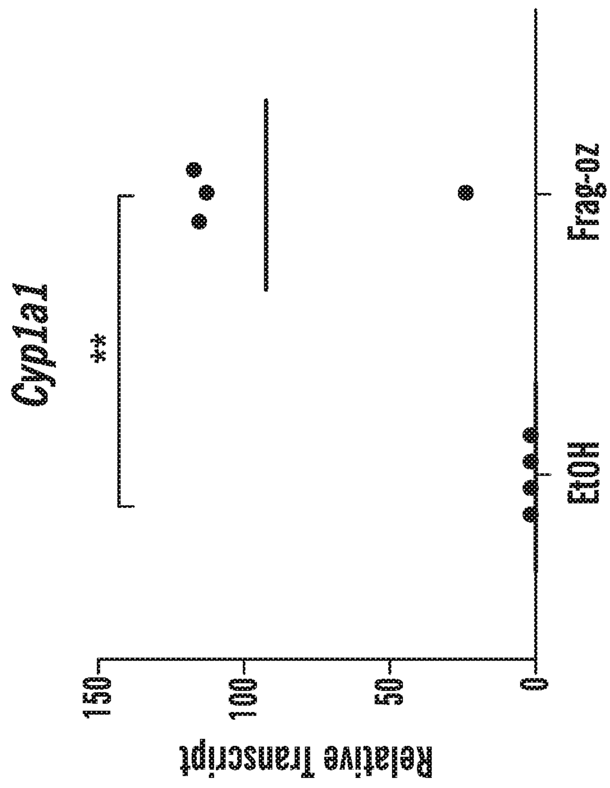

Next, it was tested whether B17 microcin derivatives could induce intestinal inflammation in vivo. Therefore, adequate quantities of a minimal B17 derivative (termed frag-oz, FIG. 2D) were synthesized to perform in vivo experiments and challenged animals via intra-rectal administration. Like oxazolone and TMO, a CD1d-dependent pathology was observed as well as induction of both Th1 and 2 cytokines from colon explants suggesting that this molecule induces inflammation in an iNKT dependent manner as inflammation and hematopoietic cell derived cytokine responses could be observed in WT, but not Cd1d−/− (CD1d KO), mice (FIG. 3A-C, FIG. 11). Decreased Mttp levels were observed and induction of Cyp1a1 in IEC enriched colonic fractions suggesting that frag-oz exerts immunomodulatory effects via the epithelial compartment in vivo (FIG. 3D-E). Though in vitro studies showed that frag-oz confers no anti-gyrase activity (Collin et al. 2013), to formally rule out the possibility that the intestinal inflammation observed was due to direct effects on the host rather than through its anti-microbial properties, GF and SPF mice were challenged with frag-oz or vehicle. Consistent with this, GF animals exhibited increased weight loss compared to animals raised under SPF conditions with severe histopathology (FIG. 3C, FIG. 3F). These studies identify an oxazole containing microbial mimic that promotes CD1d-dependent intestinal inflammation independent of its classical anti-microbial activity.

Activation of Epithelial Aryl Hydrocarbon Receptor Pathways Exacerbates Responses to Dietary and Microbial Oxazole Compounds by Limiting IL-10 Responses.

The data presented support a model in which exposure to a broad class of oxazole (or thiazole) ring containing compounds can direct transcriptional changes in responsive tissue compartments, such as the intestinal epithelium, that influence CD1d-restricted antigen presentation pathways resulting in compromised barrier integrity at mucosal sites, thereby augmenting iNKT (or non-invariant NKT) cell inflammatory responses, leading to colitis. These data also suggest the presence of cellular sensor(s) that are responsible for recognizing and transducing oxazole dependent signals. Review of the previous microarray analyses identified two signature aryl hydrocarbon receptor (AhR) targets, Cyp1a1 and Ido1, involved in P450 and tryptophan metabolism, respectively, as inducible gene targets in the colonic epithelium (Olszak et al. 2014). Here it was demonstrated that oxazolone, vinclozin, an industrial agent, and the dietary and microbial oxazole ligands, TMO and frag-oz, induced expression of these genes in vitro and in vivo. Interestingly, vinclozolin, an antifungal agent to which humans are exposed through agriculture and which affects CD1d-restricted pathways as an OxC as shown here, has been described as an AhR activator (Wambaugh et al. 2014, Dierickx 2004).

Figure 4B:
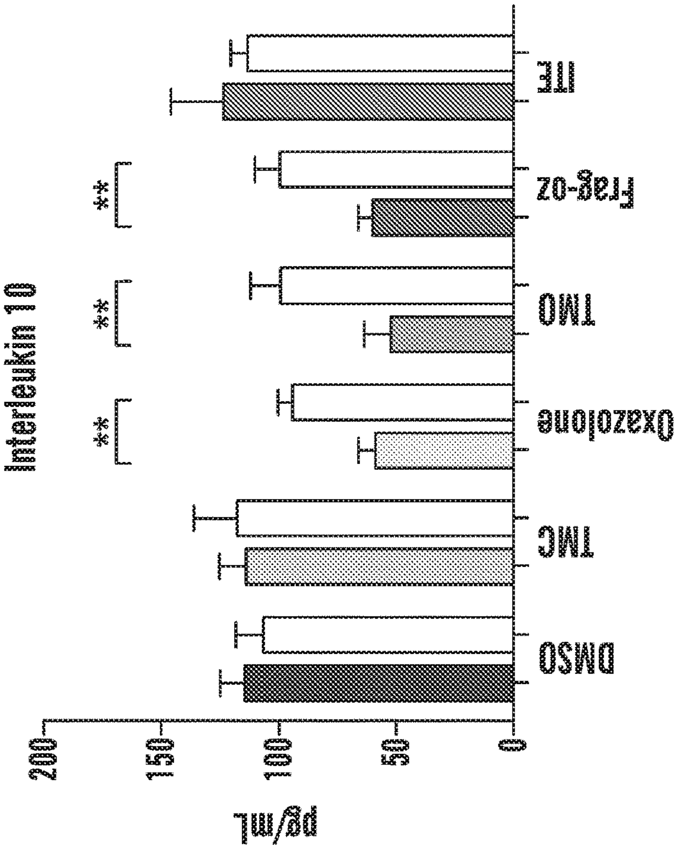
FIG. 4A-H shows activation of Aryl Hydrocarbon Receptor by dietary and microbial derived oxazole compounds.
Figure 4A:
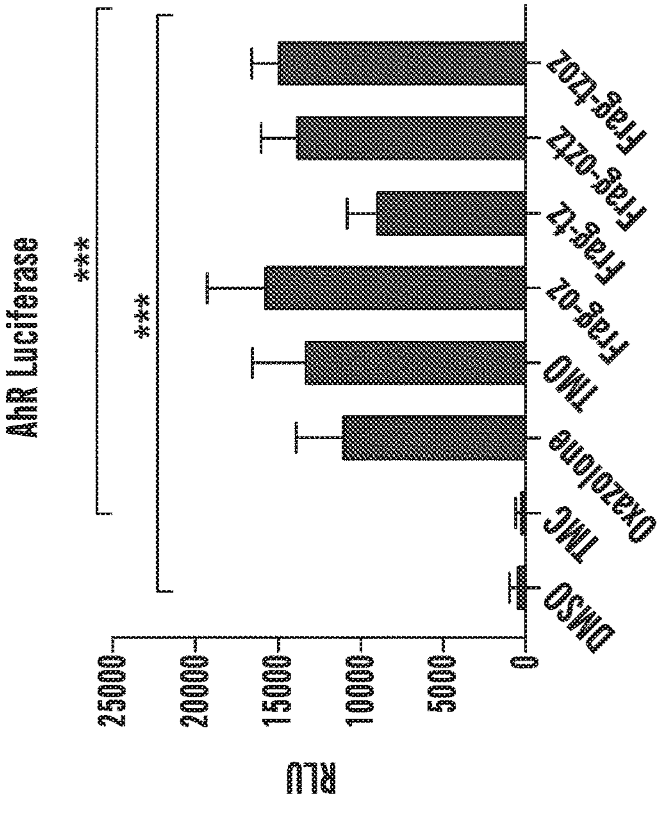
Figure 4D:
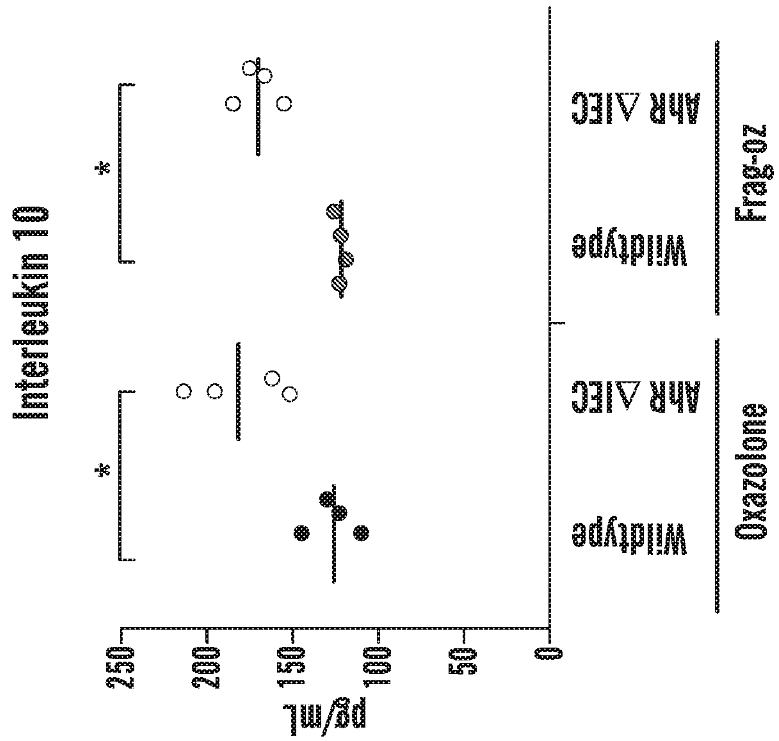
Figure 4C:
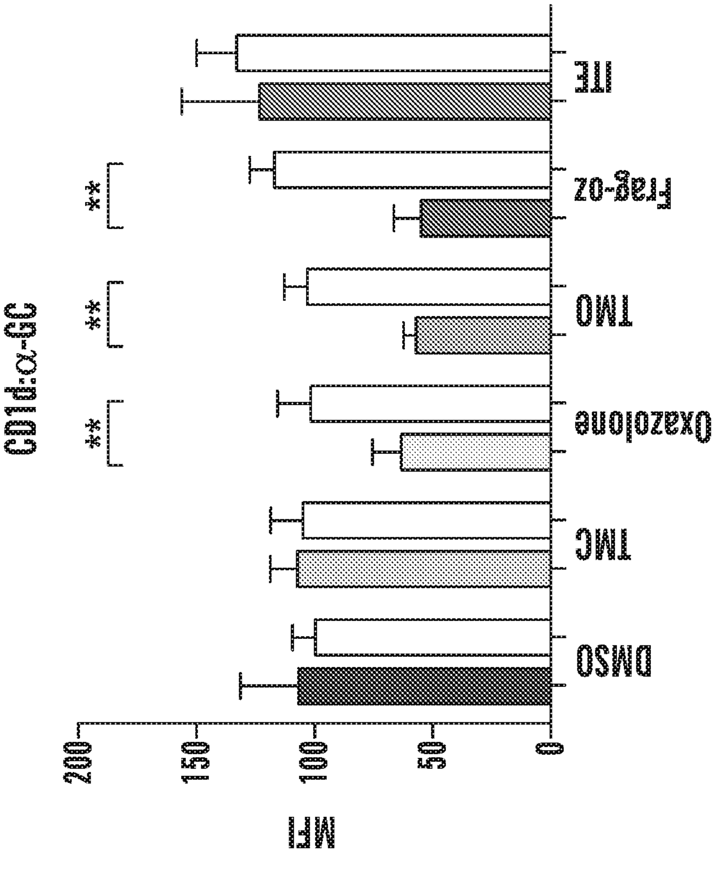
Figure 10B:
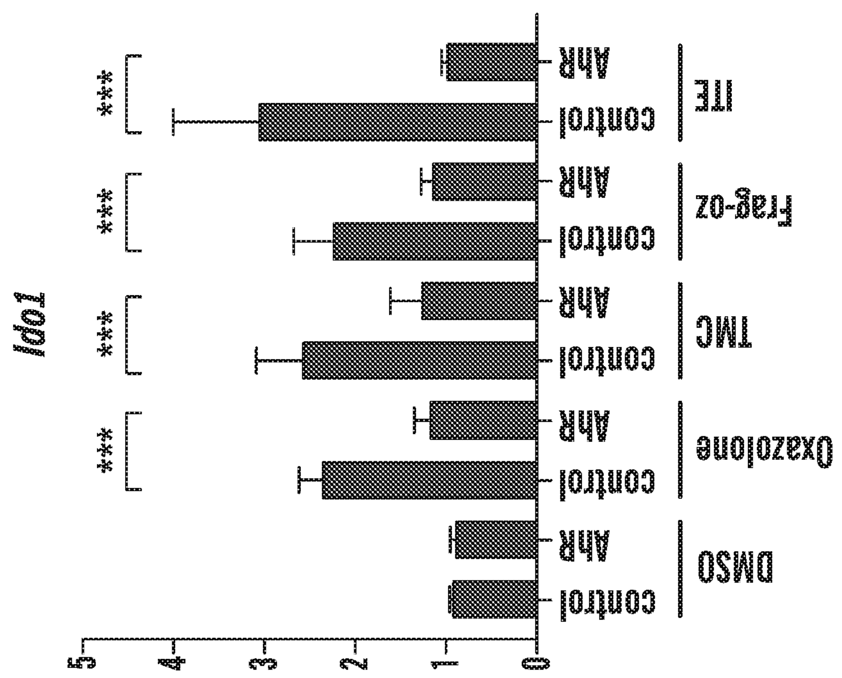
FIG. 10A-C demonstrates that the Aryl hydrocarbon receptor mediates expression of a subset of gene targets in response to oxazole containing compounds. MODE-K cells transfected with control or AhR specific siRNA, conditioned with the indicated compounds and relative transcript abundance was measured normalized to β-actin.
Figure 10A:
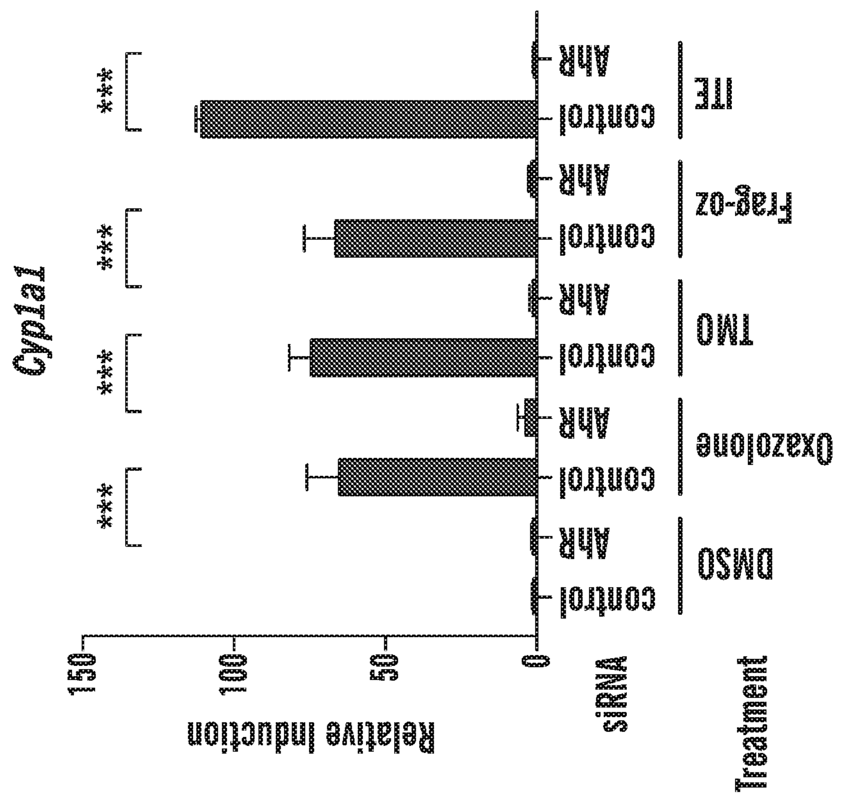
Figure 11:
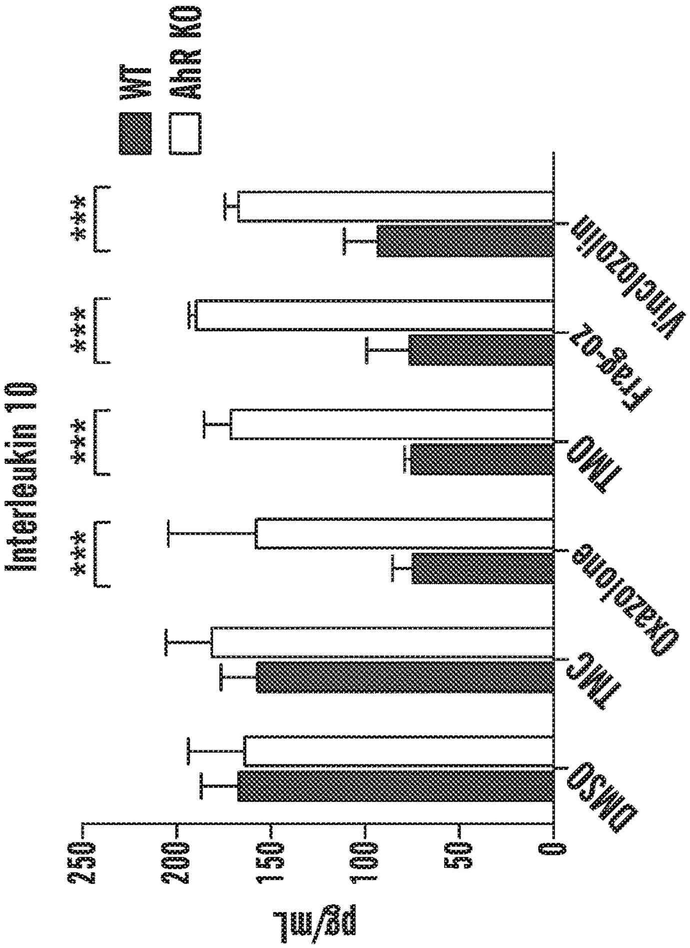
FIG. 11 shows the Aryl hydrocarbon receptor attenuates CD1d-restricted responses in primary hepatocytes: Interleukin 10 production from primary hepatocytes derived from WT or AhR-deficient (KO) animals were conditioned with the indicated compounds, loaded with a-galactosyl ceramide followed by co-culture with 24.7 iNKT hybridoma. *** p<0.001 (Student's t-test).
Figure 10C:
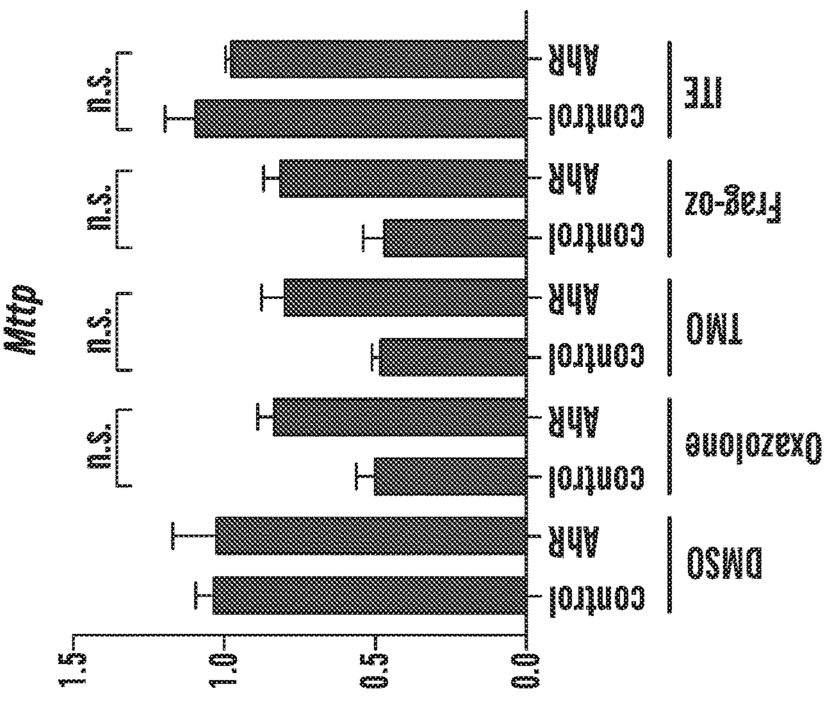

Therefore, IECs were transfected with an AhR firefly luciferase reporter and observed that oxazolone, TMO and 5 additional dietary oxazoles, as well as 4 synthetic MccB17 derivatives induced robust AhR transcriptional activity compared to vehicle or a non-oxazole heterocyclic control, 1,2,4-trimethylcyclopentane (FIG. 4A, FIG. 13). Consistent with this, siRNA mediated knockdown of AhR in MODE-K cells abrogated induction of Cyp1a1 and IDO and partially restored Mttp expression (FIG. 10A-C). Given that AhR regulates MTP expression, it was determined whether this pathway could modulate epithelial derived CD1d-restricted responses. Indeed, AhR deficiency caused by silencing AhR expression in epithelial cells reversed oxazolone, TMO or frag-oz induced inhibition of CD1d-restricted IL-10 production in IEC:iNKT cell co-cultures and reduction of cell surface CD1d lipid antigen loading (FIG. 4B, 4C). This was confirmed in hepatocytes obtained from Ahr−/− mice, which also exhibited resistance to the effects of oxazolone, TMO, frag-oz or vinclozin induced inhibition of IL-10 production in response to iNKT cells in the presence of α-GC (FIG. 11). Interestingly, these effects were not attributed to general AhR function, but instead reflected a specific response to oxazole containing molecules as a human cognate AhR ligand, 2-(H-Indol-3-carbonyl)-4-thiazolecarboxylic acid methyl ester (ITE), did not modulate Mttp expression or CD1d-restricted responses (FIG. 4B-C).

Figure 4E:
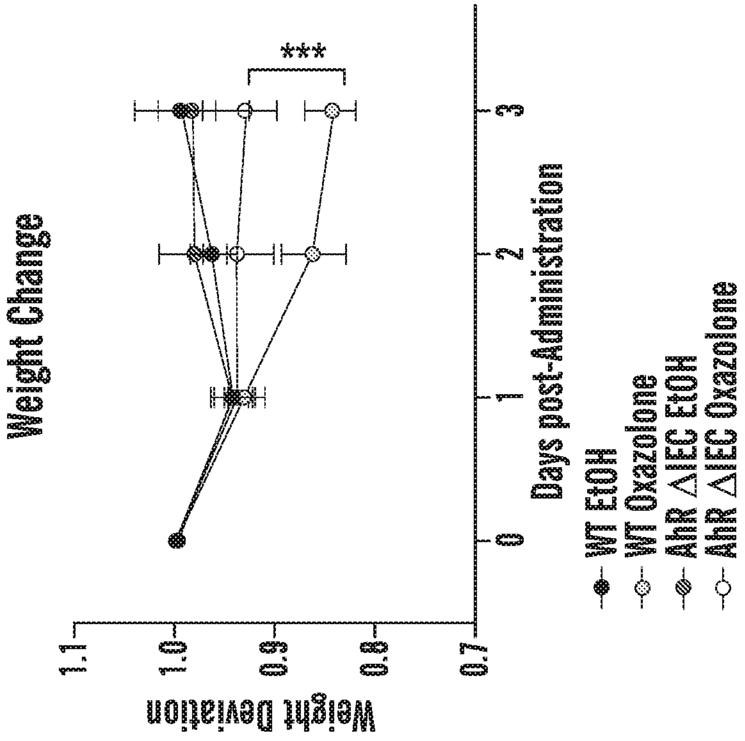

These studies reveal a novel role for epithelial derived AhR signals in promoting mucosal inflammation when exposed to OxC. Consistent with this hypothesis, deletion of Ahr specifically in IECs (generated by crossing Ahrfl/fl to Villin-Cre transgenic animals, AhrΔIEC) resulted in elevated IL-10 production in colonic explants after oxazolone or frag-oz compared to widltype controls (FIG. 4D), and conferred host protection to oxazolone (FIG. 4E-F) and frag-oz (FIG. 4G-H) after intra-rectal challenge as characterized by diminished weight loss and disease manifestations relative to that observed in Ahrfl/fl mice.

Oxazoles Induce the Generation of Tryptophan Derived Metabolites that Attenuate Epithelial CD1d-Restricted Responses in an AhR Dependent Manner.

Figure 5B:
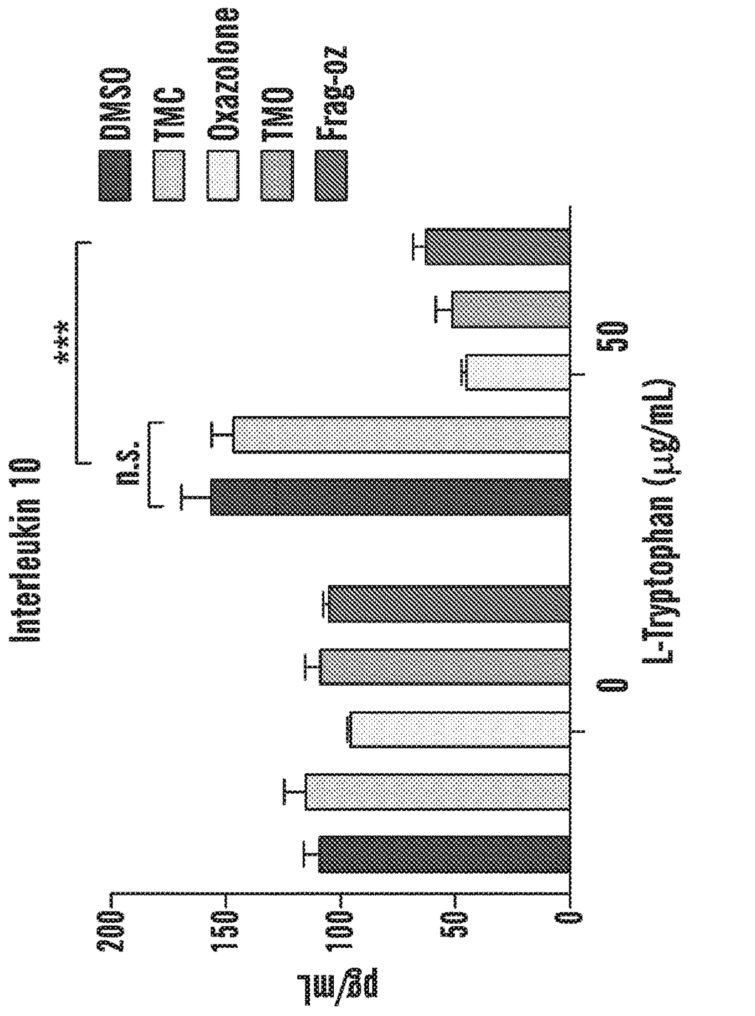
FIG. 5A-E demonstrates oxazoles induce the generation of tryptophan derived metabolites that attenuate epithelial CD1d-restricted responses in an AhR dependent manner.
Figure 5A:
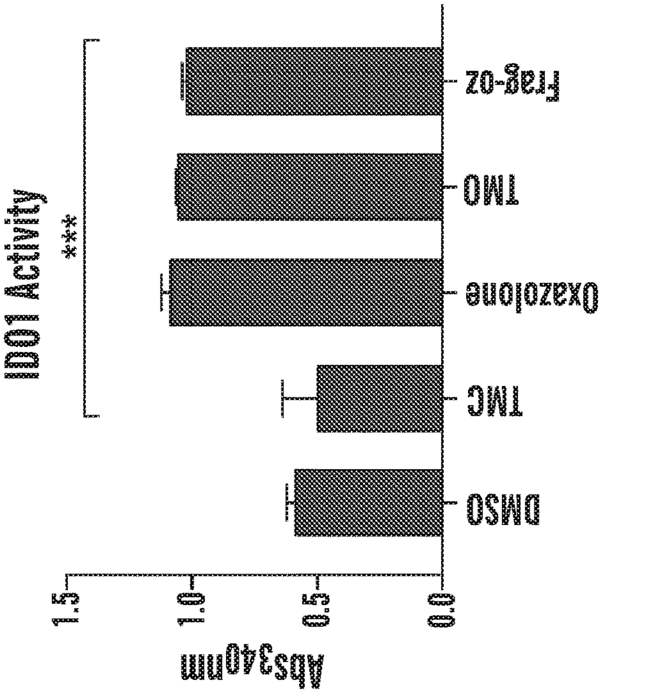
Figure 5D:
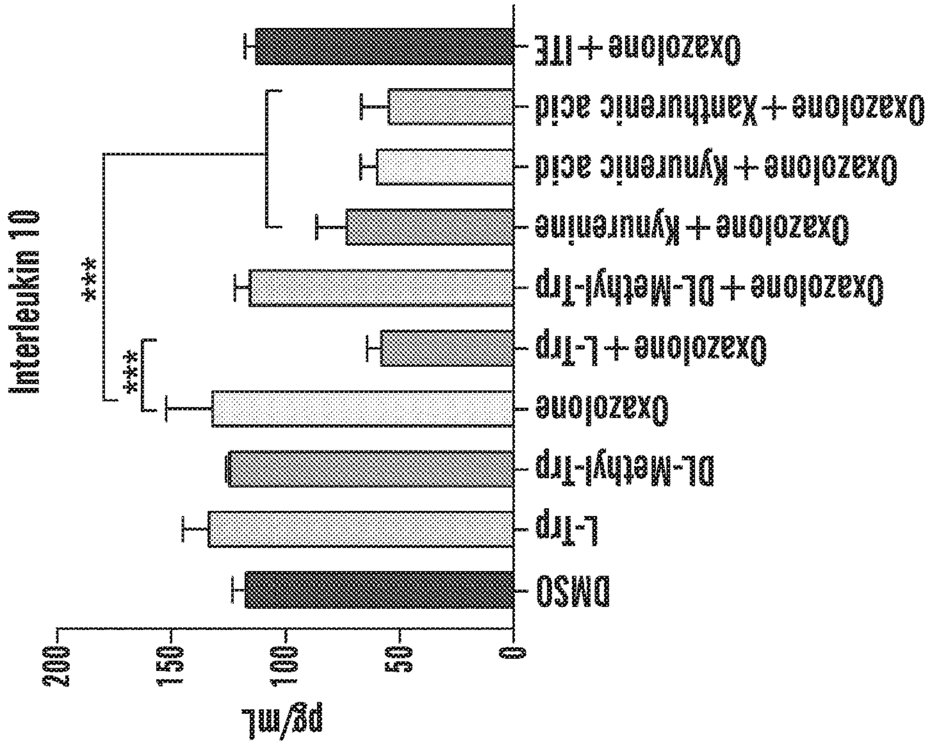
Figure 5C:
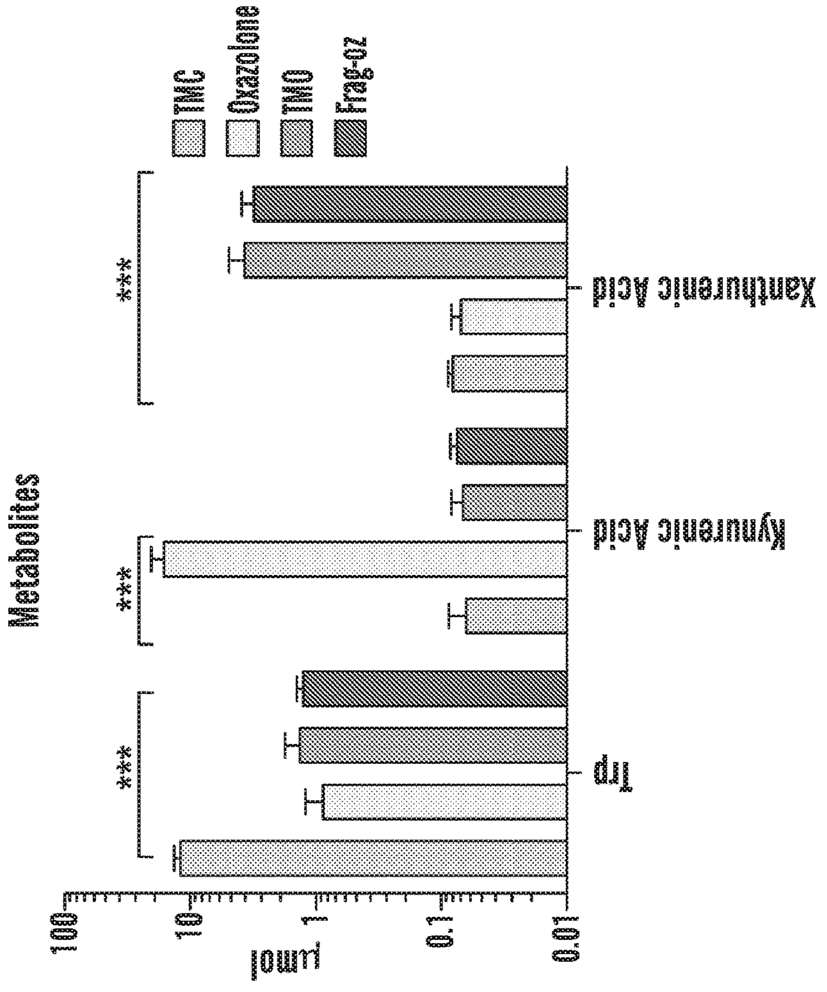
Figure 5E:
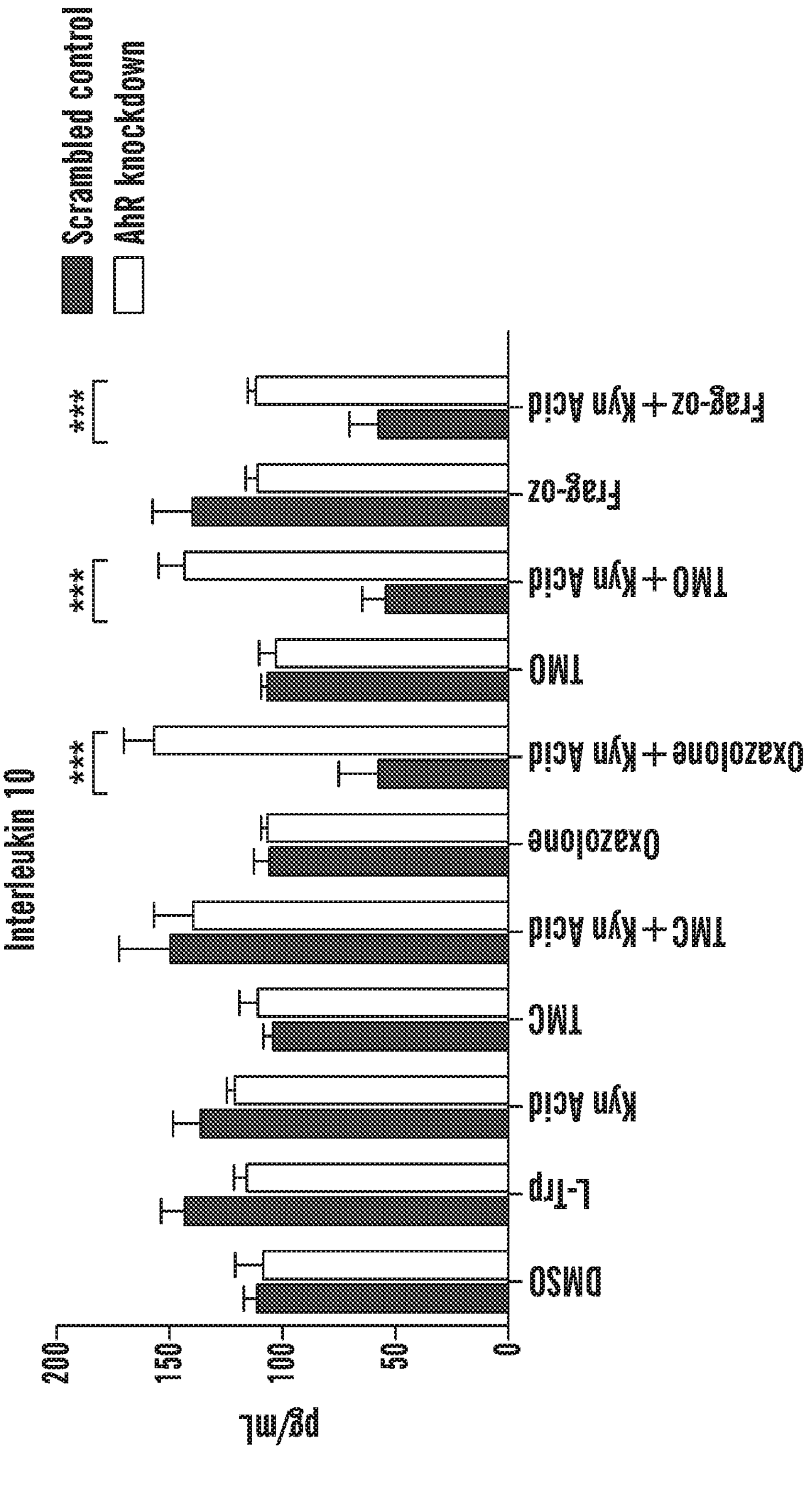
Figure 6:
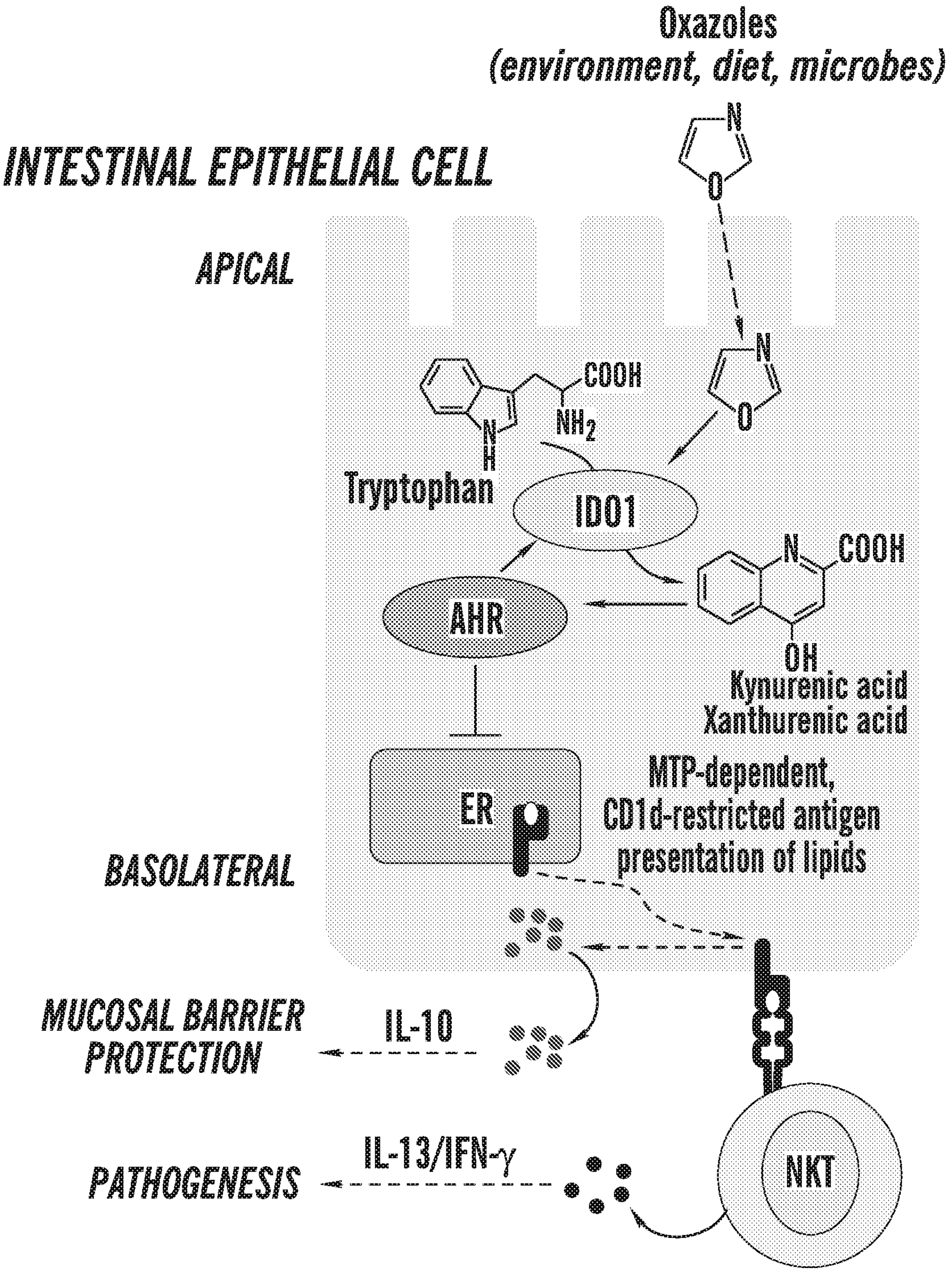
FIG. 6 shows exposure to environmental oxazoles (from diet or microbes) influences CD1d-restricted responses in intestinal epithelial cells through production of tryptophan derivatives that activate the aryl hydrocarbon receptor pathway. Intestinal epithelial cells (IEC) promote mucosal barrier protection through microsomal triglyceride protein (MTP) mediated CD1d-restricted production of Interleukin 10 (IL-10, blue circles). Upon exposure to oxazole compounds (derived from diet, microbes or other environmental sources), these CD1d-restricted responses are attenuated through a mechanism involving the production of tryptophan derived metabolites (kyneurenic acid, xanthurenic acid, orange squares), through the activity of IDO1, that activate the aryl hydrocarbon receptor (AhR). Decreased, CD1d-restricted IL-10 production results in unrestrained inflammatory responses (IL-13/IFNγ, red dots) and resulting pathology. ER (endoplasmic reticulum), IFN-γ (Interferon γ).
Figure 7A:
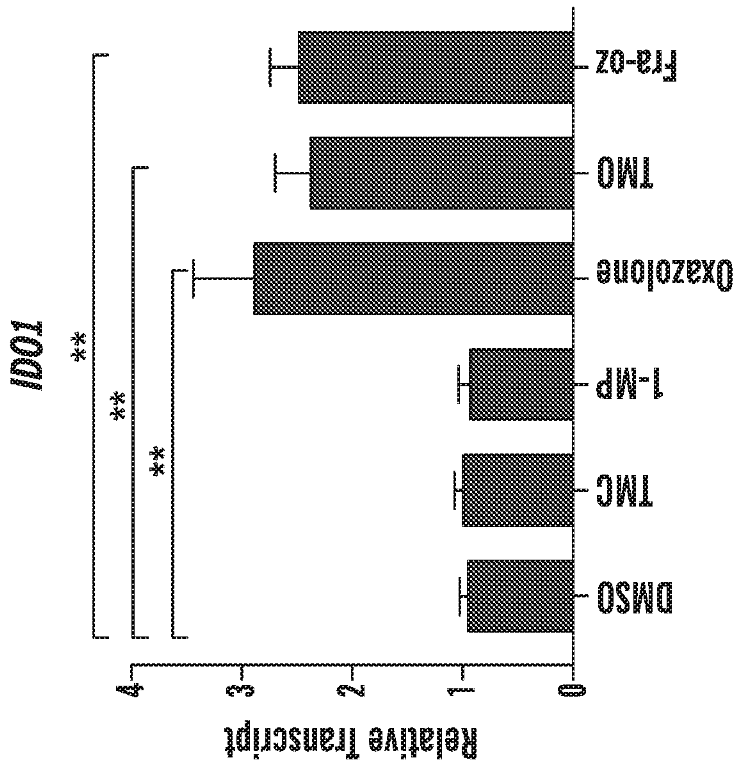
FIG. 7A-D shows a minimal oxazole structure modulates intestinal epithelial transcriptional and antigen presentation capacity to invariant and non-variant nkt cells, related to FIG. 1.
Figure 7B:
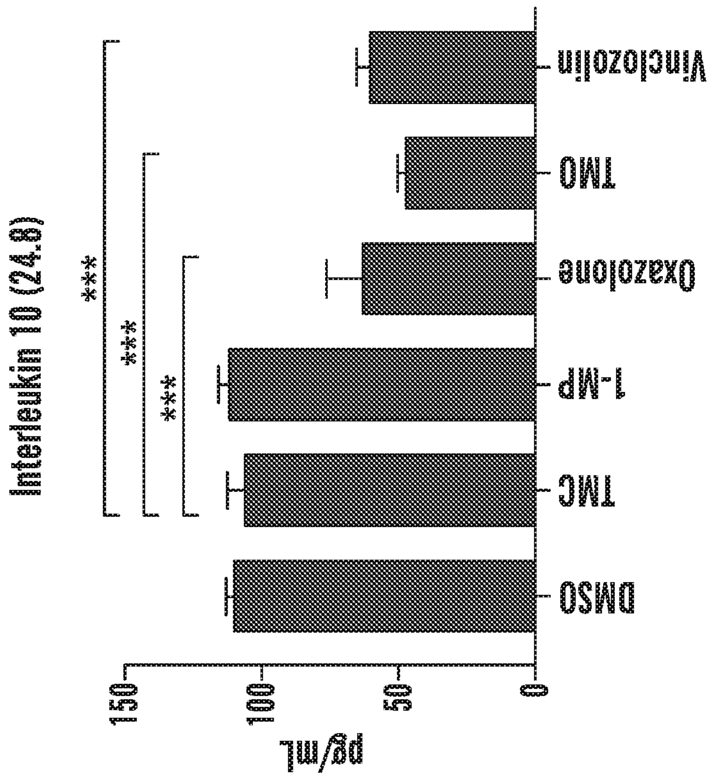
Figure 7D:
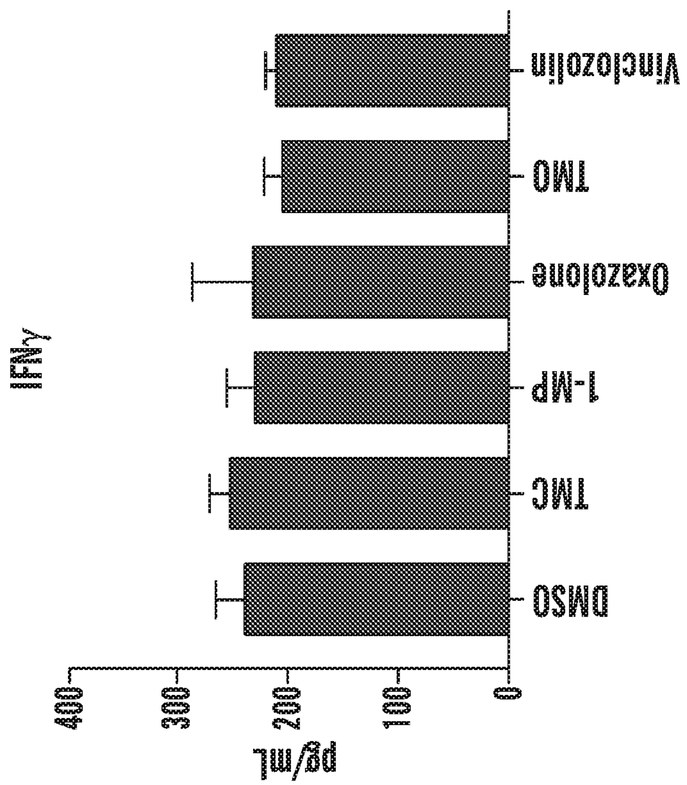
Figure 7C:
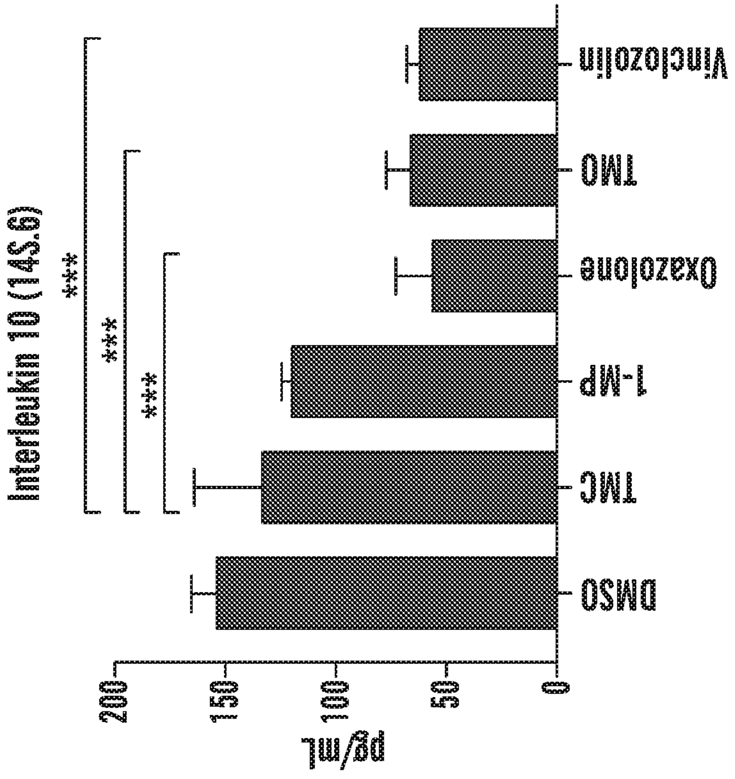

These studies show that although AhR regulates CD1d-restricted responses to oxazole containing compounds, this is not a property of all AhR ligands (such as ITE). This suggests that epithelial responses to OxC generate AhR agonists uniquely capable of attenuating IL-10 production through CD1d-restricted mechanisms. It was therefore of interest that IDO1 was upregulated in IECs exposed to oxazoles (FIG. 7A-D). IDO1 is a rate-limiting enzyme involved in tryptophan catabolism that generates formyl-kyneurenine which can be further metabolized into a variety of AhR agonists (Higuchi and Hayaishi Arch Biochem Biophys 1967, Nguyen and Bradfield 2008, Zelante et al. 2014). Indeed, incubation of recombinant IDO1 with oxazolone, TMO or frag-oz enhanced the ability of IDO1 to convert tryptophan to formyl-kyneurenine compared to control (TMC) or vehicle indicating that oxazole compounds may function to enhance IDO1 enzymatic activity through direct means (FIG. 5A). To test whether tryptophan metabolism is therefore involved in the AhR effects were observed, IECs were cultured in tryptophan-deficient media and found that CD1d-restricted IL-10 production was no longer attenuated by stimulation with oxazolone, TMO or frag-oz when compared to TMC or vehicle controls (FIG. 5B). On the other hand, supplementation with exogeneous L-tryptophan (L-Trp) restored responses to oxazolone, TMO and frag-oz resulting in attenuation of CD1d-restricted IL-10 production supporting a role for tryptophan-derived metabolites in this process (FIG. 5B). To specifically identify these tryptophan derived products, IECs were cultured with deuterated L-trp (D5-Trp) and performed high performance liquid chromatography mass spectrometry (LC-MS) on lysates stimulated with oxazolone, TMO, frag-oz or TMC control (FIG. 5C). The uptake of D5-Trp was detected in TMC stimulated IECs that was further metabolized to kyneurenic acid and 3-hydroxy kyneurenic acid (referred to as xanthurenic acid) only upon stimulation with oxazolone or TMO and frag-oz, respectively, within 6 hours of exposure to oxazoles (FIG. 5C). To further investigate whether tryptophan-derived metabolites attenuate CD1d-restricted responses, IECs were cultured in tryptophan-deficient media supplemented with L-Trp, kyneurenic acid, xanthurenic acid, or an upstream tryptophan product, kyneurenine, in the presence or absence of oxazolone. Supplementation with exogenous tryptophan or its downstream products of catabolism restored IEC responses to oxazolone as shown by reduced CD1d-restricted IL-10 production (FIG. 5D). In contrast, supplementation with DL-methyl tryptophan (DL-Mtrp) a tryptophan competitive inhibitor of IDO1, did not restore suppression of CD1d-restricted IL-10 production in IECs cultured in tryptophan-deficient conditions and stimulated with oxazolone (FIG. 5D). Finally, to ascertain whether these same metabolites identified in the LC-MS analyses, functioned through the AhR pathway, siRNA-mediated knockdown of AhR was performed in IECs cultured under tryptophan-deficient conditions in the presence of exogenously administered kyneurenic acid and measured CD1d-restricted IL-10 production after stimulation with OxC compounds (FIG. 5E). Incubation of IECs with L-Trp or kyneurenic acid alone or in conjunction with TMC stimulation had no effect on CD1d-restricted IL-10 production (FIG. 5B, SD). In contrast, IECs cultured under tryptophan-deficient conditions and stimulated with oxazolone, TMO or frag-oz when supplemented with kyneurenic acid led to decreased IL-10 production that was reduced when AhR was silenced (FIG. 5E). Taken together these latter studies are consistent with a model in which exposure of IECs to oxazole containing compounds leads to the activation of IDO1 and generation of tryptophan-derived metabolites that induce the AhR pathway to downregulate CD1d-restricted responses associated with the production of IL-10 (FIG. 6).

Summary of Results

In the studies described herein, structural analyses of oxazolone, a compound previously shown to be capable of inducing inflammation of the colon was determined (Boirevant et al. 1998, Heller et al. 2002, Dietrich and Hess 1970), to identify a new and broad class of dietary, microbial, and other environmental derived factors within the human exposome (Melby et al. 2011, Wambaugh et al. 2014, Donia et al. 2014, Asensio and Perez-Diaz 1976). As shown here, these compounds are capable of direct induction of intestinal inflammation through crosstalk of CD1d-restricted and aryl hydrocarbon receptor pathways in intestinal epithelial cells. These structures, which named oxazole-containing compounds (OxC), include a variety of chemicals used in agriculture (e.g. vinclozolin), food additives and processing (e.g. TMO) and microbial factors (e.g. bacterial microcins). In the latter case, it was demonstrated that in addition to their well-established role as anti-microbial peptides, bacterial microcins are capable of inducing host responses. Together, this suggests that environmental agents capable of activating CD1d-restricted pathways can do so by phenocopying host responses to microbial factors. In light of the wide presence of OxC in the environment including a number of microbial sources (Melby et al. 2011), these results have important implications for understanding potential environmental triggers that influence susceptibility to inflammation associated with the body surfaces associated with skin (e.g. dermatitis and contact hypersensitivity), intestines (e.g. IBD, allergy), esophagus (e.g. eosinophilic esophagitis), lungs (e.g. asthma) and others that involve the activity of CD1d-restricted pathways in susceptible hosts at the body surfaces and perhaps elsewhere (Rossjohn et al. 2012, Nieuwenhuis et al. 2002, Lexmond et al. 2014, Leavy 2006).

Environmental and lifestyle factors have been identified as critical risk elements for development of disorders of chronic inflammation, such as IBD (Molodecky and Kaplan 2010). Consistent with this, chemical induced models of intestinal inflammation have been crucial experimental tools in investigating the pathophysiology and testing of therapeutic strategies for IBD. (Wirtz et al. 2007, Blumberg et al. 1999) Here, the colitogenic activity within oxazolone has been isolated to a five-membered heterocyclic oxazole moiety. Based on these observations, it was inquired whether oxazolone is representative of a broader class of environmental factors that may be involved in the pathogenesis of IBD and possess conserved or shared sub-structure. Oxazolone, first synthesized in 1883 by Erlenmeyer and Ploechl (Plochl 1884, Erlenmeyer 1893), has been widely utilized as a synthetic building block for compounds with a range of pharmacological properties including amino acids, antibiotics and pharmaceuticals (Kupera et al. 2011, Akram et al. 2014, Witvrouw et al. 1999, Sierra et al. 2002, Madkour et al. 2002, Khan et al. 2006, Abdel et al. 2009). Oxazole ring containing compounds are also naturally abundant in diet as a component of many thermally processed foods including roasted coffee, roasted peanuts and heated beef or as flavor enhancers such as in fish products, as well as additives to fruits and vegetables through use of pesticides and fungicides, and contained in other environmental sources such as cigarette smoke (Vitzthum et al. 1975, Stoffesima et al. 1968, Lee et al. 1981, Chang et al. 1968, Ho and Hartman 1968). Previous epidemiologic studies have attempted to explore the relationship between food intake and IBD, and have shown varying associations between coffee, peanuts, meat intake, margarine and IBD (Barthel et al. 2015, Imanzadeh et al. 2015, Eaton et al. 2015, Hou et al. 2011, Ng et al. 2015, Jowett et al. 2004). In addition, these studies have suggested that processed foods (in particular red meat and margarine) may be associated with colonic inflammation (Hou et al. 2011, Ng et al. 2015). However, dietary intake was predominantly measured from food recall diaries or weighted dietary records, and the mode of processing was not studied or discussed in detail in any of these studies. It would therefore be interesting to know if the positive associations observed were linked to oxazole-rich food compounds. The findings of the study certainly warrant more in-depth exploration of the association between intake of thermally processed, oxazole-rich food and the incidence and prognosis of IBD as well as a variety of other allergic and inflammatory conditions that involve CD1d and NKT cells in their pathogenesis.

In addition, microbes are another abundant source of oxazoles as part of a structurally functionally diverse class of ribosomally derived peptides dubbed thiazole/oxazole modified microcins (TOMMs) generated through post-translational installation of heterocycles derived from cysteine, serine, and threonine residues. TOMMS are widely disseminated across the phylogenetic spectra of bacterial secretion systems, including potential pathobionts associated with IBD pathogenesis or skin inflammation including Bacteroidetes and Corynebacteriae, respectively (Melby et al. 2011, Bagley et al. 2005, Vizan et al. 1991, Carvalho et al. 2012, Mukhopadhya et al. 2012). Together, this supports the convergence of environmental and microbial derived chemical structures on conserved host immune responses.

The micromolar exposure to select oxazole species modulate CD1d-restricted responses in epithelial cells in vitro which are characterized by down-regulation of Mttp and reduced IL-10 production after CD1d crosslinking with NKT cell associated receptors. This mechanism has been previously shown to reduce epithelial barrier activity in response to similar concentrations of oxazolone in the colon leading to exacerbated inflammatory responses (Olzsak et al. 2014). To what degree oxazole products accumulate within the intestinal tract and the physiological concentrations and circumstances required for triggering inflammatory responses are unknown. Interestingly, at least two of the structures identified, 2,4,5-trimethyl-1,3-dihydro-oxazole (TMO) and vinclozolin have been detected in human urine through studies associated with defining the human exposome (Wambaugh et al. 2014). Although not directly addressed in this study, it is interesting to consider whether accumulated exposure to oxazoles derived from multifactorial sources, including diet, microbes, industry and/or agriculture acts in an additive or combinatorial manner that includes other potential non-oxazole agents in modulating host responses that are associated with disease pathogenesis.

The gene expression profiling of intestinal epithelial cells exposed to oxazole compounds have identified a several genes (FIG. 1B, FIG. 2C, FIG. 2F, FIG. 3E, FIG. 7A-D, FIG. 9B-C) involved in xenobiotic metabolism and tryptophan catabolism, including indoleamine 2,3,dioxygenase 1 (IDO1), a marker highly expressed in patients suffering from IBD as well as in many animal models of colitis (Olszak et al. 2014, Barcelo-Batllori et al. 2002, Ferdinande et al. 2008, Dickgraefe et al. 2000, Wolf et al. 2004, Hansen et al. 2009). Data presented here suggest that oxazole compounds enhance the ability of IDO1, the rate limiting enzyme in tryptophan catabolism, to metabolize tryptophan (FIG. 5A). This supports a role for the aryl hydrocarbon receptor (AhR) as a potential cytosolic sensor or signal transducer of oxazole induced products in the intestinal epithelium (Nguyen and Bradfield 2008). Indeed, specific depletion of the AhR in the epithelium was shown to alleviate the oxazole-induced suppression of CD1d-restricted anti-inflammatory responses including production of IL-10 (FIG. 4B). Mass spectrometry analyses identified at least two products of tryptophan catabolism, kyneurenic acid and xanthurenic acid, that are specifically generated in intestinal epithelial cells exposed to oxazolone or dietary and/or microbial oxazoles and their capacity to activate the AhR pathway in a manner that results in attenuation of CD1d-restricted IL-10 production. This observation is interesting given that levels of tryptophan and its byproducts in the serum have provided a robust marker for gastrointestinal pathology in clinical settings (Ciorba 2013).

Figure 4F:
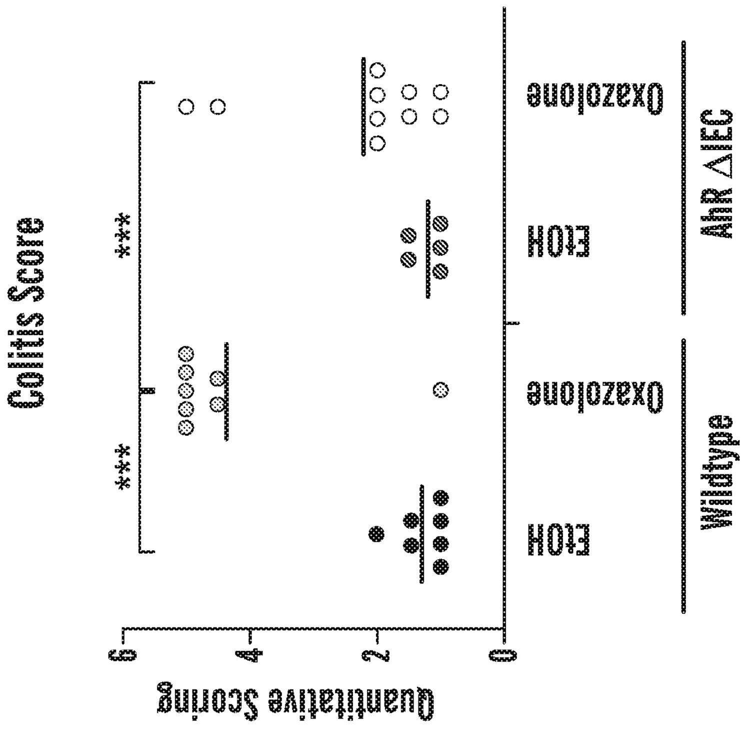
Figure 4H:
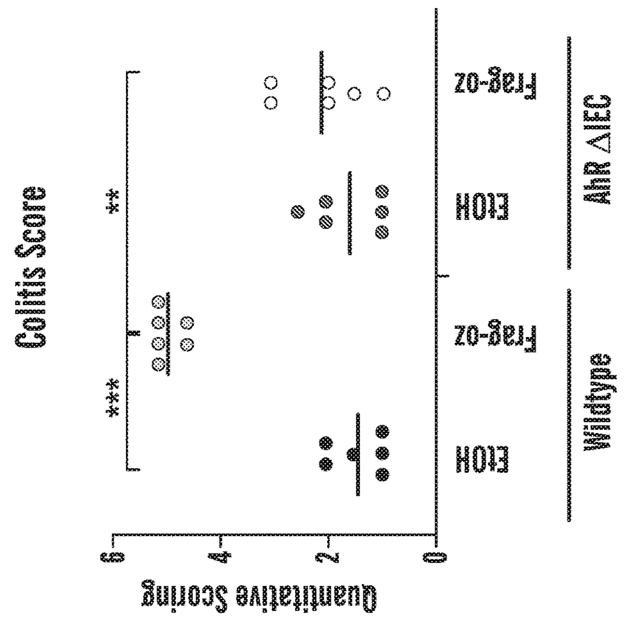
Figure 4G:
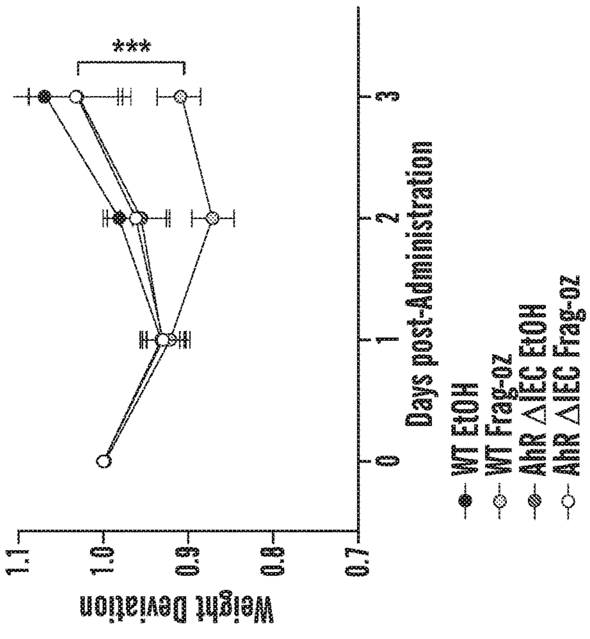

In the hematopoietic system, elevated IDO1 expression and subsequent AhR activation have been associated with immune tolerance implicating this pathway in maintaining intestinal homeostasis (Apetoh et al. 2010, Li et al. 2011, Gandhi et al. 2010, Kiss et al. 2011, Bessede et al. 2014, Veldhoen et al. 2008, Qui et al. 2012). Thus loss of of AhR activity in hematopoietic cells can be deleterious resulting in decreased regulatory T cells or group 3 innate like lymphoid cells that together normally restrain inflammation, maintain intestinal epithelial barrier function through production of interleukin-22 (Apetoh et al. 2010, Li et al. 2011). Similarly, both IDO1 and AhR are highly expressed within the intestinal epithelial compartment, however their role in promoting or preventing intestinal inflammation is poorly understood (Ciorba 2013, Schiering et al. 2017, Lanis et al. 2017). Here, it was shown that specific depletion of AhR within the intestinal epithelium, modulates CD1d-restricted responses in vitro and confers protection against the induction of intestinal pathology by oxazolone and a microbial oxazole compound in vivo (FIG. 4F, 4H). These data implicate a novel role for AhR in regulating NKT cell lipid antigen sensing specifically in IECs which, in contrast to the effects on the hematopoietic system (Apetoh et al. 2010, Li et al. 2011), has a deleterious effect on the host in the context of colitis. This can occur through enhanced production of tryptophan derived metabolites as a result of oxazole induction of the enzymatic activity of IDO1 which results in AhR suppression of CD1d-restricted responses involved in the IEC production of IL-10 (FIG. 6)

In addition, it has been shown herein that oxazoles also downregulate MTP that is normally responsible for the loading of phospholipid antigens onto CD1d (Dougan et al. 2005, 2007). Consistent with the observations, altering MTP expression or activity has been previously shown to prevent transfer of phospholipids to CD1d or the ability of CD1d to acquire exogenous lipid antigens such as α-GC (Dougan et al. 2005). Further, loss of MTP in IECs has been shown to disable the ability of iNKT cells to induce the barrier protective cytokine, IL-10, by this cell type as it has been shown (Olszak et al. 2014). Together, the data suggest that oxazoles alter presentation of lipid auto-antigens (FIG. 8A-B) and exogenous lipid antigens as shown with α-GC (FIG. 1D-E, FIG. 4C) to CD1d-restricted invariant and non-invariant NKT cells in a pathway that is dependent on AhR through the generation of tryptophan-derived metabolites. As both oxazolone and frag-oz induce inflammation in animals under GF conditions (Olszak et al. 2012, FIG. 3D-E), NKT-mediated responses to host-derived lipid antigens may be particularly important to oxazole-induced inflammation and further suggest oxazoles may thus modulate autoimmune responses to self-lipid antigens.

Conversely, it is also interesting to consider whether microbes use oxazole products to target CD1d in order to establish their niche during primary colonization potentially resulting in mucosal inflammation and pathology. Previous studies have demonstrated an important physiological role for CD1d during initial colonization of commensal and pathogenic bacteria (Nieuwenhuis et al. 2005, 2009). Specifically, CD1d-deficient animals re-derived and raised under GF conditions are unable to control colonization against gram-negative (*Pseudomonas aeruginosa. Escherichia coli*) and gram-positive (*Staphylococcus aureus, Lactobacillus gasseri*) bacteria. As a result, recently colonized CD1d-deficient GF animals exhibit an abnormal distribution of bacteria within the gastrointestinal tract and specific pathogen free, CD1d-deficient animals exhibit an altered composition of their microbiota relative to that observed in wildtype or heterozygotic littermates (Nieuwenhuis et al. 2009). Consequently, generation of products that modulate CD1d activity such as oxazoles, which are capable of specifically inhibiting intestinal epithelial cell function may affect the ability of microbes to colonize the intestine.

Intestinal inflammation is often accompanied by microbial blooms, including Enterobacteria as compared to healthy intestine, potentially resulting in dysbiosis (Winter and Baumler Cell Microbiol. 2014, Ng et al. Nature 2013, Winter et al. Science 2013). Recent studies have suggested production of microcins H47 and microcin M by the probiotic *E. coli* Nissle 1917 limited growth of competing microbes in the inflamed intestine (Sassone-Corsi et al. Nature 2016). Both H47 and microcin M possess relatively broad-spectrum activity against a variety of gram-negative commensals and pathogens. However, the mechanism of action has not been well characterized. In contrast, the MccB17 toxin which was initially isolated from human infants (Asensio and Perez-Diaz 1976) has been well delineated as an inhibitor of DNA gyrases with activity against a broad spectrum of gram-positive and gram-negative microbes linked to the presence of post-translational oxazole/thiazole installations within the MccB17 peptide (Roy 1999). Interestingly, some low molecular weight fragments of MccB17 isolated after bacterial lysis or generated by cleavage by microbial proteases retain their inhibitory activity while others lose their affinity for the MccB17 transporters, OmpF and SbmA and thus may accumulate in the intestinal lumen (Lavina J Gen. Microbiol 1986). Microcin compounds were identified as putative modulators of host mediated CD1d-restricted epithelial responses based on their shared substructure with synthetic and dietary derived oxazoles. While full length MccB17 itself shared relatively low structural similarity with oxazolone, derivative products below 270 Da generated either by alkaline hydrolysis or proteolytic cleavage showed relatively high similarity with both oxazolone and TMO (FIG. 13). Importantlyit was observed that both the natural products and their synthetic analogs display similar ability to attenuate CD1d-lipid antigen presentation and subsequent CD1d-restricted IL-10 production as well as activate AhR responses specifically in IECs resulting in inflammation associated with decreased epithelial derived IL-10 That inflammation to MccB17 derivatives occurs in GF animals confirms that the effects of these compounds are directly impacting the host and not a result of their anti-microbial capacity. It is therefore intriguing to consider then that the accumulation of oxazole compounds derived from MccB17 producing and other TOMM producing bacterial strains during a period of microbial competition may have a bystander effect on host immune responses resulting in intestinal inflammation or other effects that benefit the organism at the expense of the host.

The data also have interesting implications for understanding the biologic mechanisms by which so-called haptens mediate their effects. Classic immunologic studies using hapten-carrier complexes have provided deep insights into concepts of B cell and T cell recognition of antigens and downstream immune responses to the hapten (e.g. oxazolone) or the protein carrier, which provides peptides for MHC class II presentation (Lemus and Karol 2008). Such pathways have been implicated in the pathogenesis of diseases such as contact hypersensitivity (Martin et al. Allergy 2011, Honda et al. J. Invest. Derm. 2013). The studies indicate that chemical haptens may have important and direct biologic effects in their own right that could represent the source of disease pathogenesis and/or modify other mechanisms. Consistent with this, oxazolone conjugated to a CD1d lipid antigen, α-GC, has no effect on α-GC CD1d binding or activity in vitro or in vivo (data not shown). Such insights may have important implications for interpreting models that use other chemical haptens (Wirtz et al. 2007).

In conclusion, these studies illustrate a novel approach for interrogating triggers of inflammation due to environmental sources by searching for mimics of well-known chemical structures with established activities. In so doing, leveraging the knowledge available from oxazolone's role as a colitogenic agent via modulation of CD1d-restricted pathways oxazole containing compounds (OxC) have been identified as a new class of potential environmental agents with inflammation inducing potential that are contained within a wide range of dietary, environmental and microbial sources. With respect to the latter, these studies further show that bacterial microcins, which are well known to play a role in microbe-microbe interactions, also possess important and previously unappreciated immune regulating properties via their effects on CD1d-restricted pathways. Further, in both the case of environmental and microbial OxC it was discovered that they involve epithelial sensing by the AhR, which in turn adversely affects CD1d-restricted presentation of lipid antigens that are associated with barrier protective production of IL-10. As a result, a novel pro-inflammatory activity of AhR sensing that is associated with the intestinal epithelium has been identified and has brought forth the environmental triggers of inflammation that are associated with IBD may function in this manner by phenocopying the activity of microbial products with similar activity.

Example 2: Characterization of IDO Enhancers

Members of a class aromatic hydrocarbon termed oxazoles induce production of tryptophan derived metabolites that subsequently activate host aryl hydrocarbon receptor responses A class of oxazole derived metabolites belong to the family of kynurenine and kynurenine-like metabolites that are byproducts of the conversion of tryptophan to formyl kynurenine by the rate-limiting enzyme indoleamine 2,3-dioxygenase (IDO1).

Figure 14A:
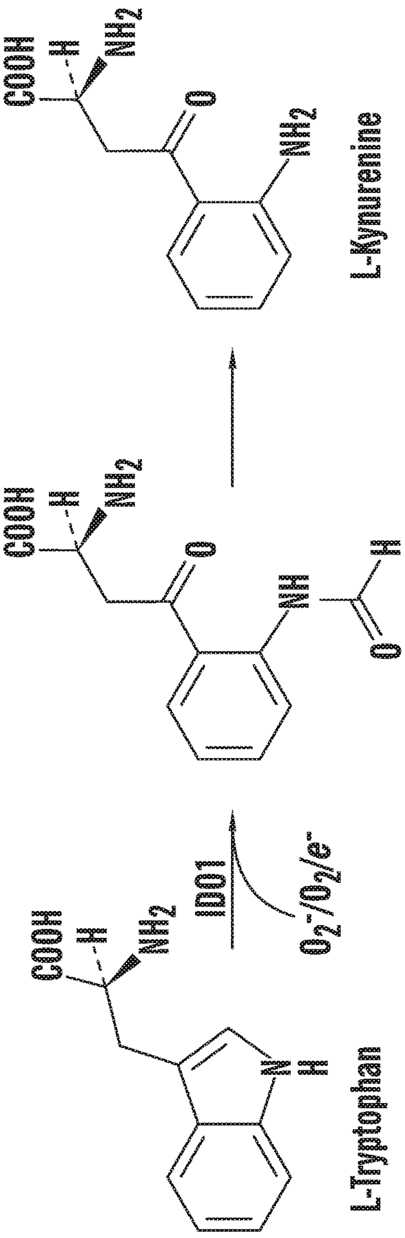
FIG. 14A-B shows oxazoles enhance degradation of tryptophan via activation of IDO1 enzymatic activity.
Figure 14B:
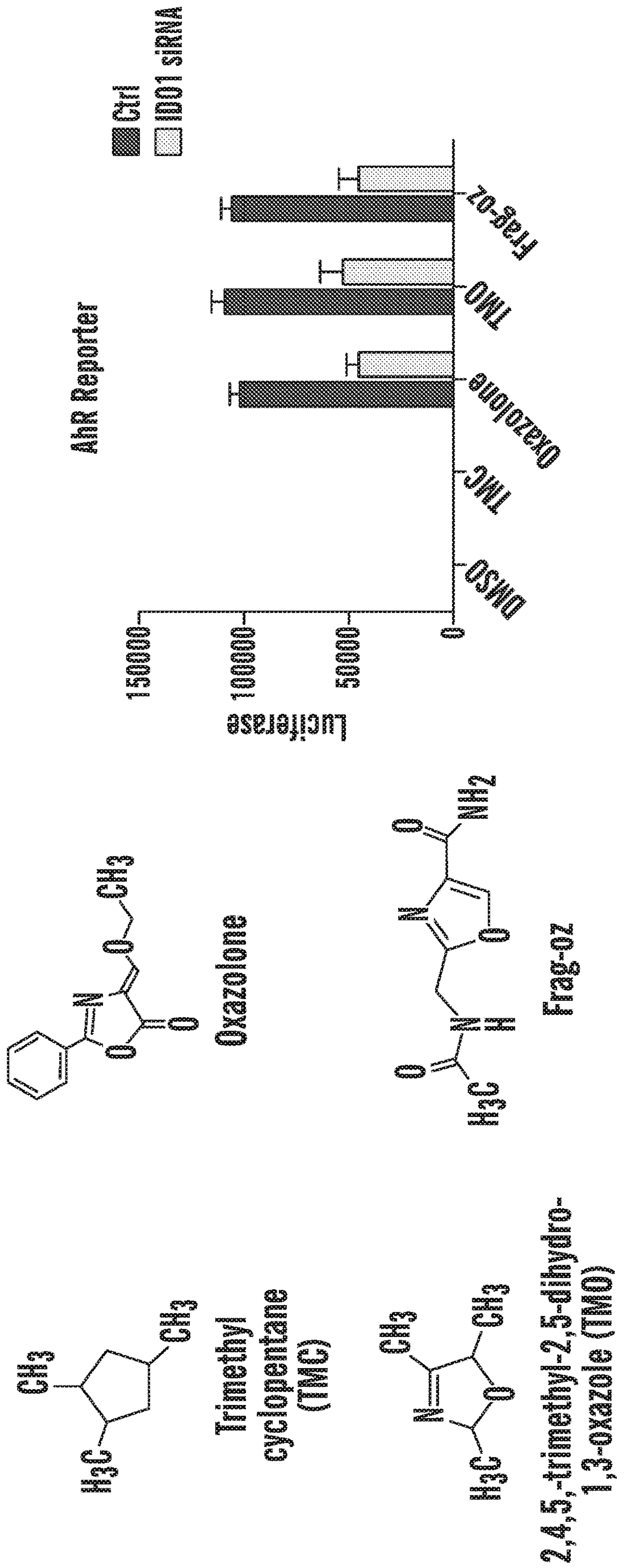

Oxazoles enhance degradation of Tryptophan via activation of IDO1 enzymatic activity. Furthermore, these compounds can enhance production of ahr agonists in idol dependent manner in intestinal epithelial cells (FIG. 14). FIG. 14A-B shows oxazoles enhance degradation of tryptophan via activation of IDO1 enzymatic activity. FIG. 14A shows IDO1 mediated conversion of tryptophan to kynurenine precursors. FIG. 14B shows oxazoles enhance production of AhR agonists in IDO1-dependent manner in intestinal epithelial cells.

An in vitro screen for IDO1 enhancers was developed based on the following categories: Synthetic, dietary, and microbial compounds with structural similarity to oxazole template.

Figure 15:
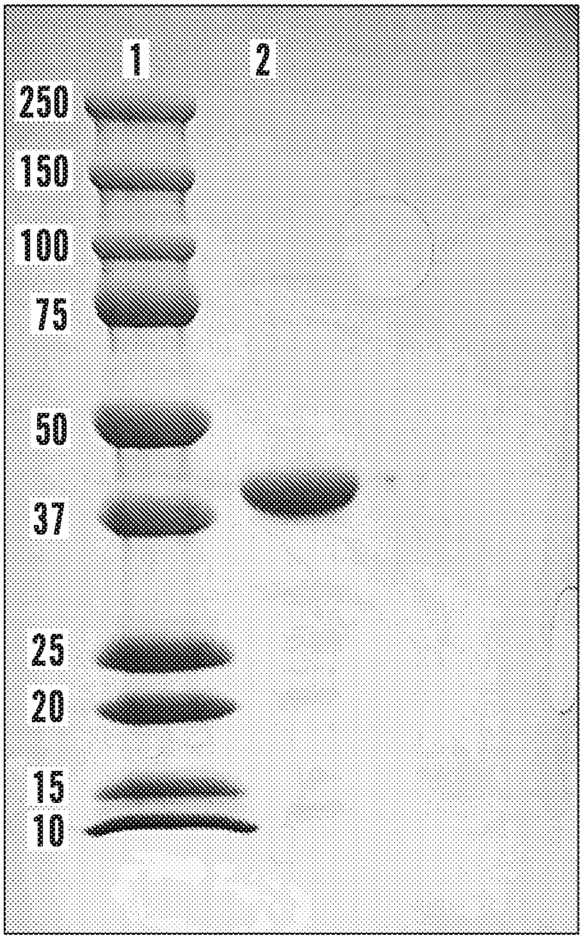
FIG. 15 shows expression and purification of human IDO1(hIDO1). SDS-PAGE gel under reducing conditions showing that hIDO1 was purified to >95% purity after HiTrap HP chelating column. Lane 1, molecular weight markers; lane 2, hIDO1.

FIG. 15 shows expression and purification of human IDO1(hIDO1). SDS-PAGE gel under reducing conditions showing that hIDO1 was purified to >95% purity after HiTrap HP chelating column.

Figure 16:
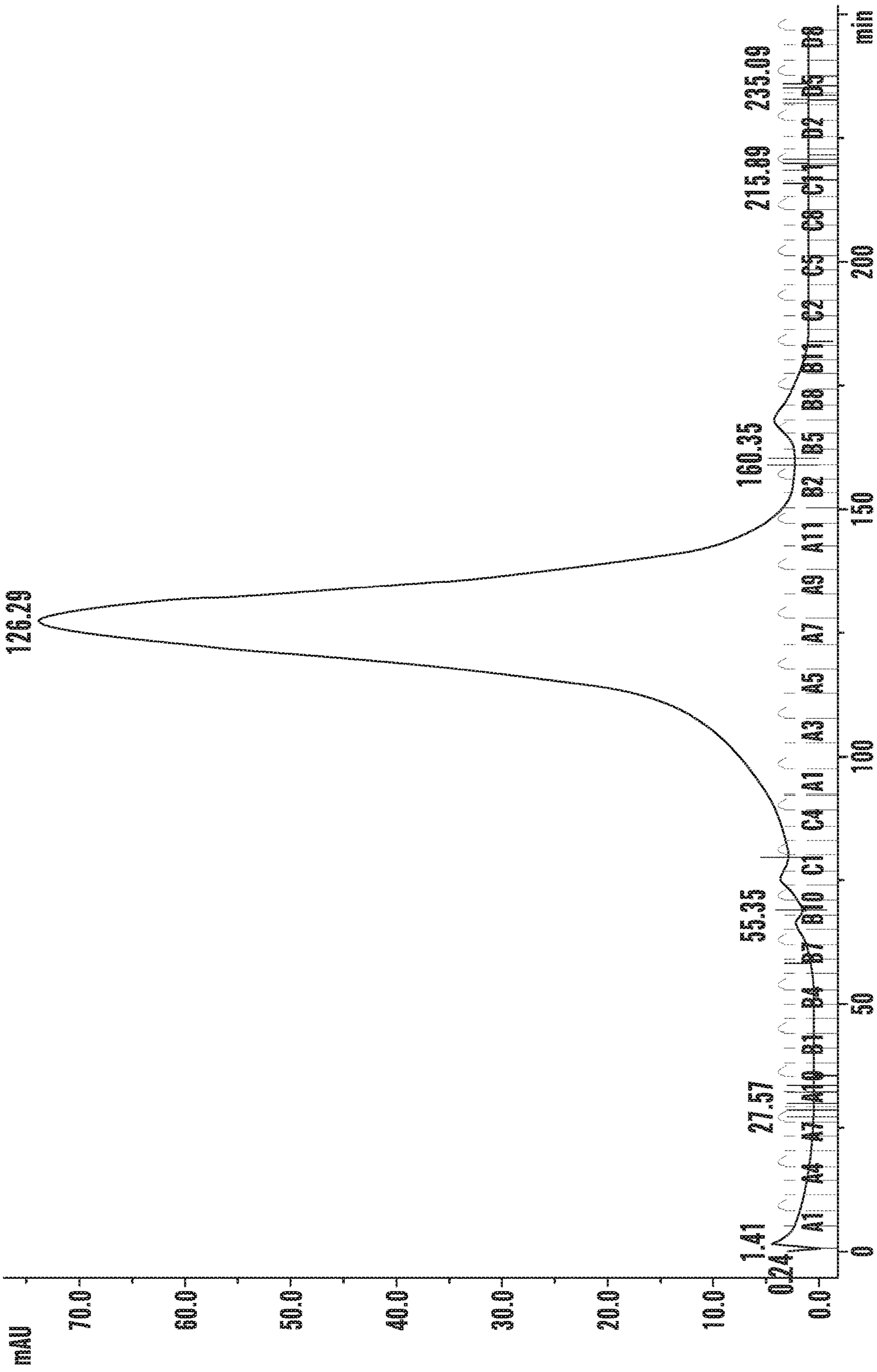
FIG. 16 shows size exclusion chromatography. HiPrep 16/60 Sephacryl S-200 HR column (GE Healthcare Life Sciences) size-exclusion chromatography in a buffer containing 10 mM HEPES buffer, 150 mM NaCl pH 7.0 of hIDO1 showing single peak and peak maximum of purified protein at 126.2 minutes.

FIG. 16 shows size exclusion chromatography of hIDO1. HiPrep 16/60 Sephacryl S-200 HR column (GE Healthcare Life Sciences) size-exclusion chromatography in a buffer containing 10 mM HEPES buffer, 150 mM NaCl pH 7.0 of hIDO1 showing single peak and peak maximum of purified protein at 126.2 minutes.

Figure 17:
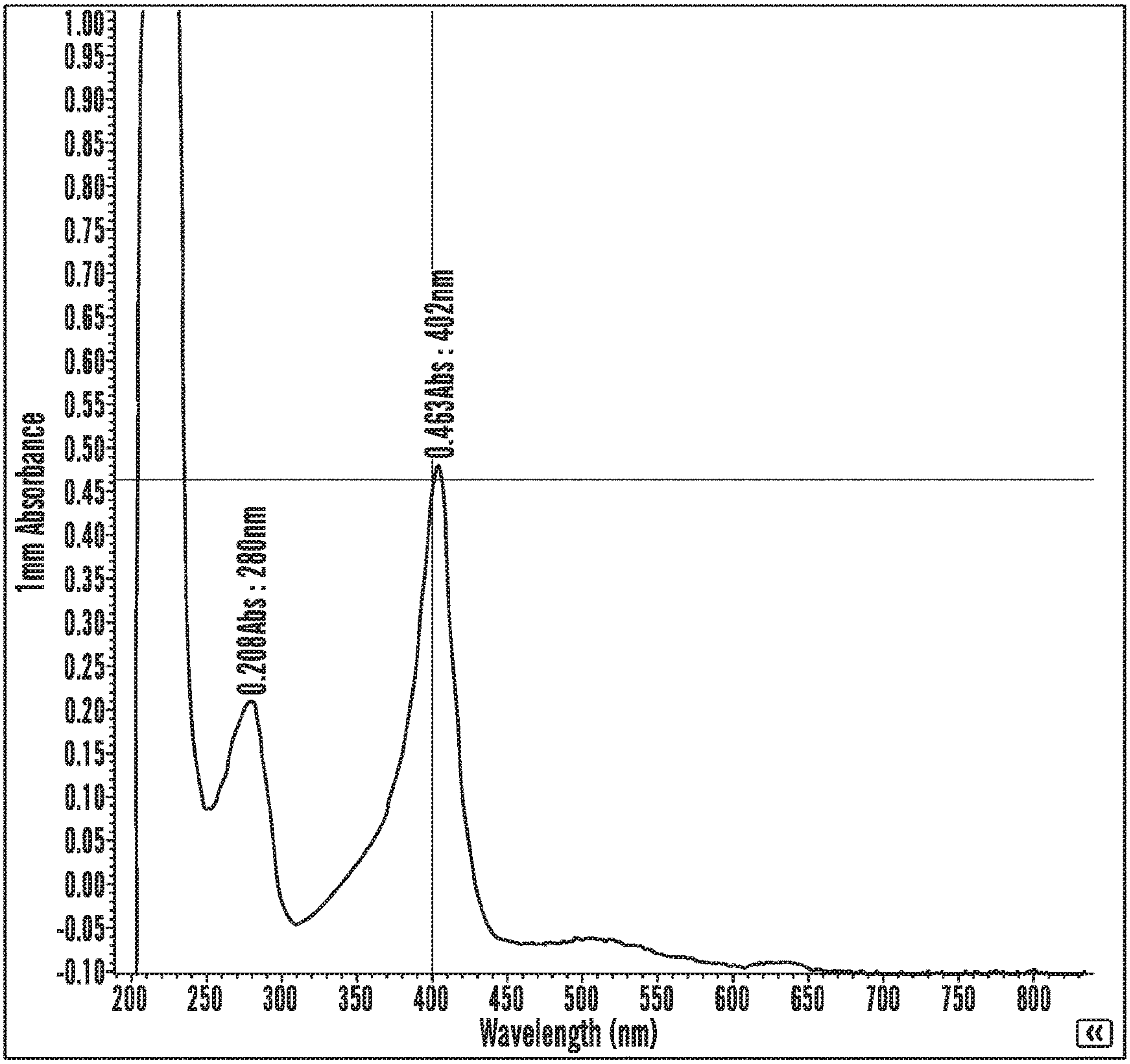
FIG. 17 shows a heme bound assay. Sizing fractions a3-a11 were checked for Heme absorbance at 402 and 280 nm. Fractions showing >2.0 Heme ratio were pooled and concentrated, and final 1.5 mg/ml concentrated protein was used for final bound heme estimation. A ratio of 2.22 at 402/280 nm confirmed heme binding to purified recombinant hIDO1 protein.

FIG. 17 shows a heme bound assay for hIDO1. Sizing fractions a3-a11 were checked for Heme absorbance at 402 and 280 nm. Fractions showing >2.0 Heme ratio were pooled and concentrated, and final 1.5 mg/ml concentrated protein was used for final bound heme estimation. A ratio of 2.22 at 402/280 nm confirmed heme binding to purified recombinant hIDO1 protein.

Figure 18:
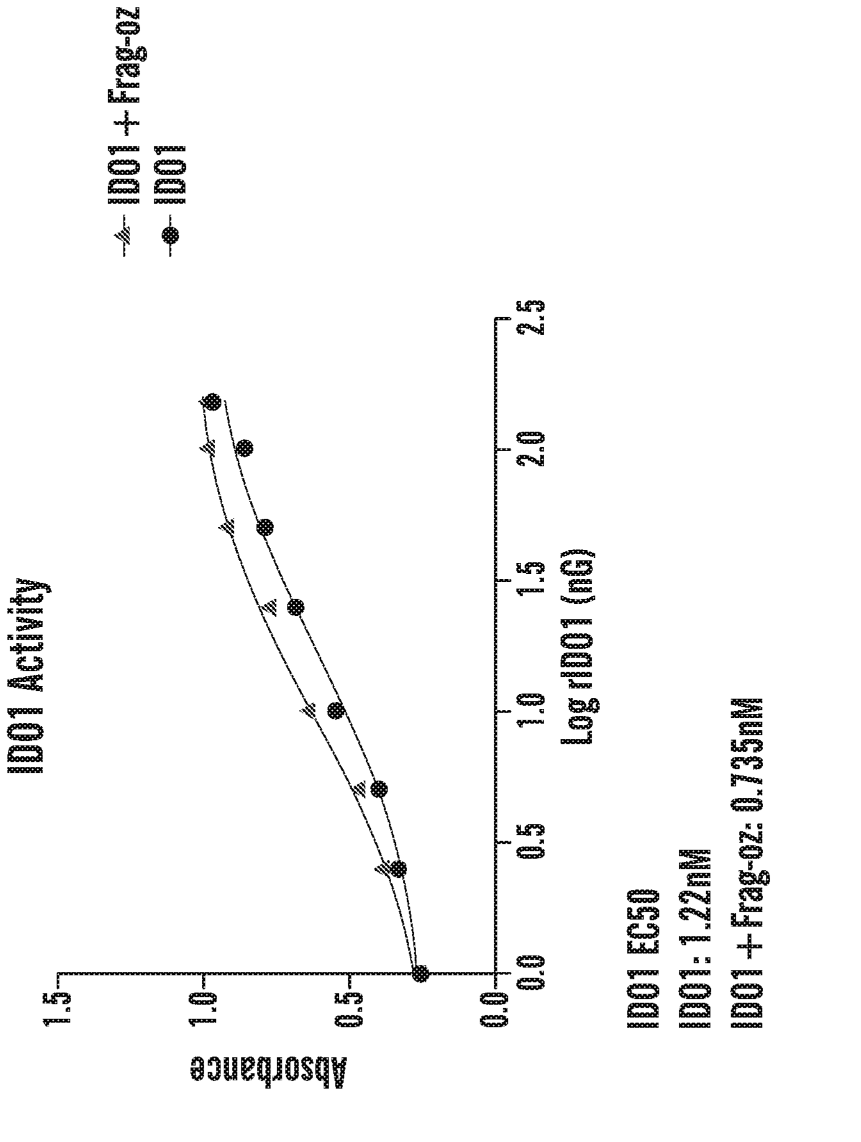
FIG. 18 shows an in vitro screening assay for IDO1 activators such as Frag-oz.

FIG. 18 shows an in vitro screening assay for IDO1 activators such as Frag-oz.

FIG. 19 shows dietary and microbial oxazole enhance IDO1 activity.

FIG. 20 shows results from the screening assay featuring synthetic and dietary compounds.

Figure 21:
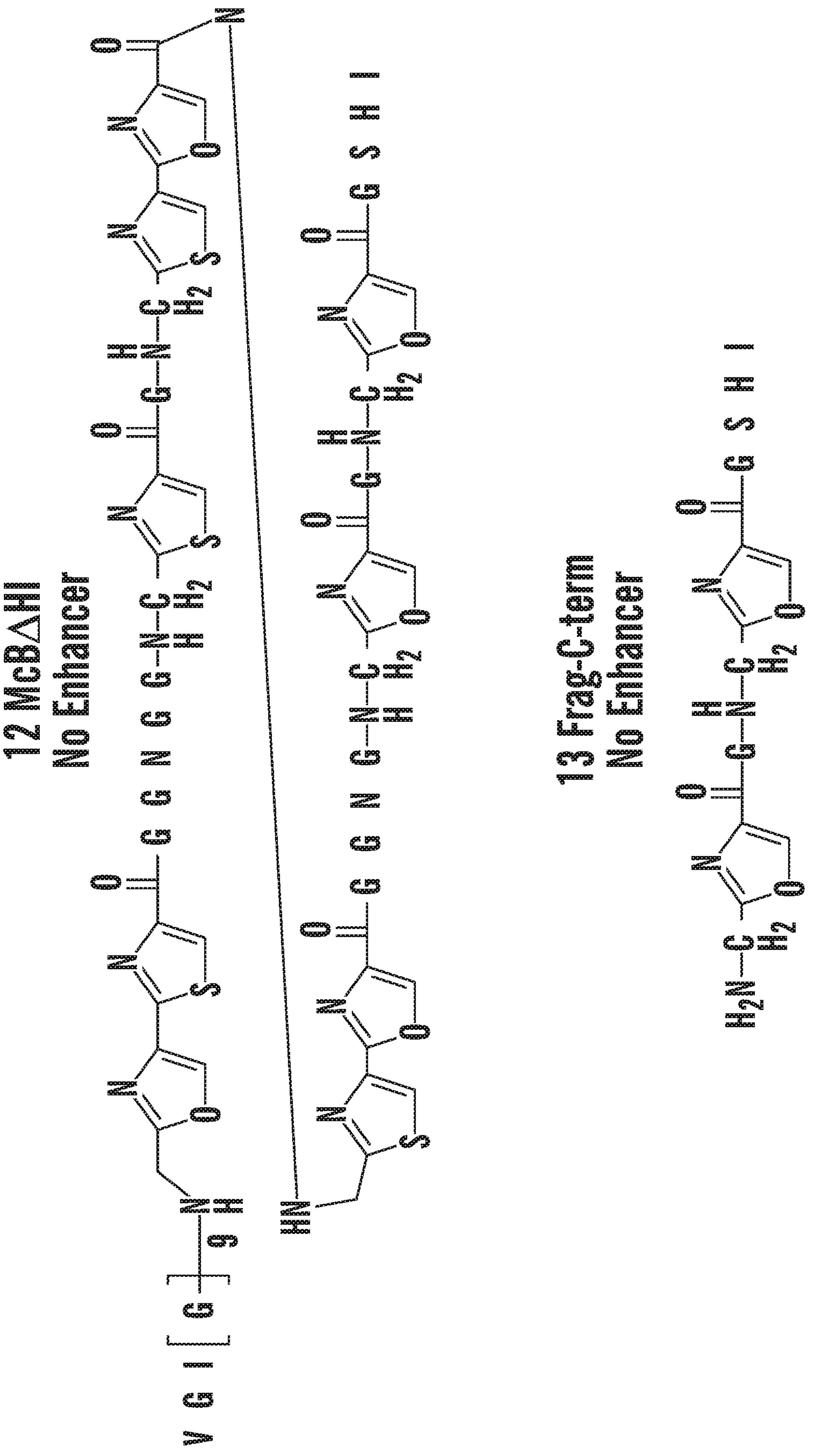
FIG. 21 shows results from the screening assay feathuring bacterial compounds.
Figure 21:
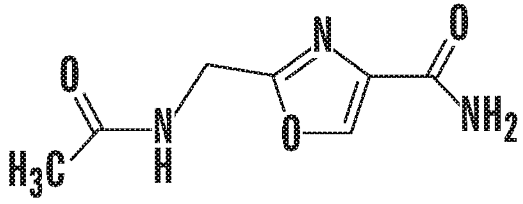

FIG. 21 shows results from the screening assay feathuring bacterial compounds.

Figure 22:
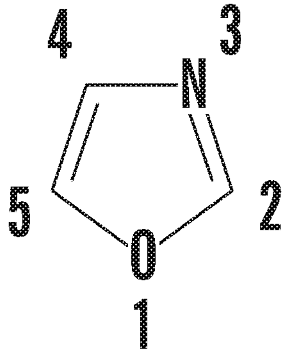
FIG. 22 shows that oxazole compounds less than 270 Da are capable of enhancing IDO1 enzymatic activity in vitro. Increased complexity of branching at 2,4,5 positions generally prevents enhancer activity.

FIG. 22 shows that oxazole compounds less than 270 Da are capable of enhancing IDO1 enzymatic activity in vitro. Increased complexity of branching at 2,4,5 positions generally prevents enhancer activity.

SEQUENCES

```
SEQ ID NO: 1 (human IDO 1 amino acid sequence,
NP_002155.1)
MAHAMENSWTISKEYHIDEEVGFALPNPQENLPDFYNDWMFIAKHLPDLI
ESGQLRERVEKLNMLSIDHLTDHKSQRLARLVLGCITMAYVWGKGHGDVR
KVLPRNIAVPYCQLSKKLELPPILVYADCVLANWKKKDPNKPLTYENMDV
LFSFRDGDCSKGFFLVSLLVEIAAASAIKVIPTVFKAMQMQERDTLLKAL
LEIASCLEKALQVFHQIHDHVNPKAFFSVLRIYLSGWKGNPQLSDGLVYE
GFWEDPKEFAGGSAGQSSVFQCFDVLLGIQQTAGGGHAAQFLQDMRRYMP
PAHRNFLCSLESNPSVREFVLSKGDAGLREAYDACVKALVSLRSYHLQIV
TKYILIPASQQPKENKTSEDPSKLEAKGTGGTDLMNFLKTVRSTTEKSLL
KEG

SEQ ID NO: 2 (human AhR amino acid sequence,
NP_001612.1)
MNSSSANITYASRKRRKPVQKTVKPIPAEGIKSNPSKRHRDRLNTELDRL
ASLLPFPQDVINKLDKLSVLRLSVSYLRAKSFFDVALKSSPTERNGGQDN
CRAANFREGLNLQEGEFLLQALNGFVLVVTTDALVFYASSTIQDYLGFQQ
SDVIHQSVYELIHTEDRAEFQRQLHWALNPSQCTESGQGIEEATGLPQTV
VCYNPDQIPPENSPLMERCFICRLRCLLDNSSGFLAMNFQGKLKYLHGQK
KKGKDGSILPPQLALFAIATPLQPPSILEIRTKNFIFRTKHKLDFTPIGC
DAKGRIVLGYTEAELCTRGSGYQFIHAADMLYCAESHIRMIKTGESGMIV
FRLLTKNNRWTWVQSNARLLYKNGRPDYIIVTQRPLTDEEGTEHLRKRNT
KLPFMFTTGEAVLYEATNPFPAIMDPLPLRTKNGTSGKDSATTSTLSKDS
LNPSSLLAAMMQQDESIYLYPASSTSSTAPFENNFFNESMNECRNWQDNT
APMGNDTILKHEQIDQPQDVNSFAGGHPGLFQDSKNSDLYSIMKNLGIDF
EDIRHMQNEKFFRNDFSGEVDFRDIDLTDEILTYVQDSLSKSPFIPSDYQ
QQQSLALNSSCMVQEHLHLEQQQQHHQKQVVVEPQQQLCQKMKHMQVNGM
FENWNSNQFVPFNCPQQDPQQYNVFTDLHGISQEFPYKSEMDSMPYTQNF
ISCNQPVLPQHSKCTELDYPMGSFEPSPYPTTSSLEDFVTCLQLPENQKH
GLNPQSAIITPQTCYAGAVSMYQCQPEPQHTHVGQMQYNPVLPGQQAFLN
KFQNGVLNETYPAELNNINNTQTTTHLQPLHHPSEARPFPDLTSSGFL

SEQ ID NO: 3 (IDO1 human gene)
See NCBI Gene ID: 3620

SEQ ID NO: 4 (AhR human gene)
See NCBI Gene ID: 196
```

The invention claimed is:

1. A method of stimulating the immune system in a subject in need thereof, the method comprising: administering an agent that increases the level or activity of indoleamine 2,3-dioxygenase (IDO1) to the subject, and wherein the agent is a compound of Formula (I):

FORMULA (I)

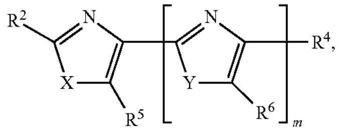

wherein:

m is 0, 1 or 2;

X and Y are independently O or S;

$R^2$, $R^4$, $R^5$ and $R^6$ are independently H, $C_1$-$C_6$alkyl, $-(CH_2)_nC(O)R^7$, $-(CH_2)_nNHC(O)-R^7$, $-(CH_2)_nC(O)N(R^7)_2$, $C_2$-$C_6$ alkenyl, $C_2$-$C_6$alkynyl, $N(R^7)_2$, $-(CH_2)_nC(O)OR^7$, halogen, $CF_3$, $SR^7$, $OR^7$, aryl, heteroaryl, cyclyl or heterocyclyl, each of which can be optionally substituted;

$R^7$ is H, $C_1$-$C_6$alkyl, heterocyclyl, heteroaryl, aryl, cyclyl, $C_2$-$C_6$alkenyl, or $C_2$-$C_6$alkynyl, each of which can be optionally substituted; and n is 0, 1,2, 3, 4, 5 or 6, or a pharmaceutically acceptable salt thereof.

2. The method of claim 1, wherein the agent is an activator of IDO1.

3. The method of claim 1, wherein m is 0 or 1.

4. The method of claim 3, wherein the compound is selected from the group consisting of: (i) 2,4-dimethyloxazole having the structure:

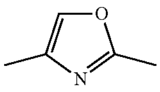
;

(ii) ethyl-4-methyloxazole-5-carboxylatre having the structure:

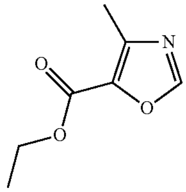
;

(iii) 2,4,5-trimethyloxazole having the structure:

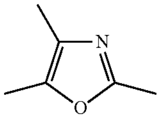
;

(iv) Frag-ortz having the structure:

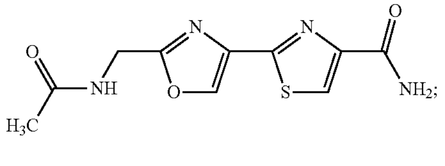 [SMILES: CC(=O)NCc1nc(-c2nc(C(N)=O)cs2)co1]

(v) Frag-tzoz having the structure:

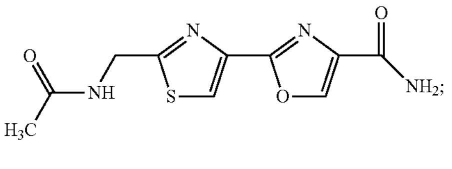 [SMILES: CC(=O)NCc1nc(-c2nc(C(N)=O)co2)cs1]

(vi) Frag-tz having the structure:

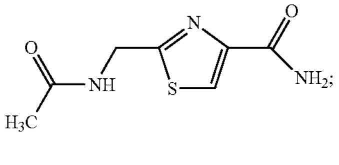

and (vii) Frag-oz having the structure:

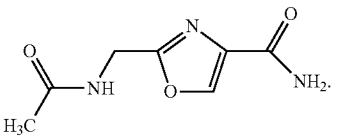

5. The method of claim 1, wherein the subject has or is diagnosed as having cancer, an immune deficiency, an autoimmune disease, an infection, or has had surgery.

6. The method of claim 1, wherein the agent is formulated with at least one pharmaceutically acceptable carrier and an adjuvant.

7. The method of claim 1, further comprising administering at least one immunotherapeutic agent or cell.

8. The method of claim 7, wherein the immunotherapeutic agent is a chemotherapeutic agent.

9. The method of claim 7, wherein the chemotherapeutic cell is a genetically engineered T cell, a dendritic cell, or a natural killer cell.

10. The method of claim 9, wherein the genetically engineered T cell is a chimeric antigen receptor (CAR) T cell.

11. The method of claim 4, wherein the compound is selected from the group consisting of: (i) Frag-ortz having the structure:

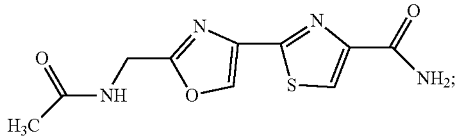 [SMILES: CC(=O)NCc1nc(-c2nc(C(N)=O)cs2)co1]

(ii) Frag-tzoz having the structure:

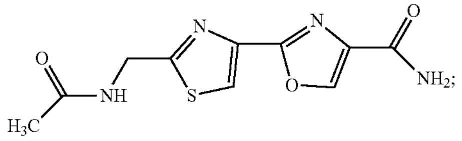 [SMILES: CC(=O)NCc1nc(-c2nc(C(N)=O)co2)cs1]

(iii) Frag-tz having the structure:

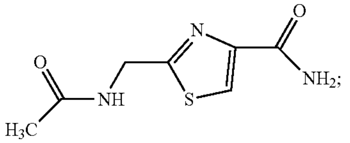

and (iv) Frag-oz having the structure:

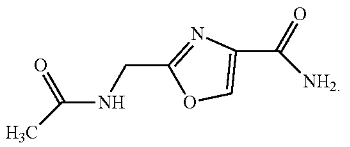

12. The method of claim 11, wherein the compound is Frag-oz having the structure:
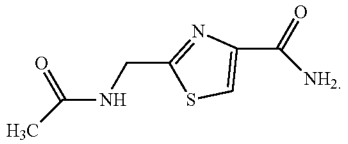
13. The method of claim 1, wherein $R^4$ is $—(CH_2)_nC(O)N(R^7)_2$.
14. The method of claim 13, wherein $R^4$ is $—C(O)NHCH_3$.
15. The method of claim 1, wherein $R^2$ is $—(CH_2)_nNHC(O)—R^7$.
16. The method of claim 15, wherein $R^2$ is $—CH_2NHC(O)CH_3$.
* * * * *

SEQUENCE LISTING

<160> NUMBER OF SEQ ID NOS: 4

<210> SEQ ID NO 1
<211> LENGTH: 403
<212> TYPE: PRT
<213> ORGANISM: Homo sapiens

<400> SEQUENCE: 1

```
Met Ala His Ala Met Glu Asn Ser Trp Thr Ile Ser Lys Glu Tyr His
1               5                   10                  15

Ile Asp Glu Glu Val Gly Phe Ala Leu Pro Asn Pro Gln Glu Asn Leu
            20                  25                  30

Pro Asp Phe Tyr Asn Asp Trp Met Phe Ile Ala Lys His Leu Pro Asp
        35                  40                  45

Leu Ile Glu Ser Gly Gln Leu Arg Glu Arg Val Glu Lys Leu Asn Met
    50                  55                  60

Leu Ser Ile Asp His Leu Thr Asp His Lys Ser Gln Arg Leu Ala Arg
65                  70                  75                  80

Leu Val Leu Gly Cys Ile Thr Met Ala Tyr Val Trp Gly Lys Gly His
                85                  90                  95

Gly Asp Val Arg Lys Val Leu Pro Arg Asn Ile Ala Val Pro Tyr Cys
            100                 105                 110

Gln Leu Ser Lys Lys Leu Glu Leu Pro Pro Ile Leu Val Tyr Ala Asp
        115                 120                 125

Cys Val Leu Ala Asn Trp Lys Lys Lys Asp Pro Asn Lys Pro Leu Thr
    130                 135                 140

Tyr Glu Asn Met Asp Val Leu Phe Ser Phe Arg Asp Gly Asp Cys Ser
145                 150                 155                 160

Lys Gly Phe Phe Leu Val Ser Leu Leu Val Glu Ile Ala Ala Ala Ser
                165                 170                 175

Ala Ile Lys Val Ile Pro Thr Val Phe Lys Ala Met Gln Met Gln Glu
            180                 185                 190

Arg Asp Thr Leu Leu Lys Ala Leu Leu Glu Ile Ala Ser Cys Leu Glu
        195                 200                 205

Lys Ala Leu Gln Val Phe His Gln Ile His Asp His Val Asn Pro Lys
    210                 215                 220

Ala Phe Phe Ser Val Leu Arg Ile Tyr Leu Ser Gly Trp Lys Gly Asn
225                 230                 235                 240

Pro Gln Leu Ser Asp Gly Leu Val Tyr Glu Gly Phe Trp Glu Asp Pro
                245                 250                 255

Lys Glu Phe Ala Gly Gly Ser Ala Gly Gln Ser Ser Val Phe Gln Cys
            260                 265                 270

Phe Asp Val Leu Leu Gly Ile Gln Gln Thr Ala Gly Gly Gly His Ala
        275                 280                 285

Ala Gln Phe Leu Gln Asp Met Arg Arg Tyr Met Pro Pro Ala His Arg
    290                 295                 300

Asn Phe Leu Cys Ser Leu Glu Ser Asn Pro Ser Val Arg Glu Phe Val
305                 310                 315                 320

Leu Ser Lys Gly Asp Ala Gly Leu Arg Glu Ala Tyr Asp Ala Cys Val
                325                 330                 335

Lys Ala Leu Val Ser Leu Arg Ser Tyr His Leu Gln Ile Val Thr Lys
            340                 345                 350

Tyr Ile Leu Ile Pro Ala Ser Gln Gln Pro Lys Glu Asn Lys Thr Ser
        355                 360                 365
```

-continued

Glu Asp Pro Ser Lys Leu Glu Ala Lys Gly Thr Gly Gly Thr Asp Leu
370 375 380

Met Asn Phe Leu Lys Thr Val Arg Ser Thr Thr Glu Lys Ser Leu Leu
385 390 395 400

Lys Glu Gly

<210> SEQ ID NO 2
<211> LENGTH: 848
<212> TYPE: PRT
<213> ORGANISM: Homo sapiens

<400> SEQUENCE: 2

Met Asn Ser Ser Ser Ala Asn Ile Thr Tyr Ala Ser Arg Lys Arg Arg
1 5 10 15

Lys Pro Val Gln Lys Thr Val Lys Pro Ile Pro Ala Glu Gly Ile Lys
20 25 30

Ser Asn Pro Ser Lys Arg His Arg Asp Arg Leu Asn Thr Glu Leu Asp
35 40 45

Arg Leu Ala Ser Leu Leu Pro Phe Pro Gln Asp Val Ile Asn Lys Leu
50 55 60

Asp Lys Leu Ser Val Leu Arg Leu Ser Val Ser Tyr Leu Arg Ala Lys
65 70 75 80

Ser Phe Phe Asp Val Ala Leu Lys Ser Ser Pro Thr Glu Arg Asn Gly
85 90 95

Gly Gln Asp Asn Cys Arg Ala Ala Asn Phe Arg Glu Gly Leu Asn Leu
100 105 110

Gln Glu Gly Glu Phe Leu Leu Gln Ala Leu Asn Gly Phe Val Leu Val
115 120 125

Val Thr Thr Asp Ala Leu Val Phe Tyr Ala Ser Ser Thr Ile Gln Asp
130 135 140

Tyr Leu Gly Phe Gln Gln Ser Asp Val Ile His Gln Ser Val Tyr Glu
145 150 155 160

Leu Ile His Thr Glu Asp Arg Ala Glu Phe Gln Arg Gln Leu His Trp
165 170 175

Ala Leu Asn Pro Ser Gln Cys Thr Glu Ser Gly Gln Gly Ile Glu Glu
180 185 190

Ala Thr Gly Leu Pro Gln Thr Val Val Cys Tyr Asn Pro Asp Gln Ile
195 200 205

Pro Pro Glu Asn Ser Pro Leu Met Glu Arg Cys Phe Ile Cys Arg Leu
210 215 220

Arg Cys Leu Leu Asp Asn Ser Ser Gly Phe Leu Ala Met Asn Phe Gln
225 230 235 240

Gly Lys Leu Lys Tyr Leu His Gly Gln Lys Lys Lys Gly Lys Asp Gly
245 250 255

Ser Ile Leu Pro Pro Gln Leu Ala Leu Phe Ala Ile Ala Thr Pro Leu
260 265 270

Gln Pro Pro Ser Ile Leu Glu Ile Arg Thr Lys Asn Phe Ile Phe Arg
275 280 285

Thr Lys His Lys Leu Asp Phe Thr Pro Ile Gly Cys Asp Ala Lys Gly
290 295 300

Arg Ile Val Leu Gly Tyr Thr Glu Ala Glu Leu Cys Thr Arg Gly Ser
305 310 315 320

Gly Tyr Gln Phe Ile His Ala Ala Asp Met Leu Tyr Cys Ala Glu Ser
325 330 335

-continued

```
His Ile Arg Met Ile Lys Thr Gly Glu Ser Gly Met Ile Val Phe Arg
            340                 345                 350

Leu Leu Thr Lys Asn Asn Arg Trp Thr Trp Val Gln Ser Asn Ala Arg
        355                 360                 365

Leu Leu Tyr Lys Asn Gly Arg Pro Asp Tyr Ile Ile Val Thr Gln Arg
    370                 375                 380

Pro Leu Thr Asp Glu Glu Gly Thr Glu His Leu Arg Lys Arg Asn Thr
385                 390                 395                 400

Lys Leu Pro Phe Met Phe Thr Thr Gly Glu Ala Val Leu Tyr Glu Ala
                405                 410                 415

Thr Asn Pro Phe Pro Ala Ile Met Asp Pro Leu Pro Leu Arg Thr Lys
            420                 425                 430

Asn Gly Thr Ser Gly Lys Asp Ser Ala Thr Thr Ser Thr Leu Ser Lys
        435                 440                 445

Asp Ser Leu Asn Pro Ser Ser Leu Leu Ala Ala Met Met Gln Gln Asp
    450                 455                 460

Glu Ser Ile Tyr Leu Tyr Pro Ala Ser Ser Thr Ser Ser Thr Ala Pro
465                 470                 475                 480

Phe Glu Asn Asn Phe Phe Asn Glu Ser Met Asn Glu Cys Arg Asn Trp
                485                 490                 495

Gln Asp Asn Thr Ala Pro Met Gly Asn Asp Thr Ile Leu Lys His Glu
            500                 505                 510

Gln Ile Asp Gln Pro Gln Asp Val Asn Ser Phe Ala Gly Gly His Pro
        515                 520                 525

Gly Leu Phe Gln Asp Ser Lys Asn Ser Asp Leu Tyr Ser Ile Met Lys
    530                 535                 540

Asn Leu Gly Ile Asp Phe Glu Asp Ile Arg His Met Gln Asn Glu Lys
545                 550                 555                 560

Phe Phe Arg Asn Asp Phe Ser Gly Glu Val Asp Phe Arg Asp Ile Asp
                565                 570                 575

Leu Thr Asp Glu Ile Leu Thr Tyr Val Gln Asp Ser Leu Ser Lys Ser
            580                 585                 590

Pro Phe Ile Pro Ser Asp Tyr Gln Gln Gln Gln Ser Leu Ala Leu Asn
        595                 600                 605

Ser Ser Cys Met Val Gln Glu His Leu His Leu Glu Gln Gln Gln Gln
    610                 615                 620

His His Gln Lys Gln Val Val Val Glu Pro Gln Gln Gln Leu Cys Gln
625                 630                 635                 640

Lys Met Lys His Met Gln Val Asn Gly Met Phe Glu Asn Trp Asn Ser
                645                 650                 655

Asn Gln Phe Val Pro Phe Asn Cys Pro Gln Gln Asp Pro Gln Gln Tyr
            660                 665                 670

Asn Val Phe Thr Asp Leu His Gly Ile Ser Gln Glu Phe Pro Tyr Lys
        675                 680                 685

Ser Glu Met Asp Ser Met Pro Tyr Thr Gln Asn Phe Ile Ser Cys Asn
    690                 695                 700

Gln Pro Val Leu Pro Gln His Ser Lys Cys Thr Glu Leu Asp Tyr Pro
705                 710                 715                 720

Met Gly Ser Phe Glu Pro Ser Pro Tyr Pro Thr Thr Ser Ser Leu Glu
                725                 730                 735

Asp Phe Val Thr Cys Leu Gln Leu Pro Glu Asn Gln Lys His Gly Leu
            740                 745                 750

Asn Pro Gln Ser Ala Ile Ile Thr Pro Gln Thr Cys Tyr Ala Gly Ala
```

-continued

```
        755                 760                 765

Val Ser Met Tyr Gln Cys Gln Pro Glu Pro Gln His Thr His Val Gly
    770                 775                 780

Gln Met Gln Tyr Asn Pro Val Leu Pro Gly Gln Gln Ala Phe Leu Asn
785                 790                 795                 800

Lys Phe Gln Asn Gly Val Leu Asn Glu Thr Tyr Pro Ala Glu Leu Asn
                805                 810                 815

Asn Ile Asn Asn Thr Gln Thr Thr Thr His Leu Gln Pro Leu His His
            820                 825                 830

Pro Ser Glu Ala Arg Pro Phe Pro Asp Leu Thr Ser Ser Gly Phe Leu
        835                 840                 845


<210> SEQ ID NO 3
<211> LENGTH: 14900
<212> TYPE: DNA
<213> ORGANISM: Homo sapiens

<400> SEQUENCE: 3

actgaggggc accagaggag cagactacaa gaatggcaca cgctatggaa aactcctgga     60

caatcagtaa agagtaccat attgatgaag aagtgggctt tgctctgcca aatccacagg    120

taagagaagg cagtaaaatg tgggaaaatg cattcttctt ctcattcctt acctggccaa    180

gttaacttct actgaacaac tgtggttcag taacttctag taaacaaaca cataaagctg    240

tgtaaaaatt agagagctgt aataactgca tctcacttaa tttgtcttac attttctccc    300

tagaaatgga gtcatctatg catttcttac ttacctaaca tggatacgga gagtggtgag    360

aaaggaaact atagaaagtg tatcagcttt acataagaat tatatagtaa aatacaaaca    420

atgaggttat tacagttgta ttttgagaaa aggtgttttg caaaagccag agttttaaat    480

gagccatgag tcaaacagaa atccctttct cttagggata taacttaaat tatgcaaaac    540

atgtgtttct aatttgatgg ggtttatgag attgcacatc aagcaccttc catgttatat    600

tatcattgct tgttatttac tgagcgtaag attcaagtga gagtctgaac tacctttttt    660

cttgtttgca agtcttacct ataaagtaca aggtatgtgg aaaaaaggtt tgccttaaaa    720

actacatttt ctagtctgtc ttctaacgaa tgctatgtaa accaatttat catcaatatt    780

ttaattatca aatacagcat ttttctaagc aatttacaaa ttaacccttt ccattctcat    840

agccatccca aaagttatgt atgttattta tttattatta ttattattat tttgagatgg    900

agtctcgctc tgtcacctgg gctggagtgc agtggcacga tctcagctca ctgcaacctc    960

tgcctcctag gttcaagcga ttctcctgcc tcagcctccc aagtagctgg gattataggc   1020

acctgccacc acacccagct actttttttgt atttttagta gagacggggt ttcaccatgt   1080

tggccaggct ggtctcgaac tcctgacctc aggtgatcca ccgatcttgg cctcccaaag   1140

tgctaggatt acaggcgtga gccactgcac ccggccagaa acgtatgtta ttatcctcat   1200

gttcctaatg agaagtataa ggcatgcaga atgtaattat caaactatgt agctagcaag   1260

tgccagaggc cagtatgagc ctaagcagcc tgtctccaga gtctatgatc ttaaaaccat   1320

tattccacac tgcctctctt aagaagggat aataagacat tgcttatttt ctttctttca   1380

atcttcagtt taacaaggta catgggattc caggagaaga tttctatgaa catgttataa   1440

taattctgta gacgagtgta tttttgtttg tagctcaaac agttacagtc cacatactag   1500

agagcacctt taaacacagc aaatgtttag tcagagattt caacctaact gtgcttagaa   1560

atgaaatcct gtaaacaatt tggtgatact ggcaaattta aagcatctac ctccttccaa   1620
```

```
tctaatttc ctcttcagat tgttaattaa agaaaatgaa aagtatactt taattttatt   1680
gccaaaagca ctagtttgct ttattcatgc aaaacaataa tactcaaact tgctatttgc   1740
ccgcagatct acaaaaatgc tgggactgga tgatttcaag gatgtactta tcaatggtac   1800
aataaaacca tctttttcag aaactactaa actttgtatc atgggttttg tttctcagat   1860
attcgattct ccttaaaaat gcaacaactg tgataattat gaatacctgt agaacagatt   1920
ccaaggagta aagcaaaacc ccaaaagaaa acaaacgaaa ctcttcctta gctacttaaa   1980
aaaaagattc tcggctgggg acgggtggct cacgcctgta atcccagcac tttgggagac   2040
ggaggcgggt ggatcatgag gtcaggagtt cgagaccagc ctggccaatg tggtgaaacc   2100
ccgtctctac taaaaaaata caaaaattcg cagggcatag tggcatacac ctgtaatcct   2160
cgctactcag gaggctgagg caggagaatc gcttgaacct gggagtcgga ggttgcagtg   2220
agctgagatc acgccaccgc actccagcct gggtgacaga gcgagactcc atctcaggaa   2280
ataataataa taatagtaat tctgacaagg tgcagtggct tacacctgta atcccagcac   2340
tttgggaggc taaggtgggt ggatcacttg aggtcaggag tttgagacca gcctggccaa   2400
catggtgaaa cccctgactc tactaaaaat gcaaaaaaaa attacccagc atgttggtgt   2460
gcccgtagtc ccagctactt gagaggctaa gacaggagaa ttgtttgaac ctgggaggcg   2520
gaggttacag tgaactgaga ttgcgccact gcactccagc ctgggtgaca gagtgaggcc   2580
ctgtctgaaa acaataacaa taataacaat tctgctagct gagatgctgc agaagctaga   2640
ttcactgtcc cggaaacatg aaaaaaaatt attggttact tttatttctt cactgaagat   2700
ctttcctaga aattatgaac caaaaaatgt ctgttttatc tctcataatc tatctgcttc   2760
ttagtccaaa ggaaaataat atgttttctg attccatata gatagataca aggcacaatc   2820
tctaatctag cagaatttga atgatcctca gtatgattca tttttaattt atattatacc   2880
atttagggat cctctgaacc agagcatatt actgattaaa ttttatactt gttgaaagtg   2940
ctgtcaaata aaatgatcat cattgtgcag aacaaaaaag tattctgtta tttggagaaa   3000
atcacaacaa ccaaaaaaat aagatgtact agatggtgaa acatagaata aaaacaacaa   3060
aaatacattt attacatttc ttttgaaagt tggaaacttc acaataaact cgatatacaa   3120
aaatcgttat gtaaactgta taagcctggg tttccttatt tatgatacag agataacttc   3180
ttgggccatt acaataatta aatatgtatc ttttatatat atgaaattat cgagcagagt   3240
gcctagtcca ctattgacat ttaaaacatc tcattttcct tccattcaaa gaacttaaaa   3300
tctagccaag ataaaccaaa gtaggccagg cgcagtggct catgcctgta atcccagcac   3360
tttgggaggc cgaggcaggc agatcacctg aggttaggag gtcgagacca acttggccaa   3420
catggcaaaa ccccatctct actaaaaata caaaaattag ccaggcatgg tggctcatgc   3480
ctgtaatccc agctacttgg gaggctgagg caggagaatt gcttgaaccc aggagacaga   3540
agttgtagtg agccaagatt gcgccactgc actccagcct gggcaacaga gtgagactcc   3600
aattcaaaaa agaaaagaaa agaaaaacca aagcagcaga taataattgt ttaacaattt   3660
gaaaaggcat aatccataga atttatagtg gaggagattg gtttcaaata gagtagtcag   3720
gaggatttta gtgaaacctt tgaggtgaac tttgaaaagc tgcaaatggc agtgtttgaa   3780
gagagaggaa gaggtggaac acagagaggg tcttcagccc tgcgtgtgca gatgacaaga   3840
cagaggctgg tgtttccaga caggtaagcc atatgccagg gcaacattgc acagaatgga   3900
tgtgaaggca aggcatacta tcagtgggaa gccaaatcta caataactgc tactactaaa   3960
taaagatctt tttttttttt caaggaaaat ctacctgatt tttataatga ctggatgttc   4020
```

-continued

```
attgctaaac atctgcctga tctcatagag tctggccagc ttcgagaaag agttgagaag   4080
gtttgacata tgtattacat ttgtcttctt gtatagcttc ttaacattgt taacttggtt   4140
ttgaagcata aaacattact gagattgatt tgagtcaatt gctccatttg ttttcagtta   4200
aacatgctca gcattgatca tctcacagac cacaagtcac agcgccttgc acgtctagtt   4260
ctgggatgca tcaccatggc atatgtgtgg ggcaaaggtc atggagatgt ccgtaaggtt   4320
tggagatttt ctcagatttc ttatgctatg tgacagattt tcatctaatt tacatttaac   4380
tttccaaaaa ttttctaaaa gcattataac tgcatcatgc aaagtttaga taacacgaca   4440
aaatgataaa gaaaatatgc cctggcttga catgtccact gttatcatta ttatattttt   4500
agtcttttac ttcatttttc atcctgtatt ttatctggca accctaatta cataaaacta   4560
atacagactg caatatctaa cctttaaaac acacatgggc ctcccagcac tttgagaggc   4620
caaggccgga ggatcacctg aggtcaggag ttcaagacca acttggctaa catagtgaaa   4680
ccccatctct actaaaaata caaaaaatag ccaggcatgg tggcaggtgc ctataatccc   4740
agctactcgg gaggctgagg tgggagaatc acttgaacct gggaggcaga ggttgcagtg   4800
agccgagatc ctgccactgc gctccagcct gggggacagg agcaagactc catctcaaaa   4860
aaaaaaaaaa aaaaaaaaac aacaacaaca acaacaaaaa acctaactac tgtattttaa   4920
tcaggtcttg ccaagaaata ttgctgttcc ttactgccaa ctctccaaga aactggaact   4980
gcctcctatt ttggtttatg cagactgtgt cttggcaaac tggaagaaaa aggatcctaa   5040
taagtatgta aacagtgata acaacaggaa tttttggagt gtgtgccgat taaataaaac   5100
aggggttgtt cattggctta attttgggca gcgcagcttt cctctcagct gggtatggtt   5160
cctctcagtt cctcggctgg gtacggtttc ttggactgct gtgtctacca ctacaaatgt   5220
acacatatgt gacaggtgta tagttaacac agtaaaatgc acaaatctta agtgttcagc   5280
ttgaatttaa ctattatata catacataca cccaccattc tcagtaagat acagaatttt   5340
ttatcacctc agaaaatttc tttgtgcctc tttcaattcc ctttcctgcc acagacaaat   5400
atatttttat ttgccttatc aaaaattaga tgatttttgt tattgggttt catatcaatg   5460
aaaccacaga gtatagactc ttgtgtctgg cttcttttga tgagcatgtc tttgagattc   5520
tattaattta atttttagc agccaattgt ggttaagagt caacacatct ttaattacag   5580
gcagcaatga ctggtttctc agagcagtct gctcaggata taggtgattt ttacccattt   5640
aggcataaga tctgctacaa taaaggaaag ggagaaccaa agcccacgtc tctgggtgtg   5700
tgcctgtaga aaaatattct gcaaatggga atatcataaa atgaaaggat tcaatctaga   5760
aagtttcttc ttattaaaaa ttagtttttt taaaaaaaaa ttcaccggga atggtggcgt   5820
atgtctgtgg tcccagctac acagggagtt aaggcaggag gatcacttca gcccaagaag   5880
ttgaggctgc agtgagccat gttcgtgcca ctgcacacca gcctgggtga cagaatgaga   5940
ccctgtctca aaaaaataaa aataaaacaa ctagttttga ctgtccatgt gtgttccttg   6000
catatttaat tatttcattc atttgtaagt tattaagtta aatgtaatgc ctactgaaga   6060
aacattttaa taagcttttt ctttttacct atgtcttacc tctgatagta gcattcaatc   6120
aaatagcaac aactcatcat tatttgatgt taaattggtt ttctttctct cttccaattg   6180
gtccattgct tcatggctgc tttcataagg cccctgactt atgagtaagt atctgattct   6240
tgtttgattc taagaattat ttgttactta tagttgaatg taggtttatc aatagactcc   6300
aaatgcattt ttaaatgatt aattgaattc agccaaaaaa taatttaagt gactatttag   6360
```

```
agaacaaata atctcagtct ttaattgtat ctatgattgt gttacaacta tgtctatctg   6420
atattatagc tatagatata tacaagaata ctactcaaat acatctgtag gaaattaata   6480
tgcaaacata caaaatgcac atacatctgt gtatctatga tttaataact cccatgtcca   6540
taactagtta ccggtgtcaa taagtaacca tataccaact tgttcttttt gacccaatcc   6600
ttactacttt tgacctataa tatatactaa acataggcta agagatggaa aacctgggct   6660
gggtgcatgg ctcacgcctg taatccctgc actttgggat gccgaggcag gtggatcacc   6720
tgaggtcagg agttcaagac cagcctgggc aacatggtga aacctcgtct ctactaaaaa   6780
tacaaaaaat tagccgggcc tggtggcggg cgcctgtaat ctcagctact caggaggctg   6840
aggcaggaga atcaattgaa cccaggaggt ggaggttgca gtgagcggaa atcacgccac   6900
tgcattccag cctgggtgac agaacaagac tccatctcaa aaaaaaaaaa aagatggaaa   6960
aactaaggta aatatcatca gtataaaccc accttggtga agctagacta atgaagagga   7020
aaggcagtat atgaaaatta tgtaaattgc gatatgataa agataaggca taagaagtta   7080
aagtattggg atccctaacc aaataaaagg agtgatgggg gaacccttga agcaagttat   7140
ttgaggaatt agctagagga aaaaggtaag agtattcata gcggaagaaa cagcaaaagt   7200
gagaccttga agtgacaaac atcttggtgc gttatcaaag ctgaaggatg gctaatgtca   7260
ctgataataa gtgataaaaa taacagtgtg agaaaaagat taattttttt ttttaaagat   7320
cgctgggaaa agtgggtgaa tcacctgagg tcaggcattc gagaccagcc tggccaacat   7380
agtgaaaacc ctcctcttct gaaaatgcaa aaattagcgg ggcatggtgg cacatgcctg   7440
taatctcagc tactcgggag actgaagcag gagaatagct tgaacccagg aggcagatgt   7500
ggcagtgaga cgagattgtg ccattgcact ccagcctggg cgacagagta agaccccatc   7560
tcaaaaaatt aaaataaaaa taaataaaga ttatgtagga ttttattagc tatgataagg   7620
agttaaaaca gtatcttaag ggagaaactg gaaggttttt aaaaacgagg atgacatcag   7680
cagtcagtct cactttacag atgagaacac caaggcagac ggtgtcatat cttgctcaag   7740
gtcacacagc aagtaagttg cagagatggt ctggcttcag ataccatgaa tttaaccacc   7800
acaaaactca tagatataca gatagtaaga ctatgtttgc accaacgccc aaacttcaat   7860
taaaaagaaa aacagggtct aatcagttat ttgaatttcg cagtcaattc ctttgtaaag   7920
catataaacc actgagaaat tgaattaggc tcacaaatta aaatgtgaat atgaatataa   7980
ttatttaaac aaaagactac ctcttaaaac tctacctcgc agatatcctg tgagaagttg   8040
acgggataat agaaacagaa ctagtttggg aatttctaat tctgagtgtt ttttgttgtt   8100
gttgttttgt tttgtttatt tgttttctga gacgagtctc gctcttgtcg cccaggctgg   8160
agtgcaatgg agtgatcttg gctcactgca acctccgcct cctgtgttca agtgattctc   8220
ctgcctcagc ctcccgagta gctgggatta caggcgccca tcaccatgcc cacctaattt   8280
ttgtattctt agtagagacg gggtttcacc acattggcca ggctggtctc aaactcctga   8340
cctcaggtga tccacccgcc ttggcctcct aaagtgccgg aattacagat acagatgtga   8400
actaccatgc ccggccctag ttctgagttc taatatgaaa ctttaggtct cagtttaacc   8460
tacttactat taattatatg atcttggaca atgggcctaa aaaaggagtc ttaatattcc   8520
caactacata atggagatag taaggcctgc cacacctctc tcataaaatt atgttgaaac   8580
taaaatagca taaataaaaa tgtcaaaaaa tatcccataa tttttgctaa acttcttgcc   8640
ttccttatcc aatttcctca ggaacatgga cgttttgttc tcatttcgtg atggagactg   8700
cagtaaagga ttcttcctgg tctctctatt ggtggaaata gcagctgctt ctgcaatcaa   8760
```

```
agtacgtcta tcctcacttc aaaatttata tgtcaattta cgtaagcaga gcaatcactt   8820
cggagcctaa actatactaa gcatgagtta actttatcct taacaagtac aacatgggat   8880
catttaattg ggggtaaagg atcaattatt tatttttgtg tattacctaa aatataaaat   8940
ctcagagcca tatacttaaa atccaacttg aaacctctgt aggagataaa aattttcaat   9000
aaaatctggc tttggaacta tgatacagtg tcataaattc aatagttttg attatcaaaa   9060
atagaaatga aacatataca actatataaa tatctttaaa ttaaatgcta tgtgaataaa   9120
aacaaatcca agcttctata aatgtaagga aattagtcaa atagagtgtc cagcccagga   9180
aagaaatgta aaaatcccaa atttaattta tggattaaga cgggggaatt tggcagggca   9240
cagtggctca cacctgtaat cccagcactt tgggaggctg aagtgggcgg atcacttgaa   9300
gtcaggagtt cgagaccagc ctggccaaca tggcgaaacc ccgtctctac taaaaatata   9360
aaaattagcc gggcatggtg gtgggcacct gtagtcccag ctactcagga ggctgaggca   9420
ggagaatggc gtgaacccgg gaggcagagc ttgcagtgag ctgagatcgc gccactgcac   9480
cccagcctgg acaactgagc gagactccgt ctcaaaaaaa aaaaaaaaaa agaaagaaag   9540
aaaaccttaa atgtttgtgt tttgtttgtt tgttttaggt aattcctact gtattcaagg   9600
caatgcaaat gcaagaacgg gacactttgc taaaggcgct gttggaaata gcttcttgct   9660
tggagaaagc ccttcaagtg tttcaccaaa tccacggcaa gtgttgtgtg cagtgcaata   9720
gtctaggctg acaagtcaaa tgttccaggt gtagaatagt tgaaaaaagg gaagcaaaaa   9780
gcaactatca cttagtatgt tttcacttta ggtattttat cttactaaac cattccactt   9840
tctatgtggt aggtttcatt atctccattt tataagtaaa gtcatctaaa ttcagaaaga   9900
cagggtaaat gacttcagat tccacaggcg gtgaagccag agttccaagc tgggtctatt   9960
taacactaag gaacttcctt gcctcccgct aaaaacctta gagaaacttt ccacatggga  10020
gggtggtttt aagtcccgaa aaaaaaaaaa tagcttctgc ttgataagaa ctccttccta  10080
attctgtttt tttacaaatt aagaaacaat acagaaaagt cattgaggtc aaaagttgtt  10140
gcaaaattaa cagctaaaaa actacccaca aaaaaacaca caaaaaagtg cataagcagt  10200
aatttgcaat aggaaatctg ccctactgaa cagactcaac aaatacttga ttgtttctct  10260
ctgggttttg agttattgct gtttagtcct tggcaagaag ctagattttc aaatcaagta  10320
gggtaggaga ctgagtgcgg tggctcatat gtgtagtttc cagctacttg ggaggctgag  10380
gtgggaagat tgcttgagcc caggagttgg ggctgcagtg agctatgatc aatacattcc  10440
agcctgagtg atgaagtgag accctgtctc caaacaattt ttaaaaattt taaaaataga  10500
gagggaaatc tagtttctag ggttttgttt tggtttgttt tgatttgttt tttttgtctt  10560
ttggtttgtt tctttatgta aacagtttac ttgttacgtc agtaagcacg taaagtaaag  10620
tagtgctaaa taaatagata cagtttaatg ggcttcctgg aagagggtag gaaagtgaat  10680
gcttatctgc aggggctttg tttagcatag actgacctaa tgccttttcc tgcagcctgt  10740
gccaaaatcc attatcagtt gtacacaaca ccttgatttc cctgtatacc tctgatgctg  10800
cttaattaaa catattccat ctttttacag atcatgtgaa cccaaaagca tttttcagtg  10860
ttcttcgcat atatttgtct gggtatgtag tcttatgttt gaatttgttt gctctcactt  10920
aacaaagaac accaccaaat tctcttggtt ggtccctaat atccattggg tttggctaac  10980
aatttacatc caaaaattca catggtagaa aaatactaga ctgttctgtt atcacttggc  11040
caggaatgta ctggagtggg ggacaggaaa gctagttatt ttaaaaagag tggtctgtgc  11100
```

```
tagtacaaag gtaagattcc attcctagaa tagttatgcc aaatctgctc aggattatat  11160
tatttactat tctcatgctt gaaaatgagc aggggcaagg gggtatgaaa aaaggatcat  11220
gaaatccatc tcttgtcacc ttctgttcag cactagtgca agatttggta cctgaaaatt  11280
agcaattaac ctaaagaatg atttttcttt ttttctttct ttcctctgat agctggaaag  11340
gcaacccccca gctatcagac ggtctggtgt atgaagggtt ctgggaagac ccaaaggagt  11400
ttgcaggggg cagtgcaggc caaagcagcg tctttcagtg ctttgacgtc ctgctgggca  11460
tccagcagac tgctggtgga ggtgagtgga aaataacaag aaataattat ctcttatgtg  11520
aatacaatag tatttggata tctacaaagc accttcccat cagcatctta tctgagctta  11580
tctgatagtt ttagcagaat caggcaagta gggatttggt tgccatgatc ccattttaaa  11640
aatgaagatg cagaaactta atgagagtca gtgacaggtt ccttgtgaac cagctagaaa  11700
gtggcagagc tggccaggtg cggtgactca agcctgtaat cctagcactt cgggagacct  11760
aggcaggtgg atcacctgag gtcaggagtt tgagaccagc ctgaccaaca tggtgaaacc  11820
cggtctctac taaaaataca aaaactagct gagtgtggtg gtgggtgcct ctaatcccag  11880
ctactcggga gactgaggca ggagaatcgc ctgaacccca caggcagagg ttgcagtgag  11940
ccaagatcgt gctactgtac tccagcctgg gcaaaagagc aaaactccat ctcaaaataa  12000
aaataaaaaa taaaaagcca ggtgcagtcg ctcacgcctg taatcctagc actttgggag  12060
gccgaggcgg gcggatcaca agatcaggag atcgagacca tcctggctaa cacggtgaaa  12120
ccctgtctct actaaaaata caaaaaagta gctgggcatg gtggcgggtg cctgtagtcc  12180
cagctactcg ggagactgag gcaggagaat ggcgtgaacc caggaggcgg agcttgcagt  12240
gaaccgatat ggcgccactg cactccagcc taggcaagag tgcgagactc catctcaaaa  12300
aaaattaata aataaaaaca aaaagaaaaa taaaataaaa taaattggca gagctttcct  12360
cacacccaag ttccatcttg aaatctgaac atgtctataa agactggttg actccggtga  12420
agccaatatc acatgctctg aaaatgtatg atcagactca gaaagagaca ctcacctgca  12480
aatgagacag ggctgttagt ggggagataa agacctcagt gacaagcaga gtctgggccc  12540
tgctcttgtt cagctgtccc gtggccccag ccacccagag caatgcctgc accaaagttt  12600
aaaggtgagc cacattcatt gtatgccttc taggggctta gctggagggg aggaataagc  12660
tccaagaaga acttcttttt aattttctct gttttgttaa acttctgttt aacagtcaaa  12720
ggggaaagca tcgggctggg taaaaacatg agtttttctt aatttgagca ctcattttta  12780
aaattttttt atcatattta actttttat tttagattca ggggatacat gtgcaggctt  12840
attacacagg tataatgggt gatgctgatg tttgggcttc taatgatccc ctcacccaag  12900
tatagaacat agtgcccaat aggtagtttt tcaacctttg ctttccttcc tccctccctc  12960
ccctatttga aatcctcact gtctattgtt cctatctttg tgtccatgtg tactcaatat  13020
ttaactccca cttatcggtg agaacatgtg gtatttggtt ttctgtttct gcattatttc  13080
acttaggcta acttaagcta atggcctcca gctgcatcca tgttgctgtg aagcgcttga  13140
tttcattctt tttcatggct gtgtagtatt ccatggtgta catgtaccac attttctttg  13200
tcccatctac cattgatggg cacctgggtt cattccatgt ctttgctgtt gttgaacact  13260
catttaaaca caatctctta aactctctta agaatcagtc ataatctgtc aaatgcagat  13320
tatatatgcc ccttgtctat accatcagct tcttacagta gaaaagagag aaagaaagtg  13380
caaacaaagg ccaggcgcgg tggctcatgc ctgtaatccc agcactttgg gaggctgagg  13440
caggtggatc atctgaggtc aggagttcga gaccagcctg accaacatgg agaaaccctg  13500
```

tctctactaa aaatacaaaa ttagccgggc atggtggcgc atgcctgaaa tcccagctac 13560
tccggaggct gaggcaggag aattgcttga gcccgggagg cacaggttgc ggcgagccga 13620
gatcgtgcca ctgcactcca gcctggccga cagagcgaga ctctgtctca aaaaaaaaaa 13680
aaaaaagcgc aaacaaaaat acttattgtg agaaaatgag tttagctcat tcagttttca 13740
aaattaataa tattttacaa taattacgat tgctagtagc aagactaata gccaaacatt 13800
agccttcaaa tagaatgacc ttgacctcag tgaatgctat attggtgatc tcctgcccac 13860
tctgacctca ctctgccttt ctctcctgga ttggggaatg ctgtgacctc cgtatttcct 13920
ctttctcttt ttcctatagg acatgctgct cagttcctcc aggacatgag aagatatatg 13980
ccaccagctc acaggaactt cctgtgctca ttagagtcaa atccctcagt ccgtgagttt 14040
gtcctttcaa aaggtgatgc tggcctgcgg gaagcttatg acgcctgtgt gaaagctctg 14100
gtctccctga ggagctacca tctgcaaatc gtgactaagt acatcctgat tcctgcaagc 14160
cagcagccaa aggagaataa gacctctgaa gacccttcaa aactggaagc caaaggaact 14220
ggaggcactg atttaatgaa tttcctgaag actgtaagaa gtacaactga gaaatccctt 14280
ttgaaggaag gttaatgtaa cccaacaaga gcacatttta tcatagcaga gacatctgta 14340
tgcattcctg tcattaccca ttgtaacaga gccacaaact aatactatgc aatgttttac 14400
caataatgca atacaaaaga cctcaaaata cctgtgcatt tcttgtagga aaacaacaaa 14460
aggtaattat gtgtaattat actagaagtt ttgtaatctg tatcttatca ttggaataaa 14520
atgacattca ataaataaaa atgcataaga tatattctgt cggctgggcg cggtggctca 14580
cgcctgtaat cccagcactt tgggaggccg aggcgggcgg atcacaaggt caggagatcg 14640
agaccatctt ggctaacacg gtgaaacccc gtctctacta aaaatacaaa aaattagccg 14700
ggcgcggtgg cgggcacctg tagtcccagc tactcgggag gctgaggcag gagaatggcg 14760
tgaacctggg aggcggagct tgcagtgagc caagattgtg ccactgcaat ccggcctggg 14820
ctaaagagcg ggactccgtc tcaaaaaaaa aaaaaaaaag atatattctg tcataataaa 14880
taaaaatgca taagatataa 14900

<210> SEQ ID NO 4
<211> LENGTH: 47496
<212> TYPE: DNA
<213> ORGANISM: Homo sapiens

<400> SEQUENCE: 4
agtggctggg gagtcccgtc gacgctctgt tccgagagcg tgccccggac cgccagctca 60
gaacaggggc agccgtgtag ccgaacggaa gctgggagca gccgggactg gtggcccgcg 120
cccgagctcc gcaggcggga agcaccctgg atttaggaag tcccgggagc agcgcggcgg 180
cacctccctc acccaagggg ccgcggcgac ggtcacgggg cgcggcgcca ccgtgagcga 240
cccaggccag gattctaaat agacggccca ggctcctcct ccgcccgggc cgcctcacct 300
gcgggcattg ccgcgccgcc tccgccggtg tagacggcac ctgcgccgcc ttgctcgcgg 360
gtctccgccc ctcgcccacc ctcactgcgc caggcccagg cagctcacct gtactggcgc 420
gggctgcgga agcctgcgtg agccgaggcg ttgaggcgcg gcgcccacgc cactgtcccg 480
agaggacgca ggtggagcgg gcgcggcttc gcggaacccg gcgccggccg ccgcagtggt 540
cccagcctac accgggttcc ggggacccgg ccgccagtgc ccggggagta gccgccgccg 600
tcggctgggc accatgaaca gcagcagcgc caacatcacc tacgccagtc gcaagcggcg 660

-continued

```
gaagccggtg cagaaaacgt gagtgtcccg agcgcgtcct catcgcgggg gctgggcgct    720
caggcacgcg ggtgcgggag gcagccccac cccgccccca aatccctgcg atcctgggat    780
taggtccatt cccggcactg cccgtggaat cgaggtttgg aggccggctg ggagacagag    840
gacttggatt ctcccgtttt caatgattgc attttaaaaa ttgtcctccc acccatcctc    900
ttcccccgca ccagtgcata cacaccctct cacatttgca actttgttct ttctgatttg    960
gtcctgattt gttgacagct ctgatctgcc ttgggctaat ggattagtta gtataaacct   1020
gtcttgaaat ctccttccac ttttcatatc cgcatgggtt aggttagagg acggtcttaa   1080
ttctcattct tcgtagagtt tggtaaggcg agatgtttta aagagctaaa cacatgctga   1140
cttttacgaa ggggctgagt gcctctaaag gtactttttg gtccccacca actggctttg   1200
tgttgcgctc atatttactt atttggcagc aattttgtag cgctcatcgt gaccatatcg   1260
gtaaagtgga tagaagtggt agcaggtggg agtggatgca acggacagga tacggtggag   1320
gatttgtatt cttcagacat ctttttcgga agcttgctta tcacttttgg ggtggcttta   1380
gggtctgtaa aataaaagat ttagaactgc atttgagaga ggttttcatt cttaacatct   1440
acctctaatt cttttcccct tcaaagtttt cttctagttg agtgagtaca aacttgcttt   1500
tgtcgttgtc ggttgatttt ggtggaatat ttgtgtgaga tggccaattt tttgtgtgtg   1560
tcagaaaaaa ctatccgtgc tcaaaacatt tcctgttgtg aggtggttgt attcatgtgt   1620
ttattccaat ttttttattt ctagatctct gagttacttt acctacatgt gtttcaagtt   1680
ttcgtaaaca attttaagaa ctcttaaacg tcttctcaga ccaaatcaga agtgtgcatt   1740
ttgcttagac tccaactatc actaatggga accagaaaaa taacacttta agatttacat   1800
ttaaaaccag ttattggttt aaagtttcat tctaaaattt tagtttcctt tcagaatttc   1860
agttatcata gttcttcaga agtatactta tgaattggca ttaacagagg ataataatct   1920
ataaatagac tgatgaaaat ttggaagttt tatggtacag tgtgtcttaa gggaatattg   1980
tcaaaccagc agttttctac cttggcagtt tgagacatcg gttattaata cttttaattt   2040
tgtagaatgg tttcttatat taaagtatgt ttgtcttatt tgacattgtc attgatggtt   2100
aaagttggga ggcatcccaa atgtctgttc tatgtgttta ttaatataat aatacactta   2160
gcatcatata taataggggt gtcatgggtt ttatgtgtat ggtgagaaaa catgaagatc   2220
tccctgatgt gtttttaaga tactgggttt cagttagggt gttatcaaag gacctggatg   2280
gctttgtaaa caaaaacaaa tgccataatt ttgtattcat tacacagttt aacatttatg   2340
gattttggtt attttgcgta aaatgtactt tttattagat tatcctaata ttatacttac   2400
ttagttttta atatacttgt attaatttct tataatataa caaaagtatt ttttccattc   2460
acccacattt tgttagcata gatgtttatc agatctctgc tgagcaccgt atattgcttc   2520
taatcataca gatgccttaa atattaccag cttgctctgt aagaataggc tagtgctggc   2580
attttcatta tcaagtgaaa gtgtttatat aaattatttt tacctgaatg aaaaattgtt   2640
aactttataa tgcagttaat caaagtttat tttagaaatg aagtcattaa acctagtatt   2700
aaatttgagt tttaaaatta aactaccagt ttgtggccta atgagcccca aaacatgcca   2760
acattgggga aaatagatct tgttttgagc tgaaaatgct atccagacct acttaacttt   2820
gacctcttaa atgagagcca ttttatttta tttacagata aaatatgctg tagcattatt   2880
ataggactgt ttaaaaagac agccaattaa atataaattt tatggaatat aagtattcca   2940
taaaattttg gagtaaagta ggtgacaatt gtaacctgaa gctctttcaa tcttgagttg   3000
aatttattaa gaaaaatcaa ccccccctag tggcggctct cacattgaaa attatcttta   3060
```

-continued

```
ttagtaggaa atacatttta aatgtgttca atttaatccc actgaagtat ctccaacata   3120
gtagactctc aataaatatt tcctttcttt ttggagtaat gaaggttggg aaattaaagg   3180
ctctgaagca actttacgtc caattcatgt tcctaccttc aagaagaaaa tatcaaagat   3240
aactttcatt atagaatcta ctataacttt gcttagactg ttgccccata cttagtgacc   3300
ctactcagaa aaagagaaca aatcctgtgt ttattttatt ctctttggaa atgaaagtgt   3360
ttatttattt tgtctcatga agatagtcaa aaaggccatt atataattaa atagaatgtt   3420
tttccctagt gataattttg tatatatttt tgtattttta aggttttaat cataaagaaa   3480
aagttgtaat ggatttcagc ttacctgtac atagaaagtt agcactgaat gttggcaaat   3540
aataggtgtt gagaaaaggg gatctacact ttaaaatgat accagctgta gtggtgatta   3600
agccattatg aagtgtcaga actggaagtc acttctgagc cttagctgat ctttctttaa   3660
aatgcatact gataaaaact tttactttta ttaacatatt aataatataa aagcattgtc   3720
ttgctattct ttttaaatgt catgaatttc atatatgtaa tactgaattg tattacttac   3780
ataatactca ttaaatgttt tctataaatt tatggtgcca tttttaaaat agcatctaaa   3840
ataaaagaat gggtcttttc atttacacaa ttatttctcc atcatttttc tttccaatag   3900
ctttagatag catatacata gtagttatgg acacttgctt attagaacta tgaaatgaag   3960
taagtgaaag tgtttagtta taggtaacat taaatggcaa aaagaggaaa caggtataaa   4020
ttgaaagcac tggatctaaa ctaaaaaatg aggtctagtt tcttcactgt tacagatctg   4080
ggcaagtttc ttgaccaata aagcacgaca gtcagcacct gtactgctac tctcacaact   4140
aaaacagaac aaaaaaaaaa tatatatata tatataaact gtgaagactg ctaaagatac   4200
aaatgaaaca gaaacgtaaa ttctattctt ttagcttaca ttatcacaga acaatcaatt   4260
cgcccgtgaa acagtaagag gcagtatacg attatgttct caattacggc tacggctgaa   4320
atgtgctact tcactggtga ataaatttac atagtacgtg cttactcatg tatttaatta   4380
agacagttac ttagaaataa ataccataca aatcttttac aacagtacct ttctactttt   4440
atgcttcttt taaaattgat attttgctag tggcttaata tgacaaaaga tgactgttta   4500
ttagcactta ttctgataca agcttgccca gttctttaca tcattttctt catttttata   4560
atagtactaa agaaaggtag tattatttaa gtttatagat agggaactga gattcaaatt   4620
cagagttgct cagataatga gaaagagttt ggatattgga tcccaggtct ttttgcttca   4680
aagcttgtgt tcttactgac ttgtgttcgt actgtccagg tgaacagatt cagtgatgca   4740
tacagtacag ccatatccta gggattttca ctgtttcttc tcagatagtg ttatggctga   4800
aataaattat ttgtcatttc ccatacataa tttgtacttg ctcatcccca tacttgtgtt   4860
tttacgtcct ttcctcttag agtcttttct cctgtcttat tgatttgcta cccacctccc   4920
ttcctcttta aaacattgtt tttaaaggct gcataatact ctgttgtact aatattctat   4980
aattttttta actgttttc ttttgggagg aaattttatt cccaaccatt taatacttta    5040
atatttcaga gaataccctt gggacgtgta aattttaatg caaatttatt tttttaggaa   5100
aaaattcctg taagggaatt ttgggataga aaagtatgtg ttgttttaag gttgaaccaa   5160
atcgtacact ccaagagata gtatcaaatt aagaaaaatt tactaattac attccatcat   5220
caatctgggg atgtgactat atctttgcat ttttgcttaa aaaatattat tgtcaatttc   5280
ataggcaaaa gtgtggttgg taattaaagt tatatgttgg gatcatggtt atgtatagga   5340
gaagcacttg tatttgcaga ttttctactt agggtgtcct ttacgtattc atttgttttg   5400
```

-continued

```
tcttacattt ttcagtcatc ttttagtttg ttctttttac ttctttctat tgaaatattg   5460
ttttaaaatg tattcctatt aaataatact ggcagatttt aaaagtcaat tatatatgtg   5520
gcacatctta agtatagcat gtgaggcctt atcttttgat gtcttactgt ggtagttagg   5580
gattttagtg ctgtcttgtc tcactttaac ctttttcacc ttcctgcatc ctcccaatat   5640
attttatcac aattttggat tatatacaca ttagtgttgt attattttttg actgtatatt   5700
gtttactgtt tagctaagta atatactgtg attatatttg ccttcctgtt ctatgctatt   5760
attgatttct tttctaccat cttcctgttt attagcatct gggtttagct gtcacttagg   5820
ttcatcggag acagagtttg tgtttctggc tcctgctttt cttgttttgg tgtggttttc   5880
tggaagagaa gggtagttgc agaaagctag atattctgcc gtcacagaaa cagaagtgtc   5940
ttgcctgtat ttaagacccg atttagatgc cacatctcca tgaactcttt tgcagcacct   6000
gtgttactga gcaatatatt atgcttgatt ttgccatgtt ataaaatata tttcctccta   6060
gtaggaaaaa gaatgtcttt aaagatagga ctattatttg tctttgaaac taccagagct   6120
tcccagtaca gtaccatgca cttagtacat atttgagatg tactaattta acaattaact   6180
accacttaaa attttttgg taatgtttta gtgattctgg taaggcagat acattttatg   6240
cgggttcgag gggggaataaa aatgtgtgtt tgcgtagaag aaggggggagg ggaaacaatg   6300
agttttccag gattatggaa ctagtagtgg tttctaggcc atatttcatt ttcctgatct   6360
tccctgctaa tgtcttgtgc tagaaactat gctgtttata tctcatcatc tctcctcagg   6420
tatagcaaac aaaagggaaa ggaaagaact catcacaatt atagggcagc agcaggaggg   6480
tggcagaaga cttctgactc attaaaagtg gcttccagcc agaattctca gaagtttttg   6540
tagatgtttt tgactcatat agggaaataa aatatccagc tgtgttcagc ctgacaatga   6600
agttggggtc tatttgtgct atgtgtcacc tccattacat taagcacata gtttatgatt   6660
gtaaatattt gaaatttata ttcagagata aatacggatg cactgaagct gggggaagga   6720
aatgaagaat gaatggggtt aagagttggg ctttattggg tgtaggtagt atggtagggg   6780
gattttattg aggaatactt cagatttcct agctgttaga tggagagtag caccatagtg   6840
ctgagaagcg ggtgcccaac tccaggggaa tgttgaatgg aagggcacag ggtcaggtac   6900
agggactgga aataaagata aacaagttat gggtaagtag accaacgcag taagagtaga   6960
ttaaatcacc ccgaggaaaa atccgataga gcaaactcag tactgtgaga ggcaatctct   7020
tgttaaaaaa cgtcactttg atctcatagg attactgaaa ccatatcttt gcatgtcatt   7080
ttgaggtttt ataatgaata ttatataaaa cagttatatt tatgagtaaa cttggttaat   7140
tttttcagct ttgcttcaaa cactggctac aaatgatgaa cctcatagac tttttgatg   7200
gagatgttaa aaaggctttc aagatagcat tcagactggc attgggcata ctgttgggcc   7260
tgttaccacc agcagttaaa gcttgcaggg cttctaaaca gaagcatggc atgcagtcag   7320
ctggagtctt gatttcataa caattttaca gattgggaca agatttttga ggtaaaggtt   7380
tcaaaaaata ataagttact cctttgcctg accaacatca tacggtctat ttcaggagat   7440
gtttgaactc cagagctccc aaatccaatc ttacagggat gtttatttat atttcaaaca   7500
ggcttttcct taaataatgg ttagcagtgt cctttcttaa agattcgaag acaatacaaa   7560
agtaaaaata ttagcgtaat ccaagtcaag tgcagttaat gtaagattac tctattttta   7620
attgttctgt atatcttcaa gatgtatgga tagatattaa atattttaac aaaatctgta   7680
catttctcac aaaatcagtg aaaaagtggg tcaaatgcat tacctttgtt agctttaaca   7740
atctgacatt ttaaaagctt caaatccagt acatctgaat tgttaagttc tgagggtact   7800
```

```
tcttagccct gaccttaatt cctctgtgta tttgactttc ttcctctgtg tatttgactt   7860
tcttctatga cctccaaaat attctaccct ggttttttc cgtctatcat ttcttctctg   7920
tgtctatgcc tcttccatag ccctatacct aaatgttggt attactgagg tctatcctca   7980
agccactttt ttccttttct ggtacagctc tcattaggaa atgtagttgt tcttctgagc   8040
tacaaatcgc agaaccattt gcaacctctc ctcactcaat ggtttcctct tccttacttc   8100
ctatagtgag ttagtttagt tcagtgaaca tttgagtctg gcttaaatct ctcttcaagc   8160
cagtcctttc ttaacctcac tgtcactgcc tttggtcagg ttgtgatcat tccttttctt   8220
ggcacttttg gtcagcaaac attaattgag aatccactct attatgctgg gcattaagga   8280
tacaaaaatg atttaagctt acatagaaat aagggtgtta ggcaaacaag tataagcaat   8340
tatgttactt gacaatggaa atttgctctc atgttaaata ttttgtaaga cacatagtaa   8400
tgcattagaa atgtagacaa ttttgcatta tgaaaagcaa gcctcagaat ctagtgtgag   8460
gctgaatatt gcaaagagcc agcacaagac aggcagcagt accacatgga gggatacctt   8520
tatgttacta ttagttctcc ctgtgtcata gcatgttgcc ttgtttcagc gtttgtgtca   8580
ctctcttctc tccagtgttt cataatcatt actggaaagc caccaagagt gcaggactgg   8640
attgtgtaca cactttctat ttctgtgaag ttgtttgtat ggaatattcc ttaatggaat   8700
cattatatta gacatttgta taagaagtca aatggggcag agttgctaat ccattgtgag   8760
gtaggtcagg gaggacttca tgaaagtgat ctacttgagc ggggacttga aaccaatggg   8820
acataacaag gaggttgtat gaaagcacta aaccacatgt tgtaactgta agtaatttct   8880
tagctctggg gtagaataga caaaagcggc ttcaatagaa gaaatgaagc cagaggggta   8940
aatgaagcta gaaagatcat gaaggatttt gtgtgctaag ctaaggaaca tggacagttc   9000
agagctactg aaggagttta atcagaggag tgacacagtc agatttatgt tttagaaaga   9060
agttcctggc atcccggaat cctaacttca gcgaaccctg ccctgctttc tgtatactct   9120
atcaccagag tcagcttggt gaaacacagg ctgatcttgt aaatctcagc tcaacactta   9180
agaacagatg cctaagtccg atttctatcg ttactttgct gtctcctcta tcttgaacat   9240
ttttgcatca gacacccaca tagctcactt cattttactc atgtctgtcc tgaaacatca   9300
catcagagag accttcctag gctgtccaaa ccagcatcac gtctgtcacc ccttagtttc   9360
ttaccttgct ttatttttct tcttagcact caccgcccta aaagttatat gtttatttgt   9420
ttatttctcc atcctccacc taggatgtaa gctccatgac aacaggagct tttgtatatt   9480
ttgtttacct gtaagtgttc tgtgctgggc acttgatagg tgttcagcat ttgttgaaag   9540
aatgtggccc caaccatcct tcttcttttc tctctttcac cctgtgcctc tcccttcatg   9600
tgggggaatt cttacagttc actaatcctt agttatgcct cttcatgaaa tcctgtccct   9660
cactcaagat ccatctcaga taccaccttt tctgtaaaat cttttttcaa gcagttgctg   9720
cttctgctta gctcccataa cactttttga atagttagga gaaaagtgtt tacctgggct   9780
gtacaggatg tgatggatat aaataaatac ttgtcagcaa gttattaatt aaccagtaga   9840
gaattacaca atgaggtaga caagcattat aggtaaagtt tgaaattcag ttggttaagt   9900
ggagaagtga agtaattagg tgtgacttga aatttgttta taaatgcaat atgattaggg   9960
gaaaatagct aggggaacca tcaccaattt ctattatata cacagttgta cagacaacct  10020
ggagaaggta tctgttgata catacataaa cacacacaca cacacacaca cacacacaca  10080
tcattttacc gatgtattac cttttttgta gaagtattta cttttcatct tctttctgcc  10140
```

-continued

```
taaagtatta cttctccaca tacatcactg aaaagaaatt atctagaaat gttttgattg  10200
ggtcatatta atagcactat gcccaggcca atttctactt tacaaaagct gatataattc  10260
catttgaatt gtcaaaaatg tctttgttgt aagaaaacgc tagataatta ctcttctggc  10320
taacaggaag gtatagaggt ataaggtata aattacttta gtttcccagt tcagcgtggg  10380
tatctgatga tttttaaatt cactttaagt gattaatgtc tgctgtgaaa tcctggctgg  10440
ggtctttgtg tgaagttatt caacttttct tttctgaact catgttcctc tttgacccat  10500
aagtgtcttt attctcaggt gaaaatcatg ctaaattgtt tagggttccg ttgaactttc  10560
taattgagac acaagctacg aaagctaata attaagtata attattgtct acatgtaaaa  10620
gcaaaagttg ctggtaatca ccattaacct ctaatatttg ccaacaagaa atgtaaatag  10680
caaaagtcaa atttattctt cttttaatat ttgaggacca cattagatgg ctggaggacc  10740
atctgcaggt gtcagagggg ctttgggaca ttatctctaa tgagttgaaa gtaaataaat  10800
acagaaagct ggtgatatga agataaatac tttatttagg gttgtccttg tttattgaca  10860
acgtcaatga tgctgagatg cttcctgtgg aagatagcaa aggaagtatg attttcatat  10920
aatttatcac aaatttctct ttttaatttt ccaccaaaca atggctaatg catttgagag  10980
gggaaaaaaa tcccagtaga tctgttaatt gggaatcact gtgctacaaa tgcttgaagt  11040
ataagcaaac attttcctat gatgagttca taagcttttt aatgaaatat tcggaagaat  11100
ttaacccatt ccctgttttt cttaagatgt gaaaggaaga ttttagaaag acttacgtaa  11160
actttaagta gactttaaaa gtttgttgtg ttagagaaat atttgaggag atgttataat  11220
gcaatagaaa tttttgcttt atattttta aaggattttt tatggtattt tgtttgtttt  11280
tcagagtaaa gccaatccca gctgaaggaa tcaagtcaaa tccttccaag cggcatagag  11340
accgacttaa tacagagttg gaccgtttgg ctagcctgct gcctttccca caagatgtta  11400
ttaataagtt ggacaaactt tcagttctta ggctcagcgt cagttacctg agagccaaga  11460
gcttctttga tggtaagaca gaagggttta atttgtctac aataacgtat aaaaaatact  11520
tgtactagat atagctgttt ctgtgttaat aactacaaaa attagccgta tttggaaaat  11580
ttattgctgt atagtaaaat ttcagtggca aagccagatt tataagtctt aaaatcaatt  11640
ttccagtttt attcacccaa cagatgcagc cactgaaatg atgcatggta tcattctttg  11700
aaaatcatat atttagaagt tacactcaaa ttgattatgt caaattccag tttcccttct  11760
acttcaatat ttaaaagtct tttttaaaaa aaaagaaaag ataaaacacc atcttgctgg  11820
attttctgtg ttttcataga catgtcattt tatttatccc tccaaactta cgtatatttc  11880
taatcttttt tttttttttt gaggcagact tttgctcttg ttgcccaggc tcgagtgcaa  11940
tgacacgatc ttggctcact gcaacctctg actcccgggt tcaagcgatt ctcctgcttc  12000
agcctcccaa gtagctggga ttataggcgc ccaccaccac gcccagctaa ttttttgtat  12060
ttttattaga gatggggttt cactatattg gccaggctgc tctcaaactc ctgacctcag  12120
gtgatctgcc cgtctcagcc tcccaaagtg ctgggattac aggcatgagc cactgcgcct  12180
ggcctatttc taatatttta cattaattgt ataccgactg caagaaatat aattaaaaca  12240
tgtttttcac tagaaagaac atttgattgt aagagtcaat agaatttgat ttcattctct  12300
attgtgtcac tgaaaactgt ttgtcattaa ccaaaccagg tagcatcccc gtatctcagt  12360
tttctcagca gtaaaggttg gggttttgag ctaggcagct ggatgatatt tgttaccttt  12420
aaattgcaat ggaagttttt gtttgcaaat gatgtttcag tgtattttct catgtaaaat  12480
taatttttga tttatctttt atctgtctat aaggcagaaa tagatttttt aaggaaatgg  12540
```

-continued

```
tctttttaaa atatcatata attttactaa ccatagcaag ttaatgataa aatctcagtg  12600
ggctatgtca gtcaatgctt ctcatacatt aatgtgctta caaatcacat agggatcttg  12660
ttaagatgca gattcttgtt cagtagcttt aggtgtgtcc ctagattttg catgtctaac  12720
aagctccgag atgatgctga tcctgctggt ctaggtcact aggaagtgcc tagacaacac  12780
gtttatggat atttgactgg taatttgtgt ttagaatatt gcaacagtta atttcccttt  12840
agatttatgt ttacataatc tgatgtgttt cgtctgagca tctttttatt gatttgcttg  12900
cttgctctcc cgtctttctt ttggacaaaa gctatttagt ttaacagttg tggtctgggc  12960
aatatacaga tttgaggata gtgatttcag gaaagattat atatttcaaa gtttcatagt  13020
acacaaattt tctctgacct atataaaaag tgtttgaatt ttcagttgcc tctataccaa  13080
acccttcatc ttgggagaag agttacgcag tattcagtga tggtctgtaa gtatgtgtgt  13140
attagctata gtcatttagc tgacatagtt ggaactagaa ctcaggtttc tagattcctt  13200
atattgtttt tcctgaccaa ataataccta ctttttctg ggaaccttcg cataggaaag  13260
cactgaggat tttttcctag acctgtggtt cttaaaagtg tagtatccag acaggcagca  13320
tcagcatcac ctgggaactt gctagaaatg caaattattg ggtccaaccc tagacctgtg  13380
gaatctaagg tggtgggacc tttggtgata gggctagatg catattgaag tttaggagcc  13440
actgctgtag attgtaactt caggcctcct cccagcgtca cggaatgctg tcctgatccc  13500
tagcatttac tcacatgctg tgcttagtgc ttgaccatgt ggtggcagat tctgtgatgt  13560
gtaagacgtg gttgccaccc ttagagattc tggagtctag aagccaagga ggcattattc  13620
tctgactctg ataaagcttt attgacttga gtcattttac ctttccattt cttgttcctt  13680
tgtaatgggg aatcaaatta tatatgttaa aaagaaaaaa aaagtatagg tttttcctct  13740
gtttagaagt agtacatatg tgtgtatcta gacagataca tataaatgtg tgtgaaacac  13800
acatatataa acagatatat ttctatattt aatgtctaca ttatgtgtgt atgtgtgttc  13860
atgtatgtat acacacagac acatacatga ttagataagt gtcctattat tcagtgcttc  13920
aagtaaagga gatctcacag tctatcttat aaagcatgtc atagtttaac acagggttca  13980
tcacggaatt gttaaaaact tttttctcag ctcttcatta atgagtttgt ctgtttttta  14040
ttctggttca gtgtatttga cagtaggatc ttattaccta tttgcatgat tccttcatca  14100
actacattat cattatcttt aacgttagat tcttttcaaa ctgcattgtg cataagaatt  14160
acctagaaag ctttttaaaa tgcaaatttg gaggcatgcc cctgctgata acaaggaagt  14220
tctgtgtaaa acccaagaat cagtatttta acaagcatgt tacggagtct gaggcagtga  14280
tttagcctag ccttgattat gccctgaaca agttaatttt tgtttctttg ccttcagaat  14340
gacaaatgca aacatacaaa atttaaagaa gtctatgaat atttttgctt gtgttatagt  14400
ggtgtacatt cagcctaagc agtttcttag attgtttgat acagaaacat acagttagat  14460
ggaaaatgaa aataataagg tttttttttt aatccccaaa tttcctccag actaccagtg  14520
gtctggaaag gcaatgcaac atttcagagc acacagagaa tgaaattata agggtgaccc  14580
ttatgaactg aaaaaatggt agatgcaaac gaagagattt gaaacatgct aacaatgatt  14640
aggatttttg tgtgcagttg gacccactct tccactatta gggaaacagt atagcgaagc  14700
gaagggaagc tcaaagtgaa taacaggatg caaacagggg gtgtgtaaat tcctgcggaa  14760
agaacaatat aaacgagtaa tcatacaatc ttgttagaaa ggaaactcaa gttttactgt  14820
aacaatagat atttttccaa gaaaatacat ctatttattg caagtttaaa taatccaact  14880
```

-continued

```
tggatggatc ttcttaaagt ttggaaccat gactatactg ctgctgctgt ctgaaaagca  14940
acactataaa gttttaagta ctacattaat atttatccat ttctaattaa ttaaaacata  15000
ttgaaatata actttaaaat acttgaacaa ggcttagcaa tttttcagtt ataaagtcga  15060
aaatagtttc tttgacatga tttaagcatt acatttaaat atattatctc tgagatggag  15120
ggtattttaa aaatttaaat aacaatggtt acaatcaata atagtttatt aatagagact  15180
aggatttggg tggttacaat ctaatctttg aaactggttg atgtgaagag aaaggattgt  15240
ttcctcctat atcatgtctc tcaaaattgt taaacagtgt acactgggct tgttgatcaa  15300
tctaatcagc attgtaatgt ttcattccta atttcagcat atctttaata caatttttaa  15360
tgagatttcc ttactatttt ttgaaatgcc cattattatg taaatatttt gttcaaatta  15420
ttctgttttt atacagctgc cccaaaattg agaattcggg aatgactact tttgttttct  15480
gtttacatac aaacacctaa tgagcctgac aaaatggagc ttagggatcc gagtttctga  15540
tttcaaagtc ttgcatttgc agctgtcata gggaatagta gtattctagt tatttttaaa  15600
acaaggtaat gttagggaaa atctaagtct tgaatcatta tacatgctta aaataatcac  15660
cattttataa aatgtagaat tatttacatg ttaaaatatt ttcattcatt aagcctaaaa  15720
atgctgtggg aagagaggat aatagttata ttatgtgatg atctaacatt tatttgaccc  15780
cattgtttat catggatctt tcttgacttt attttaaatt aaaaattaca agtgctctgt  15840
tcttggtctt ccttttgcag atgctttaac agttcattcc cagttcatta ggttttccaa  15900
agagagctat tgtgtttatt catcttcagc ttgtgcattt ctctgaattt cagttgtttt  15960
ggtatctctc tagatcagaa cattattctt gaaaaacaag tatacgtaca tgtgtatatg  16020
caaagaacaa gcttgaacaa gcagtaaaaa tgaagtaatg cacttctaag tgttgatgtt  16080
ttataaaatc taatagattt gtatgtctgc tttttcattc atgagaattc tataatttca  16140
tctgctttgt tgtaatttta aaatttctgt gtgtcaagta atttaccaaa gtttcagtat  16200
gatagtatca tagcaaatgt tatttcttaa ttctaggact atccaaagta ggtttgtttg  16260
cataacagtt tagcacattt gaaatcacca aataaagtat ttgttgaatt tgatttaccc  16320
atggcattat ccatcttaaa tggtgattta actgttatct tttttcctaa ttcacatttt  16380
aaaacatgaa actctaatta caatattcat gataactttc atagctaaaa ctatataaac  16440
ctaggttctt ttaaaatttt aatttatgga accccctgcag atttaaacat gaataaatac  16500
aaagaatagt agcgcattct tattgaatga atatacaaat cctggctctc atatttaata  16560
ttgtgacctc tttggttcag gaatttaatc tctcttttcc tcagatatcc caatttacag  16620
tataagattt attagattat atgaataaat taatatgata gaactttata taggatactt  16680
ttatctctgc ttttgtttgc tttgacaact attttgaaga acacagtgac aaatatctga  16740
gattcaaaca atctaaactc attgtatcat atattatgta ttttgctgct ttcctgtctc  16800
ttttaaattt actgatttaa tggatttctc tttgatcatt acctagtctt gcatggttct  16860
agaatccttg cttatttggc catgaacagg tcattagtca tcattttttt tctttttagg  16920
gagactaccg tgggctaaca ttaaaatcac caactttcag caattttcct tttttagaaa  16980
attttcaaat acagacattt aaaaatctgt agttaagtct taagatattt cgtgagggtt  17040
tgtgatctgg ttaatggaaa tgtacacctt catgttatag tgttttataa aacatattca  17100
tatataatat taattatatt aaaatctgaa gaaattttta tttggtaata tttgtatatt  17160
atttttaaat cttgctctta cagccttttg acttttcaat caatgaattt taatgagtaa  17220
ctcaaattcg tttatttgct tatggctgga gatttagatt ttagagtcat tttatcgtca  17280
```

-continued

```
gaataacatt ttaagccatt aaagtgaata aaatattcca gggggagaac atgtagaata  17340
agaggaaaag taccaaagat aagatgtttt aaggatgagc aggggtagta aaaagtgaaa  17400
tctgtggagt atgaaagtat gctaaggtga tagagttgac ttaagatact ttcatttgat  17460
gtgttcttaa attggagagc cagagagaaa actgtacatg aaagtgaaaa ctgaaatgaa  17520
atgaaagtgt aaactgaaat gaaatgaaag tgtaaactga aatgcaatga aagtgtgtac  17580
agaaaaataa taacactaga gaaggtgatt tctgttcctt gtttgtccat agaggccaaa  17640
aagccattca gttgttagca gtgggagatt aagagggaga caaatgtctg ggctctgtgg  17700
ctcatgcctg taatcccagc attttgagaa gccaaagcag gaggactgct tgaaagcagg  17760
agttcgagac cagccaggac aacgtagtga gacctcgtct ccatacaaaa taaaaaatta  17820
gctgggcttg gtggtgtact tctgtatccc agttattcgt gacactgagg tgggaagata  17880
tcttgagccc aggatgtcaa ggctgcattg agccatgatc gtgccactga acttcaggag  17940
tgagactgtt tcacacacac acaaaagacg gagacaagta gtctgatggg attggttgac  18000
ataaagaacc ttaatgaatt gtacctactg aattcttcat gtattttcta gcctgaaatt  18060
ttctcataca attgtcatat ttacagagca ttctgttgtc agctggattt tttttatcg   18120
tgtctaattt ctgtgttatg gagacatttc atctctttat ctcagcatgg tagagggagg  18180
ttgtgttttg tgattaaagc actgacagca ggagctgtgg atgctagttc agttaacgaa  18240
tcttgtgttt tttgatagac tttaacctca ctgttccaca gggtcttcat cttctcagca  18300
tgtttgataa agatgcttgc ttgccctgat atattaggtt tgtagtaaat tctaaaaatg  18360
agagatctgt gaaaaatttt tataattaaa attgttactg ttatggaaat catagttatt  18420
tcctgcagaa tcctgatatt tcacttgttt tagtggagaa ttttgttttt ttttttttt   18480
ttgaatatgc ataagggcct ttacggacct ggtattaata tcaattgaga atccctttgt  18540
ttaattaatt tcatattttt tatttagaga tggaaatttg ttaataaact gtttttcccc  18600
ttttgatata atacataata atttacttac atatactgtt ttcttttatc gaaagtggca  18660
catattccaa atctggacac ttggaaaagt gtgatagctt gctttggtga ggatagaaat  18720
tttgggcatt gtatgctact tgctttattg ggatacatgt caaattttct gttattgcgc  18780
tatgtcttaa gataggtgct tcagcttttg tgtttgtaaa attgttatta tttcccgaag  18840
aagttcacaa taataactgt gctgaacagc atggaatgat aattttaaga agtatgaggg  18900
aattcaatcc agaacatacg tgagttattt cctaaatcct gaggttctaa gtctctgttt  18960
ctcaaagaat ggcacctcat tctcagcatc actggggaac ttgttaccta tgcaaactgt  19020
aaagccctat cctagaccta ctgaatcaga aattctagag gtgtggctaa gcattgtatt  19080
ttaagccttc caggtgattc taatgtctgt gaaagcttaa ggatcactgc cctcattgag  19140
tatttacatt atgttactta aaatgcaatt taaatactac tcttgtatat atgaaaagct  19200
aagtgcaact cattccccac tgaaaaggtc aattaactgc tcttgttcca ttaatgcaga  19260
gatttgtcat atagttatag aggaattgta taaaactgag tgcgtaccaa tgagtaactg  19320
gaagaatgtt aaacatcttt ggaagtcagt ttttatgtaa gagtttggat agaacaaact  19380
tttaaggact accctgccaa agtagtaaag gggatggtaa atattatgaa attaattgaa  19440
tttatagcag cagttaggga ctaaaagggg atatgctttc cctggcaaga tcatctttct  19500
gtttaaatgc aaactatagt aacaaaatac aaaatatagt ttaccactat tcggtattcc  19560
tcatgaattt ttttttcctt gaccaattca aagcatgtga tatgaagaga tgtggcattt  19620
```

-continued

```
agggagtagg ggaaatctga gcttagatgt ctaaggaagg aaagtaccgt attaggaaac  19680
atggatatgg ttaaatgcat gtgggaataa aacttgagtc atctgtggta tgaccatttg  19740
ataatgctgt gatgtatttg cactctaaat tccatcattt gttagattaa attcttattt  19800
gtattgtacg actccttcat agatctttca atgaggaaat agtggaaata ttttggtggt  19860
ttactatctt aacattctac tgaatgttca gagtctgatt ctcacacttt ggaaagtggt  19920
acatatcctc actgatgggg aagattttaa caaatgccca ttacggtaca gcagatactt  19980
cccagctggt gacctatttt cagatactac attttgtttc tgtggactgt cataaattta  20040
attccagtgg tgtaatattt aaagtgtcgt tatgcatata atttatgtaa caatttacag  20100
ttttgaagta tagttgaccc ttgaacaatg cattaataac atgaacagcc gattaatgtg  20160
tcttttgtat atgtattata tactgtattc ttaaagtagg ccagagaaaa gaaaatgtta  20220
ttaagaaaat cataaggaag agaaaatata tttactgttc attaagtgga gtggatcatc  20280
atacaggtct tcatcctcat tgtcttcatg ttgagtaggc tgaggaaggg ttggtcttgc  20340
tggcttggga gtggcagagg catgtaagtg gacttgcata gttcaaaccc atgttgttca  20400
agggtcagct gtactttcaa atgtgtcata tagttaccat agtaatccta ttagatacta  20460
attactgctt tccacttaaa gatgataaaa atactcagtt acctccttag gggcacttta  20520
attgtaagtt tctcatcatg gtttgagggt gtataaagtc agcatagact tcgttacctc  20580
tgtccttgat tgtcagtgat tgattccagg cattaccctg gtattgtaca tgttatttta  20640
atcctcacaa gaatttgtct caagaggtag cattgtcctc atttaaagat gaggaaacta  20700
aaggtcaaag gtagttagca aagtgggcgg tggctaataa tagctcacac actgaggtct  20760
ggctacctga gtttttgtct aagctctgcc acttaaatct ctatgactct gaacattttc  20820
tcaatctcct taagtctcac ctttctaata tattgaaata acagtgtcag tctcatagaa  20880
ctattatgaa gattaaatag gatataatac gtggaaagtg ctaggtgtac agtgtgtgcc  20940
caatatcaca tatgagtact aagtaaggtc actccaatgg taggaagcag ctcttgtgac  21000
agtgtctcat gtcactttct tactcattgt tttctttcta atcagcacaa gcaatatata  21060
catgaaaatg agtagtattg atagagcctc tagtaattta ctaagttaga ggtagtaggc  21120
atgagagcaa gaaatagaag aaaaacttca tgcaggggta gacattacat agtttaggct  21180
gaaaggccat gacataaaat gtttcctgaa aaagcacagc agtgtttttt taaatgattt  21240
taaaagtcca cccttctcag actcatcttt gcacaatatt tacttcaatt atttaccagt  21300
gattaacctt aaacacaaga gcaacagaaa tatttgcata tttgtttttg gtagaaacct  21360
ccagtgatca ttccgccaaa tgaacttgtc acttttccta cttatgtagt agttacacat  21420
attatctatc atccttccaa catttggaat tataagcatt gttgtttaga aagaatttgt  21480
tctttttatt ttttctctac ttcaagttcc tgtaatactt taattaaacc ctattctggt  21540
acttagtatt tttgacattg ttttctagtt atttccatag cttatatccc ctacttaaag  21600
acagggtctg actcaagtgt ctaattacat tggctaatac tcccagtaca agcccaagaa  21660
caaattataa attactctaa gatgaatggt ctctttcatt gcttagtcat cttctcagtg  21720
atcaagtagt tatctcttaa tatttatgtt tttctactgc cagtgactct aggtggaact  21780
aatatcaatt gtgttgatta aatattaatt ttaagagatt ccaaacaata atttagatat  21840
ataaagtctg acactgttat tgtccgtttt taggcttatt tcataatgta agggtttggc  21900
tttgttgttt tctttttaaa agcaagtgtt actgatgctt cataccagag cttttagaaa  21960
agtaacagaa tatagttgac tctgacgttg tatggtttta gtgcattcaa gcaaatgtgg  22020
```

ccattagtaa gcaagcaaca acataactta ccgaatagaa agggagaaaa ggccattctc 22080
tcttctgcca ttctctctgt gtacagatta aacatttcct ttggtcttga tgaactgtta 22140
ggtcagttta cctcaaactg ttttttggcc taaggaaatc tgttctctgg ccttttgaag 22200
ttacattcag agaccgtgct tttggctgtt tcttgcaaag agatatgttt taacttctgc 22260
aaaggccaga atggcatgag attctggtgt gacacattca ctgatgattt accagaaaat 22320
acactgcaaa tatgaaagac tgcagacagg ttttatatgt ggaactctgc tcagactgag 22380
agaaagtcta gttattagta aatctctagt tttttcagag ctggattatt ttgtcacata 22440
aaaatatagt gagataaatg ttaagaggac tgccagagtc agttttattt aatggtttct 22500
cttattcaaa tatcacaggt taaaagaagg tcagaaagtg gcaagtatct aaaagattat 22560
gctttataac caagcaatcc ataagctctg agaaatattt ctactaatta cagctactgt 22620
ttgttgaaca gtattgatcc actatgtgtc agaaacttta catatattct cattactctt 22680
cacaacagcc ctgcaagatg tgctttaaaa tttttttttt taattaccac ctcacatatt 22740
aggagacagg ctcaaataac tcccactttt agtaaatgtc agaggtaagg tttgagccca 22800
attctgtcag ttaccaatat ccacatgctt ttaagtgaga taatatttga aagtgcttgg 22860
caaaatgttt aagtggtagc tgttattatt tctattcagc tgcgcttcct cccagactat 22920
aaatacatac ataccacaca catacacaca cacacacaca cacacacagt gaggaaaaaa 22980
aagaagagat agcattataa catgacacct ccaatagtaa gcatcctatc atgccatcag 23040
actttccttc acatatataa tccacaagca gttaaaagct ataccggaaa agccacttta 23100
caagatgtaa tacctaggag taaatataaa gatacctgtg cacatctttt ttgtagacaa 23160
ctttaaaaca ttctagcagg acaaaatata gacttgaaca aatggaaaga aatgtatgtt 23220
cttggataga atgattcaag attataaaga cattaattct ccatgagtta atttataaat 23280
ttaacatgaa cctattaaat agtcacagta attaacagtt tttacccaaa tgctggacaa 23340
gaagattcca aacatcagaa atccatctct caataaggtg tatagttgct tttttctcc 23400
tcaccaccac cagttcccta atatttcaat aaatacataa aaatgttgga ttcattttta 23460
taggttacat tatggagaac tttagtctcc taagaaagga ggtaggagtg gagaggagtg 23520
tttgtaacag tgttgtgcag ttctttgaaa ctcctaagtt ttgtgacaaa attatatcgt 23580
gaactcatca aaaattattt ttaacaatct gtcagctgac aacttgacta aacccttcag 23640
ttttgttact agcatagaat aaggagctac ccactggcaa caggattact tacctagtat 23700
ttattattta ccttgtttta gccaaatact aaaaatacca gtggatgcca gtatttcaaa 23760
ttgtctttgt ttggtgttca gaagttttct attatagctc tttactcttg cttactttta 23820
aaatcattgt ttttcctttt tttccatagt tgcattaaaa tcctccccta ctgaaagaaa 23880
cggaggccag gataactgta gagcagcaaa tttcagagaa ggcctgaact tacaagaagg 23940
agaattctta ttacaggtaa attttagtaa atatagtttc ttacactaag gacagttgta 24000
aatggaaaat gaattaataa gtcttttagt aattccctgt ttacttagga tttgctcaat 24060
gtttttttgcc actttcatct gaactgcgat agtgaatgat gcttaataca tgaaaaactg 24120
gaattatagt catgcaccat ataatgatgt ttcagttaac aacagaccac atatgcgaca 24180
gtggtcccgt aagattatac catatttttt actgtaattt ttctagttta gatacaaaaa 24240
tgcttaccat gtgttaaaat tgcctacagt attcagtata gtaacatgct gtacaggtct 24300
gtagccttgg agcaataagt tatactgtat agcgtaagtg tatggtagac tataccatct 24360
aggtttgtgt aagtacactc tatgatgttt gcatgatgat gaaaatcacc taaccacata 24420
tttctttgaa tgtgtccctg ttaagtaatg catgactgta tatgaagtag attagttaga 24480
agaccggtca accccttctg ttgtattaat atttcttcaa acagcaagaa ctcctagagt 24540
attttagagg ttctaattta agatgttgaa tttatatata tttttatgga atgtatctct 24600
attaaaattg ttaaatgcat ttcttaaata gtttaaaata gttcttaacc caaatttcat 24660
tttgccaata tgttataact tacattttat tttagcaact gtttgtgact tattaacata 24720
ctaaagattt tctcaacaac tccaatccct atttttatgc ttcagaattt agtttctaat 24780
ttgtctatga aagcatttg catctttttt tactcttttt tttagaattg atgccatgat 24840
tgattctcac ttaaaattct cagatactta ttttgttgaa aaaagataga ataaagatgt 24900
gtgccatgtg tgctgtcacc gctatgtgat cattatcagt ttcacccact gaactgacta 24960
gaaaaacttc accattgtta caaaaagtaa ccctaagttt cggtaactcc actagttcat 25020
tcagtggatg gtgatgtgcc taataatata acatttttat tacaattgtg taatcacatt 25080
caaagtcctg ttagcaaaaa ttaacttatg ttaaacaaag taaatctatt aaagcatgag 25140
tcctccccta gccccaactg aggatcttca tgtatatgta aacccaaaca taaagactcc 25200
ttattcaggt cataggaaag cattttaata attgctattt aagatgatta aacacacctc 25260
ttgggttttc tactaagggc ctaatgaaat cccgtatttc aggtgaaata gacagatatg 25320
tactgattga cgtaacactt ggcaagttgg tttaaattat gggccatttt tattttttttc 25380
ccaaaacatt taggcaaatt gtgtacatac cctatgtcag ggaaacagaa taacaataat 25440
atgaatgcaa agctgtaaag ctataattat atggaatata tatattttaa attatctgca 25500
aattggtaac ccttaagaag ttaaaataaa cttacctgtt tatattgaat accatttgta 25560
gattgctctt ttaataggaa gactcacatt ctctatgatt ttcttaggat tgtgcttata 25620
tgttatcttt ttatgaagaa gatgactaaa aacattatag atatgtggaa atggctgttt 25680
gattataaca attgcataat gacatctgac tttatattgc aaccgacggt tatcagccaa 25740
ttaccactac agtgtgaaag gtgttaccag aggttctgta taccatatgg cctaaaactt 25800
ttgaggagaa atattttcct ttgcttaaca aaggcatatg aagaaaatgt tacaaaaatt 25860
tttattaaag gccaggtgcg gtggctcacg cctgtgatcc cagcactttg ggaggccaag 25920
gcgggcagat cacgaggtca ggagttcaag accagcctgg ccaacatagg gaaaccccat 25980
ctctactaaa aatacaaaaa attagctggg tgtggtggcg ggtgcctgta atcctagata 26040
cccaggaggc tgaggcccga gaatcgcttg aagccaggag gcagtagttg cagtgagcag 26100
agatcacacc actgcactcc agcccgggtg acaatgcgag actccatctg aaaaaaaaaa 26160
aaaatttatt aaaagtttaa gacatctttc taggttagct tcaatttatt actattttac 26220
aaggaataaa aatgaaacaa tgtgaataac tgtgtcttta tttacttcac atgtttattt 26280
cataagttta aaatatatct cttgctattt aatactgtat tgttaaaatc ttgcagcttt 26340
gtttttcagt gacaggagtt gaaattttat ataacagtat tgcagtttct ctgaaataat 26400
aagtgagctt aacaaaattt tcagataggt tgagtgaatc tttgtgacta aaagaatgat 26460
gatctctttt atttaattag catattaatt ccttctgtta atttattgag agaaatcaat 26520
acaagtaata accttgggtc tcctggtact tgagatcatt tgagatatat aaaaattgat 26580
gtgcatctat cgtttctaga tttttatttc tgataataac atttgtctaa agagatttga 26640
taactgtact taaattatcc ttctgtcttc tggcatgtac accaatgagt ttattggaat 26700
gtgactaaat ttgtttcact gtttgaaaaa gtatgatgtt ctacaaaata atatgaatgt 26760

```
gatcaatgga taatcttccc tagaagcaga tattttcagg atgaatcagt gcaatgacgg  26820
atatatagtg ttactgccaa gagaatttaa gaatatccaa ttttgaatgt gttagtcatt  26880
aactattcaa gttcttatgg gtagaatcac cattgtttat cctaagagaa ttgccaggta  26940
ttacatatca tatttgcagt caaaaacctg agagcctgct tgtggttaaa gggacatgga  27000
tggagccgga ggccattatc cttagcaagc taccacagga acagaaaaac caaataccac  27060
atgttctccc ttataagtga gagctaaatg atgagaacac atggacacac agaggggaac  27120
aacacacact ggggccgttt agaggctgca gggtgggagg agggagagag gatcaggaaa  27180
aataactgat aagtactagg cttaatacct gggtgatgaa ataatctgta caacaaaccc  27240
tcatgacaca agtttaccta tgtaacaaac ctgcacttgt accactgaac ttaaaagtaa  27300
aaaaatagaa caaaacagtc agaaccatgc accaatttgg gatcgataac acataaaggc  27360
agcatatcat gttatttaag tgagtacgct ttggagccag actgaattta tctcctggat  27420
cagccatttt ctggctatgt gaccttgggc aagttacttt taaaggtata gtccttgacc  27480
tcagtttctt ctattgtaaa actggaacat ggcacttacc tcattgggtt tttgggagaa  27540
gaaaccactc aaatacataa aaacatttag aaaaaggaat actaaataat agttgttatc  27600
tttgtagtca agttcttaga agtataatat agatcaagaa tcttgaaggt ggaaagtaat  27660
tggagtggaa agagagacag tcactgtatt tcatttattt catctgataa tgaagatatc  27720
gactggacta tatgtgagca gcataagcac tagggcaaag acttgttaac tcttaaatcc  27780
cagtacttag catacatatc tcctcttggg tatgtaatag tttattacgt gttgaataaa  27840
tgaatcacta ttatttatat agctctttat agttctcaaa gcatggtgat ataaatcttt  27900
atttgctcat ttctacaacc atataacatt gtaccttatt acactgagtg ctggctctgt  27960
gccaagcatt gagttaggtg ggatatcgtc attatatcta cctgatgaag tgccagtttt  28020
tgaaataaca ctgaagccta aaaagcagta aatagcttaa ccaaagccac acagctagta  28080
atagacagag acaggagtcc agaccaaatc tgtctgacta cacagtacaa ttcttaaact  28140
aaaccatact gtgtttctcc ttacatgaaa aacagggtgt tagaagacat tagctgtgat  28200
cacatagtaa agaatagatc aagtaccaaa ttgaactcaa ggagaaaata gtgagggctt  28260
gtagaattaa aatatatgat aataataaag tgatctatga tactattgtt atccaagagg  28320
agaataaagg tattagttga tattggactt gaattatcca gtaataggaa aagaaactat  28380
aacatccaaa ctaaagagta tggctaata aaaaataatg gacccaaagt aggcaaaaca  28440
gagagaaaaa gaaacattat acatgtgaat gtgctgtgaa caaatagaaa taacacatat  28500
aaaatgataa atttaggtat gtgttcataa tgacattaaa ttttagtgga ctaaattcac  28560
tgtatgcttg ctttacatgt gtattatagt ttaattacat gtatatttta tatatatagt  28620
gttttcctgt aaaagtctta aaatgttctg tgacttaaaa tgttagcatc agtgcttgaa  28680
atgtctttgt acaagaagag ttttctatta atgttcccag tttaagaatc taatcaacat  28740
ctttgcctcc tgtttccctc taaaaaaaag cagtgtgata gactatagtg aatgatgtct  28800
agtttgtttt ttaaaaaata tatacaatat atttaaaaga gaaaatctga aacatgaaga  28860
agatgaattc catattctac caaagttatt ctgattgagc attaaattta gccatttttc  28920
catagacaaa tcaaaaggta tgaatagata tttcttagtc caggagtgta tgttttggct  28980
gtgtttgtga aatgtgacaa ttttaactat tttgaagaga agaattttca gagataaaag  29040
taataacctt tatctgatgg tcaatattaa gtcatattac taattttaga acttcctttc  29100
```

cttgtaggct ctgaatggct ttgtattagt tgtcactaca gatgctttgg tcttttatgc 29160
ttcttctact atacaagatt atctagggtt tcagcaggta agtatatatt atttatatca 29220
tttatattat tatatcattt actttttata tatatttagg acacagttgg ccatttgtat 29280
gtataaagta tcaatatatg ctgtagaata cagtatgtat ttgtagctaa taattttttc 29340
taatattaat aatttactgc actataattc ctttaaacct ttatgtgatt catggttact 29400
gtgtttcttc tttcgcttat caagaatctt atatataaga aactttcagg cacgtagggt 29460
ctaggggaga agatacaaaa ttatttgcta tcaaataact tatggatagc agaggatata 29520
tgacaactat gaaatgaatg agatgctgtt aaaaagtaca agtaaaatcc tatgatttat 29580
acctttaatt ctgatttatt tggattatgg aagttaccct aaatcaaatg gtatgtaagc 29640
tgacctaaat aatgtgtaac aggtgggtgg tcaagaaaac ataggaatat tgaagtactg 29700
taagcattag actggaagtc attgaaggaa acagacgtgt ctgacttgtt tgatgttatt 29760
gaatgaacag tgaatagatg gaattataaa tatttgatat attggaaggg caagaacatc 29820
ttttatggtt tgagaacaga ttgtaacatt tgaatgcttg ctattctcat atatctggtt 29880
ctcaaattgt actgtgcaca agaatcacct gaagaccttg ataaaacttg gtcatccctg 29940
tgagccccat tgtcagatat tctgaatcag tagttcacag tggggcccat gaatttgcat 30000
ttctattaag ctcacaaggc tgctggtctt aataacagtt atatagacta gagcttcaac 30060
tatattatat acccagtgga aaccactgaa gggttttgtt acagggggtg tgtatatttc 30120
aacttgtgtt tcagatgcaa cttttggaaa ttgtgtaatg gttggcatca agatgattta 30180
atactagaag attaggttcc taggaagatt taagtgtaga tgactaaagt agtggtatct 30240
agctactact gctaccacaa agtctaaact cctgatttct tgcattctaa agaaaataca 30300
ttaatgtcca tagaaaagcc tgtttgaagc ctaatgtatt atataactgt cttaatcagg 30360
atttgatatt gtgatttata ttagtaagaa aatcagagag attagccatt ttccaatcca 30420 ttttttttctc gcatatacac atggattttt ttcctaaaag aatattcata tctgacgcaa 30480
gtggtagatt aagacaccat ttttaaaact gcaagttatg actcgctcat gggtatgcag 30540
tcgagacagt ggatcactat caaactgttt tttagttgtt taggatagaa taaaataata 30600
tagaatacac agtgttatct catgtaataa tggtaagtgt tttgtgaaac ttttccatgt 30660
gtttatgtct gtgcacacac ctgtgacaga tggaaatgta ttttttatca taacttgcag 30720
ttaaaaaaaa aggaaaactc tggtttaagc actaaggact cagcaccgta gtaaatggtg 30780
agaggcaaga gaaggaaagt gggtttaata tggtaaaggc acaatccctt gctcttgtgg 30840
agtctacttg gagtgaaaat tttatatgaa gaaaatttta gagaacagtg aaggaaatac 30900
ataaagaata ccattaagct tagagaagtc aaagaggcct ggggtggtta ggaaaagctg 30960
catggaagag ataagaatct aaaaactaac aaatgaatat ggaacataaa cagattttaa 31020
tatgttgcat ttaaggaatg gggatgtgac ttatttgagc aagagcattc atgttgggaa 31080
ctgatgacaa gtaacttttg gcttatctgt tgtagtgcca gtctctttag ctttttctac 31140
cttaggttct atcttaggtg actagggaat tttaggaatc attcaattcg tattcatcac 31200
cactagcaag cacccactaa tctaaatagg ctttaaaatt aatttagcca tattttttaa 31260
tcagtccttt tgttgtattc cttgtatctt ttttctttag tctgatgtca tacatcagag 31320
tgtatatgaa cttatccata ccgaagaccg agctgaattt cagcgtcagc tacactgggc 31380
attaaatcct tctcagtgta cagagtctgg acaaggaatt gaaggtaaga attgatggta 31440
caaaaaatag tgttggtagt ttttaaatat gagtctgtga aaggaggctg ggaacctgta 31500
gggtcataga actccatgat agggaagtag tggaaagatg taaagtctgc aatcataggc 31560
cacagctagg tcacaaagag cctgatgagc taaggaatat tttggcaaat gagagccatt 31620
taatgagttt caggcaacag agtattgcca tagtcagtaa tgtattttat aaaaataagt 31680
agtaccttca tgaaagatgg aaggaaggta caaggttgat acctgagtgc atgtaaatta 31740
ttgtgtttaa aatgcaccaa agaaaaaagt aagctagcat atgcaagtat aaaaatgctt 31800
ttctcaatgc aaaaaatgtt tttggaaatt tgttaaagtg ttaagaaaac aaaaatgcat 31860
tagaaaatat gaaaattgtt gacagtgata gctcaataaa aatttaaaaa attatgcaag 31920
ttctatctga taaaagtgat atttaataaa cttttagttt cttgtcatta gctcttttga 31980
aaatgatttt tttgtattca gaacacagac tccagtttag aaactaatac aaattttacc 32040
tattcaagtg cttaatttta cagcaaaatg gaaagtaaat tttgttttgc ctttatttct 32100
acagaagcca ctggtctccc ccagacagta gtctgttata acccagacca gattcctcca 32160
gaaaactctc ctttaatgga gaggtgcttc atatgtcgtc taaggtgtct gctggataat 32220
tcatctggtt ttctggtaag gtacaaaatt ttatgatact ggcttttact attgttacaa 32280
taaaagcttg aggcaaattt aatttagcaa aatataattc agcagagaac tattcccaaa 32340
tcaggcaacc ctcagaacca gagagcttca gagagctcac ttaaaaacat gggctggagc 32400
atttatgaac agaaaatgca agtgaggtac agaaatggct tgattgatta cagcttggga 32460
tttgccttat ttgaagatga tctgattagt tggccacctg tgactgactg agactcagct 32520
atttggttac aaaagtttaa ttctactgtt aggctttccg ttagcttata tagtaaatga 32580
agttgcaatt ccttggtaag gacttaagga gcagaggcat cttcagccca aatttagttt 32640
aacattaagt tatagaaaaa acaagccaat tttctttggt tatctttgat ttcagcttta 32700
aaaatctgct accaaataat ttgataaagg aaagtaacat tttaaagtaa ttatttctga 32760
ttttgactat cttctataac tcagaaaact gttctttagg atatagtaac aaaaattgag 32820
tgaaataaca cgaagccttg tattttgact attttaggat ttttaaggta tgagagaatt 32880
atgtagccct tttttaatag gaggatgctt accatcttgg gattgaatgc ctgctagaca 32940
gagaaattat ggcctttcca tatgtctcaa ataactgcca catagaaaaa cgattgtata 33000
ttcatgattg tggaatcatc atttgatagg agatgctgtt ttcttgttac aaagtctgaa 33060
cacctgcata ggagttgact gtagggaaca gcttaggatt cctcagagtg gacttgtctg 33120
ttatctcatt gtatccttag ctcatgttac caagtacagg agaagaaaat acaaagtata 33180
ttgtatattc tttttgtgaa taacaaggaa tttgaaacag ataatcaaat cttaaattaa 33240
cattaccaag caatgatttt tgtttatgtg tttatttctg aagaggattt tgctgaccca 33300
gaattagaat tatgctttga gacagttttc ccagtgttat tgctcatgaa caattagtat 33360
gtagagtcat gtcctgcata atgatgcttt ggtcaataac agaccatgta tatgatggta 33420
gtcccatgag atcataatgg agccgaaaaa tccctatcac ttaatgatgt catagcattg 33480
ctcacatgtt gatggtgatg ctgatggaag caaacctgtg ttgccagtca tataaaaagt 33540
atagcacata caattatata tgatacataa tacttgaaaa taaaacaata ataaatcact 33600
atgtatttac tattaatcat tattttactt tatttttaaa tgtattatac ttttaattat 33660
tttattttaa tcattatttt agaataaggt taactgtaaa acaggctcag gcaggtcctt 33720
caggaaatat tccaaaagaa ggcattgtta tcacaggaga tgacagctcc atgcatgtta 33780
ttgcccccgc agaccttcca gtgggacaag atgtagaggt ggaagatagg atcattaatg 33840

-continued

```
atcctcaccc tgtacagacc taagctaatg tgtgggtttg tgtcttagtt tttaacaaaa  33900
aaagtttaaa aagtaaaaaa attaaaaatt aaaaaataga agaaagctta tagaataagg  33960
atataaagaa agaaaatgtt tttgtatggc tgtacactgt gtttaagtgt tattacagaa  34020
gagtcaaaag ttaaaaatgc aaaagtttat gaagtaaaaa tgttacagta aactgtgctg  34080
ggattacagg cataagccac tgcacctggc caaaaggaaa atatttttta taaattcagc  34140
gtagcctaag tgtatagtgt ttataaactc tatagtagtg tacggtaatg tctcaggcct  34200
tcacattcac tcaccactca ctcactgact aaaccaaagc aactttcagt cctgcctacc  34260
ttgtttacaa taagtgctct tatacaggta taccattttt tgtcttttat actgtatttt  34320
tactgtatat tttctatgtt tagatacaca aatacttacc atcatgttac aattgcttta  34380
agtattcagt acgatagcat gctgtacagg tttgtagcct aggaacaaaa ggctatactg  34440
tatagcttag atgcgtagta agctatacca tctaggtttg tgaacctacc ctctgatgtt  34500
cacaggataa tgaaattgcc taaggacaca tttcacagaa catgcccctt ttgttaaatg  34560
acatgtgagt gtatgtctga ggtggaatat ctgtgtgcag gagggccttt tcctccttgt  34620
gctgctatta ttttgatgtc agaaccatcc cttggactgg ttgatattgt tttaagcaat  34680
taaatatatc atgttcatgt ttaagtgcct ttgttttccc tgtcttctaa atttcttcca  34740
tatctttact cagtagggct ctgcattctt tatatgtttt catgatgatt cattttagtg  34800
tcttaataaa attatatttt gcctctatag aaaagattat gaactatgca gtatgctatg  34860
agctgtgata tagttcatgt atgcttgaaa atgaatgttt actttaggac tttatcacca  34920
ttcaggatat attgattgcc tggtgtgcaa ggagctgtgt gaggtgaaaa tgatagggta  34980
atggcaagct tggaaaatga tataggtttt catgttatga ccattaggaa caaggagtgg  35040
ttcacttatc cctttagaat atttttcata ttactctttg agatagattt aatgggcgtc  35100
ccatggagag aggagtgaag gaaactaaca gttctcagct tcaggaatat ttatggaatt  35160
atcaagaacc ctagaggcag ccataatgga gccttttaaa aaggcactat tttatattgt  35220
taattttaat gaactttttt gttgttgttg ctttttttaag gcaatgaatt tccaagggaa  35280
gttaaagtat cttcatggac agaaaaagaa agggaaagat ggatcaatac ttccacctca  35340
gttggctttg tttgcgatag ctactccact tcagccacca tccatacttg aaatccggac  35400
caaaaatttt atctttagaa ccaaacacaa actagacttc acacctattg gttgtgatgc  35460
caagtaagtg agactttttc acttttattt tattggatgt acattatgtt tcagtaagtc  35520
tctcttagca tgtaaaacat acagtgtatg taatattgtt tattattaga ttggctatta  35580
tcgtacattc ttccagtgta gccttttaca gtaaaataat ttaatcaggc tcacaaatca  35640
tctttttaat ttttgcaata cttgtctcaa atgatgatgt tcttatatat tagtaaggtt  35700
tattcttctg atgacattta tgttggtttg ttttacattt ttaaatggca caaatgttat  35760
ttgatttcta gccccagaag ttttagtaac tttcagaaaa ttgtgagcag gagtctgata  35820
ttaaacattt atatcatatc aaacatatca gtgcttttct cctttctaat gtgggaatgc  35880
agagaggtaa ttagaaaaac cttcttccct aaaaatagat tataaaaaca ttccagattt  35940
ttattaaaga tgttctgtta cccatacatc tgctctatta gattcatttt tagcatacta  36000
atttccatgg atttattcag gaaaagaaaa taggctgaaa ctgaaatttg caatcataag  36060
caaagaagat cagtttacat ggatgtgttt aatttcacat ctacttatgt gaaattctaa  36120
atgtgaacta aaacatattg cagaaactag cgtaaaacca atgaatttat cttggttatt  36180
tcatttatgt taaatcttaa tccattctta ttttaccttt ttttatttta aacagaggaa  36240
```

```
gaattgtttt aggatatact gaagcagagc tgtgcacgag aggctcaggt tatcagttta  36300
ttcatgcagc tgatatgctt tattgtgccg agtcccatat ccgaagtaag ttgtagttcc  36360
ttatgaacat gtcagaagaa aacggcatat actgttgtac atgtttcaaa ttcttacgta  36420
atgtaaagtg tttaagtaaa gtatatggat aaacttctac ttagtaacat atcattatga  36480
ttaaccaggg ttacactctt tgttcattaa cttgtctaca cctgccatgt agaaatattg  36540
ttgtttagtt attaaaaaat gaccattttg gcccatgaag ttttgcttgg gaattttta  36600
attacatcgt tatcaattca taaatctatg ttaatattgt aacaataata gtgttaataa  36660
ttctagttta aaattataaa gtattaggct gtaggaaaat attccctatt taaaatgaaa  36720
ataatttttt ccccaactta tgttctctct atactttcct gtgttactag aattgtttgg  36780
tacataatct tccctttaac atttaaaata ataaatttaa aacaactctg aaaaactatt  36840
tccatgcctt ttattatttt ttgtttaaaa tttattgtct ttggggataa aggaaataca  36900
tccagaacta tgtcacaaga gctttgtttt aggaataatc tttactatat tgatttgggg  36960
gtttgataat ttaatttttt aattttattt tagtgattaa gactggagaa agtggcatga  37020
tagttttccg gcttcttaca aaaaacaacc gatggacttg ggtccagtct aatgcacgcc  37080
tgctttataa aaatggaaga ccagattata tcattgtaac tcagagacca ctaacgtaag  37140
cacaaataat gtttcctgtt ttaacagttt tgttttcata agtcctctta tgtgaaagca  37200
taaaaataat tcaagcagac tttagtctgt aaataaaaat tgaaaagttt aattcatcta  37260
gaaagaagag cacaggtgag agacattgag aagatagaat tgacgaactt gattgagagc  37320
tacatgtgca gagctataga aagaataata aaactctagg gttttatctt gggcatatga  37380
aagacacatg aaaagctagt gtcattggta aaaaagaaga aaaatataac aatgctttat  37440
ttagaatata ttctctaaac ccagcagtga ttttaagagt ttcttacaca tgctgcagat  37500
gagtccttta tcaaatattt gtattgcaaa tgtttcctcc cactctggag aattgatttt  37560
tgtctgtagc ttgaggtaag gattgattcc ccccagccat tatacgtata cccaattgac  37620
cagtaacatt gaaaagatga tttaccgaga aggtcattgt ttcccggctg cgctgtattt  37680
tgatcagggg attttgtctg tggttctctg tctggattgt gttgttctat taatagctcc  37740
attagtgcag ttgtctattt tgtctagcat tacactgtct tagttattct atctttatta  37800
tatatttcta tgtcagagtg tgtcattttg tttgttttgc ctttttttgtt ctccttcaag  37860
attgccttgg ttcttctttg ccctctataa ttccatatac attttagaaa gcagttgtct  37920
gaaaatctgt tgagattttg agtgcaatta ccttgaaact gtagatcatt tggggagaat  37980
taacatcttt ttaatactga atctttgagc ccatgaacat gatgaatgta tgtatgtgta  38040
taagtaccca tggaagtaca tgagtatgtg tgtaccatat gtatatgagt gcatgggtat  38100
gtgtgtacct ctacaaattt gtcacttctc ccttgatcaa tgtttctaga aggcactttt  38160
tttaattaga ttttattagt ctttattagg atccaacttt tggtttattg atttttttct  38220
attttataca tttgttttca attttaatta tgtctgctca ttattatttt cttccttcta  38280
ctttctttgg gtataattta tcatttttg caacttttaa aaaatatata cttaaacata  38340
tatatcagtt tccctttaag tacagcatta caaccctcat cttttgctat cttattttta  38400
ttatttaatt gaaaatactg gctaatttgt ttttattttt attcatgaat tatttagaaa  38460
tacagtgtta ctgtactttt tggtgtttgg ggatttttct agttgccttt ttatgattga  38520
cttttagctt aattccattg tagtcagaaa atattctctg gatggatttc agttttttg  38580
```

aaatttgtgg tgacttattt tatgatctaa tacatggtct atgttggtaa aatatcccat 38640
gtaatcctat gaagaataca tgttctgtag tttgggagta tcttattttt atatatcaga 38700
agtctagttt gttaattgtg ttcatatttg tatacatttg ttgatatttt atgtgcttct 38760
gttagttact aagacatttt gttttcattt attactgaag gggggcatct ttttacatct 38820
ttctgttttt tttttttttt tgagatggag tctcgctctg tcgcccaggc tggagtgcag 38880
tggcgggatc tcggctcact gcaagctccg ccacccgggt tcacgccatt ctcctgcctc 38940
agcctcccaa gtagctggga ctacaggcgc ccgccactac gcccggctaa ttttttgta 39000
tttttagtag agatggggtt tcaccgtttt agccaggatg gtctcaatct cctgacctcg 39060
tgatccgccc gcctcagcct cccaaagtgc tgggattaca ggcgtgagcc accgcgcccg 39120
gcccttttta cgtttttcta tgacattttt cttttataaa ttacatttgt atcatttacc 39180
tgtttttctg ttgagttgtt tgcctctctc tcagactcta ttggagctct ttattatgga 39240
tatgaaattt tataagtata ttaaattata aatacattat gttacaaata ttttctttaa 39300
aaattctatt gcccgaggcg ggcggatcac gaggtcagga gatcgagacc atcctggcta 39360
acacggtgaa accccgtctc tactaaaaat acaaaaaatt agccgggcgt tgtagcgggc 39420
gcctgtagtc ccagctactc gggaggctga ggcaggagaa tggcgtgaac ccgggaggcg 39480
gagcttgcag tgagccgaga tcgcgccact gcactccagc ctgggcgaca gagcgagact 39540
ccgtctcaaa aaaaaaaaaa aaaatctatt gcaaaaatac aaatacttta atattaagta 39600
attttcatat tattatgcca atctgtcttt atagctgctg ggttttatta tagaggttag 39660
ttgtttcaga ttcttaactt tctaattcct aatttttta tttttttatt attattattt 39720
ttgagacagg atcttactct gtcacctatg ctggaatgca gtggcacaaa tgtggctcac 39780
tgaagcctta acctccaggc tcaggcagtc ctcctgcctc agactccaga gtagctgaag 39840
actgtaggca tgtgccacca tgcccagcta gtttttattt ttttgtagag gtgagggtct 39900
tgccatgttg cccaggtttg tctcaaaatc ctgggctcaa gcaattcaca cacatcagcc 39960
tcccaaagtg ctgcaattac aggcatgcac caccatgcct ggcccctaaa ttctcgtagt 40020
ctgtttttat gtgtagatat ttattccaca caaatttatt atttttttct ttttttgcag 40080
ggtgtcaggt agggatgtaa cctgaccatg gaattaacta agttattttt taaaaattaa 40140
atcatttaaa tatgcttgtc tgaaaaacaa ttttatagca ccagtcatga gaataattga 40200
ggtgaaaata aaatatgtcc ctttctgaat tcaattacaa tgtattttgc tttatgtttt 40260
tctttttaa attattttta ttttaaaatg tttgatagaa tttttttcta agactttttt 40320
gtacacaatt ttagagatga ggaaggaaca gagcatttac gaaaacgaaa tacgaagttg 40380
ccttttatgt ttaccactgg agaagctgtg ttgtatgagg caaccaaccc ttttcctgcc 40440
ataatggatc ccttaccact aaggactaaa aatggcacta gtggaaaaga ctctgctacc 40500
acatccactc taagcaagga ctctctcaat cctagttccc tcctggctgc catgatgcaa 40560
caagatgagt ctatttatct ctatcctgct tcaagtactt caagtactgc accttttgaa 40620
aacaactttt tcaacgaatc tatgaatgaa tgcagaaatt ggcaagataa tactgcaccg 40680
atgggaaatg atactatcct gaaacatgag caaattgacc agcctcagga tgtgaactca 40740
tttgctggag gtcacccagg gctctttcaa gatagtaaaa acagtgactt gtacagcata 40800
atgaaaaacc taggcattga ttttgaagac atcagacaca tgcagaatga aaaatttttc 40860
agaaatgatt tttctggtga ggttgacttc agagacattg acttaacgga tgaaatcctg 40920
acgtatgtcc aagattcttt aagtaagtct cccttcatac cttcagatta tcaacagcaa 40980
cagtccttgg ctctgaactc aagctgtatg gtacaggaac acctacatct agaacagcaa 41040
cagcaacatc accaaaagca agtagtagtg gagccacagc aacagctgtg tcagaagatg 41100
aagcacatgc aagttaatgg catgtttgaa aattggaact ctaaccaatt cgtgcctttc 41160
aattgtccac agcaagaccc acaacaatat aatgtcttta cagacttaca tgggatcagt 41220
caagagttcc cctacaaatc tgaaatggat tctatgcctt atacacagaa ctttatttcc 41280
tgtaatcagc ctgtattacc acaacattcc aaatgtacag agctggacta ccctatgggg 41340
agttttgaac catccccata ccccactact tctagtttag aagattttgt cacttgttta 41400
caacttcctg aaaaccaaaa gcatggatta aatccacagt cagccataat aactcctcag 41460
acatgttatg ctggggccgt gtcgatgtat cagtgccagc cagaacctca gcacacccac 41520
gtgggtcaga tgcagtacaa tccagtactg ccaggccaac aggcattttt aaacaaggta 41580
agggtgttat caaactgaat taaatctttc agtgattctt tttaccttat agacatgtta 41640
cacatttttt atgtcagctg attttaatcg gttatctaca gcattcatgg agacagcatt 41700
ttttattata tctgtgacta cctttttttt ttttacaagc ctgtactttt tccagtatgt 41760
tactaatata tcattcacct gattcatgag ggagaaagat atcaaggaat gaagcaacat 41820
gaatgtgtcc ttaatataag atgacctaaa ttaccaggtg aaattagttt ttagaagtat 41880
tttgtttaaa atagataatt tggtttattc tttctggatt ctttaaaaat tatatggcta 41940
tttaaaaatt caagctttaa aaaacgtatt gcaattttta agaataattt cttcaaagct 42000
ctattttttt atatatgttt gaaattgagt taaactcaaa tttaagtgtg ctttcttaca 42060
atgcctctga aaccctagat taattatatc cctggaattc agtcctaggc acctccatgt 42120
tctctagcta ttcctccaca ttacctcccc tatcctcatc tcatccttta aggtagaatg 42180
gctttctttt ctggctttct taaaagaggt aactcagctg gctttctgtc atggaaatca 42240
agcttgatag tgcattttttg ttgtttaaat gtgtcatcag aatccgtctg gcagtgagca 42300
cactttaaat ctaaaaatga tcacttaaaa aaaaaaagtt aacataatgt cagtaactgc 42360
tgtctctggc cactcaggaa tacatcatgt ttgcatttat gctttttcca ttagaaaata 42420
tttagttcat tttaaagtat atttaagttt agttttaaag aatatcttga ctaaaattaa 42480
gctccttgac ccctgtttac tctgtattag agtataataa ttaaaagtat gacctgaagc 42540
tttatcttta attgtatttt ctggcttttt catacatttt gcttgtctaa tcgtatatga 42600
gctttttaat agaaaaggac agtgaaaatt tttcttattc cttacatcct tcaattatat 42660
taaaattgaa taatattcag ttatagtccg tctcacaaaa ttgctatgaa agtatatttt 42720
actcttgagt aaagcaaatt gtacagaagt taattctgta aaattacatt ttgaataagg 42780
agttgcatga gtaccacata agttctttgc agtgttttcc cctcactact tttcactgct 42840
tctttgtaaa taaccaaata attctataga cctacatatg ttccagagta catgttattg 42900
agctaagaca ctcaatattg agccactgag tagctgttca gcacttgaaa tgtggctagt 42960
ccaaattgag atgtgctgtg tgaagtacac attggatttt tggattttga agacttggct 43020
tgaaaaaaga atgtaaaata tctcatcttt tattattgat ttcatgttga aatgattagt 43080
tttttcagta gccgcattac aaaagtaaaa agaaacaggt aaaattaact ttagaaatgt 43140
attttattta atctactgta gccaaaaatt taagttctgt atgtggctca cattatattt 43200
ctattggatt acactgctgt gtacagtatg tttaaagaga atggtgacat gaattgtgtt 43260
atgagtaatg agaaaaaatc attttaaact caccattatc tggccaggta atactaactt 43320

-continued

```
tttatttaaa gaatttacag tgttgccatt cattgaagat acaggttata tgatttttac  43380
tatagatttt atatatgttt tggaggatct gtgaagtaat taacattttg attactgaag  43440
ccagttatgt aggctttaca aaggtagatt ttatttgaag caattaagga tatgatttta  43500
atctgtttta aagtttccag aacgtccact aactaaaata taaaggctct gtaatctata  43560
aaactctaca gagctataca tcttcatgtc cttccttttt atttttcttt tttctactag  43620
cagttataga aaccagattc attgcagtgt aagaaaacaa gacagagcat tttcttttgg  43680
taacttgatt ctgtaattag aactatgctt tcagtagtat tcattaatta aaagtatatt  43740
atgaataaga aatcggttaa gaaaatcata cctgtggtgt aatattttag gaatatttag  43800
aaacatttag aaaatcagaa gctgcctttt ttggaaaagt tttgcattcc agtgtaagat  43860
tcctgaatat aatcaattca ttgatacgta taacttcaaa cctggtcaaa gcaaacctac  43920
ttatgataga gaatatttaa ctgtaatttg tgacttgtgc tgtttgaccc atcaattcct  43980
acctgaccca aaggcaatct gaaatgagac agctgcatca ctcatctgta ccatgttcaa  44040
aatttcctgt caaattaatg gaaaaacagg ttataaatgc aactaataca taatatgtcc  44100
tcagtatgtc ttcactgtgt gaaagattta aaatttagca acagtaaagg aacttgaagt  44160
ttacaactct caggggtaag attttaaaaa tacatgttaa tgttatttac tggcttaaga  44220
tacttggaag atctattcca ataagttgca tcaccatttt tgttttcagt ttcagaatgg  44280
agttttaaat gaaacatatc cagctgaatt aaataacata aataacactc agactaccac  44340
acatcttcag ccacttcatc atccgtcaga agccagacct tttcctgatt tgacatccag  44400
tggattcctg taattccaag cccaattttg accctggttt ttggattaaa ttagtttgtg  44460
aaggattatg gaaaaataaa actgtcactg ttggacgtca gcaagttcac atggaggcat  44520
tgatgcatgc tattcacaat tattccaaac caaattttaa tttttgcttt tagaaaaggg  44580
agtttaaaaa tggtatcaaa attacatata ctacagtcaa gatagaaagg gtgctgccac  44640
ggagtggtga ggtaccgtct acatttcaca ttattctggg caccacaaaa tatacaaaac  44700
tttatcaggg aaactaagat tcttttaaat tagaaaatat tctctatttg aattatttct  44760
gtcacagtaa aaataaaata ctttgagttt tgagctactg gattcttatt agttccccaa  44820
atacaaagtt agagaactaa actagttttt cctatcatgt taacctctgc ttttatctca  44880
gatgttaaaa taaatggttt ggtgcttttt ataaaaagat aatctcagtg ctttcctcct  44940
tcactgtttc atctaagtgc ctcacatttt tttctaccta taacactcta ggatgtatat  45000
tttatataaa gtattctttt tctttttttaa attaatatct ttctgcacac aaatattatt  45060
tgtgtttcct aaatccaacc attttcatta attcaggcat attttaactc cactgcttac  45120
ctactttctt caggtaaagg gcaaataatg atcgaaaaaa taattattta ttacataatt  45180
tagttgtttc tagactataa atgttgctat gtgccttatg ttgaaaaaat ttaaaagtaa  45240
aatgtctttc caaattattt cttaattatt ataaaaatat taagacaata gcacttaaat  45300
tcctcaacag tgttttcaga agaaataaat ataccactct ttacctttat tgatatctcc  45360
atgatgatag ttgaatgttg caatgtgaaa aatctgctgt taactgcaac cttgtttatt  45420
aaattgcaag aagctttatt tctagctttt taattaagca aagcacccat ttcaatgtgt  45480
ataaattgtc tttaaaaact gttttagacc tataatcctt gataatatat tgtgttgact  45540
ttataaattt cgcttcttag aacagtggaa actatgtgtt tttctcatat ttgaggagtg  45600
ttaagattgc agatagcaag gtttggtgca aagtattgta atgagtgaat tgaatggtgc  45660
attgtataga tataatgaac aaaattattt gtaagatatt tgcagttttt cattttaaaa  45720
```

-continued

| | | | | | | |
|---|---|---|---|---|---|---|
| agtccatacc | ttatatatgc | acttaatttg | ttggggcttt | acatacttta | tcaatgtgtc | 45780 |
| tttctaagaa | atcaagtaat | gaatccaact | gcttaaagtt | ggtattaata | aaaagacaac | 45840 |
| cacatagttc | gtttaccttc | aaactttagg | ttttttaat | gatatactga | tcttcattac | 45900 |
| caataggcaa | attaatcacc | ctaccaactt | tactgtccta | acatggttta | aaagaaaaaa | 45960 |
| tgacaccatc | ttttattctt | tttttttttt | ttttttgaga | gagagtctta | ctctgccgcc | 46020 |
| caaactggag | tgcagtggca | caatcttggc | tcactgcaac | ctctacctcc | tgggttcaag | 46080 |
| tgattctctt | gcctcagcct | cccgagttgc | tgggattaca | ggcatgtgcc | accatgccca | 46140 |
| gctaattttt | gtatttttag | tagaaacggg | tttcaccatg | ttggccagac | tggtctcaaa | 46200 |
| ctcctgacct | caggtgagcc | tcccaccttg | gcctcccaaa | gtgctgggat | tacaggcgtg | 46260 |
| agccactgca | ttcagctctt | cttttcttta | gatatgagag | ctgaagagct | tagacacatt | 46320 |
| ttgcatgtat | tatttgaaaa | tctgatggaa | tcccaaactg | agatgtatta | aaatacaatt | 46380 |
| tttggccggg | tgcagtggct | cacgcctgta | atcccagcac | ttggggaggg | cgaggagggt | 46440 |
| ggatcacgag | gtcaagagat | ggagaccatc | ctgaccaaca | tggtgaaacc | ctgtctctac | 46500 |
| taaaaataca | gaaattagct | gggcatggtg | gcgtgagcct | gtagtcctag | ctactcagga | 46560 |
| ggctgaggca | ggagaatagc | ctgaacctgg | gaatcggagg | ttgcagagcc | aagatcgccc | 46620 |
| cactgcactc | cagcctggca | atagaccgag | actccgtctc | caaaaaaaaa | aaaaatacaa | 46680 |
| tttttatttc | ttttactttt | tttagtaagt | taatgtatat | aaaaatggct | tcggacaaaa | 46740 |
| tatctctgag | ttctgtgtat | tttcagtcaa | aactttaaac | ctgtagaatc | aatttaagtg | 46800 |
| ttggaaaaaa | tttgtctgaa | acatttcata | atttgtttcc | agcatgaggt | atctaaggat | 46860 |
| ttagaccaga | ggtctagatt | aatactctat | ttttacattt | aaacctttta | ttataagtct | 46920 |
| tacataaacc | atttttgtta | ctctcttcca | catgttactg | gataaattgt | ttagtggaaa | 46980 |
| ataggctttt | taatcatgaa | tatgatgaca | atcagttata | cagttataaa | attaaaagtt | 47040 |
| tgaaaagcaa | tattgtatat | ttttatctat | ataaaataac | taaaatgtat | ctaagaataa | 47100 |
| taaaatcacg | ttaaaccaaa | tacacgtttg | tctgtattgt | taagtgccaa | acaaaggata | 47160 |
| cttagtgcac | tgctacattg | tgggatttat | ttctagatga | tgtgcacatc | taaggatatg | 47220 |
| gatgtgtcta | atttagtctt | ttcctgtacc | aggtttttct | tacaatacct | gaagacttac | 47280 |
| cagtattcta | gtgtattatg | aagctttcaa | cattactatg | cacaaactag | tgtttttcga | 47340 |
| tgttactaaa | ttttaggtaa | atgctttcat | ggctttttc | ttcaaaatgt | tactgcttac | 47400 |
| atatatcatg | catagatttt | tgcttaaagt | atgatttata | atatcctcat | tatcaaagtt | 47460 |
| gtatacaata | atatataata | aaataacaaa | tatgaa | | | 47496 |